(12) United States Patent
Hull, III et al.

(10) Patent No.: US 9,388,176 B2
(45) Date of Patent: Jul. 12, 2016

(54) METHOD OF TREATING CONDITIIONS WITH KINASE INHIBITORS

(71) Applicant: Allergan, Inc., Irvine, CA (US)

(72) Inventors: Clarence E. Hull, III, Mission Viejo, CA (US); Thomas C. Malone, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 13/796,928

(22) Filed: Mar. 12, 2013

(65) Prior Publication Data

US 2013/0237537 A1 Sep. 12, 2013

Related U.S. Application Data

(60) Provisional application No. 61/609,742, filed on Mar. 12, 2012.

(51) Int. Cl.
*C07D 471/04* (2006.01)
*C07D 487/04* (2006.01)
*A61K 31/437* (2006.01)
*A61K 31/4375* (2006.01)
*A61K 31/519* (2006.01)

(52) U.S. Cl.
CPC ............ *C07D 471/04* (2013.01); *A61K 31/437* (2013.01); *A61K 31/4375* (2013.01); *A61K 31/519* (2013.01); *C07D 487/04* (2013.01)

(58) Field of Classification Search
CPC A61K 31/437; A61K 31/4375; A61K 31/519
See application file for complete search history.

(56) References Cited

U.S. PATENT DOCUMENTS

| 4,166,452 A | 9/1979 | Generales et al. |
| 4,256,108 A | 3/1981 | Theeuwes |
| 2010/0226992 A1* | 9/2010 | Kabra ........................... 424/489 |

FOREIGN PATENT DOCUMENTS

| WO | 2005-107706 | 11/2005 |
| WO | 2008-054749 | 5/2008 |
| WO | 2011-101806 | 8/2011 |

OTHER PUBLICATIONS

Arora, Amit et al, Role of Tyrosine Kinase Inhibitors in Cancer Therapy, Journal of Pharmacology and Experimental Therapeutics, 2005, 971-979, 315(3).
Barakat, Mark et al, VEGF Inhibitors for The Treatment of Neovascular Age-Related Macular Degeneration, Expert Opin. Investig. Drugs, 2009, 637-646, 18(5).
Bergers, Gabriele et al, Benefits of Targeting Both Pericytes and Endothelial Cells in the Tumor Vasculature With Kinase Inhibitors, J. Clin. Invest., 2003, 1287-1295, 111.
Campochiaro, Peter, Molecular Targets for Retinal Vascular Diseases, Journal of Cellular Physiology, 2007, 575-581, 210.
Chappelow, Aimee et al, Neovascular Age-Related Macular Degeneration, Drugs, 2008, 1029-1036, 68(8).
Cowan-Jacob, S.W., Structural Biology of Protein Tyrosine Kinases, Cell. Mol. Life Sci., 2006, 2608-2625, 63.
Guttman, Cheryl, PTERYGIA: Anti-Angiogenic Therapy Supported by Scientific Rationale, But Not by Trial Results, Cornea, 2013, 1 Page, 17/18 (12/1).
Heidenreich, Regina et al, Angiogenesis: The New Potential Target for The Therapy of Psoriasis?, Drug News Perspect, Mar. 2008, 97-105, 21(2).
Jo, Nobuo et al, Inhibition of Platelet-Derived Growth Factor B Signaling Enhances the Efficacy of Anti-Vascular Endothelial Growth Factor Therapy in Multiple Models of Ocular Neovascularization, American Journal of Pathology, Jun. 2006, 2036-2052, 168(6).
Ni, Zhang et al, Emerging Pharmacologic Therapies for Wet Age-Related Macular Degeneration, Ophthalmologica, 2009, 401-410, 223.
Peng, Mei-Ling et al, Vascular Endothelial Growth Factor Gene Polymorphism and Protein Expression in the Pathogenesis of Pterygium, Br. J. Ophthalmol, 2014, 556-561, 98.
Remington's Pharmaceutical Sciences, 16th Edition, 10 Pages, 1980.
Schon, Uwe et al, An Improved Synthesis of N-aryl and N-heteroaryl Substituted Piperidones, Tetrahedron Letters, 2007, 2519-2525, 48.
Stommel, Jayne et al, Coactivation of Receptor Tyrosine Kinases Affects the Response of Tumor Cells to Targeted Therapies, Science, 2007, 287-290, 318.
Zhang, Xinyuan et al, Vascular Endothelial Growth Factor-A: A Multifunctional Molecular Player in Diabetic Retinopathy, The International Journal of Biochemistry & Cell Biology, 2009, 2368-2371, 41.
Patent Cooperation Treaty, Notification of Transmittal of the International Search Report and the Written Opinion of the International Searching Authority, or the Declaration, Form PCT/ISA/220, Int. App. No. PCT/US2013/030625, May 14, 2013.

* cited by examiner

*Primary Examiner* — Zohreh Fay
(74) *Attorney, Agent, or Firm* — Jonathan Bass

(57) ABSTRACT

The present invention relates to a method of treating ophthalmic diseases and conditions, e.g. diabetic retinopathy, age-related macular degeneration, retinopathy of prematurity, etc., in a subject comprising administering to said subject a therapeutically effective amount of at least one compound of formula I

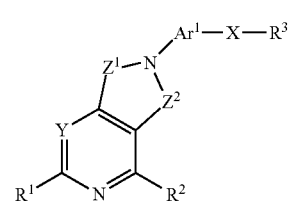

or a prodrug, pharmaceutically acceptable salt, racemic mixtures or enantiomers of said compound. The compounds of formula I are capable of modulating tyrosine kinase signal transduction in order to regulate, modulate and/or inhibit abnormal cell proliferation.

2 Claims, 1 Drawing Sheet

Hypothetical Orientation of Example 1 in ATP site of VEGFR2 receptor. $R^1$ and $R^8$ substituents are oriented towards solvent exposed protein surface.
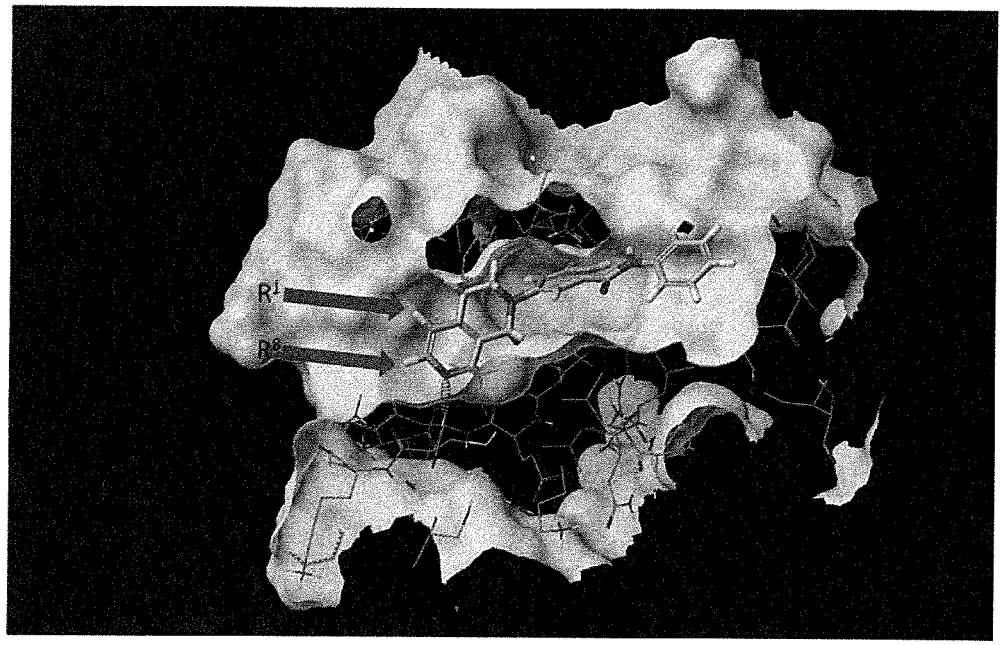

METHOD OF TREATING CONDITIIONS WITH KINASE INHIBITORS

CROSS REFERENCE TO RELATED APPLICATIONS

This application claims the benefit of U.S. Provisional Application Ser. No. 61/609,742, filed on Mar. 12, 2012, all of which is incorporated herein by reference herein in its entirety.

BACKGROUND OF THE INVENTION

1. Field of the Invention

The present invention is directed to methods of regulating, modulating or inhibiting tyrosine kinases, whether of the receptor or non-receptor class, for the prevention and/or treatment of disorders related to unregulated tyrosine kinase signal transduction, including cell growth, metabolic disorders and blood vessel proliferative disorders.

2. Description of the Related Art

Protein tyrosine kinases (PTKs) comprise a large and diverse class of proteins having enzymatic activity. The PTKs play an important role in the control of cell growth and differentiation. For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 2996, 63, 2608-2625 which is incorporated herein by reference.

There are a number of examples where RTK kinases, have been found to be involved in cellular signaling pathways leading to pathological conditions, including wet age-related macular degeneration (Ni et al. Ophthalmologica 2009 223 401-410; Chappelow et al. Drugs 2008 68 1029-1036), diabetic retinopathy (Zhang et al Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105) and hyper immune response. In ophthalmic diseases such as neovascular age-related macular degeneration and diabetic retinopathy aberrant activation of VEGF receptors can lead to abnormal blood vessel growth. The importance of VEGFR signaling in the neovascular age-related macular degeneration disease process is evident by the clinical success of multiple anti-VEGF targeting agents including Lucentis®, Avastin®, and EYLEA™ (Barakat et al., Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as neovascular age-related macular degeneration and diabetic retinopathy the inhibition of both VEGFR and PDGFR may provide a greater therapeutic effect in by causing regression of existing neovascular blood vessels present in the disease (Adamis et al., Am. J. Pathol. 2006 168 2036-2053). In cancer inhibition of multiple RTK signaling pathways has been suggested to have a greater effect than inhibiting a single RTK pathway (DePinho et al., Science 2007 318 287-290; Bergers et al., J. Clin Invest. 2003 111 1287-1295).

The identification of effective small compounds which specifically inhibit signal transduction by modulating the activity of receptor and non-receptor tyrosine kinases to regulate and modulate abnormal or inappropriate cell proliferation is therefore desirable and one object of this invention.

WO2011/101806 which discloses certain bicyclic compounds, comprising a pyrimidine and a pyridine ring, which are reported to be useful as dual c-SRC/JAKJ inhibitors.

These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to the use of organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration, pterygium and retinopathy of prematurity, autoimmune diseases and transplant rejection.

In one illustrative embodiment, the compounds utilized in the method of the present invention have the following general formula I:

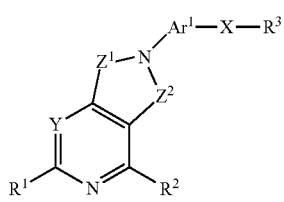

wherein
$R^1$ is selected from the group consisting of hydrogen, $C_1$ to $C_8$ alkyl, $NR^9R^{10}$, $C(O)NR^9R^{10}$, $(CR^{11}R^{12})_pNR^9R^{10}$, $(CR^{11}R^{12})_pC(O)OR^{13}$, $(CR^{11}R^{12})_pOR^{13}$, $NR^9C(O)(CR^{11}R^{12})_pNR^{10}R^{10}$, $NR^9C(O)(CR^{11}R^{12})_pC(O)OR^{13}$, $NR^9C(O)(CR^{11}R^{12})_pOR^{13}$, $C(O)(CR^{11}R^{12})_pNR^9R^{10}$, $C(O)(CR^{11}R^{12})_pC(O)OR^{13}$, $C(O)(CR^{11}R^{12})_pCOR^{13}$, $C(O)NR^9(CR^{11}R^{12})_pNR^9R^{10}$, $C(O)NR^9(CR^{11}R^{12})_pC(O)OR^{13}$, $C(O)NR^9(CR^{11}R^{12})_pCOR^{13}$, $NR^9C(O)NR^{10}(CR^{11}R^{12})_pNR^9R^{10}$, $NR^9C(O)NR^{10}(CR^{11}R^{12})_pC(O)OR^{13}NR^9C(O)NR^{10}(CR^{11}R^{12})_pOR^{13}$, $SR^{19}$, $S(O)R^{19}$ and $S(O)_2R^{19}$;
wherein each $R^9$ independently is hydrogen or alkyl;
each $R^{10}$ independently is hydrogen or alkyl;
each $R^{11}$ independently is hydrogen or alkyl;
each $R^{12}$ is hydrogen or alkyl;
each $R^{13}$ independently is hydrogen or alkyl;
each $R^{19}$ independently is hydrogen or alkyl;
each p independently is 0 or an integer of 1 to 6;
$R^2$ is hydrogen or $NH_2$;
$R^3$ is hydrocarbyl or substituted hydrocarbyl;
$Z^1$ is $(CR^4R^5)_n$;
$Z^2$ is $(CR^6R^7)_m$;
X is selected from the group consisting of:

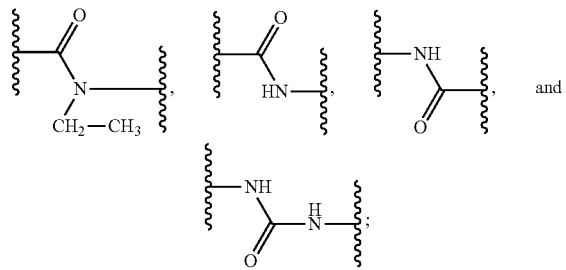

Y is $CR^8$ or N;
n is an integer of 1 or 2;
m is an integer of 1 or 2;
provided however that both n and m are not 2;
$Ar^1$ is aryl, wherein said aryl may be optionally substituted with alkyl, halogen, or haloalkyl, or wherein when said aryl has two substituents on adjacent carbon atoms, said substituents taken together with the carbon atoms to which they are attached form a phenyl which may be optionally substituted with alkyl, halogen or haloalkyl;
each $R^4$ independently is hydrogen or alkyl;
each $R^5$ independently is hydrogen or alkyl;
each $R^6$ independently is hydrogen or alkyl;
each $R^7$ independently is hydrogen or alkyl;
$R^8$ is selected from the group consisting of hydrogen, halogen, $CF_3$, $C_1$ to $C_8$ alkyl, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}C(O)(CR^{16}R^{17})_pCOR^{18}$, $C(O)NR^{14}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$, and $NR^{14}C(O)NR^{15}(CR^{16}R^{17})_pOR^{18}$;
wherein each $R^{14}$ independently is hydrogen or alkyl;
each $R^{15}$ independently is hydrogen or alkyl;
or $R^{14}$ and $R^{15}$ may be taken together with N to form a heterocyclic ring;
each $R^{16}$ independently is selected from the group consisting of hydrogen, alkyl, halogen, trifluoromethyl and hydroxy;
each $R^{17}$ independently is hydrogen, alkyl, halogen, trifluoromethyl or hydroxy;
each $R^{18}$ independently is hydrogen or alkyl;
or a prodrug, pharmaceutically acceptable salt, racemic mixtures or enantiomers of said compound.

In another embodiment, the compounds utilized in the method of the present invention have the following general formula I:

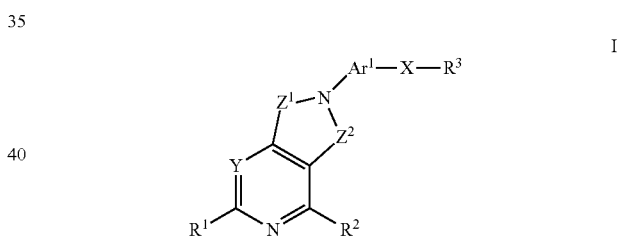

wherein
$R^1$ is selected from the group consisting of hydrogen, $C_1$ to $C_8$ alkyl, $NR^9R^{10}$, $C(O)NR^9R^{10}$, $(CR^{11}R^{12})_pNR^9R^{10}$, $(CR^{11}R^{12})_pC(O)OR^{13}$, $(CR^{11}R^{12})_pOR^{13}$, $NR^9C(O)(CR^{11}R^{12})_pNR^9R^{10}$, $NR^9C(O)(CR^{11}R^{12})_pC(O)OR^{13}$, $NR^9C(O)(CR^{11}R^{12})_pOR^{13}$, $C(O)(CR^{11}R^{12})_pNR^9R^{10}$, $C(O)(CR^{11}R^{12})_pC(O)OR^{13}$, $C(O)(CR^{11}R^{12})_pCOR^{13}$, $C(O)NR^9(CR^{11}R^{12})_pNR^9R^{10}$, $C(O)NR^9(CR^{11}R^{12})_pC(O)OR^{13}$, $C(O)NR^9(CR^{11}R^{12})_pCOR^{13}$, $NR^9C(O)NR^{10}(CR^{11}R^{12})_pNR^9R^{10}$, $NR^9C(O)NR^{10}(CR^{11}R^{12})_pC(O)OR^{13}$ and $NR^9C(O)NR^{10}(CR^{11}R^{12})_pOR^{13}$,
wherein $R^9$ is hydrogen or alkyl;
$R^{10}$ is hydrogen or alkyl;
$R^{11}$ is hydrogen or alkyl;
$R^{12}$ is hydrogen or alkyl;
$R^{13}$ is hydrogen or alkyl;
p is 0 or an integer of 1 to 6,
$R^2$ is hydrogen or $NH_2$,
$R^3$ is hydrocarbyl or substituted hydrocarbyl, preferably aryl, wherein said substituted hydrocarbyl, e.g. said aryl, may be optionally substituted with alkyl, halogen, or trifluoromethyl, $Z^1$ is $(CR^4R^5)_n$,
$Z^2$ is $(CR^6R^7)_m$,
X is

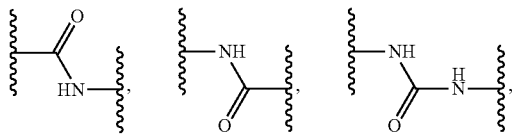 [SMILES: *NC(*)=O ; *NC(*)=O ; *NC(=O)N*]

Y is $CR^8$ or N,
n is an integer of 1 or 2,
m is an integer of 1 or 2,
provided however that both n and m are not 2,
$Ar^1$ is aryl, wherein said aryl may be optionally substituted with alkyl, halogen, or trifluoromethyl,
$R^4$ is hydrogen or alkyl,
$R^5$ is hydrogen or alkyl,
$R^6$ is hydrogen or alkyl,
$R^7$ is hydrogen or alkyl,
$R^8$ is selected from the group consisting of hydrogen, halogen, $CF_3$, $C_1$ to $C_8$ alkyl, $NR^{14}R^{15}$, $C(O)NR^{14}R^{15}$, $(CR^{16}R^{17})_p NR^{14}R^{15}$, $(CR^{16}R^{17})_p C(O)OR^{18}$, $(CR^{16}R^{17})_p OR^{18}$, $NR^{14}C(O)(CR^{16}R^{17})_p NR^{14}R^{15}$, $NR^{14}C(O)(CR^{16}R^{17})_p C(O)OR^{18}$, $NR^{14}C(O)(CR^{16}R^{17})_p OR^{18}$, $C(O)(CR^{16}R^{17})_p NR^{14}R^{15}$, $C(O)(CR^{16}R^{17})_p C(O)OR^{18} C(O)(CR^{16}R^{17})_p COR^{18}$, $C(O)NR^{14}(CR^{16}R^{17})_p NR^{14}R^{15}$, $C(O)NR^{14}(CR^{16}R^{17})_p C(O)OR^{18}$, $C(O)NR^{14}(CR^{16}R^{17})_p COR^{18}$, $NR^{14}C(O)NR^{15}(CR^{16}R^{17})_p NR^{14}R^{15}$, $NR^{14}C(O)NR^{15}(CR^{16}R^{17})_p C(O)OR^{18}$, $NR^{14}C(O)NR^{15}(CR^{16}R^{17})_p OR^{18}$,
wherein $R^{14}$ is hydrogen or alkyl,
$R^{15}$ is hydrogen or alkyl,
and $R^{14}$ and $R^{15}$ may be taken together with N to form a heterocyclic ring,
$R^{16}$ is selected from the group consisting of hydrogen, alkyl, halogen, trifluoromethyl and hydroxy,
$R^{17}$ is hydrogen, alkyl, halogen, trifluoromethyl or hydroxy and
$R^{18}$ is hydrogen or alkyl and
prodrugs, pharmaceutically acceptable salts, racemic mixtures and enantiomers of said compound.

In one aspect of the invention, in formula I, Y is N or $CR^8$, wherein $R^8$ is selected from the group consisting of hydrogen, $(CR^{16}R^{17})_p C(O)OR^{18}$, $C(O)NR^{14}(CR^{16}R^{17})_p NR^{14}R^{15}$, $C(O)NR^{14}(CR^{16}R^{17})_p C(O)OR^{18}$; wherein:
each p independently is 0 or an integer of 1 to 6;
each $R^{14}$ independently is hydrogen or alkyl;
each $R^{15}$ independently is hydrogen or alkyl;
or $R^{14}$ and $R^{15}$ may be taken together with N to form a heterocyclic ring;
$R^{16}$ is selected from the group consisting of hydrogen, alkyl, halogen, trifluoromethyl and hydroxy;
each $R^{17}$ independently is hydrogen, alkyl, halogen, trifluoromethyl or hydroxy; and
each $R^{18}$ independently is hydrogen or alkyl.

In another aspect of the invention, in formula I, $R^1$ is $NH_2$ and $R^2$ is hydrogen.

In another aspect of the invention, in formula I, $R^1$ or $R^8$ is a solubility enhancing moiety that is a polar radical which increases the hydrophilicity of the molecule as compared to the same molecule wherein $R^1$ or $R^8$ is hydrogen. While not intending to be bound by theory, it is believed that, as show in the FIGURE, $R^1$ and $R^8$ resides outside of the receptor during binding and activation, therefore $R^1$ and $R^8$ are unexpectedly convenient sites for adding a polar radical to increase the solubility to the otherwise hydrophobic compound.

In another aspect of the invention, in formula I, $Ar^1$ is selected from the group consisting of phenyl, imidazolyl, thiazolyl, oxazolyl, pyridinyl, and benzopyridinyl.

In another aspect of the invention, in formula I, $R^1$ is selected from the group consisting of H, $NH_2$, $SR^{19}$, and $S(O)R^{19}$, wherein each $R^{19}$ independently is alkyl.

In another aspect of the invention, in formula I, $R^2$ is hydrogen

In another aspect of the invention, in formula I, $R^3$ is selected from the group consisting of phenyl, alkyl, and cycloalkyl.

In another aspect of the invention, in formula I, $R^3$ is alkyl is alkyl which is optionally substituted with a cycloakyl.

In another aspect of the invention, in formula I, $R^3$ is cycloalkyl which is optionally substituted with an alkyl.

In another aspect of the invention, in formula I, $R^3$ is phenyl which is substituted with a substituent selected from the group consisting of alkyl, alkyloxy, —O-Heterocyclyl, halogen and haloalkyl.

In another aspect of the invention, in formula I, $R^3$ is phenyl which is substituted with a substituent selected from the group consisting of $C_1$ to $C_7$ alkyl, which alkyl may be substituted with a fluoro, and $C_1$ to $C_7$ alkyloxy, which alkyloxy may be substituted with a nitrogen heteroatom.

In another aspect of the invention, in formula I, $R^3$ is phenyl which is substituted with a substituent selected from the group consisting of methyl, trifluoromethyl, ethyl, isopropyl, n-butyl, t-butyl, 3,3 dimethylbutyl, cyclopentyl, cyclohexyl cyclohexylmethyl, methyloxy and 1-methylpiperidin-4-yloxy.

In another aspect of the invention, in formula I, $Ar^1$ is pyridyl, which is unsubstituted, benzofused or substituted with methyl.

In another aspect of the invention, in formula I, $Ar^1$ is imidazole, which is optionally substituted with methyl.

In another aspect of the invention, in formula I, $Ar^1$ is unsubstituted oxazolyl or thiazolyl.

In another aspect of the invention, in formula I, $R^3$ is phenyl, wherein said phenyl is substituted with a substituent selected from the group consisting of alkyl, alkyloxy, halogen, and haloalkyl.

For example, said substituent may be selected from the group consisting of $C_1$ to $C_7$ alkyl, which alkyl may be substituted with a fluoro, and $C_1$ to $C_7$ alkyloxy, which alkyloxy may be substituted with a nitrogen heteroatom.

In another aspect of the invention, in formula I, $R^3$ is alkyl, e.g., ethyl, n-butyl, 3,3 dimethylbutyl, 4-t-butylcyclohexyl, cyclohexylmethyl, cyclopentyl, etc.

In another aspect of the invention, in formula I, $R^4$ is hydrogen.

In another aspect of the invention, in formula I, $R^5$ is hydrogen.

In another aspect of the invention, in formula I, $R^6$ is hydrogen.

In another aspect of the invention, in formula I, $R^7$ is hydrogen.

In another aspect of the invention, in formula I, $R^8$ is hydrogen.

In another aspect of the invention, in formula I, Y is CH or N.

In another aspect of the invention, in formula I, X is —C(O)—N(H)—.

In another aspect of the invention, in formula I, Y is N or CH.

In another aspect of the invention, in formula I, Ar¹ is aryl, which is optionally substituted with halogen, lower alkyl or halogen-substituted lower alkyl. In another embodiment, the substituents are selected from the group consisting of methyl, fluoro, chloro and trifluoromethyl.

Compounds of formula I are useful as kinase inhibitors. As such, compounds of formula I will be useful for treating diseases related to unregulated tyrosine kinase signal transduction, for example, cancer, blood vessel proliferative disorders, fibrotic disorders, and neurodegenerative diseases. In particular, the method of the present invention is useful for treatment of mesangial cell proliferative disorders and metabolic diseases, pterygium, arthritis, restenosis, hepatic cirrhosis, atherosclerosis, psoriasis, diabetes mellitus, wound healing, inflammation and neurodegenerative diseases. The compounds of formula I are especially preferred for treating ophthalmic diseases and conditions, such as diabetic retinopathy, age-related macular degeneration, retinopathy of prematurity, etc.

In another aspect, the present invention provides compound that is a 5,6,7,8-tetrahydropyrido[4,3-d]pyrimidine-N-hydrocarbyl(aryl)(carboxamide) or a 6,7-dihydro-5H-pyrrolo[3,4-d]pyrimidine-N-hydrocarbyl(aryl)(carboxamide), wherein said compound is a tyrosine kinase inhibitor that blocks the PDGR and VEGF receptors.

In another aspect, the 5,6,7,8-tetrahydropyrido[4,3-d]pyrimidine-N-hydrocarbyl(aryl)(carboxamide) or the 6,7-dihydro-5H-pyrrolo[3,4-d]pyrimidine-N-hydrocarbyl(aryl)(carboxamide) is a 2 or 4-amino-5,6,7,8-tetrahydropyrido[4,3-d]pyrimidine-N-hydrocarbyl(aryl)(carboxamide) or a 2 or 4-amino-6,7-dihydro-5H-pyrrolo[3,4-d]pyrimidine-N-hydrocarbyl(aryl)(carboxamide) and binds to the tyrosine kinase receptor.

In another aspect, the present invention provides a method for treating diseases related to unregulated tyrosine kinase signal transduction, by inhibiting/blocking the VEGF and/or PDGF receptors, the method comprising the step of administering to a subject in need thereof a therapeutically effective amount of at least one compound represented by the general formula I as set forth above.

In another aspect, the present invention provides a method of treating ophthalmic diseases and conditions in subject, comprising administering to said subject a pharmaceutical composition comprising a therapeutically effective amount of at least one compound represented by the general formula I as set forth above, or a prodrug, pharmaceutically acceptable salt, racemic mixtures, or enantiomers of said compound; and at least one pharmaceutically acceptable carrier or excipient.

In another aspect, the present invention provides a method of inhibiting the VEGF and/or PDGF receptors in a subject, comprising administering to said subject a therapeutically effective amount of a compound represented by the general formula I as set forth above, or a prodrug, pharmaceutically acceptable salt, racemic mixtures or enantiomers of said compound. In another aspect, the compound has an $IC_{50}$ value for compound inhibition in the VEGFR2 Kinase Assay of less than 1000 nM. In another aspect, compound has an $IC_{50}$ value for compound inhibition in the PDGFRβ Kinase Assay of less than 1000 nM. In another aspect, compound has an $IC_{50}$ value for compound inhibition in the VEGFR2 Kinase Assay and in the PDGFRβ Kinase Assay of less than 1000 nM.

BRIEF DESCRIPTION OF THE DRAWINGS

The drawing FIGURE shows the hypothetical orientation of the compound of Example 1 in ATP site of VEGFR2 receptor. The $R^1$ and $R^8$ substituents are oriented towards solvent exposed protein surface.

DETAILED DESCRIPTION OF THE INVENTION

The present invention is further directed to the use of pharmaceutical compositions comprising a pharmaceutically effective amount of the above-described compounds and a pharmaceutically acceptable carrier or excipient for treating diseases related to unregulated tyrosine kinase signal transduction. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"

"Ac" refers to acetyl

"COMU" refers to (1-Cyano-2-ethoxy-2-oxoethylidenaminooxy)dimethylamino-morpholino-carbenium hexafluorophosphate "DMA" refers to dimethylacetamide "DMF" refers to dimethylformamide "Et" refers to ethyl "EtOH" refers to ethanol "HBTU" refers to O-Benzotriazole-N,N,N',N'-tetramethyl-uronium-hexafluorophosphate "iPr" refers to i-propyl "Me" refers to methyl "MeOH" refers to methanol "PDGF" refers to platelet derived growth factor "PDGFRβ" refers to platelet derived growth factor receptor beta "Ph" refers to phenyl "PTKs" refers to protein tyrosine kinase "RTKs" refers to receptor tyrosine kinase "tBu" refers to t-butyl "TFA" refers to trifluoroacetic acid "THF" refers to tetrahydrofuran "VEGF" refers to vascular endothelial growth factor "VEGFR" refers to vascular endothelial growth factor receptor "Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts may also refers to those salts which retain the biological effectiveness and properties of the free acid and which are obtained by reaction with inorganic bases such as sodium hydroxide, calcium hydroxide, magnesium hydroxide, zinc hydroxide or by organic bases such as tromethamine, choline, diethylamine and lysine and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, NO₂, halogen, dimethyl amino, and SH.

"Alkoxy" refers to O-alkyl.

"Alkoxycarbonyl" refers to —C(O)O-alkyl or —C(O)O-aryl.

"Heterocyclyl" refers to a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, NO₂, amine, thioether, cyano, alkoxy, alkyl, and amino "Carbocyclic aryl" refers to an aryl group wherein the ring atoms are carbon.

"Heteroaryl" or "heterocyclic aryl" refers to an aryl group having from 1 to 3 heteroatoms as ring atoms, the remainder of the ring atoms being carbon. Heteroatoms include oxygen, sulfur, and nitrogen. Thus, heteroaryl groups include furanyl, thienyl, pyridyl, pyrrolyl, N-lower alkyl pyrrolo, pyrimidyl, pyrazinyl, imidazolyl and the like.

The compounds of this invention may be prepared by the general reaction schemes set forth below.

-continued

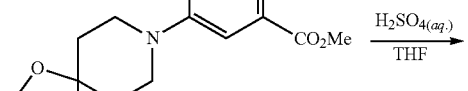

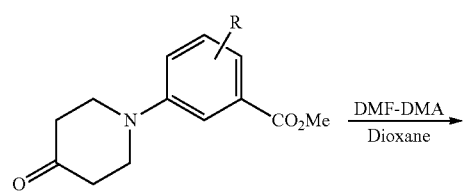

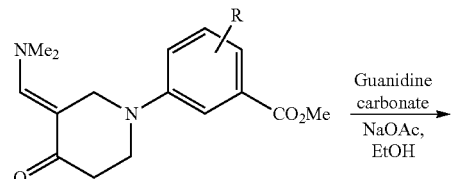

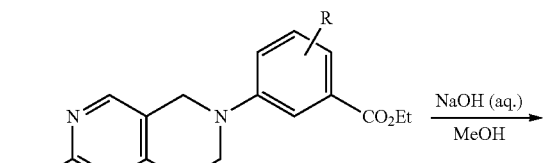

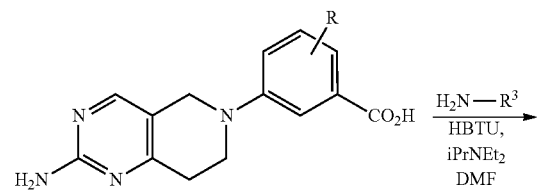

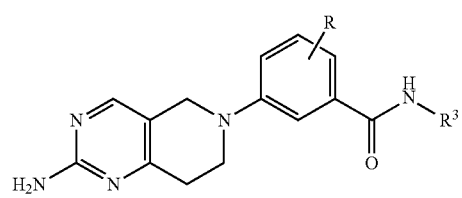

Scheme 1

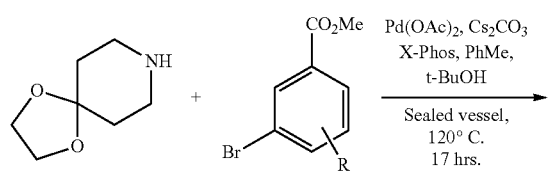

Scheme 2

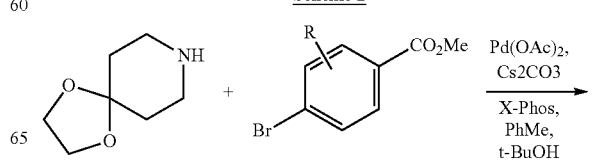

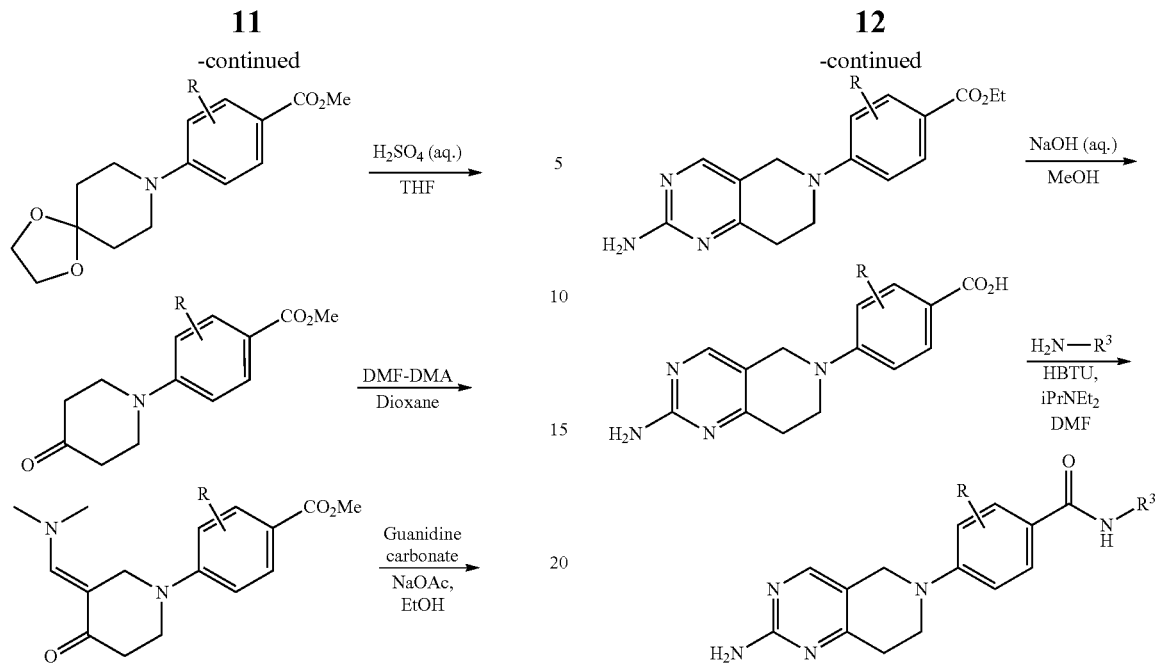
Scheme 3
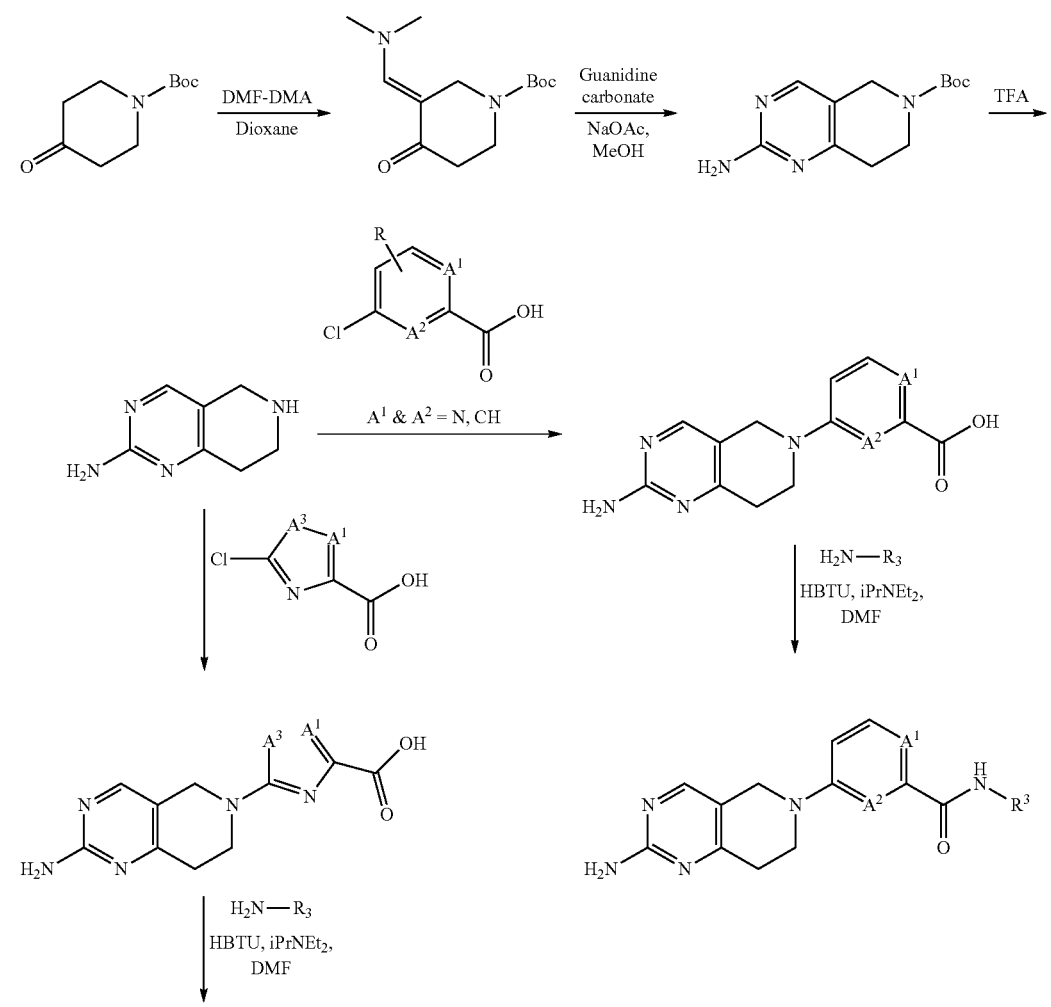

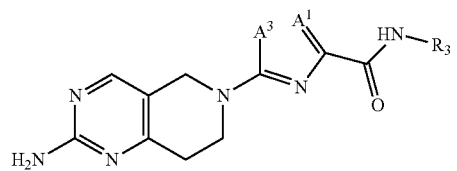
-continued
Scheme 4
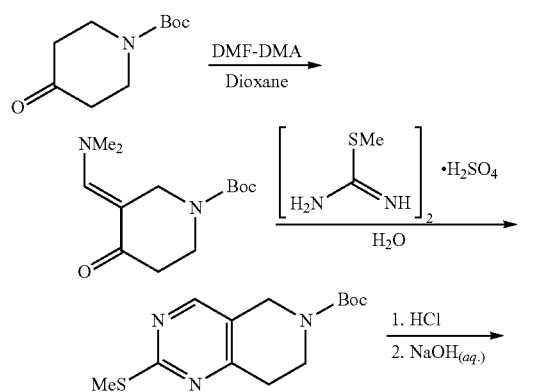
Scheme 5
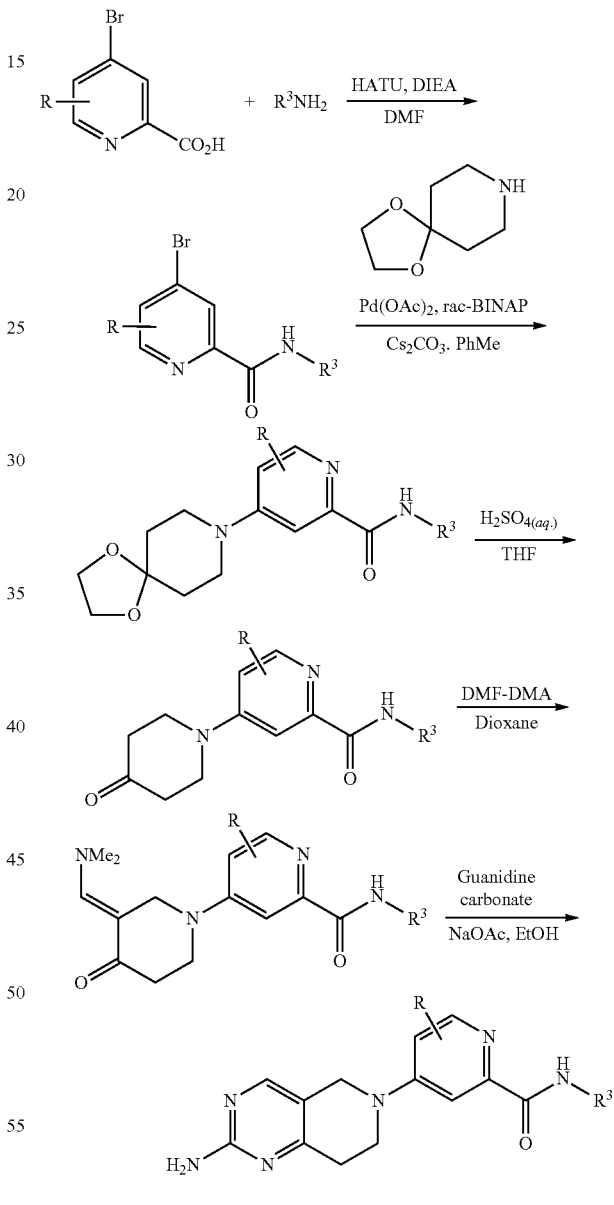
Scheme 6
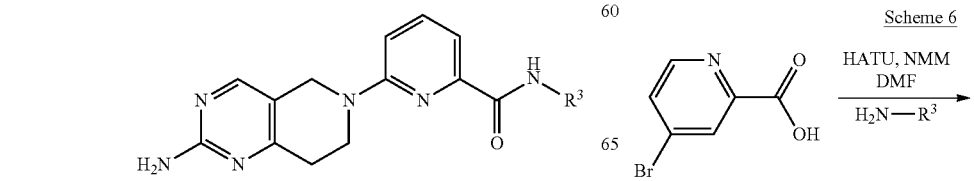

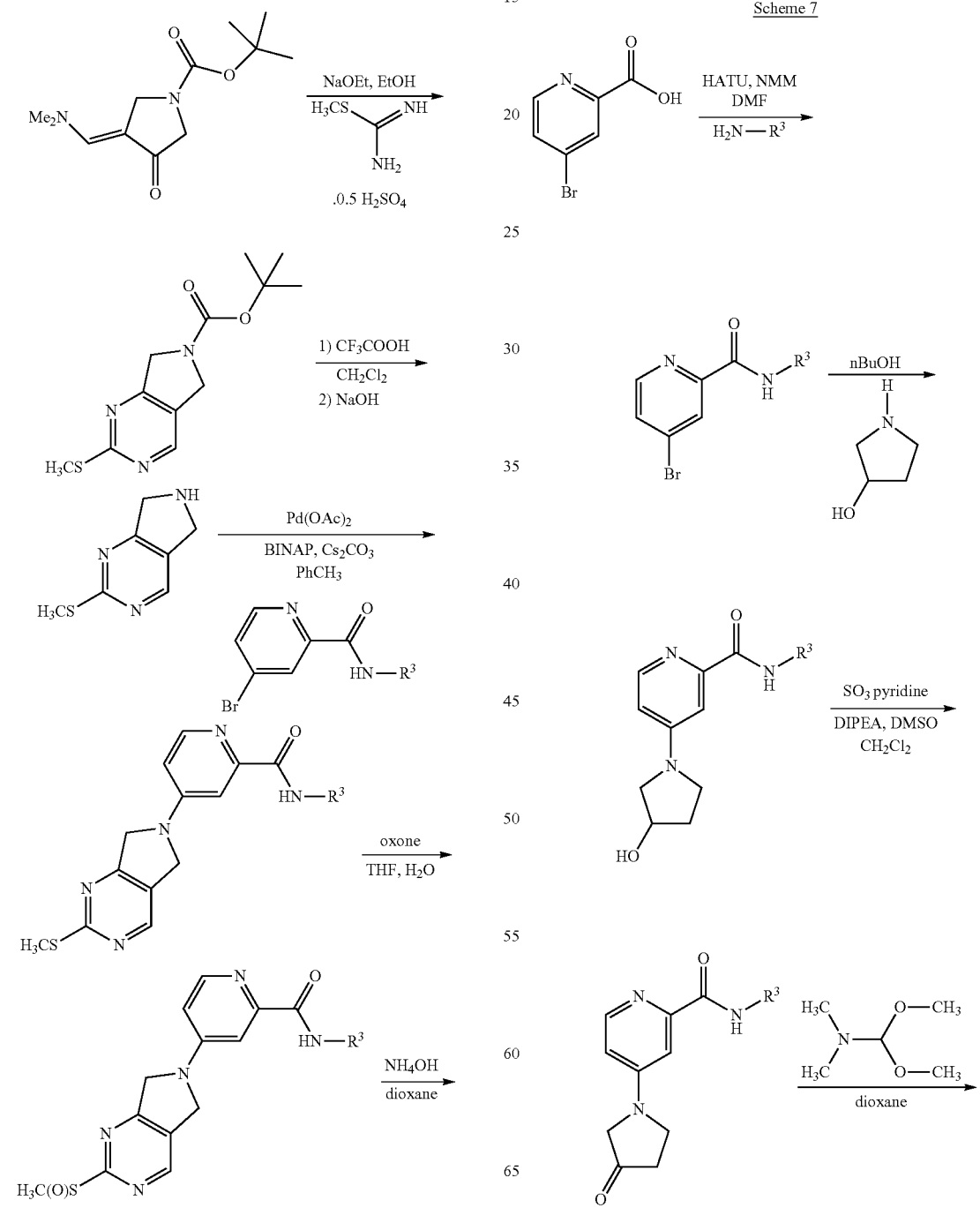
Scheme 7

-continued
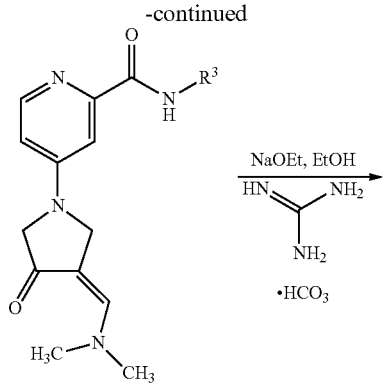
Scheme 8
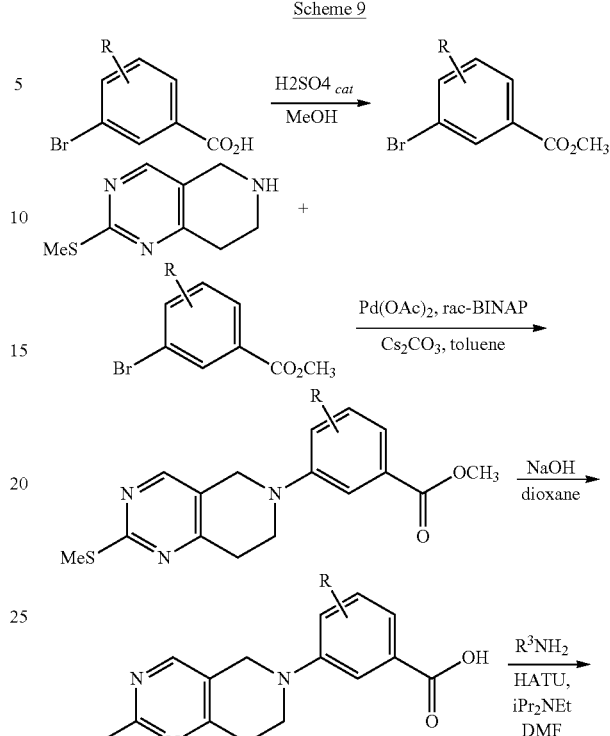
Scheme 9
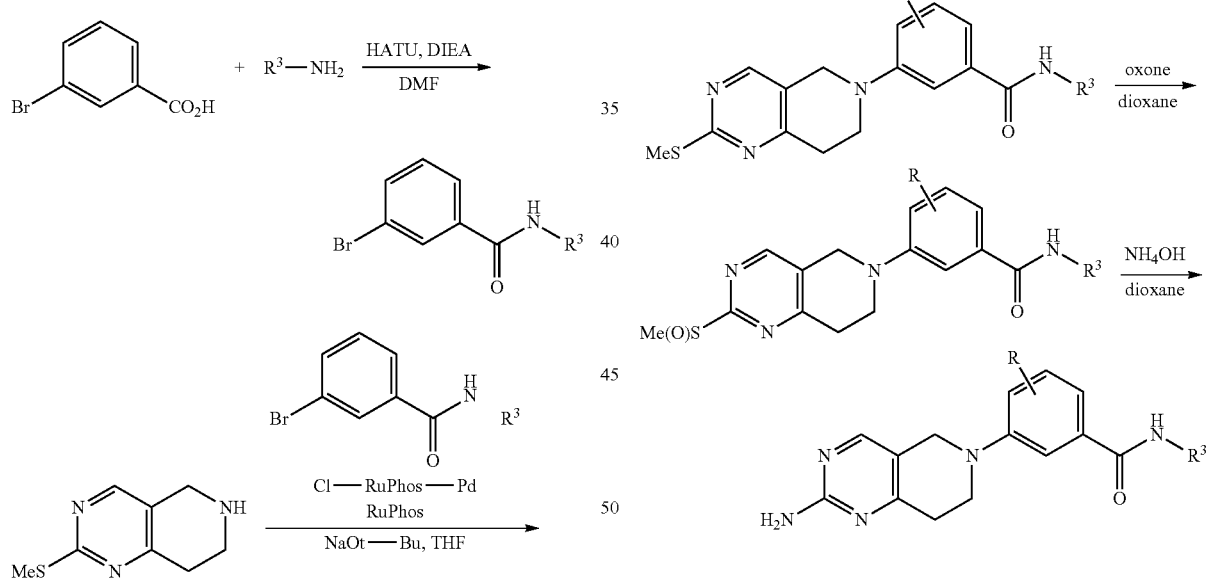
Scheme 10
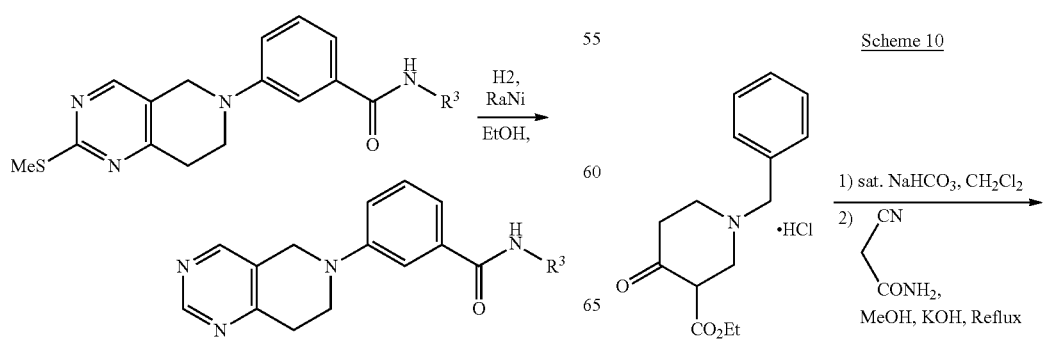

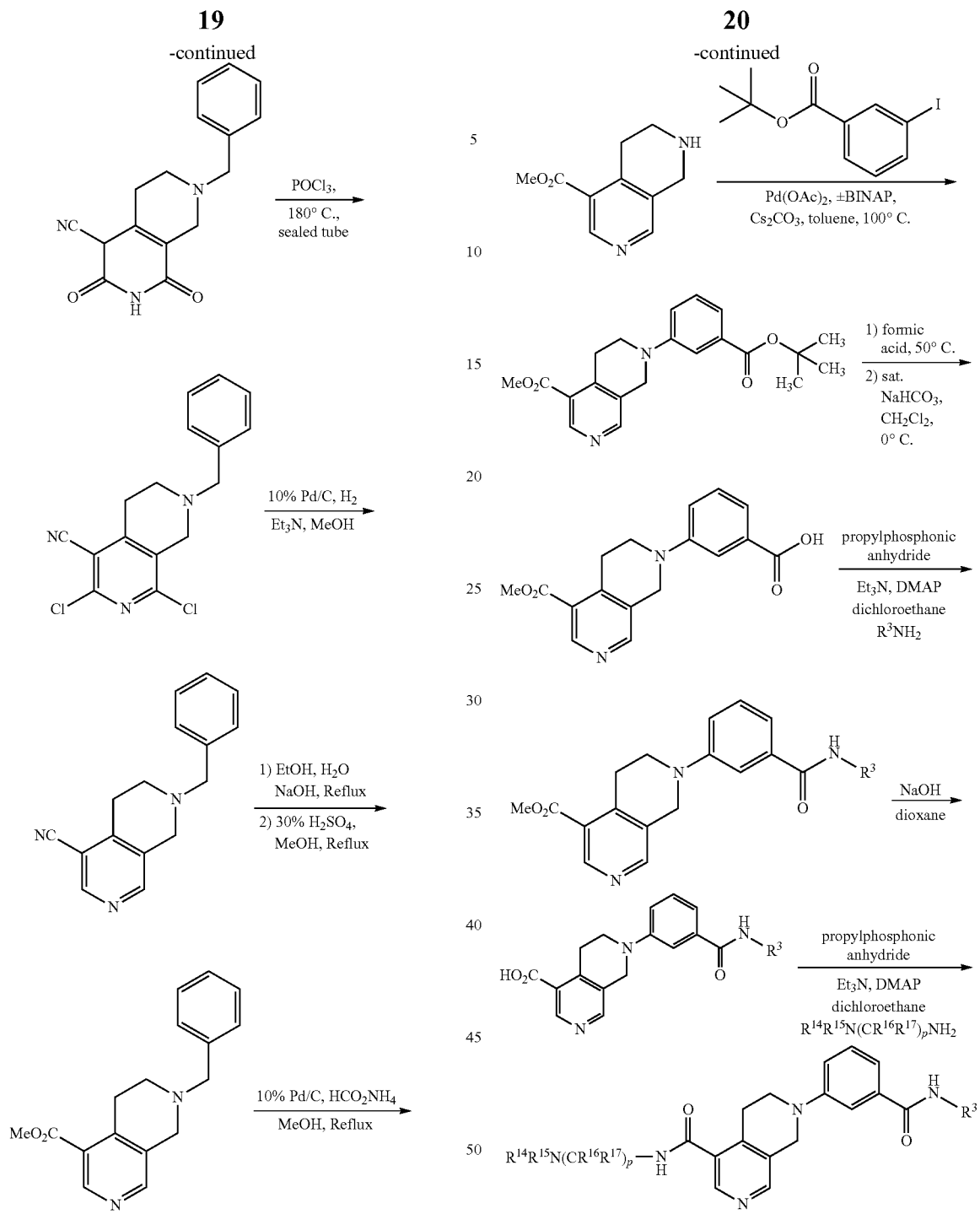
Scheme 11
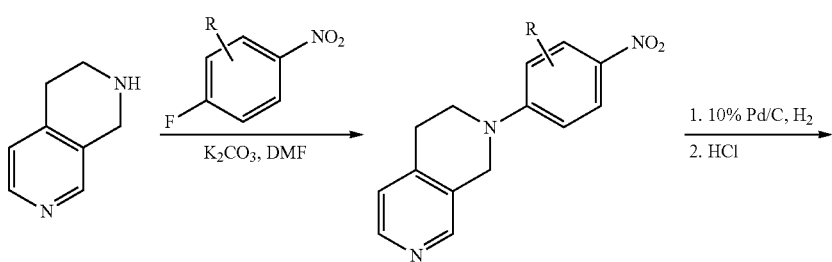

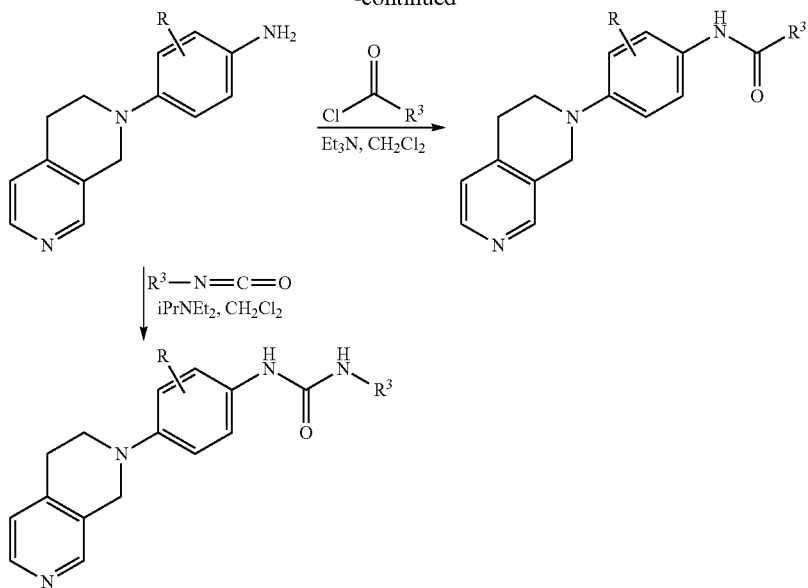

In particular the compounds used in the practice of the method of the present invention are selected from the compounds of Table 1, below. In Table 1 the compounds of the present invention are exemplified by any combination of Ar¹, R¹ and R² attached to the core template illustrated.

TABLE 1

| Example Number | Structure | Compound Name |
| --- | --- | --- |
| 1 | 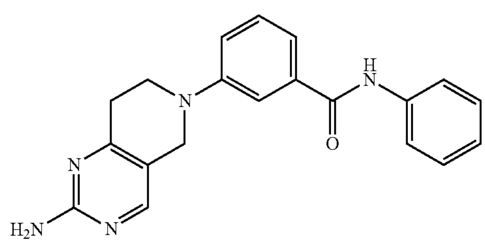 | 3-(2-amino-7,8-dihydropyrido[4,3-d]pyrimidin-6(5H)-yl)-N-phenylbenzamide |
| 2 | 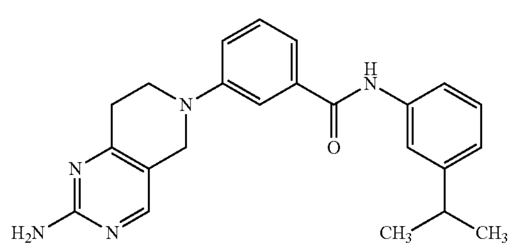 [SMILES: CC(C)c1cccc(NC(=O)c2cccc(N3CCc4nc(N)ncc4C3)c2)c1] | 3-(2-amino-7,8-dihydropyrido[4,3-d]pyrimidin-6(5H)-yl)-N-(3-isopropylphenyl)benzamide |
| 3 | 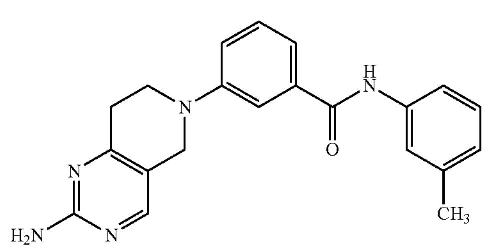 | 3-(2-amino-7,8-dihydropyrido[4,3-d]pyrimidin-6(5H)-yl)-N-(3-methylphenyl)benzamide |

TABLE 1-continued

| Example Number | Structure | Compound Name |
|---|---|---|
| 4 | 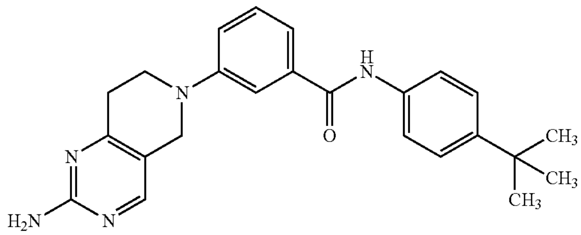 [SMILES: CC(C)(C)c1ccc(NC(=O)c2cccc(N3CCc4nc(N)ncc4C3)c2)cc1] | 3-(2-amino-7,8-dihydropyrido[4,3-d]pyrimidin-6(5H)-yl)-N-(4-tert-butylphenyl)benzamide |
| 5 | 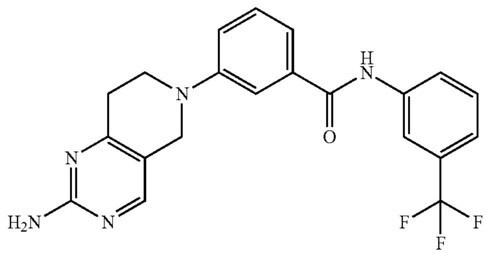 [SMILES: Nc1ncc2c(n1)CCN(c1cccc(C(=O)Nc3cccc(C(F)(F)F)c3)c1)C2] | 3-(2-amino-7,8-dihydropyrido[4,3-d]pyrimidin-6(5H)-yl)-N-[3-(trifluoromethyl)phenyl]benzamide |
| 6 | 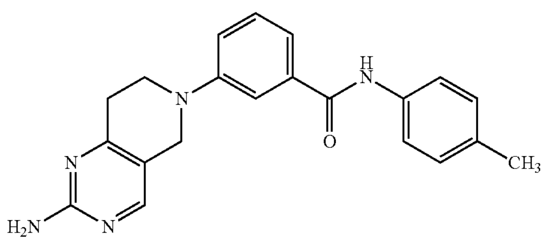 [SMILES: Cc1ccc(NC(=O)c2cccc(N3CCc4nc(N)ncc4C3)c2)cc1] | 3-(2-amino-7,8-dihydropyrido[4,3-d]pyrimidin-6(5H)-yl)-N-(4-methylphenyl)benzamide |
| 7 | 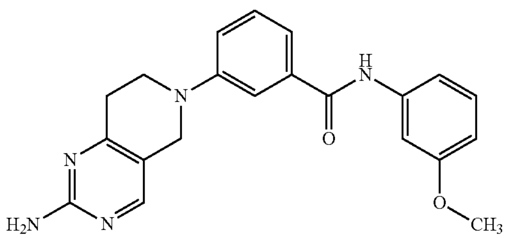 [SMILES: COc1cccc(NC(=O)c2cccc(N3CCc4nc(N)ncc4C3)c2)c1] | 3-(2-amino-7,8-dihydropyrido[4,3-d]pyrimidin-6(5H)-yl)-N-(3-methoxyphenyl)benzamide |
| 8 | 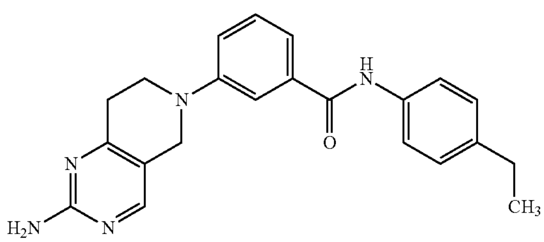 [SMILES: CCc1ccc(NC(=O)c2cccc(N3CCc4nc(N)ncc4C3)c2)cc1] | 3-(2-amino-7,8-dihydropyrido[4,3-d]pyrimidin-6(5H)-yl)-N-(4-ethylphenyl)benzamide |
| 9 | 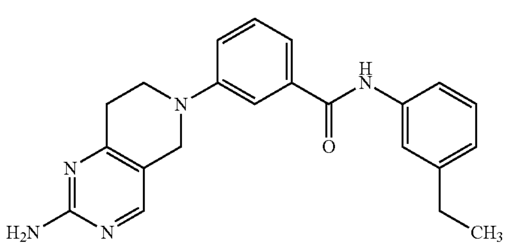 | 3-(2-amino-7,8-dihydropyrido[4,3-d]pyrimidin-6(5H)-yl)-N-(3-ethylphenyl)benzamide |

TABLE 1-continued

| Example Number | Structure | Compound Name |
|---|---|---|
| 10 | 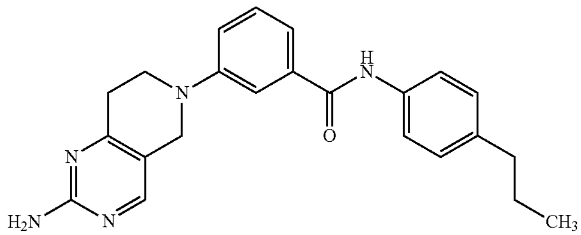 [SMILES: CCCc1ccc(NC(=O)c2cccc(N3CCc4nc(N)ncc4C3)c2)cc1] | 3-(2-amino-7,8-dihydropyrido[4,3-d]pyrimidin-6(5H)-yl)-N-(4-propylphenyl)benzamide |
| 11 | 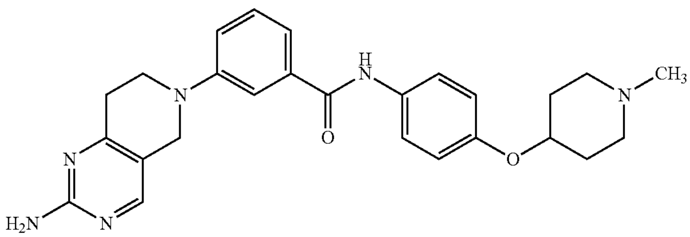 [SMILES: CN1CCC(Oc2ccc(NC(=O)c3cccc(N4CCc5nc(N)ncc5C4)c3)cc2)CC1] | 3-(2-amino-7,8-dihydropyrido[4,3-d]pyrimidin-6(5H)-yl)-N-{4-[(1-methylpiperidin-4-yl)oxy]phenyl}benzamide |
| 12 | 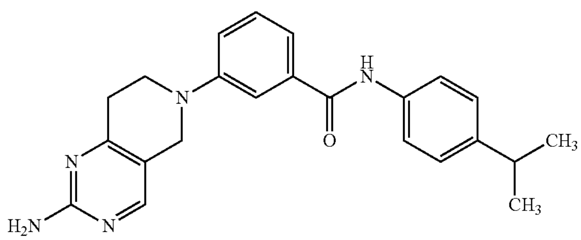 [SMILES: CC(C)c1ccc(NC(=O)c2cccc(N3CCc4nc(N)ncc4C3)c2)cc1] | 3-(2-amino-7,8-dihydropyrido[4,3-d]pyrimidin-6(5H)-yl)-N-(4-isopropylphenyl)benzamide |
| 13 | 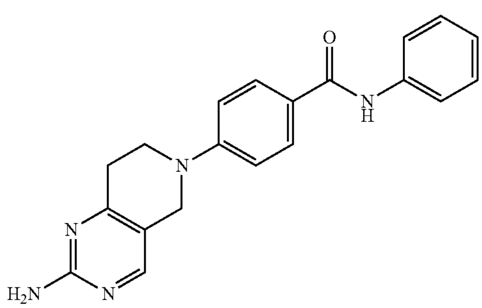 [SMILES: Nc1ncc2c(n1)CCN(c1ccc(C(=O)Nc3ccccc3)cc1)C2] | 4-(2-amino-7,8-dihydropyrido[4,3-d]pyrimidin-6(5H)-yl)-N-phenylbenzamide |
| 14 | 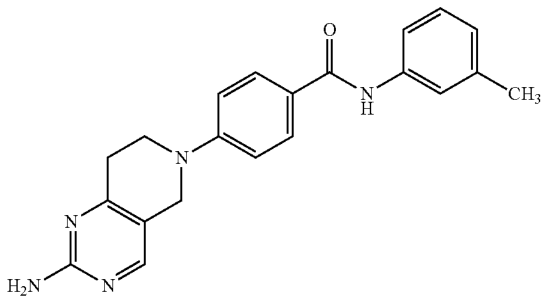 [SMILES: Cc1cccc(NC(=O)c2ccc(N3CCc4nc(N)ncc4C3)cc2)c1] | 4-(2-amino-7,8-dihydropyrido[4,3-d]pyrimidin-6(5H)-yl)-N-(3-methylphenyl)benzamide |

TABLE 1-continued

| Example Number | Structure | Compound Name |
| --- | --- | --- |
| 15 | 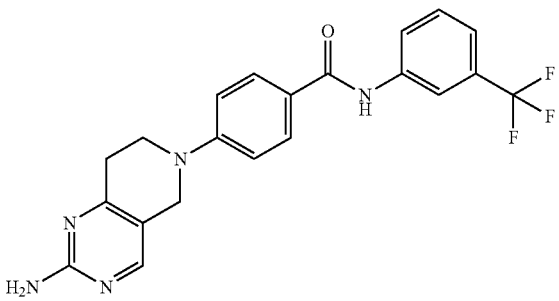 [SMILES: Nc1ncc2c(n1)CCN(c1ccc(C(=O)Nc3cccc(C(F)(F)F)c3)cc1)C2] | 4-(2-amino-7,8-dihydropyrido[4,3-d]pyrimidin-6(5H)-yl)-N-[3-(trifluoromethyl)phenyl]benzamide |
| 16 | 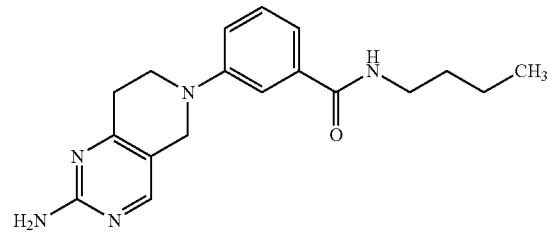 [SMILES: CCCCNC(=O)c1cccc(N2CCc3nc(N)ncc3C2)c1] | 3-(2-amino-7,8-dihydropyrido[4,3-d]pyrimidin-6(5H)-yl)-N-butylbenzamide |
| 17 | 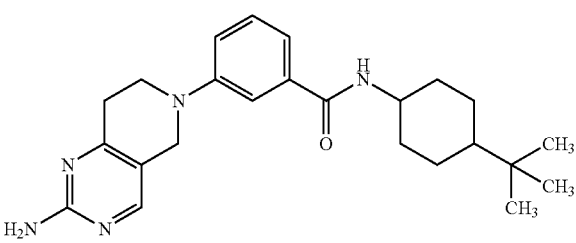 [SMILES: CC(C)(C)C1CCC(NC(=O)c2cccc(N3CCc4nc(N)ncc4C3)c2)CC1] | 3-(2-amino-7,8-dihydropyrido[4,3-d]pyrimidin-6(5H)-yl)-N-(4-tert-butylcyclohexyl)benzamide |
| 18 | 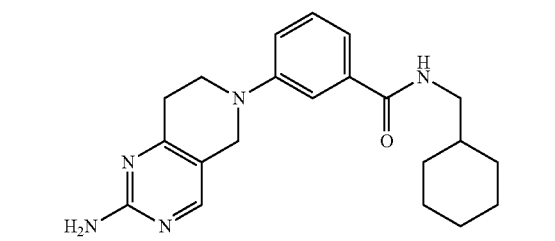 [SMILES: Nc1ncc2c(n1)CCN(c1cccc(C(=O)NCC3CCCCC3)c1)C2] | 3-(2-amino-7,8-dihydropyrido[4,3-d]pyrimidin-6(5H)-yl)-N-(cyclohexylmethyl)benzamide |
| 19 | 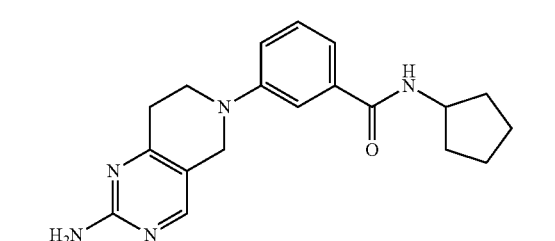 | 3-(2-amino-7,8-dihydropyrido[4,3-d]pyrimidin-6(5H)-yl)-N-cyclopentylbenzamide |
| 20 | 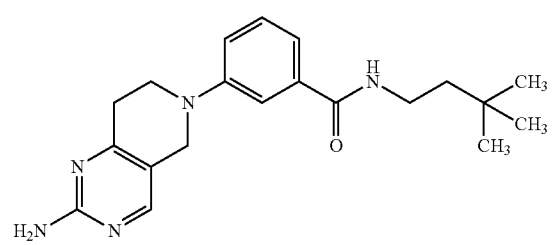 [SMILES: CC(C)(C)CCNC(=O)c1cccc(N2CCc3nc(N)ncc3C2)c1] | 3-(2-amino-7,8-dihydropyrido[4,3-d]pyrimidin-6(5H)-yl)-N-(3,3-dimethylbutyl)benzamide |

TABLE 1-continued

| Example Number | Structure | Compound Name |
|---|---|---|
| 21 | 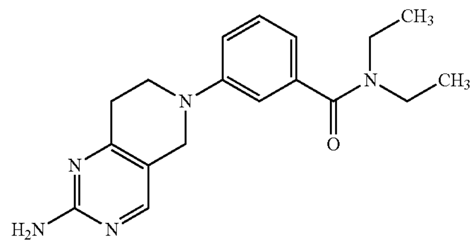 [SMILES: CCN(CC)C(=O)c1cccc(N2CCc3nc(N)ncc3C2)c1] | 3-(2-amino-7,8-dihydroprido[4,3-d]pyrimidin-6(5H)-yl)-N,N-diethylbenzamide |
| 22 | 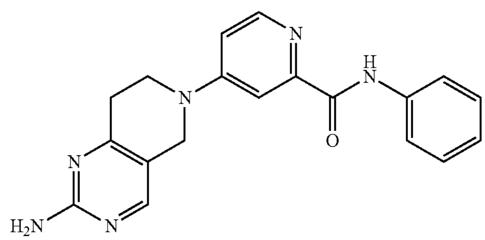 [SMILES: Nc1ncc2c(n1)CCN(c1ccnc(C(=O)Nc3ccccc3)c1)C2] | 4-(2-amino-7,8-dihydropyrido[4,3-d]pyrimidin-6(5H)-yl)-N-phenylpyridine-2-carboxamide |
| 23 | 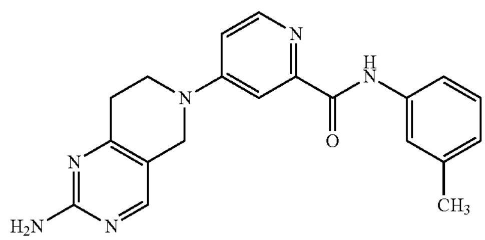 [SMILES: Cc1cccc(NC(=O)c2cc(N3CCc4nc(N)ncc4C3)ccn2)c1] | 4-(2-amino-7,8-dihydropyrido[4,3-d]pyrimidin-6(5H)-yl)-N-(3-methylphenyl)pyridine-2-carboxamide |
| 24 | 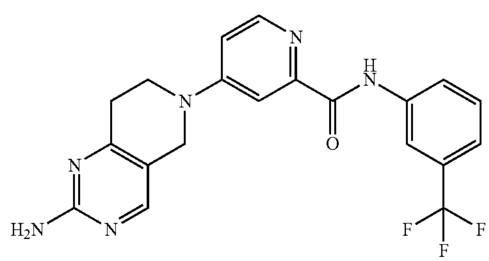 [SMILES: Nc1ncc2c(n1)CCN(c1ccnc(C(=O)Nc3cccc(C(F)(F)F)c3)c1)C2] | 4-(2-amino-7,8-dihydropyrido[4,3-d]pyrimidin-6(5H)-yl)-N-[3-(trifluoromethyl)phenyl]pyridine-2-carboxamide |
| 25 | 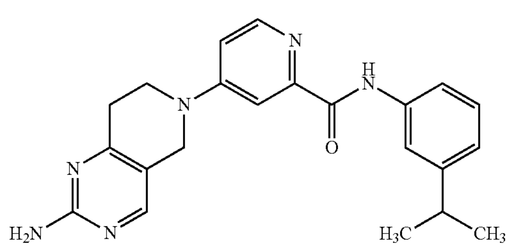 [SMILES: CC(C)c1cccc(NC(=O)c2cc(N3CCc4nc(N)ncc4C3)ccn2)c1] | 4-(2-amino-7,8-dihydropyrido[4,3-d]pyrimidin-6(5H)-yl)-N-(3-isopropylphenyl)pyridine-2-carboxamide |
| 26 | 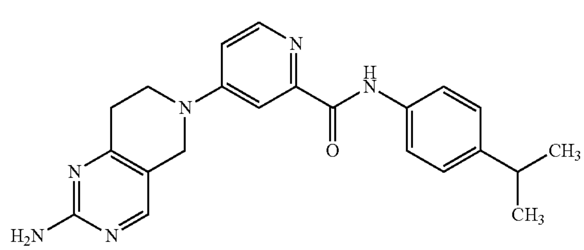 [SMILES: CC(C)c1ccc(NC(=O)c2cc(N3CCc4nc(N)ncc4C3)ccn2)cc1] | 4-(2-amino-7,8-dihydropyrido[4,3-d]pyrimidin-6(5H)-yl)-N-(4-isopropylphenyl)pyridine-2-carboxamide |

TABLE 1-continued

| Example Number | Structure | Compound Name |
|---|---|---|
| 27 | 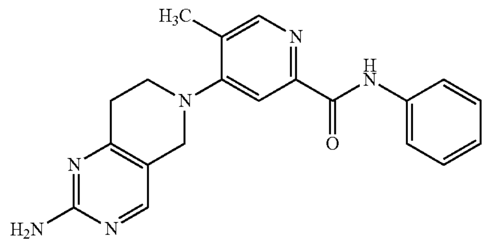 [SMILES: Cc1cnc(C(=O)Nc2ccccc2)cc1N1CCc2nc(N)ncc2C1] | 4-(2-amino-7,8-dihydropyrido[4,3-d]pyrimidin-6(5H)-yl)-5-methyl-N-phenylpyridine-2-carboxamide |
| 28 | 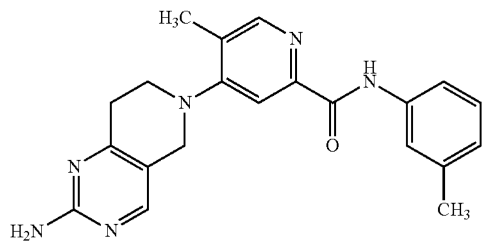 [SMILES: Cc1cccc(NC(=O)c2cc(N3CCc4nc(N)ncc4C3)c(C)cn2)c1] | 4-(2-amino-7,8-dihydropyrido[4,3-d]pyrimidin-6(5H)-yl)-5-methyl-N-(3-methylphenyl)pyridine-2-carboxamide |
| 29 | 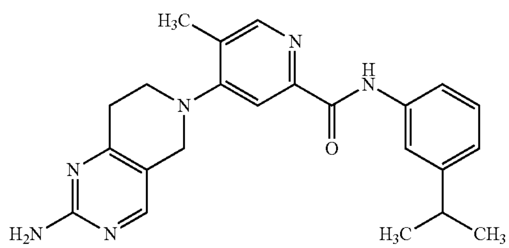 | 4-(2-amino-7,8-dihydropyrido[4,3-d]pyrimidin-6(5H)-yl)-N-(3-isopropylphenyl)-5-methylpyridine-2-carboxamide |
| 30 | 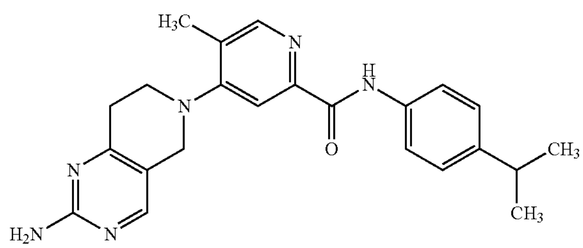 | 4-(2-amino-7,8-dihydropyrido[4,3-d]pyrimidin-6(5H)-yl)-N-(4-isopropylphenyl)-5-methylpyridine-2-carboxamide |
| 31 | 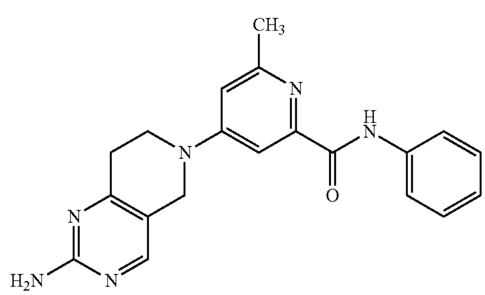 [SMILES: Cc1cc(N2CCc3nc(N)ncc3C2)cc(C(=O)Nc2ccccc2)n1] | 4-(2-amino-7,8-dihydropyrido[4,3-d]pyrimidin-6(5H)-yl)-6-methyl-N-phenylpyridine-2-carboxamide |
| 32 | 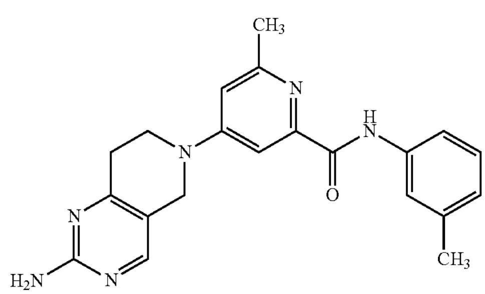 [SMILES: Cc1cccc(NC(=O)c2cc(N3CCc4nc(N)ncc4C3)cc(C)n2)c1] | 4-(2-amino-7,8-dihydropyrido[4,3-d]pyrimidin-6(5H)-yl)-6-methyl-N-(3-methylphenyl)pyridine-2-carboxamide |

TABLE 1-continued

| Example Number | Structure | Compound Name |
|---|---|---|
| 33 | 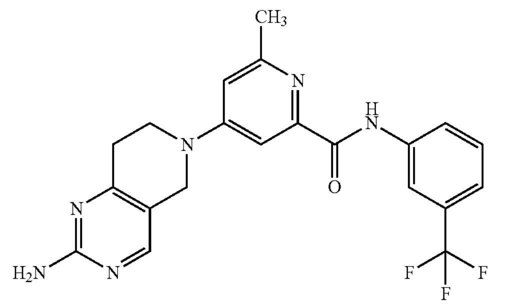 [SMILES: Cc1cc(N2CCc3nc(N)ncc3C2)cc(C(=O)Nc2cccc(C(F)(F)F)c2)n1] | 4-(2-amino-7,8-dihydropyrido[4,3-d]pyrimidin-6(5H)-yl)-6-methyl-N-[3-(trifluoromethyl)phenyl]pyridine-2-carboxamide |
| 34 | 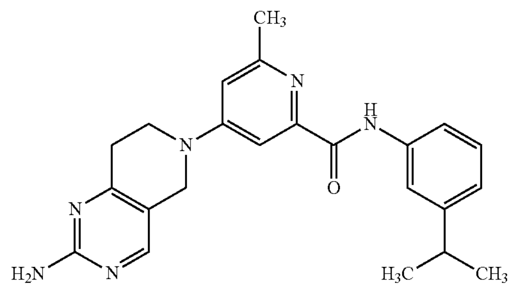 | 4-(2-amino-7,8-dihydropyrido[4,3-d]pyrimidin-6(5H)-yl)-N-(3-isopropylphenyl)-6-methylpyridine-2-carboxamide |
| 35 | 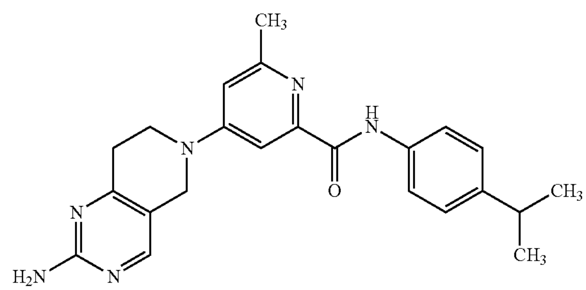 [SMILES: Cc1cc(N2CCc3nc(N)ncc3C2)cc(C(=O)Nc2ccc(C(C)C)cc2)n1] | 4-(2-amino-7,8-dihydropyrido[4,3-d]pyrimidin-6(5H)-yl)-N-(4-isopropylphenyl)-6-methylpyridine-2-carboxamide |
| 36 | 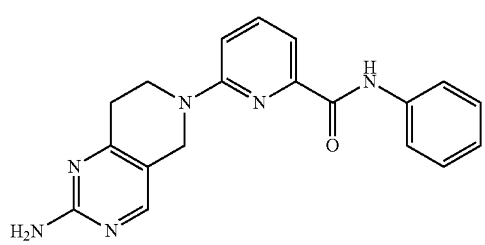 [SMILES: Nc1ncc2c(n1)CCN(c1cccc(C(=O)Nc3ccccc3)n1)C2] | 6-(2-amino-7,8-dihydropyrido[4,3-d]pyrimidin-6(5H)-yl)-N-phenylpyridine-2-carboxamide |
| 37 | 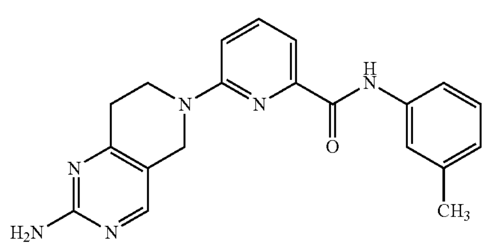 [SMILES: Cc1cccc(NC(=O)c2cccc(N3CCc4nc(N)ncc4C3)n2)c1] | 6-(2-amino-7,8-dihydropyrido[4,3-d]pyrimidin-6(5H)-yl)-N-(3-methylphenyl)pyridine-2-carboxamide |

TABLE 1-continued

| Example Number | Structure | Compound Name |
|---|---|---|
| 38 | 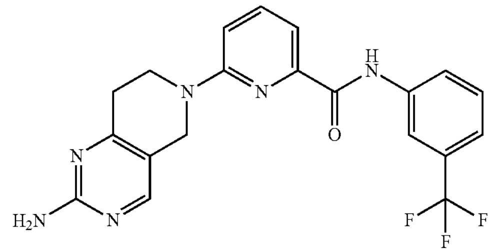 [SMILES: Nc1ncc2c(n1)CCN(c1cccc(C(=O)Nc3cccc(C(F)(F)F)c3)n1)C2] | 6-(2-amino-7,8-dihydropyrido[4,3-d]pyrimidin-6(5H)-yl)-N-[3-(trifluoromethyl)phenyl]pyridine-2-carboxamide |
| 39 | 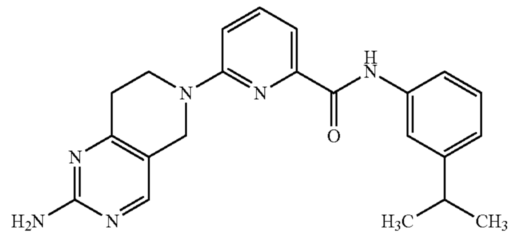 [SMILES: CC(C)c1cccc(NC(=O)c2cccc(N3CCc4nc(N)ncc4C3)n2)c1] | 6-(2-amino-7,8-dihydropyrido[4,3-d]pyrimidin-6(5H)-yl)-N-(3-isopropylphenyl)pyridine-2-carboxamide |
| 40 | 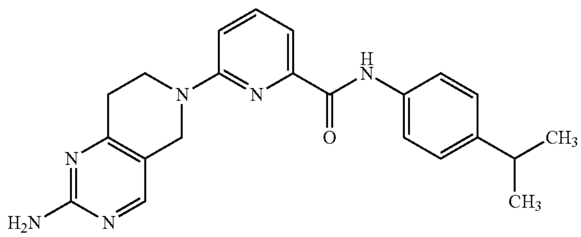 [SMILES: CC(C)c1ccc(NC(=O)c2cccc(N3CCc4nc(N)ncc4C3)n2)cc1] | 6-(2-amino-7,8-dihydropyrido[4,3-d]pyrimidin-6(5H)-yl)-N-(4-isopropylphenyl)pyridine-2-carboxamide |
| 41 | 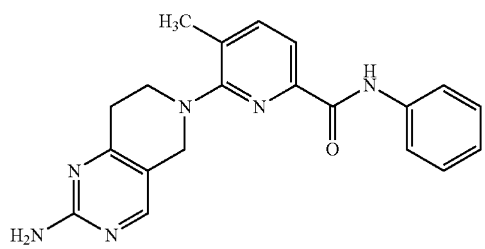 [SMILES: Cc1ccc(C(=O)Nc2ccccc2)nc1N1CCc2nc(N)ncc2C1] | 6-(2-amino-7,8-dihydropyrido[4,3-d]pyrimidin-6(5H)-yl)-5-methyl-N-phenylpyridine-2-carboxamide |
| 42 | 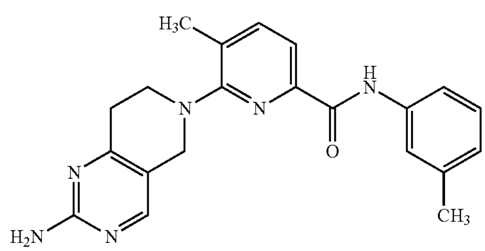 [SMILES: Cc1cccc(NC(=O)c2ccc(C)c(N3CCc4nc(N)ncc4C3)n2)c1] | 6-(2-amino-7,8-dihydropyrido[4,3-d]pyrimidin-6(5H)-yl)-5-methyl-N-(3-methylphenyl)pyridine-2-carboxamide |
| 43 | 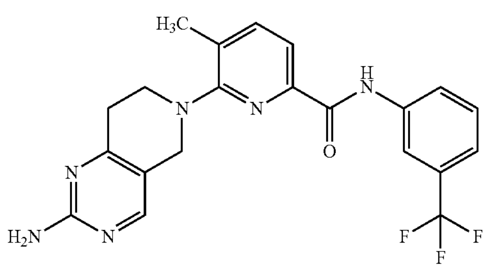 [SMILES: Cc1ccc(C(=O)Nc2cccc(C(F)(F)F)c2)nc1N1CCc2nc(N)ncc2C1] | 6-(2-amino-7,8-dihydropyrido[4,3-d]pyrimidin-6(5H)-yl)-5-methyl-N-[3-(trifluoromethyl)phenyl]pyridine-2-carboxamide |

TABLE 1-continued

| Example Number | Structure | Compound Name |
|---|---|---|
| 44 | 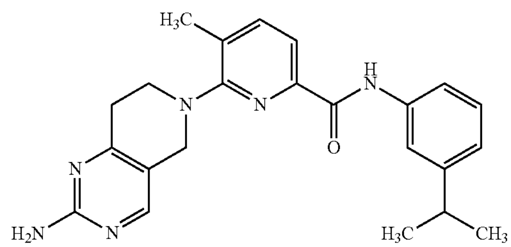 | 6-(2-amino-7,8-dihydropyrido[4,3-d]pyrimidin-6(5H)-yl)-N-(3-isopropylphenyl)-5-methylpyridine-2-carboxamide |
| 45 | 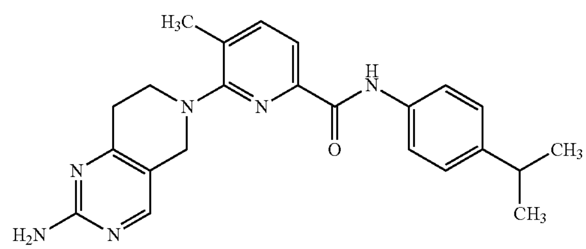 [SMILES: Cc1ccc(C(=O)Nc2ccc(C(C)C)cc2)nc1N1CCc2nc(N)ncc2C1] | 6-(2-amino-7,8-dihydropyrido[4,3-d]pyrimidin-6(5H)-yl)-N-(4-isopropylphenyl)-5-methylpyridine-2-carboxamide |
| 46 | 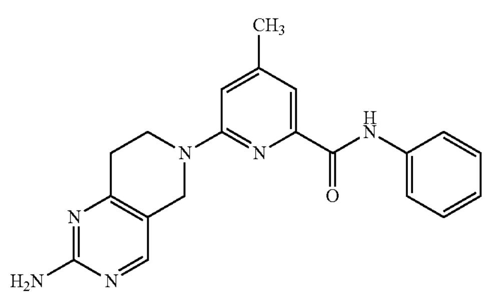 | 6-(2-amino-7,8-dihydropyrido[4,3-d]pyrimidin-6(5H)-yl)-4-methyl-N-phenylpyridine-2-carboxamide |
| 47 | 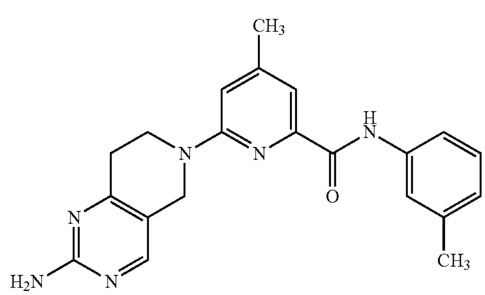 [SMILES: Cc1cccc(NC(=O)c2cc(C)cc(N3CCc4nc(N)ncc4C3)n2)c1] | 6-(2-amino-7,8-dihydropyrido[4,3-d]pyrimidin-6(5H)-yl)-4-methyl-N-(3-methylphenyl)pyridine-2-carboxamide |
| 48 | 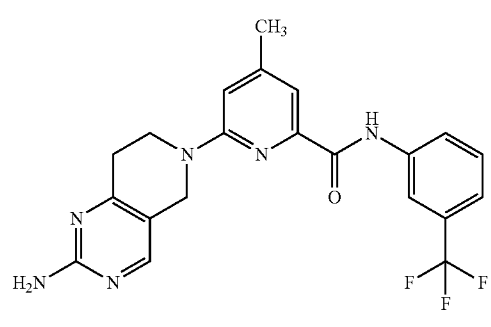 [SMILES: Cc1cc(C(=O)Nc2cccc(C(F)(F)F)c2)nc(N2CCc3nc(N)ncc3C2)c1] | 6-(2-amino-7,8-dihydropyrido[4,3-d]pyrimidin-6(5H)-yl)-4-methyl-N-[3-(trifluoromethyl)phenyl]pyridine-2-carboxamide |

TABLE 1-continued

| Example Number | Structure | Compound Name |
|---|---|---|
| 49 | 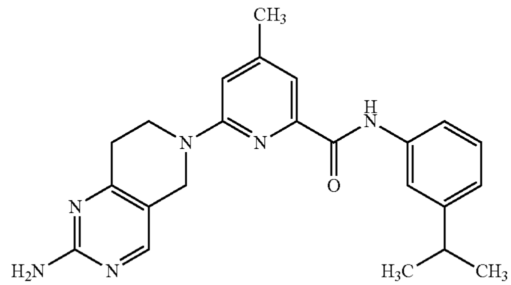 [SMILES: Cc1cc(C(=O)Nc2cccc(C(C)C)c2)nc(N2CCc3nc(N)ncc3C2)c1] | 6-(2-amino-7,8-dihydropyrido[4,3-d]pyrimidin-6(5H)-yl)-N-(3-isopropylphenyl)-4-methylpyridine-2-carboxamide |
| 50 | 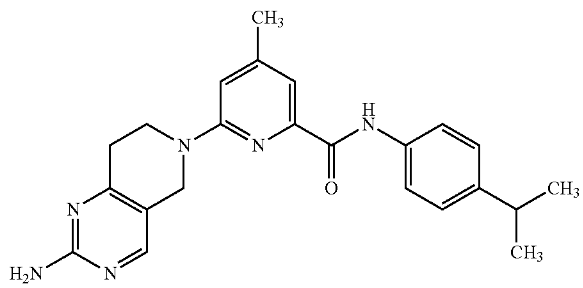 [SMILES: Cc1cc(C(=O)Nc2ccc(C(C)C)cc2)nc(N2CCc3nc(N)ncc3C2)c1] | 6-(2-amino-7,8-dihydropyrido[4,3-d]pyrimidin-6(5H)-yl)-N-(4-isopropylphenyl)-4-methylpyridine-2-carboxamide |
| 51 | 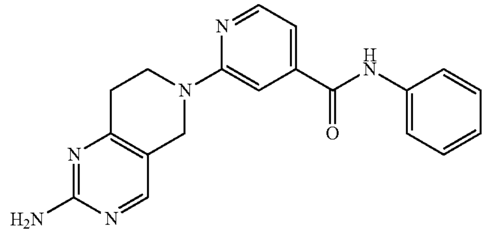 [SMILES: Nc1ncc2c(n1)CCN(c1cc(C(=O)Nc3ccccc3)ccn1)C2] | 2-(2-amino-7,8-dihydropyrido[4,3-d]pyrimidin-6(5H)-yl)-N-phenylisonicotinamide |
| 52 | 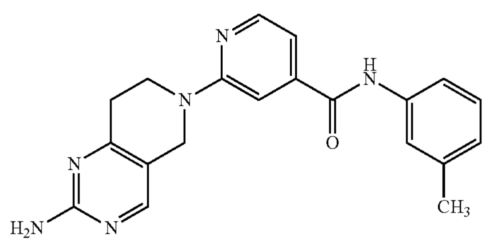 [SMILES: Cc1cccc(NC(=O)c2ccnc(N3CCc4nc(N)ncc4C3)c2)c1] | 2-(2-amino-7,8-dihydropyrido[4,3-d]pyrimidin-6(5H)-yl)-N-(3-methylphenyl)isonicotinamide |
| 53 | 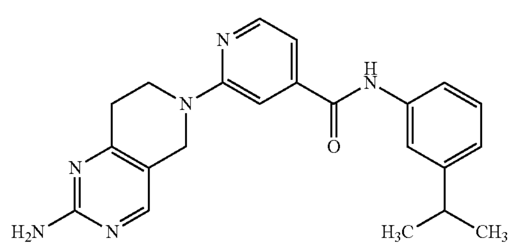 [SMILES: CC(C)c1cccc(NC(=O)c2ccnc(N3CCc4nc(N)ncc4C3)c2)c1] | 2-(2-amino-7,8-dihydropyrido[4,3-d]pyrimidin-6(5H)-yl)-N-(3-isopropylphenyl)isonicotinamide |
| 54 | 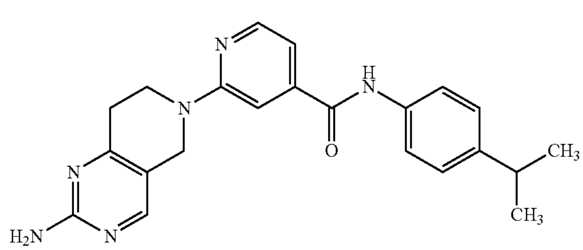 [SMILES: CC(C)c1ccc(NC(=O)c2ccnc(N3CCc4nc(N)ncc4C3)c2)cc1] | 2-(2-amino-7,8-dihydropyrido[4,3-d]pyrimidin-6(5H)-yl)-N-(4-isopropylphenyl)isonicotinamide |

TABLE 1-continued

| Example Number | Structure | Compound Name |
|---|---|---|
| 55 | 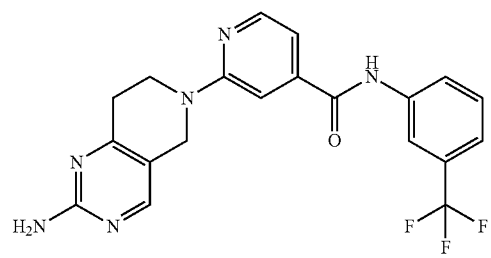 | 2-(2-amino-7,8-dihydropyrido[4,3-d]pyrimidin-6(5H)-yl)-N-[3-(trifluoromethyl)phenyl]isonicotinamide |
| 56 | 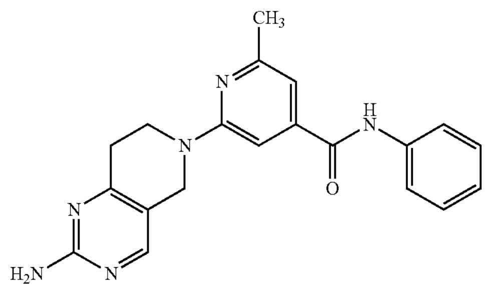 [SMILES: Cc1cc(C(=O)Nc2ccccc2)cc(N2CCc3nc(N)ncc3C2)n1] | 2-(2-amino-7,8-dihydropyrido[4,3-d]pyrimidin-6(5H)-yl)-6-methyl-N-phenylisonicotinamide |
| 57 | 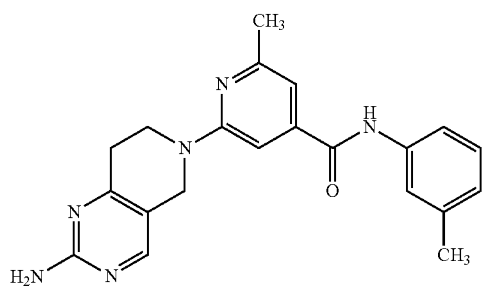 [SMILES: Cc1cccc(NC(=O)c2cc(C)nc(N3CCc4nc(N)ncc4C3)c2)c1] | 2-(2-amino-7,8-dihydropyrido[4,3-d]pyrimidin-6(5H)-yl)-6-methyl-N-(3-methylphenyl)isonicotinamide |
| 58 | 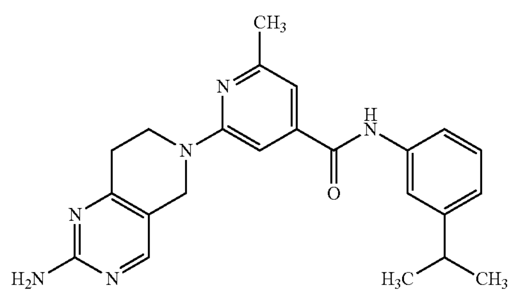 | 2-(2-amino-7,8-dihydropyrido[4,3-d]pyrimidin-6(5H)-yl)-N-(3-isopropylphenyl)-6-methylisonicotinamide |
| 59 | 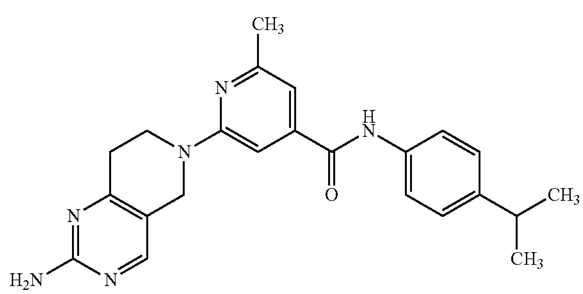 [SMILES: Cc1cc(C(=O)Nc2ccc(C(C)C)cc2)cc(N2CCc3nc(N)ncc3C2)n1] | 2-(2-amino-7,8-dihydropyrido[4,3-d]pyrimidin-6(5H)-yl)-N-(4-isopropylphenyl)-6-methylisonicotinamide |

TABLE 1-continued

| Example Number | Structure | Compound Name |
|---|---|---|
| 60 | 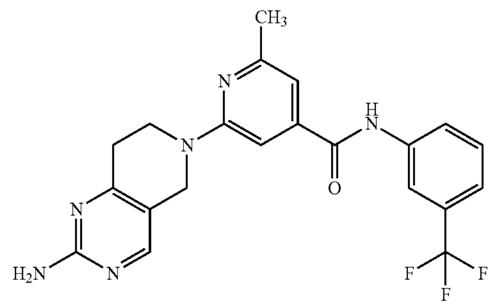 [SMILES: Cc1cc(C(=O)Nc2cccc(C(F)(F)F)c2)cc(N2CCc3nc(N)ncc3C2)n1] | 2-(2-amino-7,8-dihydropyrido[4,3-d]pyrimidin-6(5H)-yl)-6-methyl-N-[3-(trifluoromethyl)phenyl]isonicotinamide |
| 61 | 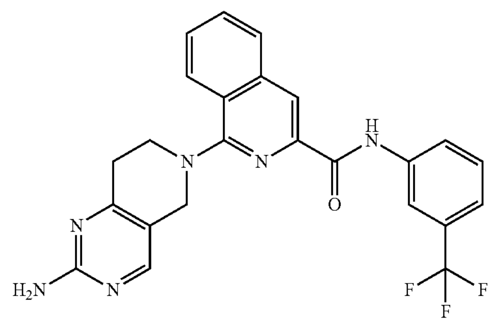 [SMILES: Nc1ncc2c(n1)CCN(c1nc(C(=O)Nc3cccc(C(F)(F)F)c3)cc3ccccc13)C2] | 1-(2-amino-7,8-dihydropyrido[4,3-d]pyrimidin-6(5H)-yl)-N-[3-(trifluoromethyl)phenyl]isoquinoline-3-carboxamide |
| 62 | 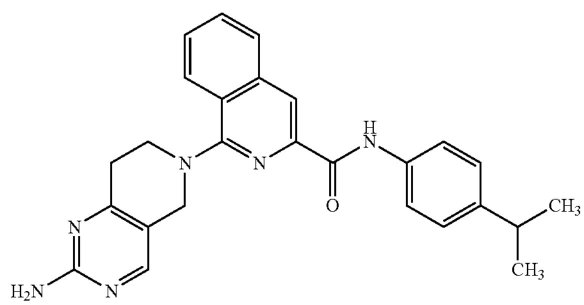 [SMILES: CC(C)c1ccc(NC(=O)c2cc3ccccc3c(N3CCc4nc(N)ncc4C3)n2)cc1] | 1-(2-amino-7,8-dihydropyrido[4,3-d]pyrimidin-6(5H)-yl)-N-(4-isopropylphenyl)isoquinoline-3-carboxamide |
| 63 | 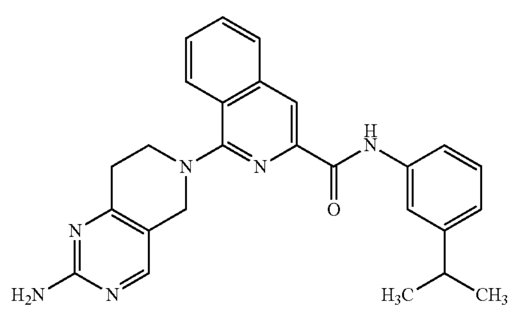 [SMILES: CC(C)c1cccc(NC(=O)c2cc3ccccc3c(N3CCc4nc(N)ncc4C3)n2)c1] | 1-(2-amino-7,8-dihydropyrido[4,3-d]pyrimidin-6(5H)-yl)-N-(3-isopropylphenyl)isoquinoline-3-carboxamide |
| 64 | 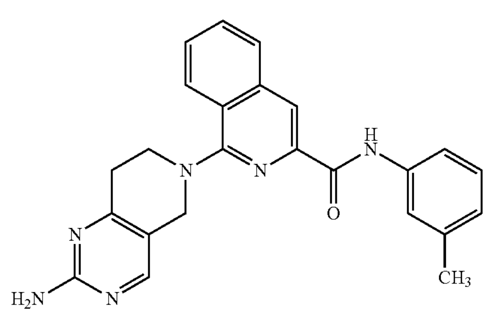 [SMILES: Cc1cccc(NC(=O)c2cc3ccccc3c(N3CCc4nc(N)ncc4C3)n2)c1] | 1-(2-amino-7,8-dihydropyrido[4,3-d]pyrimidin-6(5H)-yl)-N-(3-methylphenyl)isoquinoline-3-carboxamide |

TABLE 1-continued

| Example Number | Structure | Compound Name |
|---|---|---|
| 65 | 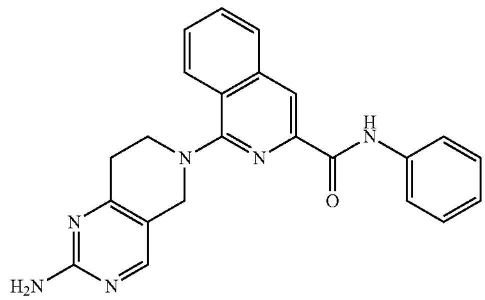 [SMILES: Nc1ncc2c(n1)CCN(c1nc(C(=O)Nc3ccccc3)cc3ccccc13)C2] | 1-(2-amino-7,8-dihydropyrido[4,3-d]pyrimidin-6(5H)-yl)-N-phenylisoquinoline-3-carboxamide |
| 66 | 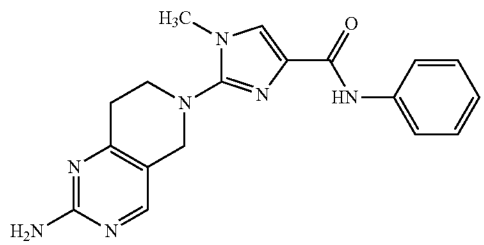 [SMILES: Cn1cc(C(=O)Nc2ccccc2)nc1N1CCc2nc(N)ncc2C1] | 2-(2-amino-7,8-dihydropyrido[4,3-d]pyrimidin-6(5H)-yl)-1-methyl-N-phenyl-1H-imidazole-4-carboxamide |
| 67 | 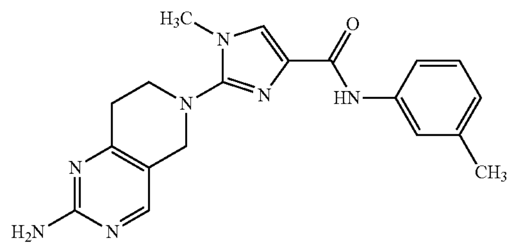 [SMILES: Cc1cccc(NC(=O)c2cn(C)c(N3CCc4nc(N)ncc4C3)n2)c1] | 2-(2-amino-7,8-dihydropyrido[4,3-d]pyrimidin-6(5H)-yl)-1-methyl-N-(3-methylphenyl)-1H-imidazole-4-carboxamide |
| 68 | 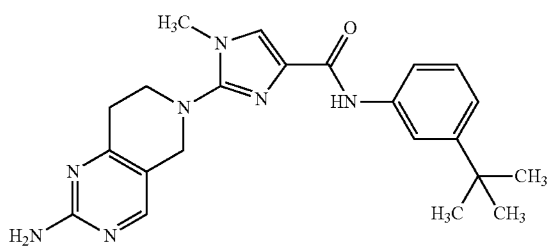 [SMILES: Cn1cc(C(=O)Nc2cccc(C(C)(C)C)c2)nc1N1CCc2nc(N)ncc2C1] | 2-(2-amino-7,8-dihydropyrido[4,3-d]pyrimidin-6(5H)-yl)-N-(3-tert-butylphenyl)-1-methyl-1H-imidazole-4-carboxamide |
| 69 | 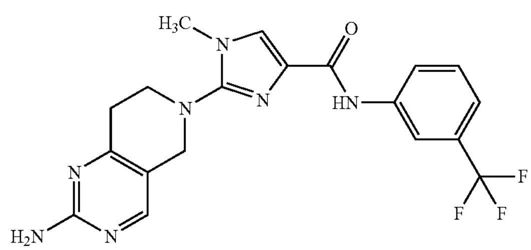 [SMILES: Cn1cc(C(=O)Nc2cccc(C(F)(F)F)c2)nc1N1CCc2nc(N)ncc2C1] | 2-(2-amino-7,8-dihydropyrido[4,3-d]pyrimidin-6(5H)-yl)-1-methyl-N-[3-(trifluoromethyl)phenyl]-1H-imidazole-4-carboxamide |
| 70 | 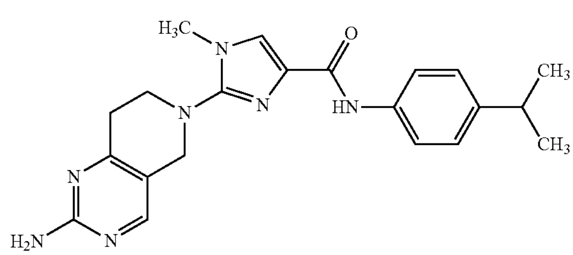 [SMILES: CC(C)c1ccc(NC(=O)c2cn(C)c(N3CCc4nc(N)ncc4C3)n2)cc1] | 2-(2-amino-7,8-dihydropyrido[4,3-d]pyrimidin-6(5H)-yl)-N-(4-isopropylphenyl)-1-methyl-1H-imidazole-4-carboxamide |

TABLE 1-continued

| Example Number | Structure | Compound Name |
|---|---|---|
| 71 | 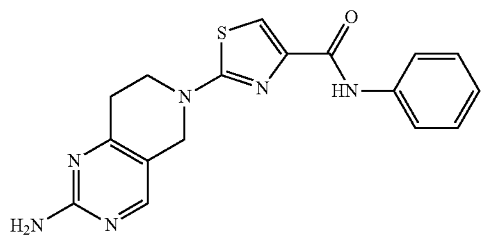 [SMILES: Nc1ncc2c(n1)CCN(c1nc(C(=O)Nc3ccccc3)cs1)C2] | 2-(2-amino-7,8-dihydropyrido[4,3-d]pyrimidin-6(5H)-yl)-N-phenyl-1,3-thiazole-4-carboxamide |
| 72 | 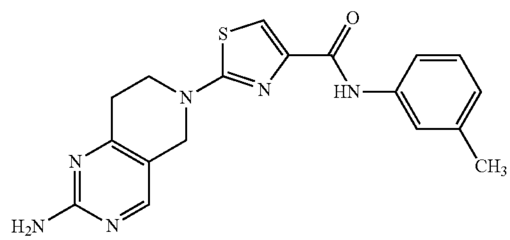 [SMILES: Cc1cccc(NC(=O)c2csc(N3CCc4nc(N)ncc4C3)n2)c1] | 2-(2-amino-7,8-dihydropyrido[4,3-d]pyrimidin-6(5H)-yl)-N-(3-methylphenyl)-1,3-thiazole-4-carboxamide |
| 73 | 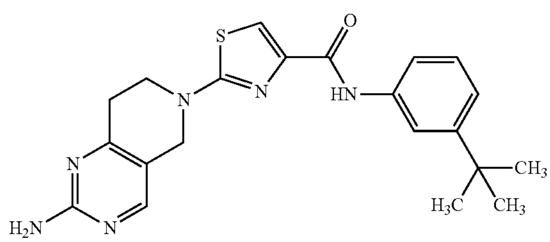 [SMILES: CC(C)(C)c1cccc(NC(=O)c2csc(N3CCc4nc(N)ncc4C3)n2)c1] | 2-(2-amino-7,8-dihydropyrido[4,3-d]pyrimidin-6(5H)-yl)-N-(3-tert-butylphenyl)-1,3-thiazole-4-carboxamide |
| 74 | 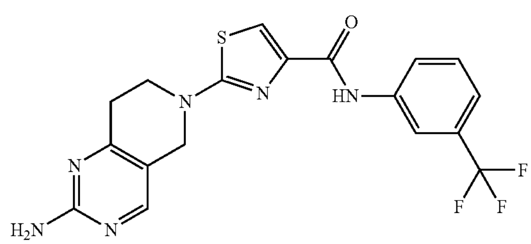 | 2-(2-amino-7,8-dihydropyrido[4,3-d]pyrimidin-6(5H)-yl)-N-[3-(trifluoromethyl)phenyl]-1,3-thiazole-4-carboxamide |
| 75 | 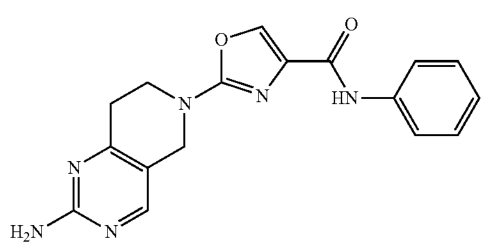 | 2-(2-amino-7,8-dihydropyrido[4,3-d]pyrimidin-6(5H)-yl)-N-phenyl-1,3-oxazole-4-carboxamide |
| 76 | 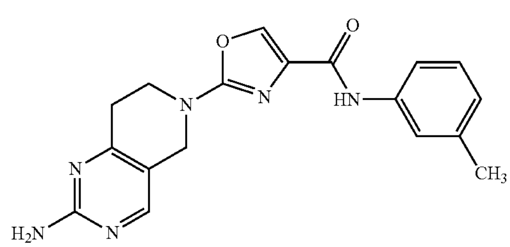 | 2-(2-amino-7,8-dihydropyrido[4,3-d]pyrimidin-6(5H)-yl)-N-(3-methylphenyl)-1,3-oxazole-4-carboxamide |

TABLE 1-continued

| Example Number | Structure | Compound Name |
|---|---|---|
| 77 | 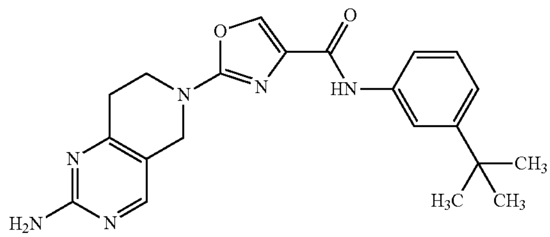 | 2-(2-amino-7,8-dihydropyrido[4,3-d]pyrimidin-6(5H)-yl)-N-(3-tert-butylphenyl)-1,3-oxazole-4-carboxamide |
| 78 | 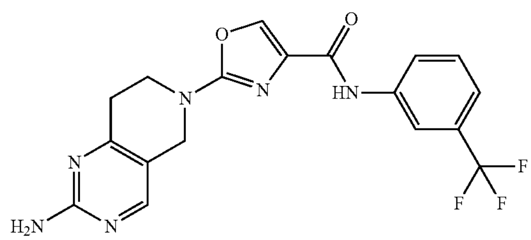 [SMILES: Nc1ncc2c(n1)CCN(c1nc(C(=O)Nc3cccc(C(F)(F)F)c3)cs1)C2] | 2-(2-amino-7,8-dihydropyrido[4,3-d]pyrimidin-6(5H)-yl)-N-[3-(trifluoromethyl)phenyl]-1,3-oxazole-4-carboxamide |
| 79 | 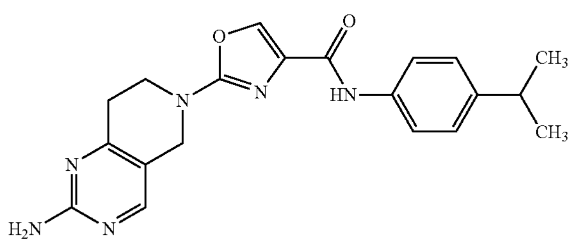 [SMILES: CC(C)c1ccc(NC(=O)c2coc(N3CCc4nc(N)ncc4C3)n2)cc1] | 2-(2-amino-7,8-dihydropyrido[4,3-d]pyrimidin-6(5H)-yl)-N-(4-isopropylphenyl)-1,3-oxazole-4-carboxamide |
| 80 | 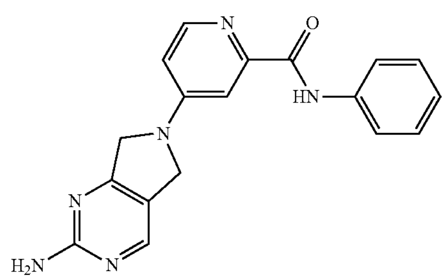 [SMILES: Nc1ncc2c(n1)CN(c1ccnc(C(=O)Nc3ccccc3)c1)C2] | 4-(2-amino-5,7-dihydro-6H-pyrrolo[3,4-d]pyrimidin-6-yl)-N-phenylpyridine-2-carboxamide |
| 81 | 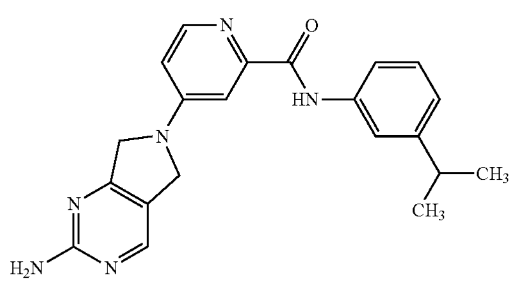 [SMILES: CC(C)c1cccc(NC(=O)c2cc(N3Cc4cnc(N)nc4C3)ccn2)c1] | 4-(2-amino-5,7-dihydro-6H-pyrrolo[3,4-d]pyrimidin-6-yl)-N-(3-isopropylphenyl)pyridine-2-carboxamide |
| 82 | 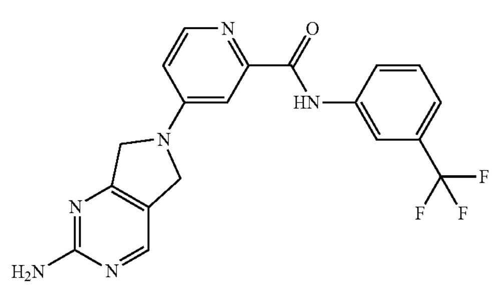 [SMILES: Nc1ncc2c(n1)CN(c1ccnc(C(=O)Nc3cccc(C(F)(F)F)c3)c1)C2] | 4-(2-amino-5,7-dihydro-6H-pyrrolo[3,4-d]pyrimidin-6-yl)-N-[3-(trifluoromethyl)phenyl]pyridine-2-carboxamide |

TABLE 1-continued

| Example Number | Structure | Compound Name |
|---|---|---|
| 83 | 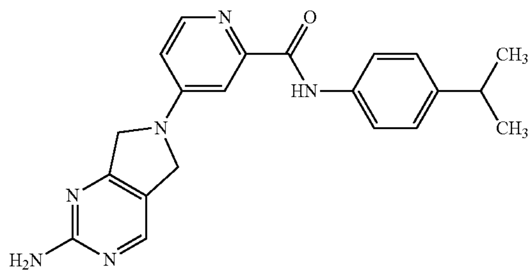 [SMILES: CC(C)c1ccc(NC(=O)c2cc(N3Cc4cnc(N)nc4C3)ccn2)cc1] | 4-(2-amino-5,7-dihydro-6H-pyrrolo[3,4-d]pyrimidin-6-yl)-N-(4-isopropylphenyl)pyridine-2-carboxamide |
| 84 | 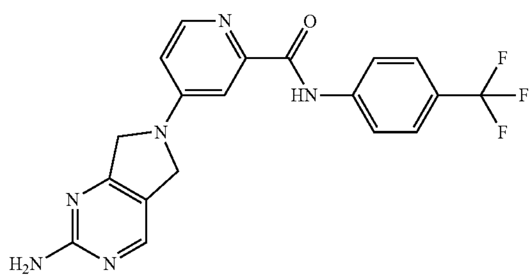 [SMILES: Nc1ncc2c(n1)CN(c1ccnc(C(=O)Nc3ccc(C(F)(F)F)cc3)c1)C2] | 4-(2-amino-5,7-dihydro-6H-pyrrolo[3,4-d]pyrimidin-6-yl)-N-[4-(trifluoromethyl)phenyl]pyridine-2-carboxamide |
| 85 | 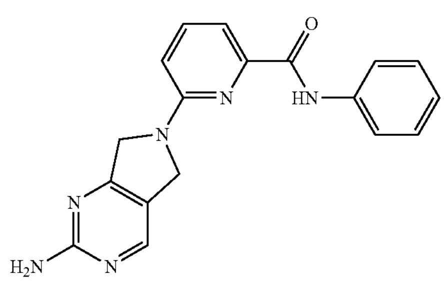 [SMILES: Nc1ncc2c(n1)CN(c1cccc(C(=O)Nc3ccccc3)n1)C2] | 6-(2-amino-5,7-dihydro-6H-pyrrolo[3,4-d]pyrimidin-6-yl)-N-phenylpyridine-2-carboxamide |
| 86 | 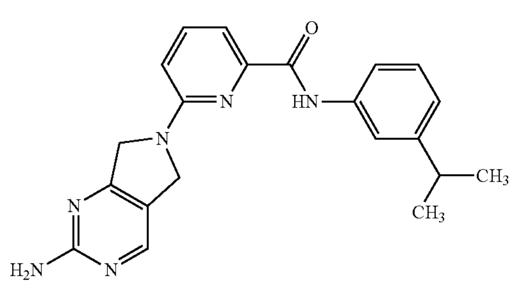 | 6-(2-amino-5,7-dihydro-6H-pyrrolo[3,4-d]pyrimidin-6-yl)-N-(3-ylphenyl)pyridine-2-carboxamide |
| 87 | 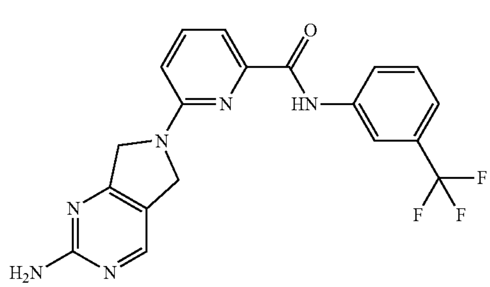 | 6-(2-amino-5,7-dihydro-6H-pyrrolo[3,4-d]pyrimidin-6-yl)-N-[3-(trifluoromethyl)phenyl]pyridine-2-carboxamide |

TABLE 1-continued

| Example Number | Structure | Compound Name |
|---|---|---|
| 88 | 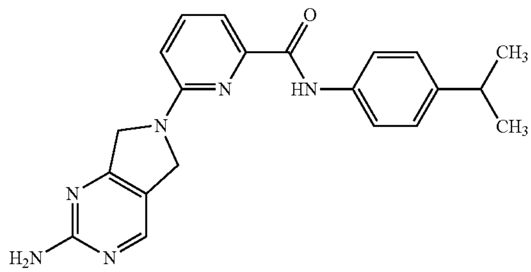 [SMILES: CC(C)c1ccc(NC(=O)c2cccc(N3Cc4cnc(N)nc4C3)n2)cc1] | 6-(2-amino-5,7-dihydro-6H-pyrrolo[3,4-d]pyrimidin-6-yl)-N-(4-isopropylphenyl)pyridine-2-carboxamide |
| 89 | 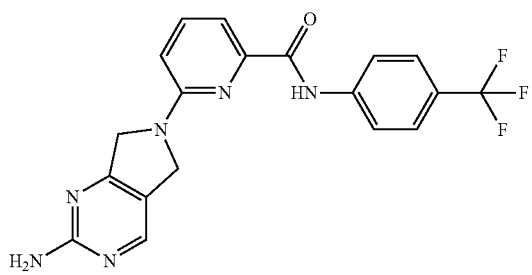 [SMILES: Nc1ncc2c(n1)CN(c1cccc(C(=O)Nc3ccc(C(F)(F)F)cc3)n1)C2] | 6-(2-amino-5,7-dihydro-6H-pyrrolo[3,4-d]pyrimidin-6-yl)-N-[4-(trifluoromethyl)phenyl]pyridine-2-carboxamide |
| 90 | 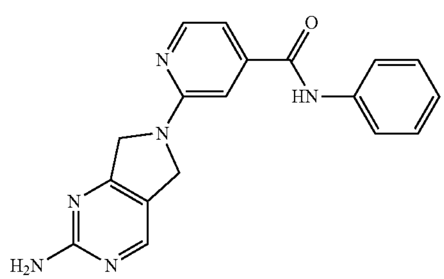 [SMILES: Nc1ncc2c(n1)CN(c1cc(C(=O)Nc3ccccc3)ccn1)C2] | 2-(2-amino-5,7-dihydro-6H-pyrrolo[3,4-d]pyrimidin-6-yl)-N-phenylisonicotinamide |
| 91 | 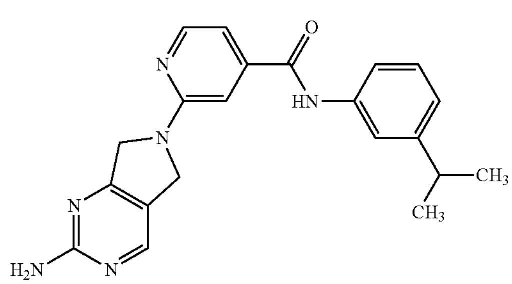 [SMILES: CC(C)c1cccc(NC(=O)c2ccnc(N3Cc4cnc(N)nc4C3)c2)c1] | 2-(2-amino-5,7-dihydro-6H-pyrrolo[3,4-d]pyrimidin-6-yl)-N-(3-isopropylphenyl)isonicotinamide |
| 92 | 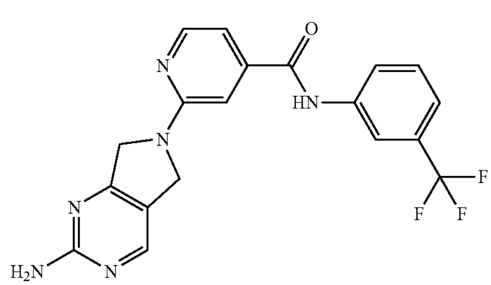 | 2-(2-amino-5,7-dihydro-6H-pyrrolo[3,4-d]pyrimidin-6-yl)-N-[3-(trifluoromethyl)phenyl]isonicotinamide |

TABLE 1-continued

| Example Number | Structure | Compound Name |
|---|---|---|
| 93 | 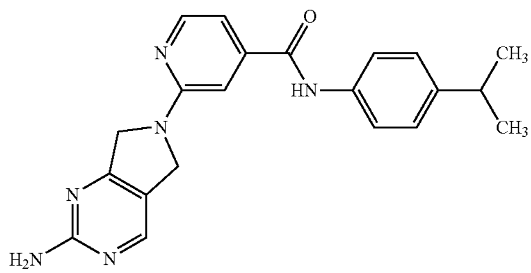 | 2-(2-amino-5,7-dihydro-6H-pyrrolo[3,4-d]pyrimidin-6-yl)-N-(4-isopropylphenyl)isonicotinamide |
| 94 | 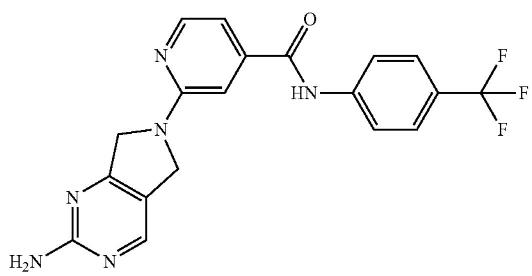 [SMILES: Nc1ncc2c(n1)CN(c1cc(C(=O)Nc3ccc(C(F)(F)F)cc3)ccn1)C2] | 2-(2-amino-5,7-dihydro-6H-pyrrolo[3,4-d]pyrimidin-6-yl)-N-[4-(trifluoromethyl)phenyl]isonicotinamide |
| 95 | 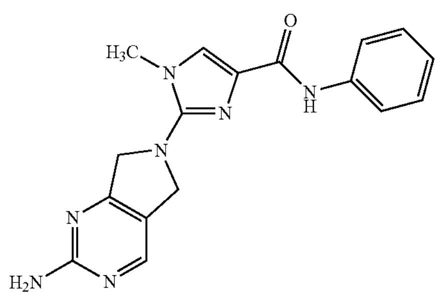 [SMILES: Cn1cc(C(=O)Nc2ccccc2)nc1N1Cc2cnc(N)nc2C1] | 2-(2-amino-5,7-dihydro-6H-pyrrolo[3,4-d]pyrimidin-6-yl)-1-methyl-N-phenyl-1H-imidazole-4-carboxamide |
| 96 | 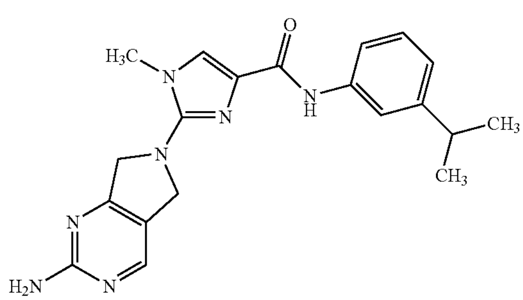 [SMILES: CC(C)c1cccc(NC(=O)c2cn(C)c(N3Cc4cnc(N)nc4C3)n2)c1] | 2-(2-amino-5,7-dihydro-6H-pyrrolo[3,4-d]pyrimidin-6-yl)-N-(3-isopropylphenyl)-1-methyl-1H-imidazole-4-carboxamide |
| 97 | 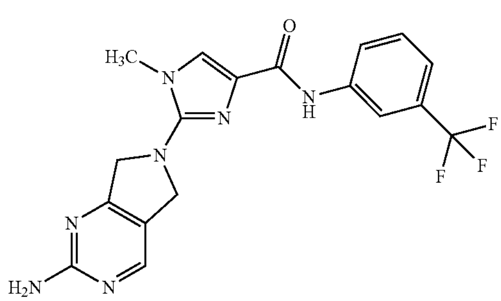 [SMILES: Cn1cc(C(=O)Nc2cccc(C(F)(F)F)c2)nc1N1Cc2cnc(N)nc2C1] | 2-(2-amino-5,7-dihydro-6H-pyrrolo[3,4-d]pyrimidin-6-yl)-1-methyl-N-[3-(trifluoromethyl)phenyl]-1H-imidazole-4-carboxamide |

TABLE 1-continued

| Example Number | Structure | Compound Name |
|---|---|---|
| 98 | 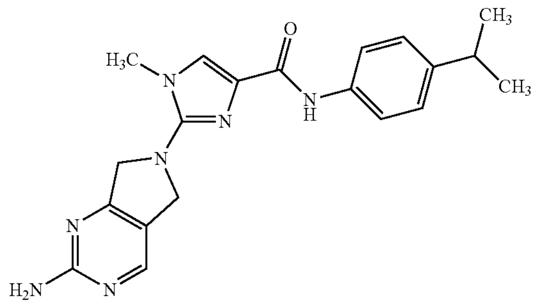 [SMILES: CC(C)c1ccc(NC(=O)c2cn(C)c(N3Cc4cnc(N)nc4C3)n2)cc1] | 2-(2-amino-5,7-dihydro-6H-pyrrolo[3,4-d]pyrimidin-6-yl)-N-(4-isopropylphenyl)-1-methyl-1H-imidazole-4-carboxamide |
| 99 | 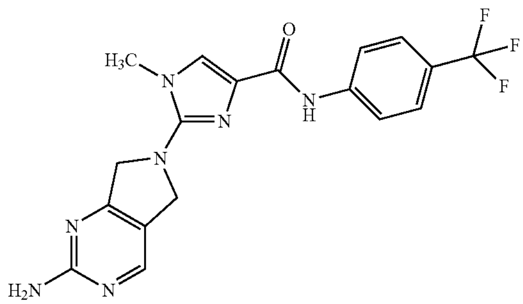 [SMILES: Cn1cc(C(=O)Nc2ccc(C(F)(F)F)cc2)nc1N1Cc2cnc(N)nc2C1] | 2-(2-amino-5,7-dihydro-6H-pyrrolo[3,4-d]pyrimidin-6-yl)-1-methyl-N-[4-(trifluoromethyl)phenyl]-1H-imidazole-4-carboxamide |
| 100 | 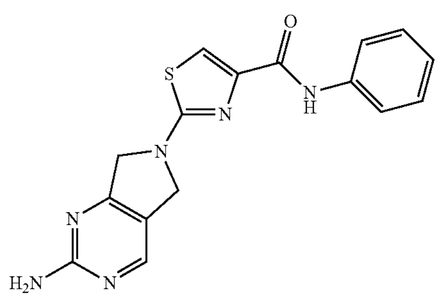 [SMILES: Nc1ncc2c(n1)CN(c1nc(C(=O)Nc3ccccc3)cs1)C2] | 2-(2-amino-5,7-dihydro-6H-pyrrolo[3,4-d]pyrimidin-6-yl)-N-phenyl-1,3-thiazole-4-carboxamide |
| 101 | 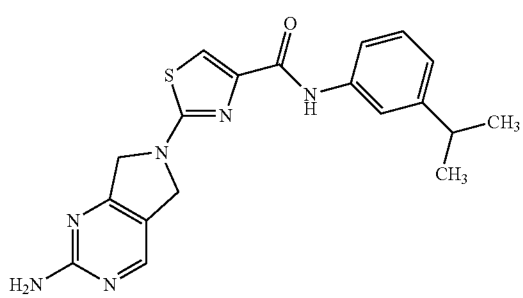 [SMILES: CC(C)c1cccc(NC(=O)c2csc(N3Cc4cnc(N)nc4C3)n2)c1] | 2-(2-amino-5,7-dihydro-6H-pyrrolo[3,4-d]pyrimidin-6-yl)-N-(3-isopropylphenyl)-1,3-thiazole-4-carboxamide |
| 102 | 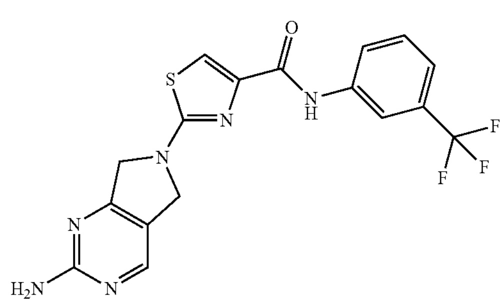 [SMILES: Nc1ncc2c(n1)CN(c1nc(C(=O)Nc3cccc(C(F)(F)F)c3)cs1)C2] | 2-(2-amino-5,7-dihydro-6H-pyrrolo[3,4-d]pyrimidin-6-yl)-N-[3-(trifluoromethyl)phenyl]-1,3-thiazole-4-carboxamide |

TABLE 1-continued

| Example Number | Structure | Compound Name |
|---|---|---|
| 103 | 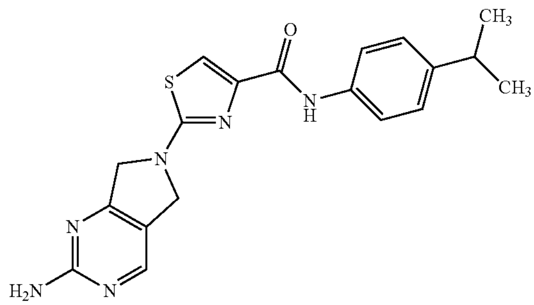 [SMILES: CC(C)c1ccc(NC(=O)c2csc(N3Cc4cnc(N)nc4C3)n2)cc1] | 2-(2-amino-5,7-dihydro-6H-pyrrolo[3,4-d]pyrimidin-6-yl)-N-(4-isopropylphenyl)-1,3-thiazole-4-carboxamide |
| 104 | 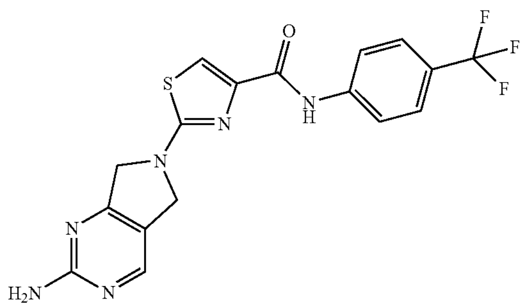 [SMILES: Nc1ncc2c(n1)CN(c1nc(C(=O)Nc3ccc(C(F)(F)F)cc3)cs1)C2] | 2-(2-amino-5,7-dihydro-6H-pyrrolo[3,4-d]pyrimidin-6-yl)-N-[4-(trifluoromethyl)phenyl]-1,3-thiazole-4-carboxamide |
| 105 | 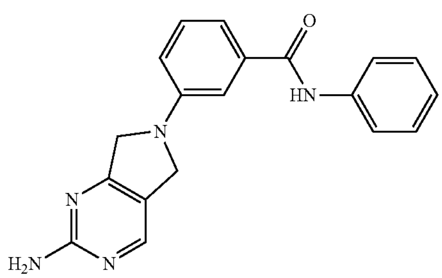 [SMILES: Nc1ncc2c(n1)CN(c1cccc(C(=O)Nc3ccccc3)c1)C2] | 3-(2-Amino-5,7-dihydro-pyrrolo[3,4d]pyrimidin-6-yl)-N-phenyl-benzamide |
| 106 | 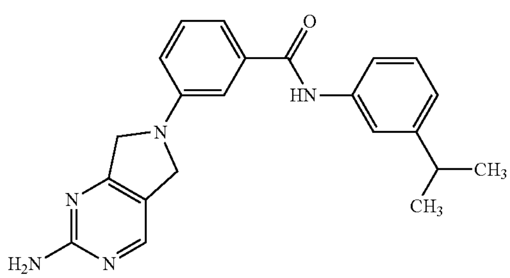 | 3-(2-Amino-5,7-dihydro-pyrrolo[3,4-d]pyrimidin-6-yl)-N-(3-isopropyl-phenyl)-benzamide |
| 107 | 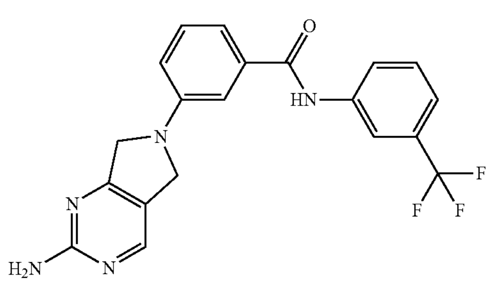 [SMILES: Nc1ncc2c(n1)CN(c1cccc(C(=O)Nc3cccc(C(F)(F)F)c3)c1)C2] | 3-(2-Amino-5,7-dihydro-pyrrolo[3,4-d]pyrimidin-6-yl)-N-(3-trifluoromethyl-phenyl)-benzamide |

TABLE 1-continued

| Example Number | Structure | Compound Name |
|---|---|---|
| 108 | 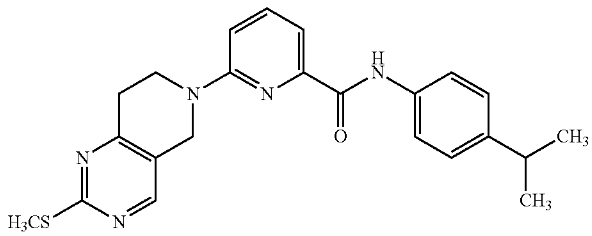 | N-(4-isopropylphenyl)-6-[2-(methylthio)-7,8-dihydropyrido[4,3-d]pyrimidin-6(5H)-yl]pyridine-2-carboxamide |
| 109 | 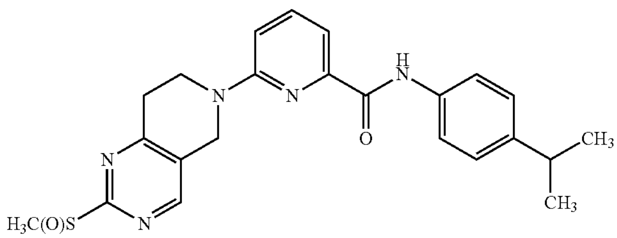 | 6-(2-Methanesulfinyl-7,8-dihydro-5H-pyrido[4,3-d]pyrimidin-6-yl)-pyridine-2-carboxylic acid (4-isopropyl-phenyl)-amide |
| 110 | 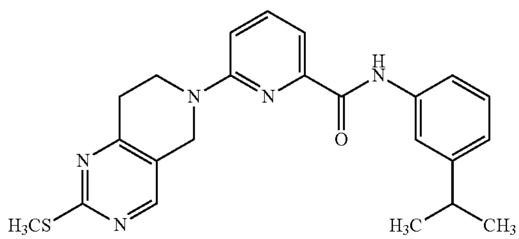 | N-(3-isopropylphenyl)-6-[2-(methylthio)-7,8-dihydropyrido[4,3-d]pyrimidin-6(5H)-yl]pyridine-2-carboxamide |
| 111 | 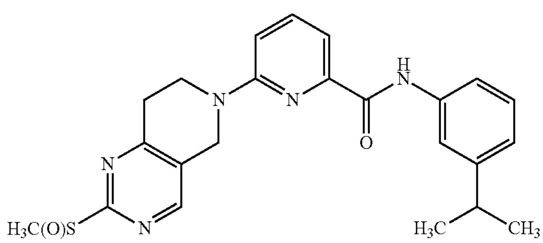 | N-(3-isopropylphenyl)-6-(2-((methylthio)oxy)-7,8-dihydropyrido[4,3-d]pyrimidin-6(5H)-yl)picolinamide |
| 112 | 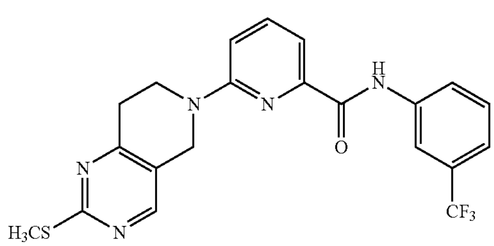 | 6-[2-(methylthio)-7,8-dihydropyrido[4,3-d]pyrimidin-6(5H)-yl]-N-[3-(trifluoromethyl)phenyl]pyridine-2-carboxamide |
| 113 | 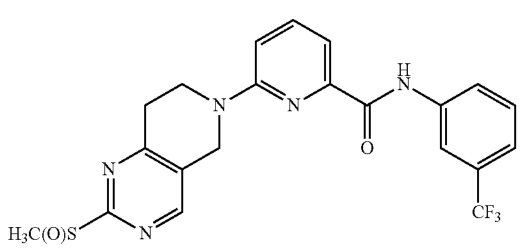 | 6-(2-((methylthio)oxy)-7,8-dihydropyrido[4,3-d]pyrimidin-6(5H)-yl)-N-(3-(trifluoromethyl)phenyl)picolinamide |

TABLE 1-continued

| Example Number | Structure | Compound Name |
|---|---|---|
| 114 | 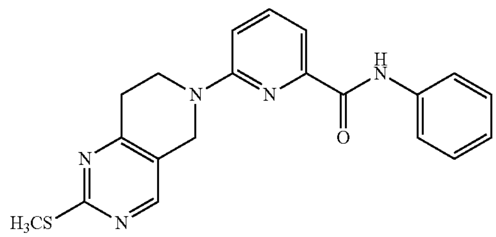 | 6-[2-(methylthio)-7,8-dihydropyrido[4,3-d]pyrimidin-6(5H)-yl]-N-phenylpyridine-2-carboxamide |
| 115 | 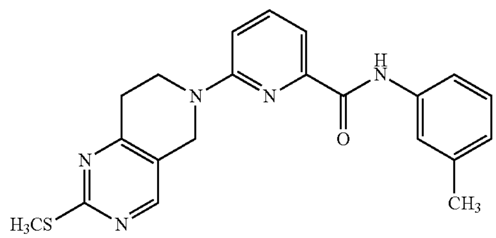 | N-(3-methylphenyl)-6-[2-(methylthio)-7,8-dihydropyrido[4,3-d]pyrimidin-6(5H)-yl]pyridine-2-carboxamide |
| 116 | 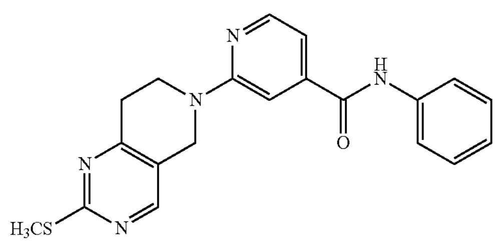 | 2-[2-(methylthio)-7,8-dihydropyrido[4,3-d]pyrimidin-6(5H)-yl]-N-phenylisonicotinamide |
| 117 | 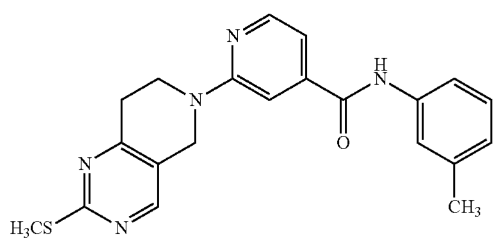 | N-(3-methylphenyl)-2-[2-(methylthio)-7,8-dihydropyrido[4,3-d]pyrimidin-6(5H)-yl]isonicotinamide |
| 118 | 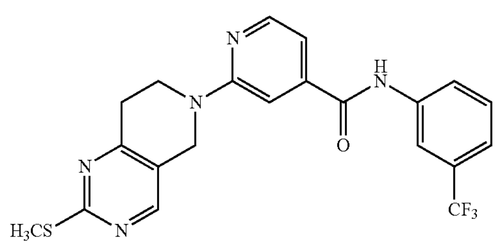 | 2-[2-(methylthio)-7,8-dihydropyrido[4,3-d]pyrimidin-6(5H)-yl]-N-[3-(trifluoromethyl)phenyl]isonicotinamide |
| 119 | 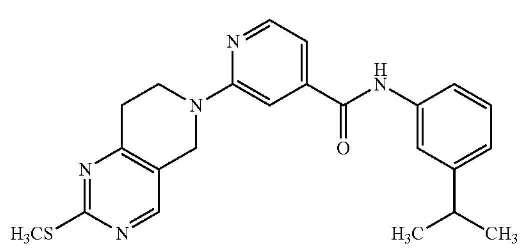 | N-(3-Isopropyl-phenyl)-2-(2-methylsulfanyl-7,8-dihydro-5H-pyrido[4,3-d]pyrimidin-6-yl)-isonicotinamide |

TABLE 1-continued

| Example Number | Structure | Compound Name |
|---|---|---|
| 120 | 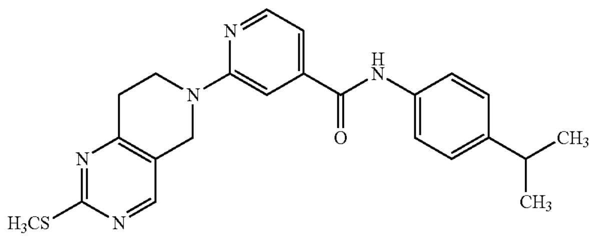 | N-(4-Isopropyl-phenyl)-2-(2-methylsulfanyl-7,8-dihydro-5H-pyrido[4,3-d]pyrimidin-6-yl)-isonicotinamide |
| 121 | 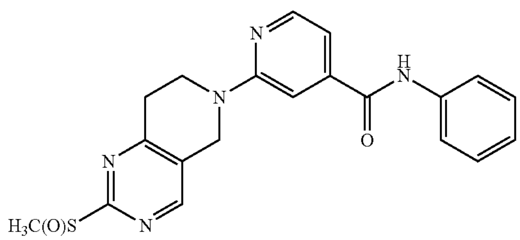 | 2-(2-(methylsulfinyl)-7,8-dihydropyrido[4,3-d]pyrimidin-6(5H)-yl)-N-phenylisonicotinamide |
| 122 | 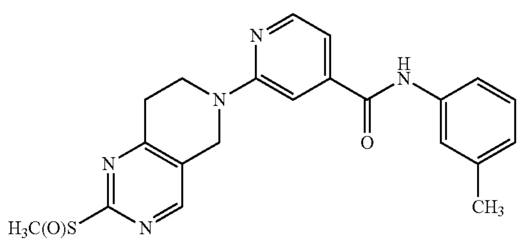 | 2-(2-(methylsulfinyl)-7,8-dihydropyrido[4,3-d]pyrimidin-6(5H)-yl)-N-(m-tolyl)isonicotinamide |
| 123 | 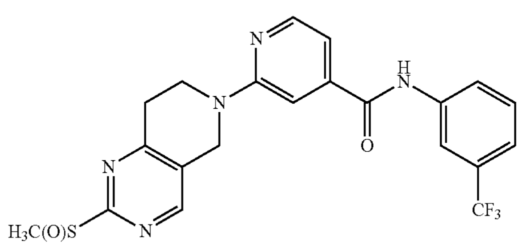 | 2-(2-(methylsulfinyl)-7,8-dihydropyrido[4,3-d]pyrimidin-6(5H)-yl)-N-(3-(trifluoromethyl)phenyl)isonicotinamide |
| 124 | 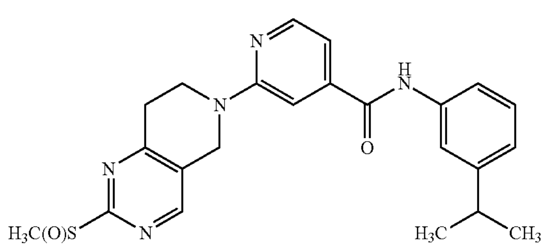 | N-(3-isopropylphenyl)-2-(2-(methylsulfinyl)-7,8-dihydropyrido[4,3-d]pyrimidin-6(5H)-yl)isonicotinamide |
| 125 | 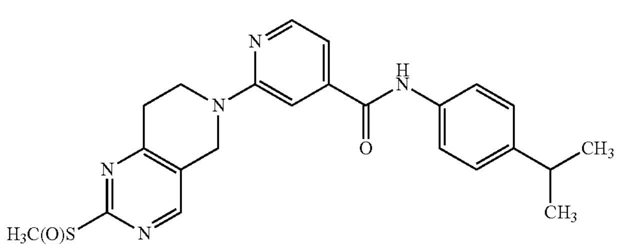 | N-(4-isopropylphenyl)-2-(2-(methylsulfinyl)-7,8-dihydropyrido[4,3-d]pyrimidin-6(5H)-yl)isonicotinamide |

TABLE 1-continued

| Example Number | Structure | Compound Name |
|---|---|---|
| 126 | 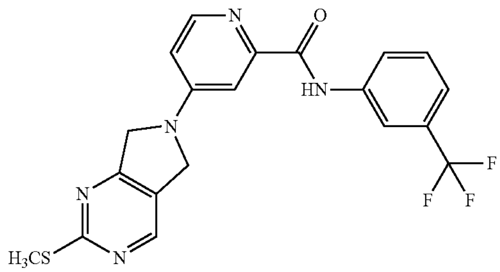 | 4-(2-Methylsulfanyl-5,7-dihydro-pyrrolo[3,4-d]pyrimidin-6-yl)-pyridine-2-carboxylic acid (3-trifluoromethyl-phenyl)-amide |
| 127 | 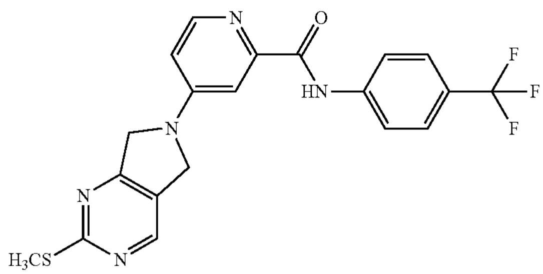 | 4-(2-Methylsulfanyl-5,7-dihydro-pyrrolo[3,4-d]pyrimidin-6-yl)-pyridine-2-carboxylic acid (4-trifluoromethyl-phenyl)-amide |
| 128 | 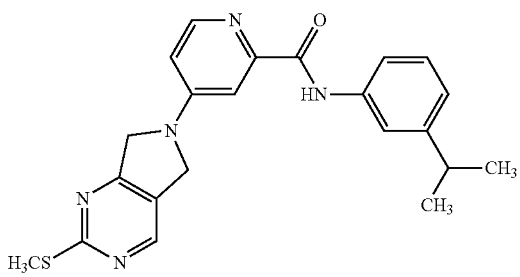 | 4-(2-Methylsulfanyl-5,7-dihydro-pyrrolo[3,4-d]pyrimidin-6-yl)-pyridine-2-carboxylic acid (3-isopropyl-phenyl)-amide |
| 129 | 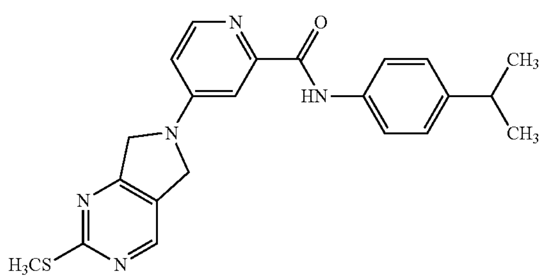 | 4-(2-Methylsulfanyl-5,7-dihydro-pyrrolo[3,4-d]pyrimidin-6-yl)-pyridine-2-carboxylic acid (4-isopropyl-phenyl)-amide |
| 130 | 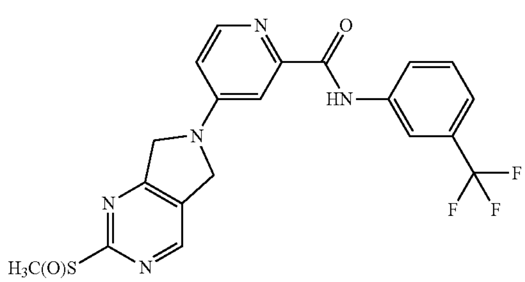 | 4-(2-(Methylsulfinyl)-5H-pyrrolo[3,4-d]pyrimidin-6(7H)-yl)-N-(3-(trifluoromethyl)phenyl)picolinamide |

TABLE 1-continued

| Example Number | Structure | Compound Name |
|---|---|---|
| 131 | 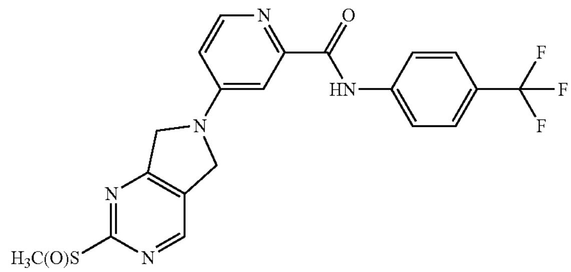 | 4-(2-Methylsulfanyl-5,7-dihydro-pyrrolo[3,4-d]pyrimidin-6-yl)-pyridine-2-carboxylic acid (4-trifluoromethyl-phenyl)-amide |
| 132 | 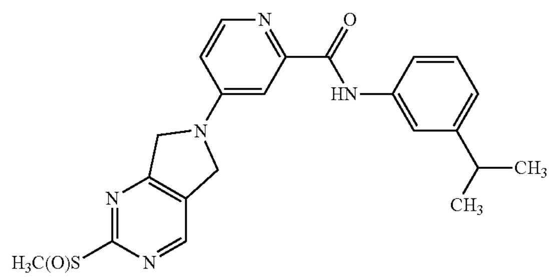 | N-(3-isopropylphenyl)-4-(2-(methylsulfinyl)-5H-pyrrolo[3,4-d]pyrimidin-6(7H)-yl)picolinamide |
| 133 | 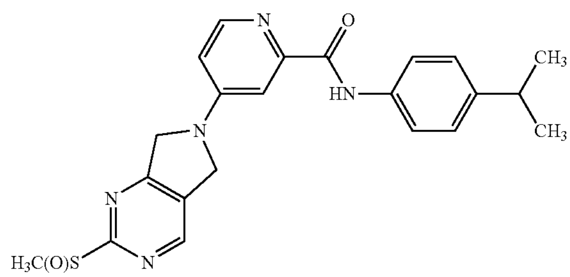 | N-(4-isopropylphenyl)-4-(2-(methylsulfinyl)-5H-pyrrolo[3,4-d]pyrimidin-6(7H)-yl)picolinamide |
| 134 | 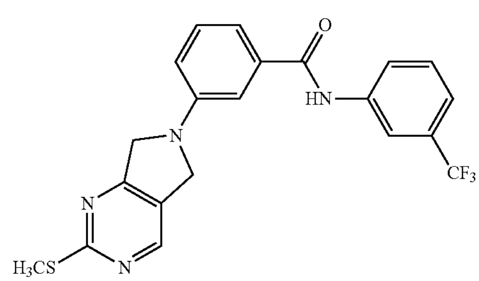 | 3-[2-(methylthio)-5,7-dihydro-6H-pyrrolo[3,4-d]pyrimidin-6-yl]-N-[3-(trifluoromethyl)phenyl]benzamide |
| 135 | 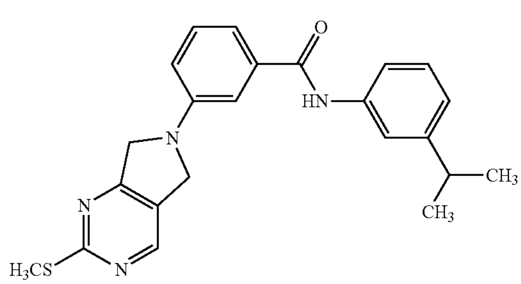 | N-(3-isopropylphenyl)-3-[2-(methylthio)-5,7-dihydro-6H-pyrrolo[3,4-d]pyrimidin-6-yl]benzamide |

TABLE 1-continued

| Example Number | Structure | Compound Name |
|---|---|---|
| 136 | 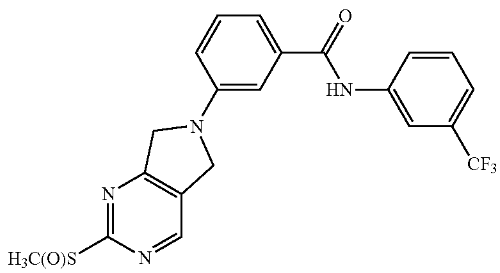 | 3-(2-(methylsulfinyl)-5H-pyrrolo[3,4-d]pyrimidin-6(7H)-yl)-N-(3-(trifluoromethyl)phenyl)benzamide |
| 137 | 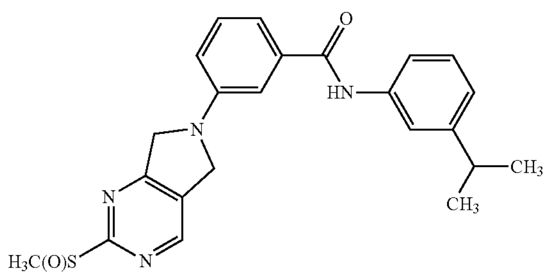 | N-(3-isopropylphenyl)-3-(2-(methylsulfinyl)-5H-pyrrolo[3,4-d]pyrimidin-6(7H)-yl)benzamide |
| 138 | 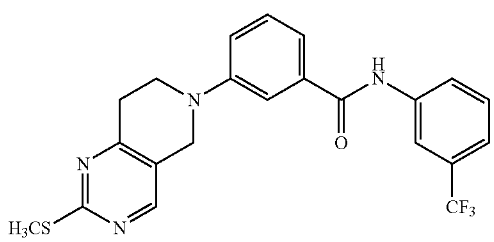 | 3-[2-(methylthio)-7,8-dihydropyrido[4,3-d]pyrimidin-6(5H)-yl]-N-[3-(trifluoromethyl)phenyl]benzamide |
| 139 | 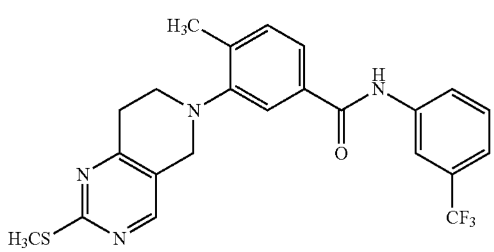 | 4-methyl-3-[2-(methylthio)-7,8-dihydropyrido[4,3-d]pyrimidin-6(5H)-yl]-N-[3-(trifluoromethyl)phenyl]benzamide |
| 140 | 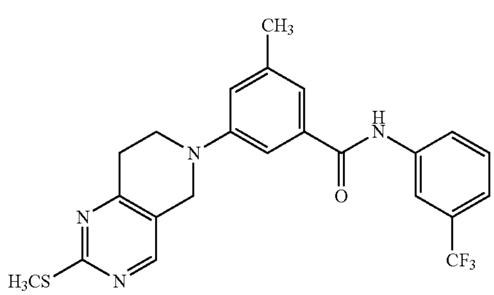 | 3-methyl-5-[2-(methylthio)-7,8-dihydropyrido[4,3-d]pyrimidin-6(5H)-yl]-N-[3-(trifluoromethyl)phenyl]benzamide |

TABLE 1-continued

| Example Number | Structure | Compound Name |
|---|---|---|
| 141 | 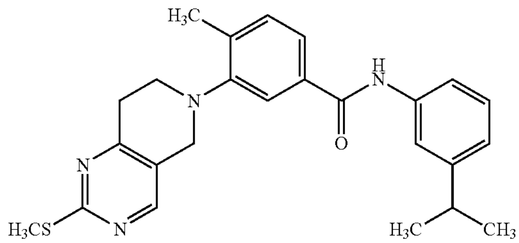 | N-(3-isopropylphenyl)-4-methyl-3-[2-(methylthio)-7,8-dihydropyrido[4,3-d]pyrimidin-6(5H)-yl]benzamide |
| 142 | 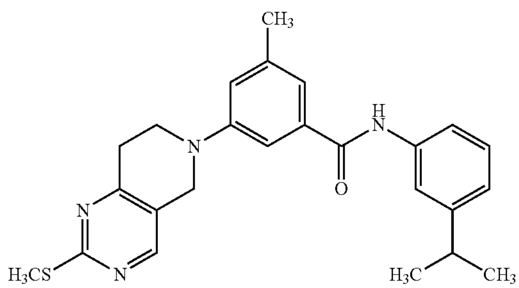 | N-(3-isopropylphenyl)-3-methyl-5-[2-(methylthio)-7,8-dihydropyrido[4,3-d]pyrimidin-6(5H)-yl]benzamide |
| 143 | 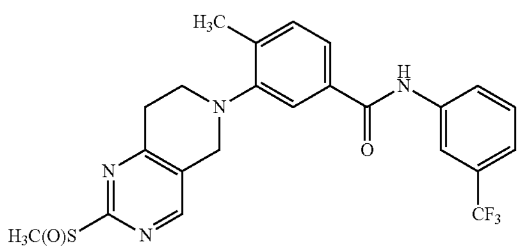 | 4-methyl-3-(2-(methylsulfinyl)-7,8-dihydropyrido[4,3-d]pyrimidin-6(5H)-yl)-N-(3-(trifluoromethyl)phenyl)benzamide |
| 144 | 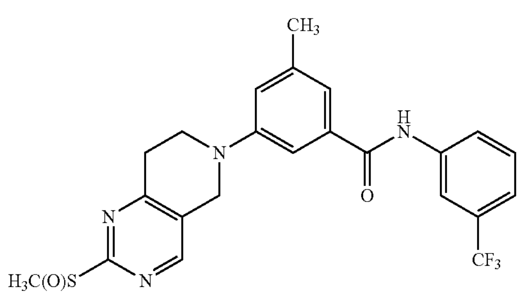 | 3-methyl-5-(2-((methylthio)oxy)-7,8-dihydropyrido[4,3-d]pyrimidin-6(5H)-yl)-N-(3-(trifluoromethyl)phenyl)benzamide |
| 145 | 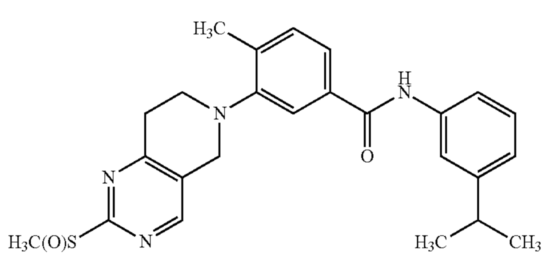 | N-(3-isopropylphenyl)-4-methyl-3-(2-(methylsulfinyl)-7,8-dihydropyrido[4,3-d]pyrimidin-6(5H)-yl)benzamide |

TABLE 1-continued

| Example Number | Structure | Compound Name |
|---|---|---|
| 146 | 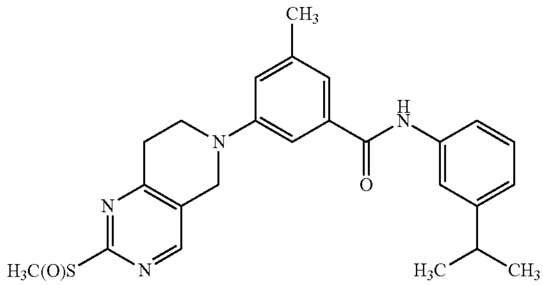 | N-(3-isopropylphenyl)-3-methyl-5-(2-(methylsulfinyl)-7,8-dihydropyrido[4,3-d]pyrimidin-6(5H)-yl)benzamide |
| 147 | 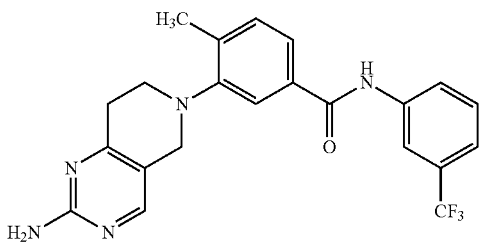 [SMILES: Cc1ccc(C(=O)Nc2cccc(C(F)(F)F)c2)cc1N1CCc2nc(N)ncc2C1] | 3-(2-amino-7,8-dihydropyrido[4,3-d]pyrimidin-6(5H)-yl)-4-methyl-N-[3-(trifluoromethyl)phenyl]benzamide |
| 148 | 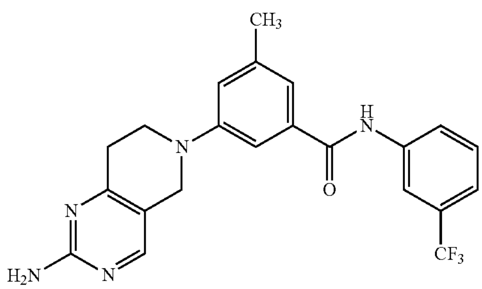 [SMILES: Cc1cc(C(=O)Nc2cccc(C(F)(F)F)c2)cc(N2CCc3nc(N)ncc3C2)c1] | 3-(2-amino-7,8-dihydropyrido[4,3-d]pyrimidin-6(5H)-yl)-5-methyl-N-[3-(trifluoromethyl)phenyl]benzamide |
| 149 | 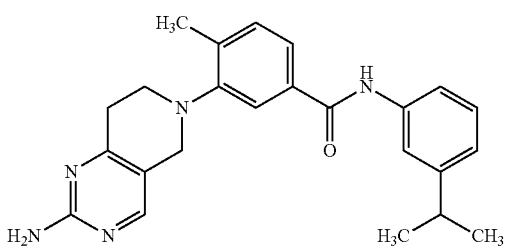 [SMILES: Cc1ccc(C(=O)Nc2cccc(C(C)C)c2)cc1N1CCc2nc(N)ncc2C1] | 3-(2-amino-7,8-dihydropyrido[4,3-d]pyrimidin-6(5H)-yl)-N-(3-isopropylphenyl)-4-methylbenzamide |
| 150 | 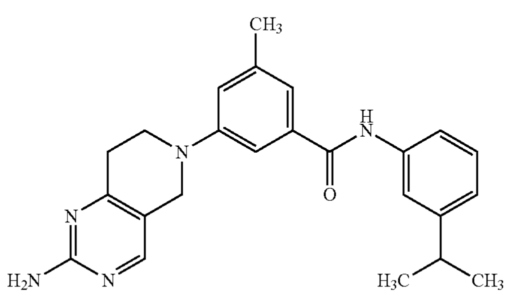 [SMILES: Cc1cc(C(=O)Nc2cccc(C(C)C)c2)cc(N2CCc3nc(N)ncc3C2)c1] | 3-(2-amino-7,8-dihydropyrido[4,3-d]pyrimidin-6(5H)-yl)-N-(3-isopropylphenyl)-5-methylbenzamide |

TABLE 1-continued

| Example Number | Structure | Compound Name |
|---|---|---|
| 151 | 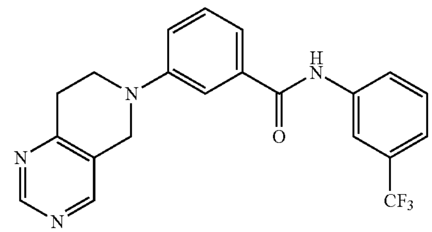 [SMILES: O=C(Nc1cccc(C(F)(F)F)c1)c1cccc(N2CCc3ncncc3C2)c1] | 3-(7,8-dihydropyrido[4,3-d]pyrimidin-6(5H)-yl)-N-[3-(trifluoromethyl)phenyl]benzamide |
| 152 | 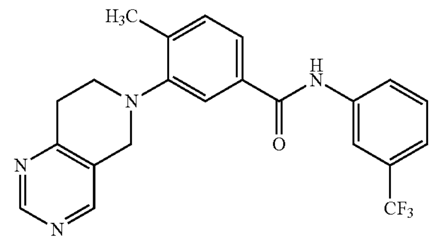 [SMILES: Cc1ccc(C(=O)Nc2cccc(C(F)(F)F)c2)cc1N1CCc2ncncc2C1] | 3-(7,8-dihydropyrido[4,3-d]pyrimidin-6(5H)-yl)-4-methyl-N-[3-(trifluoromethyl)phenyl]benzamide |
| 153 | 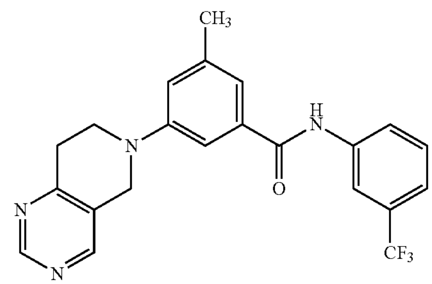 [SMILES: Cc1cc(C(=O)Nc2cccc(C(F)(F)F)c2)cc(N2CCc3ncncc3C2)c1] | 3-(7,8-dihydropyrido[4,3-d]pyrimidin-6(5H)-yl)-5-methyl-N-[3-(trifluoromethyl)phenyl]benzamide |
| 154 | 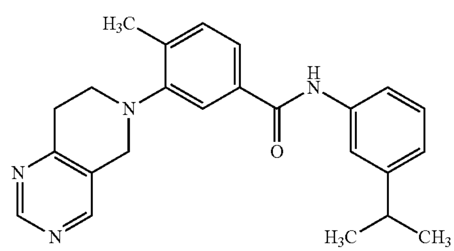 [SMILES: Cc1ccc(C(=O)Nc2cccc(C(C)C)c2)cc1N1CCc2ncncc2C1] | 3-(7,8-dihydropyrido[4,3-d]pyrimidin-6(5H)-yl)-N-(3-isopropylphenyl)-4-methylbenzamide |
| 155 | 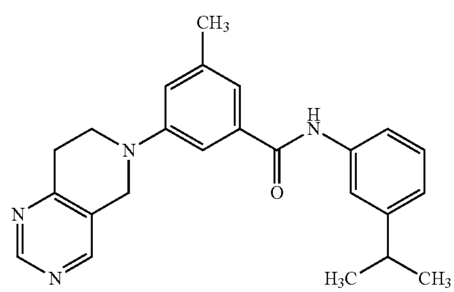 [SMILES: Cc1cc(C(=O)Nc2cccc(C(C)C)c2)cc(N2CCc3ncncc3C2)c1] | 3-(7,8-dihydropyrido[4,3-d]pyrimidin-6(5H)-yl)-N-(3-isopropylphenyl)-5-methylbenzamide |
| 156 | 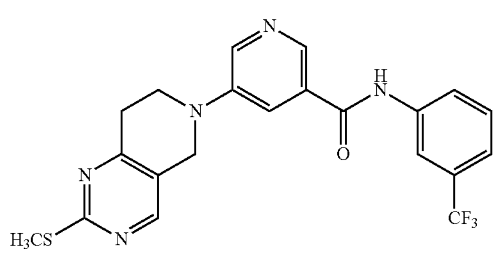 | 5-(2-Methylsulfanyl-7,8-dihydro-5H-pyrido[4,3-d]pyrimidin-6-yl)-N-(3-trifluoromethyl-phenyl)-nicotinamide |

TABLE 1-continued

| Example Number | Structure | Compound Name |
|---|---|---|
| 157 | 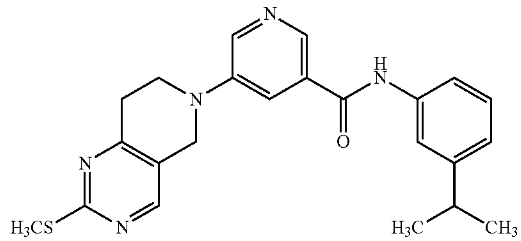 | N-(3-Isopropyl-phenyl)-5-(2-methylsulfanyl-7,8-dihydro-5H-pyrido[4,3-d]pyrimidin-6-yl)-nicotinamide |
| 158 | 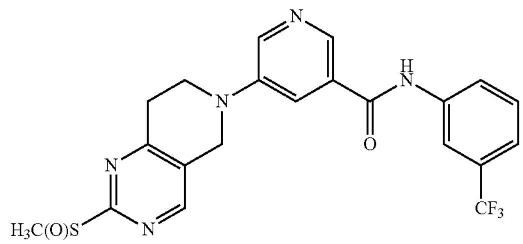 | 5-(2-(methylsulfinyl)-7,8-dihydropyrido[4,3-d]pyrimidin-6(5H)-yl)-N-(3-(trifluoromethyl)phenyl)nicotinamide |
| 159 | 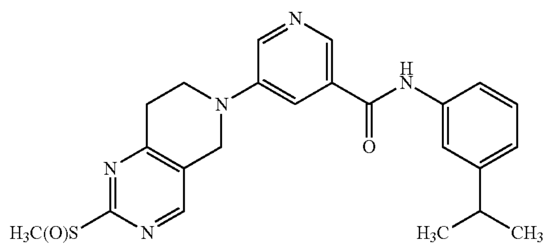 | N-(3-isopropylphenyl)-5-(2-(methylsulfinyl)-7,8-dihydropyrido[4,3-d]pyrimidin-6(5H)-yl)nicotinamide |
| 160 | 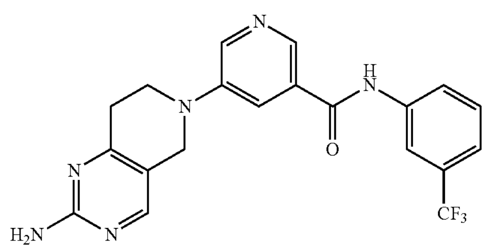 [SMILES: Nc1ncc2c(n1)CCN(c1cncc(C(=O)Nc3cccc(C(F)(F)F)c3)c1)C2] | 5-(2-amino-7,8-dihydropyrido[4,3-d]pyrimidin-6(5H)-yl)-N-[3-(trifluoromethyl)phenyl]nicotinamide |
| 161 | 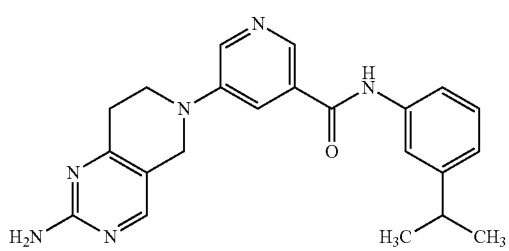 [SMILES: CC(C)c1cccc(NC(=O)c2cncc(N3CCc4nc(N)ncc4C3)c2)c1] | 5-(2-amino-7,8-dihydropyrido[4,3-d]pyrimidin-6(5H)-yl)-N-(3-isopropylphenyl)nicotinamide |
| 162 | 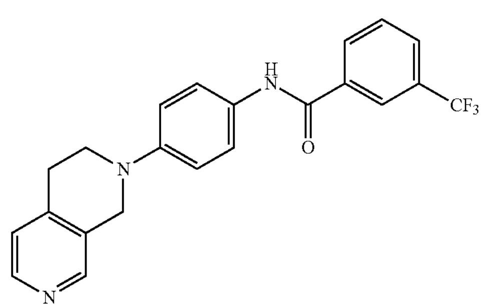 [SMILES: O=C(Nc1ccc(N2CCc3ccncc3C2)cc1)c1cccc(C(F)(F)F)c1] | N-[4-(3,4-dihydro-2,7-naphthyridin-2(1H)-yl)phenyl]-3-(trifluoromethyl)benzamide |

TABLE 1-continued

| Example Number | Structure | Compound Name |
|---|---|---|
| 163 | 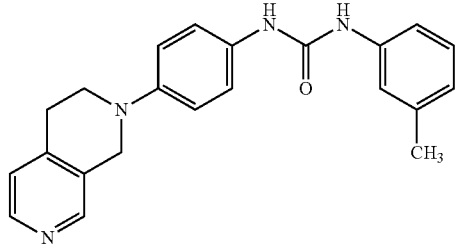 [SMILES: Cc1cccc(NC(=O)Nc2ccc(N3CCc4ccncc4C3)cc2)c1] | 1-[4-(3,4-dihydro-2,7-naphthyridin-2(1H)-yl)phenyl]-3-(3-methylphenyl)urea |
| 164 | 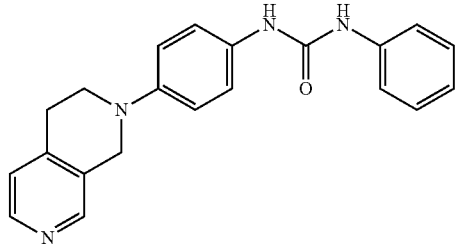 [SMILES: O=C(Nc1ccccc1)Nc1ccc(N2CCc3ccncc3C2)cc1] | 1-[4-(3,4-dihydro-2,7-naphthyridin-2(1H)-yl)phenyl]-3-phenylurea |
| 165 | 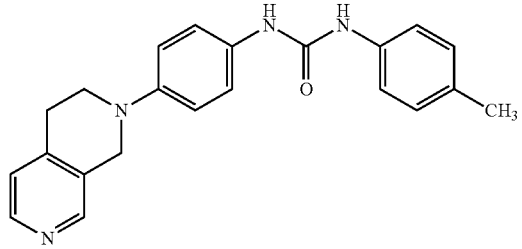 [SMILES: Cc1ccc(NC(=O)Nc2ccc(N3CCc4ccncc4C3)cc2)cc1] | 1-[4-(3,4-dihydro-2,7-naphthyridin-2(1H)-yl)phenyl]-3-(4-methylphenyl)urea |
| 166 | 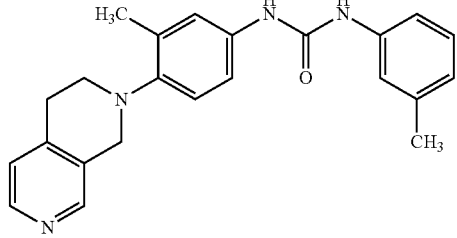 | 1-[4-(3,4-dihydro-2,7-naphthyridin-2(1H)-yl)-3-methylphenyl]-3-(3-methylphenyl)urea |
| 167 | 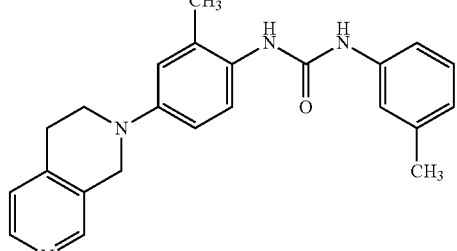 | 1-[4-(3,4-dihydro-2,7-naphthyridin-2(1H)-yl)-2-methylphenyl]-3-(3-methylphenyl)urea |
| 168 | 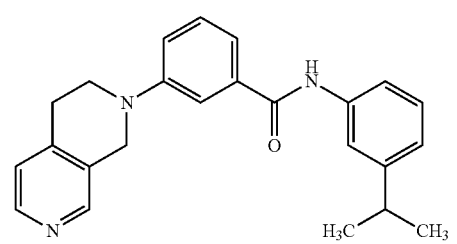 | 3-(3,4-dihydro-2,7-naphthyridin-2(1H)-yl)-N-(3-isopropylphenyl)benzamide |

TABLE 1-continued

| Example Number | Structure | Compound Name |
|---|---|---|
| 169 | 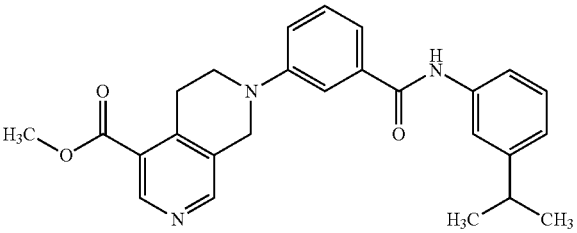 [SMILES: COC(=O)c1cncc2c1CCN(c1cccc(C(=O)Nc3cccc(C(C)C)c3)c1)C2] | methyl 7-(3-{[(3-isopropyl-phenyl)amino]carbonyl}phenyl)-5,6,7,8-tetrahydro-2,7-naphthyridine-4-carboxylate |
| 170 | 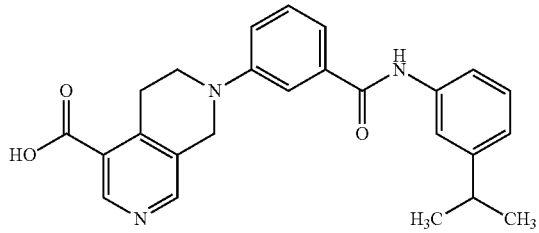 [SMILES: CC(C)c1cccc(NC(=O)c2cccc(N3CCc4c(cncc4C(=O)O)C3)c2)c1] | 7-(3-{[(3-isopropyl-phenyl)amino]carbonyl}phenyl)-5,6,7,8-tetrahydro-2,7-naphthyridine-4-carboxylic acid |
| 171 | 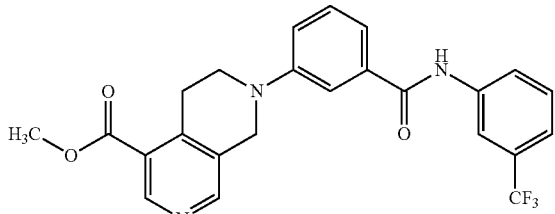 | methyl 7-[3-({[3-(trifluoro-methyl)phenyl]amino}carbonyl)phenyl]-5,6,7,8-tetrahydro-2,7-naphthyridine-4-carboxylate |
| 172 | 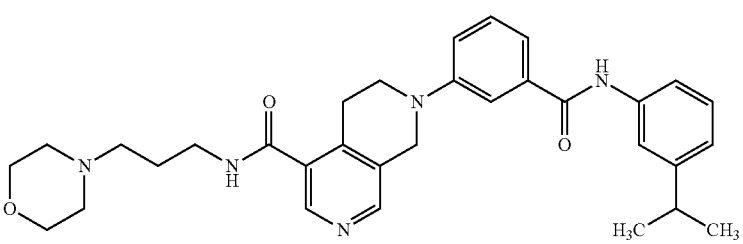 [SMILES: CC(C)c1cccc(NC(=O)c2cccc(N3CCc4c(cncc4C(=O)NCCCN4CCOCC4)C3)c2)c1] | 7-(3-{[(3-isopropyl-phenyl)amino]carbonyl}phenyl)-N-(3-morpholin-4-ylpropyl)-5,6,7,8-tetrahydro-2,7-naphthyridine-4-carboxamide |
| 173 | 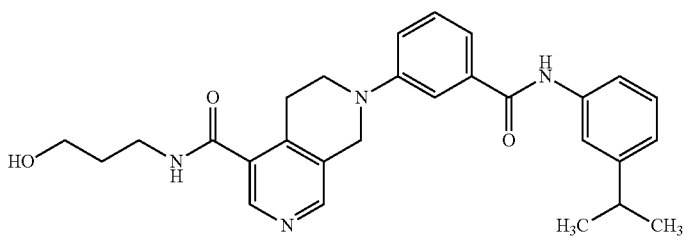 [SMILES: CC(C)c1cccc(NC(=O)c2cccc(N3CCc4c(cncc4C(=O)NCCCO)C3)c2)c1] | N-(3-hydroxypropyl)-7-(3-{[(3-isopropyl-phenyl)amino]carbonyl}phenyl)-5,6,7,8-tetrahydro-2,7-naphthyridine-4-carboxamide |
| 174 | 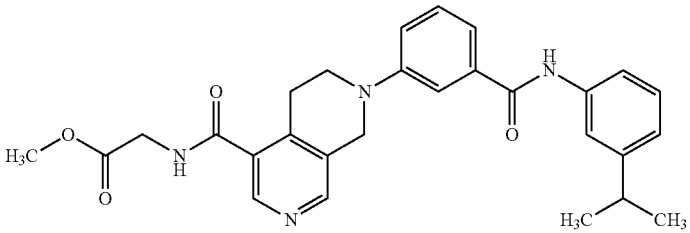 [SMILES: COC(=O)CNC(=O)c1cncc2c1CCN(c1cccc(C(=O)Nc3cccc(C(C)C)c3)c1)C2] | methyl ({[7-(3-{[(3-isopropyl-phenyl)amino]carbonyl}phenyl)-5,6,7,8-tetrahydro-2,7-naphthyridin-4-yl]carbonyl}amino)acetate |

TABLE 1-continued

| Example Number | Structure | Compound Name |
|---|---|---|
| 175 | 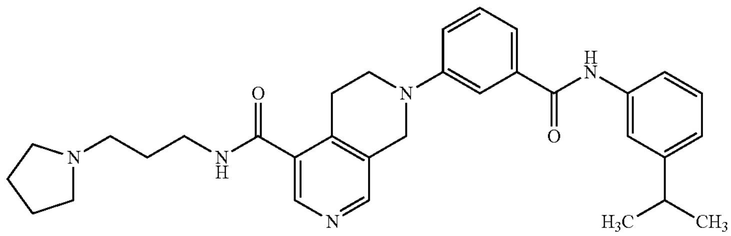 [SMILES: CC(C)c1cccc(NC(=O)c2cccc(N3CCc4c(cncc4C(=O)NCCCN4CCCC4)C3)c2)c1] | 7-(3-{[(3-isopropyl-phenyl)amino]carbonyl}phenyl)-N-(3-pyrrolidin-1-ylpropyl)-5,6,7,8-tetrahydro-2,7-naphthyridine-4-carboxamide |
| 176 | 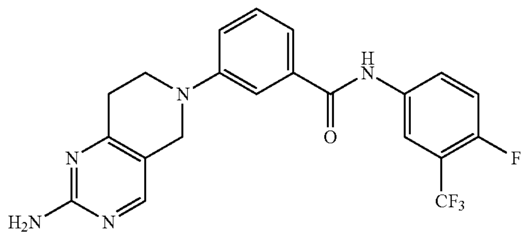 [SMILES: Nc1ncc2c(n1)CCN(c1cccc(C(=O)Nc3ccc(F)c(C(F)(F)F)c3)c1)C2] | 3-(2-amino-7,8-dihydropyrido[4,3-d]pyrimidin-6(5H)-yl)-N-[4-fluoro-3-(trifluoromethyl)phenyl]benzamide |
| 177 | 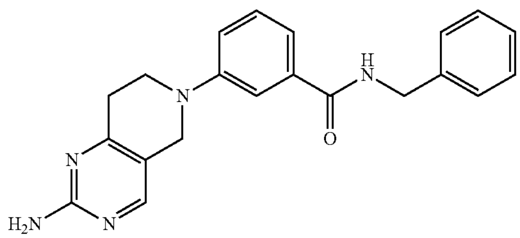 [SMILES: Nc1ncc2c(n1)CCN(c1cccc(C(=O)NCc3ccccc3)c1)C2] | 3-(2-amino-7,8-dihydropyrido[4,3-d]pyrimidin-6(5H)-yl)-N-benzylbenzamide |

As discussed above, the present invention relates to methods of treating various conditions with compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to the use of compounds which regulate, modulate and/or inhibit tyrosine kinase signal transduction by affecting the enzymatic activity of the RTKs and/or the non-receptor tyrosine kinases and interfering with the signal transduced such proteins. More particularly, the present invention is directed to the use of compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Biological data for the compounds of the present invention was generated by use of the following assays.

VEGFR2 Kinase Assay:

Biochemical KDR kinase assays were performed in 96 well microliter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N H$_2$SO$_4$ to each well and read using a microplate ELISA reader set at 492 nm. IC$_{50}$ values for compound inhibition were calculated directly from graphs of optical density (arbitrary units) versus compound concentration following subtraction of blank values.

PDGFRβ Kinase Assay

Biochemical PDGFRβ kinase assays were performed in 96 well microliter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-β protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of 0-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N H$_2$SO$_4$ to each well and read using a microplate ELISA reader set at 492 nm. IC$_{50}$ values for compound inhibition were calculated directly from graphs of optical density (arbitrary units) versus compound concentration following subtraction of blank values.

IC$_{50}$ values for test compounds were calculated from % inhibition of PDGF-BB stimulated responses in the absence of inhibitor.

TABLE 2

| Example Number | Structure | VEGFR2 Kinase (IC$_{50}$, nM) | PDGFRβ Kinase (IC$_{50}$, nM) |
|---|---|---|---|
| 1 | 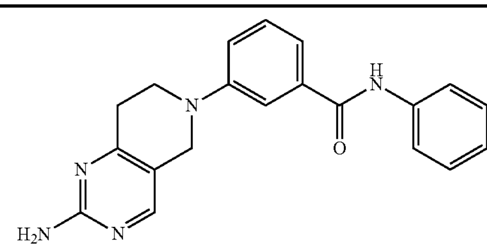 | 2980 | |
| 2 | 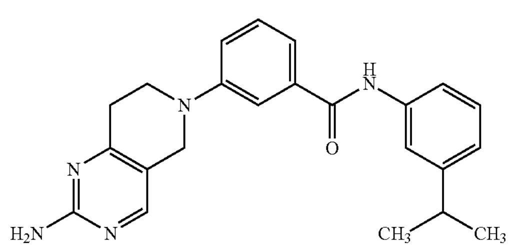 [SMILES: CC(C)c1cccc(NC(=O)c2cccc(N3CCc4nc(N)ncc4C3)c2)c1] | 12 | 21 |
| 3 | 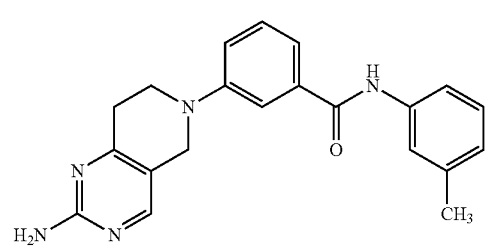 | 114 | 116 |

TABLE 2-continued

| Example Number | Structure | VEGFR2 Kinase (IC$_{50}$, nM) | PDGFRβ Kinase (IC$_{50}$, nM) |
|---|---|---|---|
| 4 | 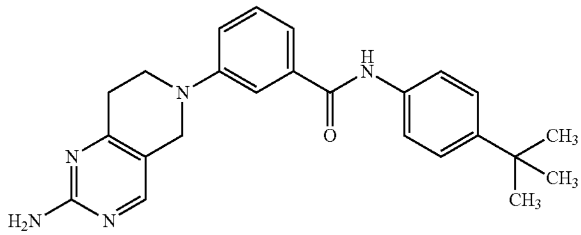 [SMILES: CC(C)(C)c1ccc(NC(=O)c2cccc(N3CCc4nc(N)ncc4C3)c2)cc1] | 41 | 109 |
| 5 | 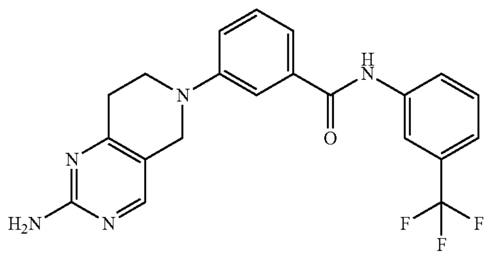 | 12 | 26 |
| 6 | 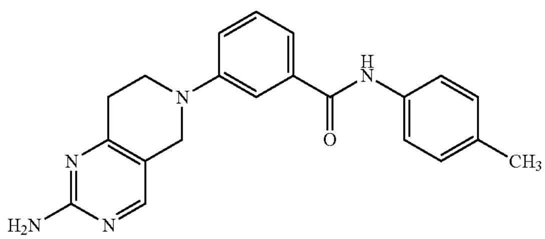 [SMILES: Cc1ccc(NC(=O)c2cccc(N3CCc4nc(N)ncc4C3)c2)cc1] | 783 | 90 |
| 7 | 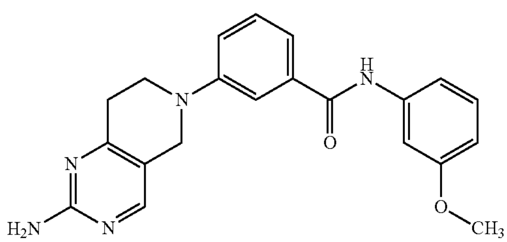 [SMILES: COc1cccc(NC(=O)c2cccc(N3CCc4nc(N)ncc4C3)c2)c1] | 102 | 1240 |
| 8 | 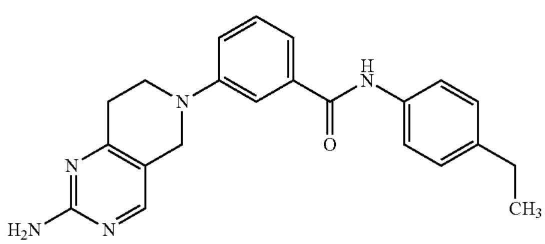 [SMILES: CCc1ccc(NC(=O)c2cccc(N3CCc4nc(N)ncc4C3)c2)cc1] | 145 | 134 |
| 9 | 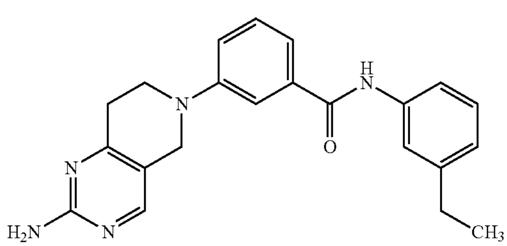 | 22 | 52 |

TABLE 2-continued

| Example Number | Structure | VEGFR2 Kinase (IC$_{50}$, nM) | PDGFRβ Kinase (IC$_{50}$, nM) |
| --- | --- | --- | --- |
| 10 | 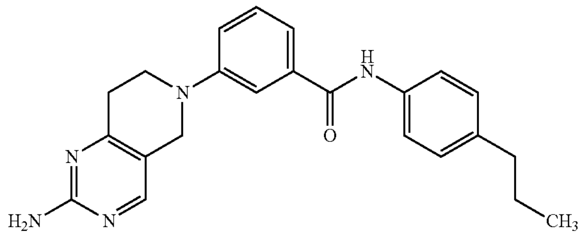 [SMILES: CCCc1ccc(NC(=O)c2cccc(N3CCc4nc(N)ncc4C3)c2)cc1] | 67 | 32 |
| 11 | 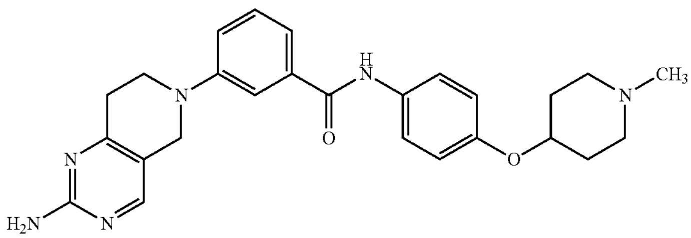 [SMILES: CN1CCC(Oc2ccc(NC(=O)c3cccc(N4CCc5nc(N)ncc5C4)c3)cc2)CC1] | 1180 | >1000 |
| 12 | 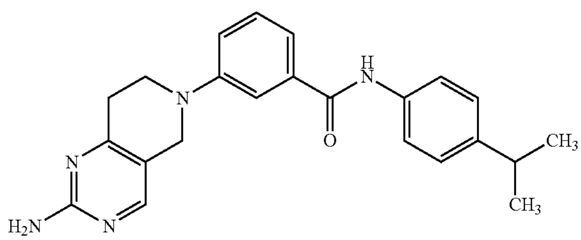 | 27 | 24 |
| 13 | 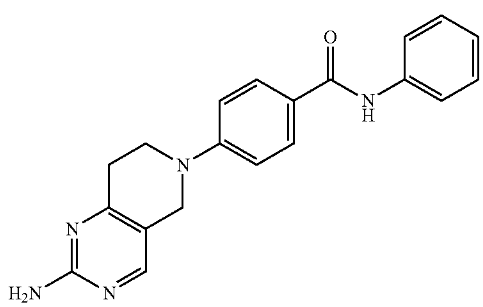 [SMILES: Nc1ncc2c(n1)CCN(c1ccc(C(=O)Nc3ccccc3)cc1)C2] | >10000 | |
| 14 | 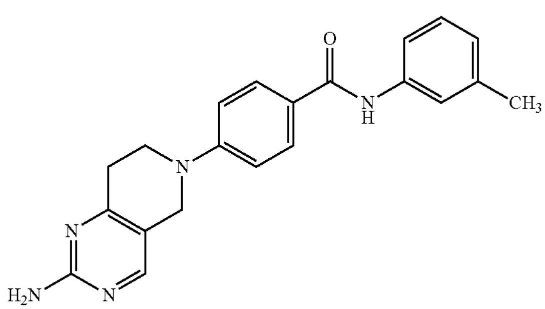 [SMILES: Cc1cccc(NC(=O)c2ccc(N3CCc4nc(N)ncc4C3)cc2)c1] | >10000 | |

TABLE 2-continued

| Example Number | Structure | VEGFR2 Kinase (IC$_{50}$, nM) | PDGFRβ Kinase (IC$_{50}$, nM) |
|---|---|---|---|
| 15 | 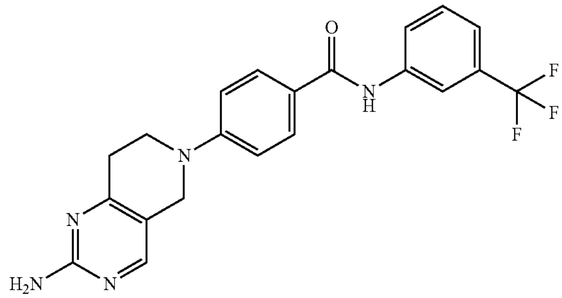 [SMILES: Nc1ncc2c(n1)CCN(c1ccc(C(=O)Nc3cccc(C(F)(F)F)c3)cc1)C2] | >10000 | |
| 16 | 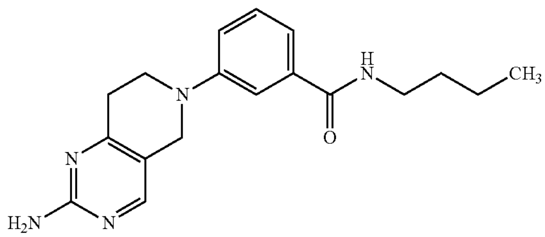 [SMILES: CCCCNC(=O)c1cccc(N2CCc3nc(N)ncc3C2)c1] | >1000 | >10000 |
| 17 | 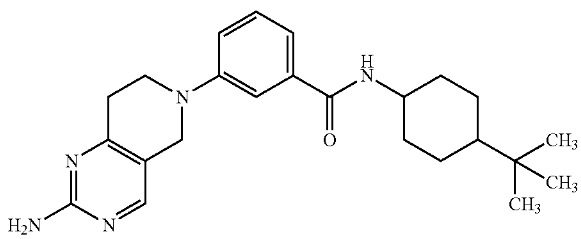 [SMILES: CC(C)(C)C1CCC(NC(=O)c2cccc(N3CCc4nc(N)ncc4C3)c2)CC1] | 307 | 246 |
| 18 | 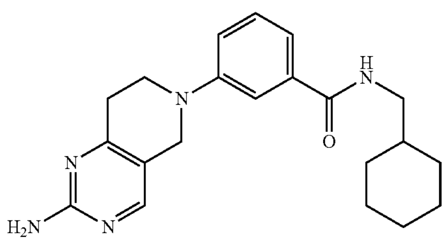 [SMILES: Nc1ncc2c(n1)CCN(c1cccc(C(=O)NCC3CCCCC3)c1)C2] | 2130 | 602 |
| 19 | 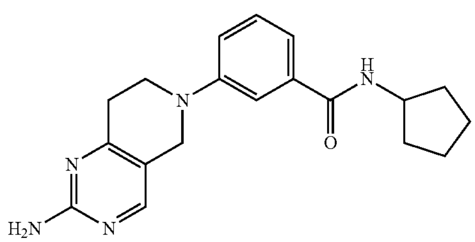 [SMILES: Nc1ncc2c(n1)CCN(c1cccc(C(=O)NC3CCCC3)c1)C2] | >10000 | >10000 |
| 20 | 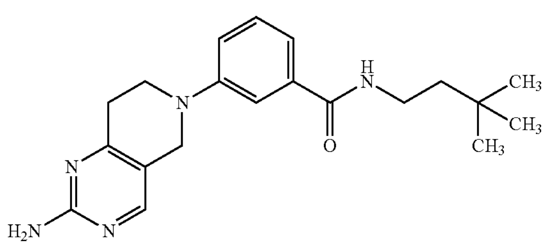 [SMILES: CC(C)(C)CCNC(=O)c1cccc(N2CCc3nc(N)ncc3C2)c1] | 566 | 164 |

TABLE 2-continued

| Example Number | Structure | VEGFR2 Kinase (IC$_{50}$, nM) | PDGFRβ Kinase (IC$_{50}$, nM) |
| --- | --- | --- | --- |
| 21 | 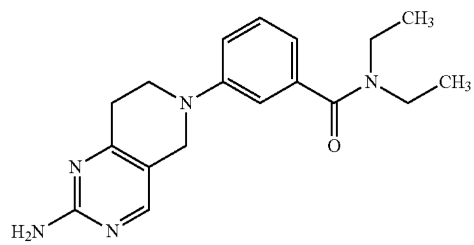 [SMILES: CCN(CC)C(=O)c1cccc(N2CCc3nc(N)ncc3C2)c1] | 1250 | >1000 |
| 22 | 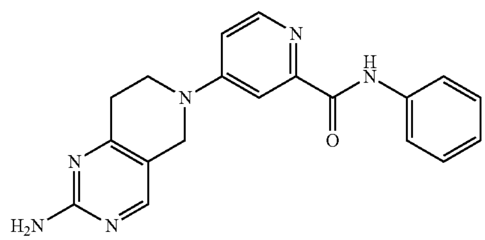 | >10000 | |
| 23 | 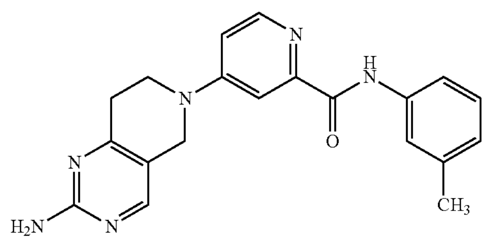 | >10000 | |
| 24 | 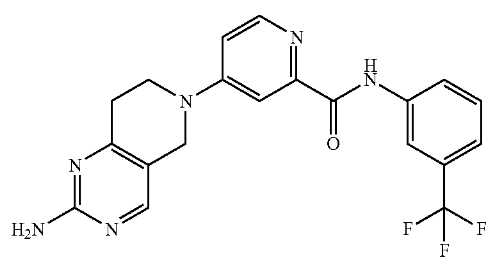 | >10000 | |
| 25 | 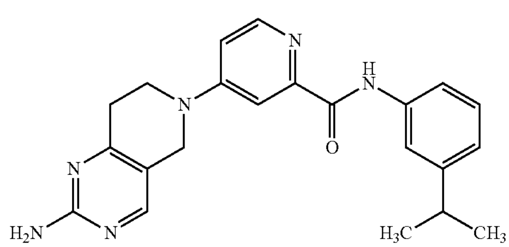 [SMILES: CC(C)c1cccc(NC(=O)c2cc(N3CCc4nc(N)ncc4C3)ccn2)c1] | >10000 | |
| 26 | 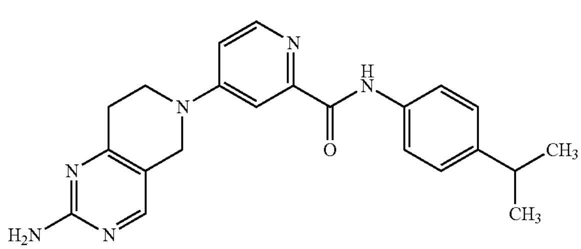 | >10000 | |

TABLE 2-continued
| Example Number | Structure | VEGFR2 Kinase (IC$_{50}$, nM) | PDGFRβ Kinase (IC$_{50}$, nM) |
|---|---|---|---|
| 36 | 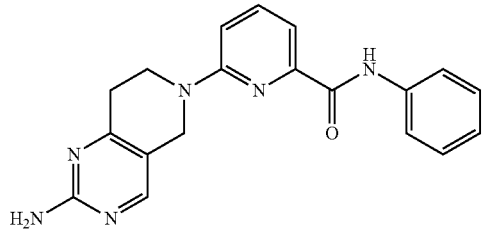 | >10000 | |
| 37 | 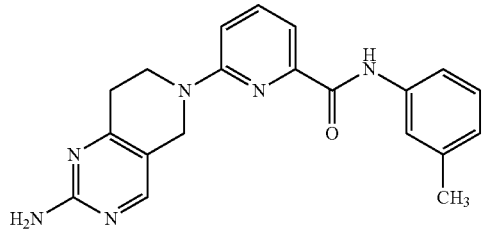 | >10000 | >10000 |
| 38 | 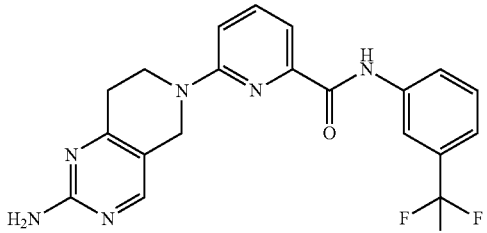 | >10000 | |
| 39 | 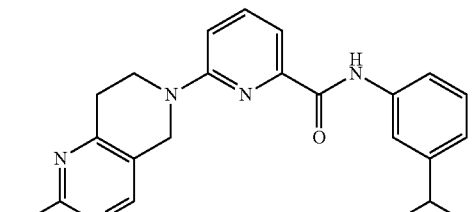 | >10000 | |
| 40 | 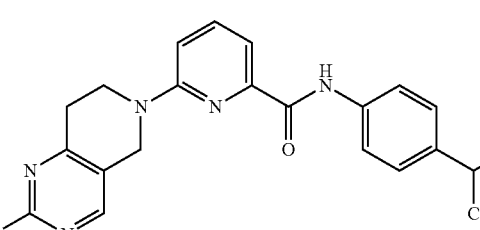 | >10000 | |
| 51 | 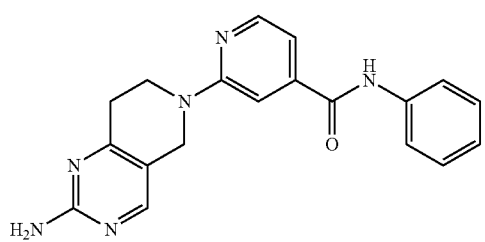 | >10000 | |

TABLE 2-continued

| Example Number | Structure | VEGFR2 Kinase (IC$_{50}$, nM) | PDGFRβ Kinase (IC$_{50}$, nM) |
|---|---|---|---|
| 52 | 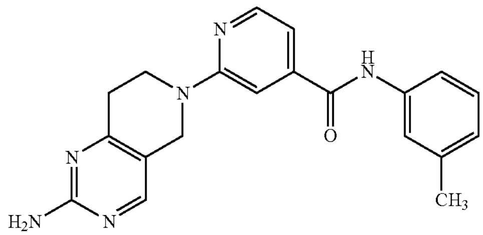 | | >10000 |
| 53 | 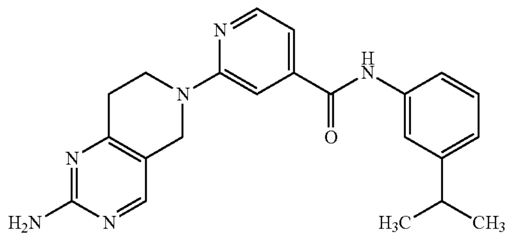 [SMILES: CC(C)c1cccc(NC(=O)c2ccnc(N3CCc4nc(N)ncc4C3)c2)c1] | | >10000 |
| 54 | 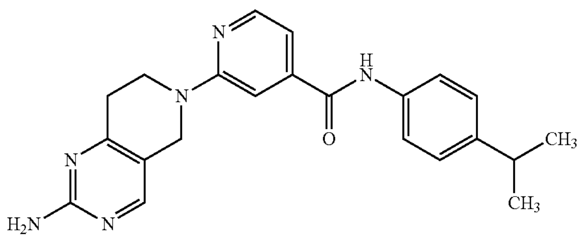 | | >10000 |
| 55 | 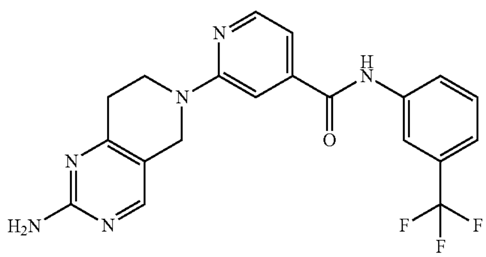 | | >10000 |
| 80 | 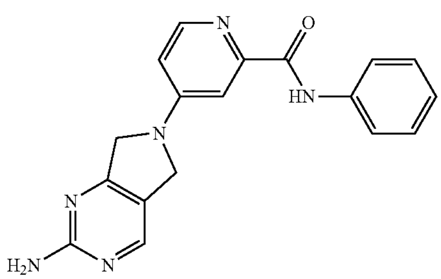 [SMILES: Nc1ncc2c(n1)CN(c1ccnc(C(=O)Nc3ccccc3)c1)C2] | | >10000 |
| 81 | 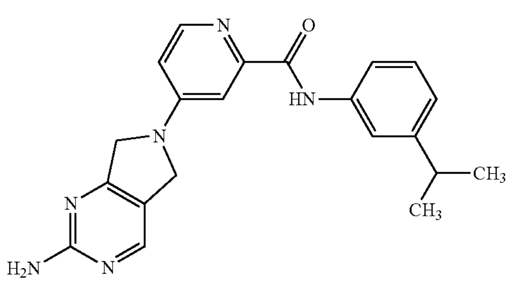 | | >10000 |

TABLE 2-continued

| Example Number | Structure | VEGFR2 Kinase (IC$_{50}$, nM) | PDGFRβ Kinase (IC$_{50}$, nM) |
| --- | --- | --- | --- |
| 82 | 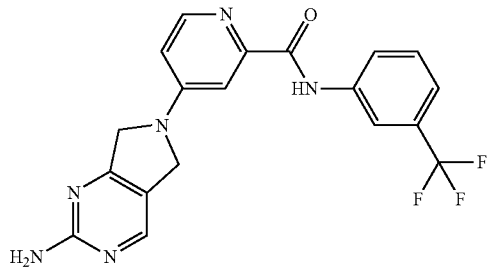 | | >10000 |
| 83 | 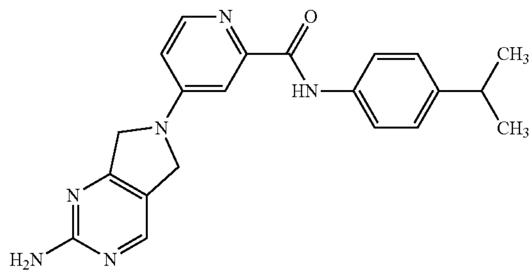 | | >10000 |
| 84 | 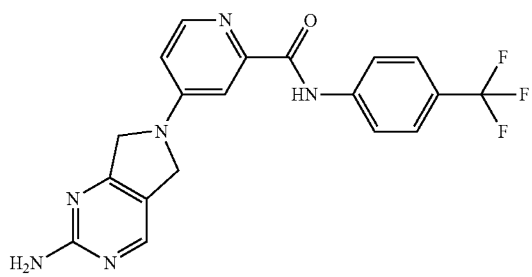 [SMILES: Nc1ncc2c(n1)CN(c1ccnc(C(=O)Nc3ccc(C(F)(F)F)cc3)c1)C2] | | >10000 |
| 106 | 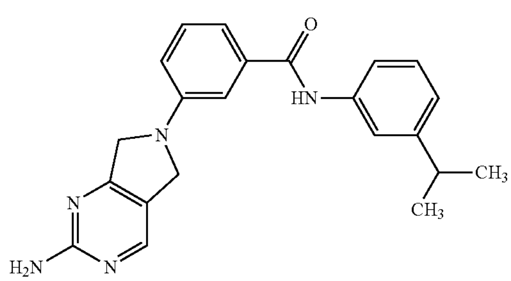 | | 6360 |
| 107 | 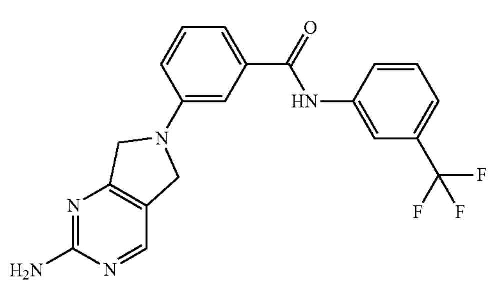 | | 2129 |

TABLE 2-continued

| Example Number | Structure | VEGFR2 Kinase (IC$_{50}$, nM) | PDGFRβ Kinase (IC$_{50}$, nM) |
|---|---|---|---|
| 108 | 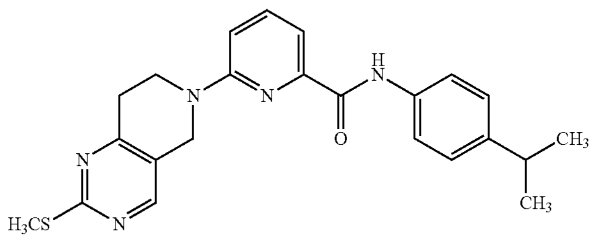 | | >10000 |
| 110 | 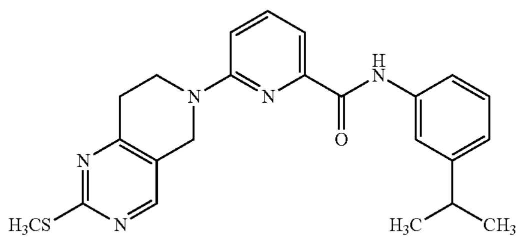 | | >10000 |
| 112 | 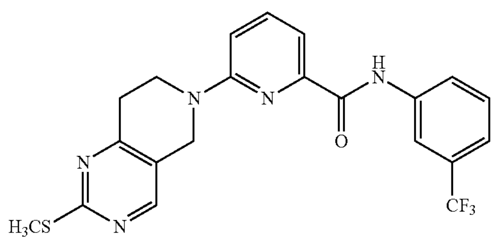 | | >10000 |
| 114 | 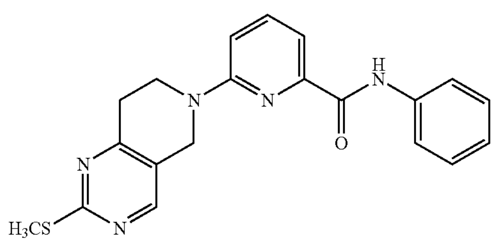 | | >10000 |
| 115 | 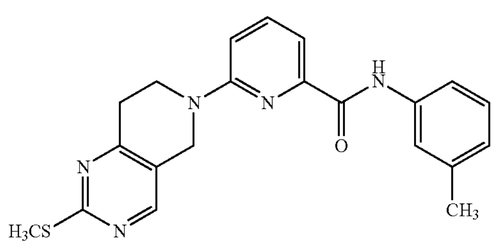 | | >10000 |
| 116 | 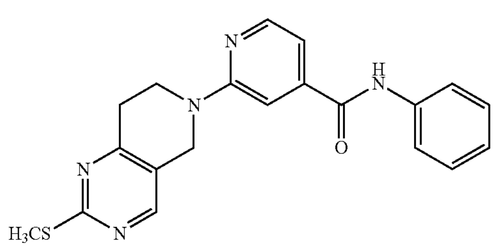 | | >10000 |

TABLE 2-continued

| Example Number | Structure | VEGFR2 Kinase (IC$_{50}$, nM) | PDGFRβ Kinase (IC$_{50}$, nM) |
|---|---|---|---|
| 118 | 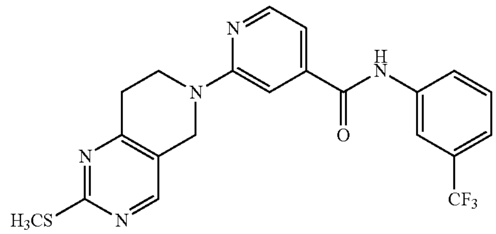 | >10000 | |
| 119 | 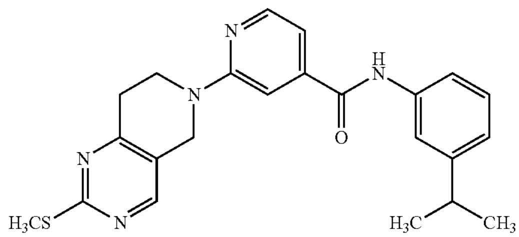 | >10000 | |
| 120 | 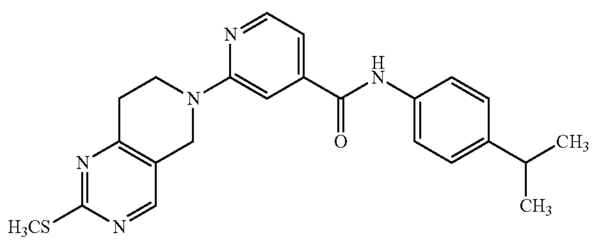 | >10000 | |
| 126 | 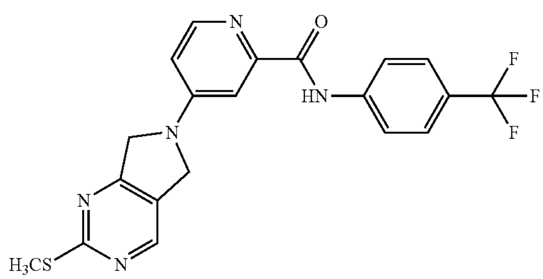 | >10000 | |
| 128 | 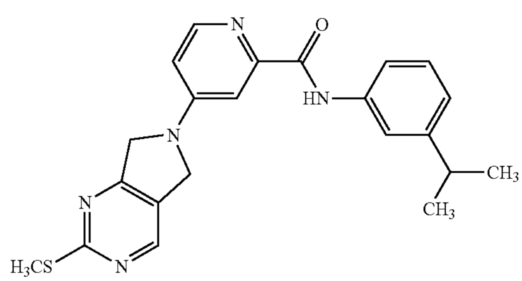 | >10000 | |
| 129 | 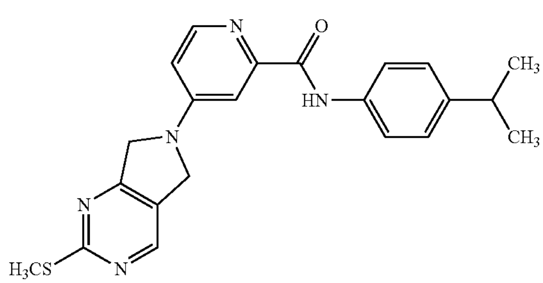 | >10000 | |

TABLE 2-continued

| Example Number | Structure | VEGFR2 Kinase (IC$_{50}$, nM) | PDGFRβ Kinase (IC$_{50}$, nM) |
|---|---|---|---|
| 138 | 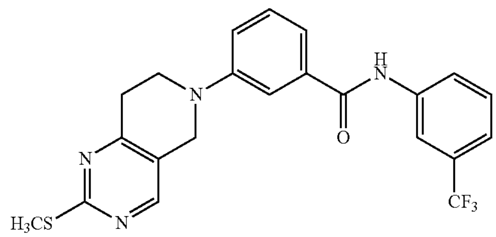 | 764 | |
| 139 | 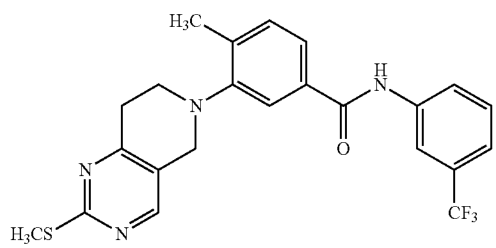 | 71 | |
| 140 | 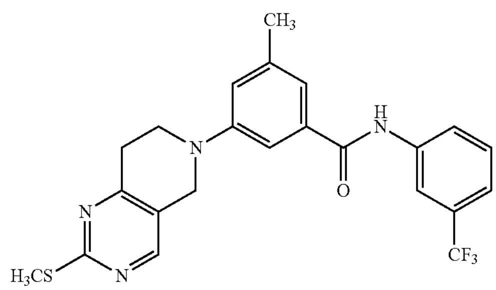 | >1000 | |
| 141 | 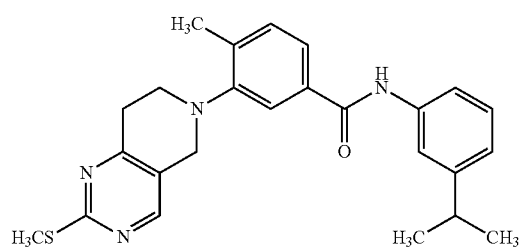 | 31 | |
| 142 | 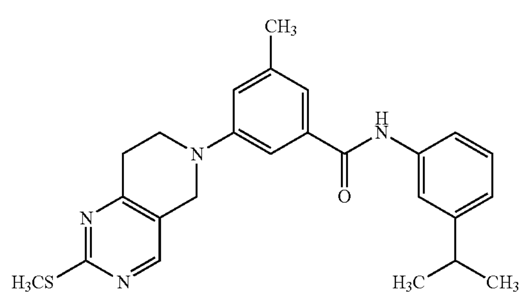 | >1000 | |
| 147 | 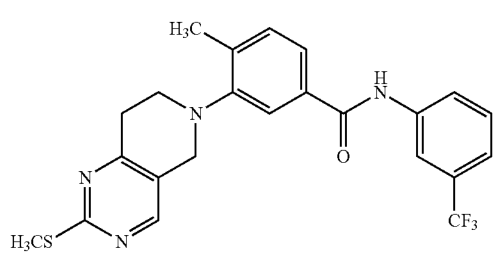 | 8 | 20 |

TABLE 2-continued

| Example Number | Structure | VEGFR2 Kinase (IC$_{50}$, nM) | PDGFRβ Kinase (IC$_{50}$, nM) |
|---|---|---|---|
| 148 | 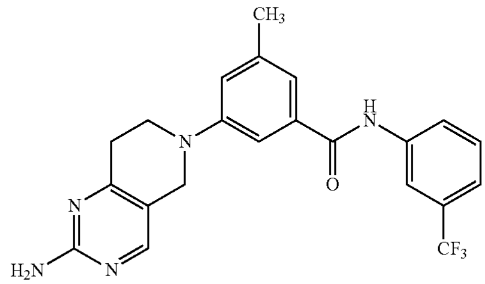 [SMILES: Cc1cc(C(=O)Nc2cccc(C(F)(F)F)c2)cc(N2CCc3nc(N)ncc3C2)c1] | 27 | 273 |
| 149 | 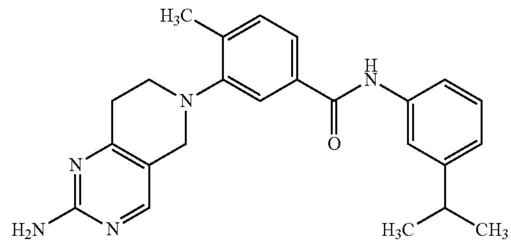 | 14 | 30 |
| 150 | 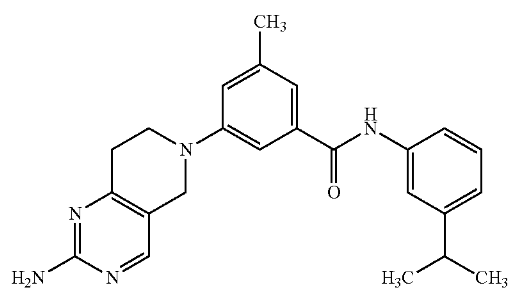 | 17 | 59 |
| 151 | 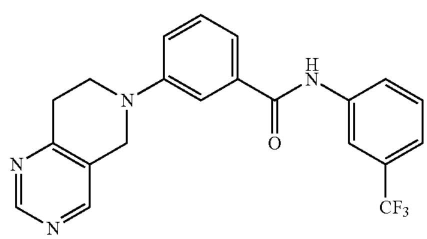 [SMILES: O=C(Nc1cccc(C(F)(F)F)c1)c1cccc(N2CCc3ncncc3C2)c1] | 19 | |
| 152 | 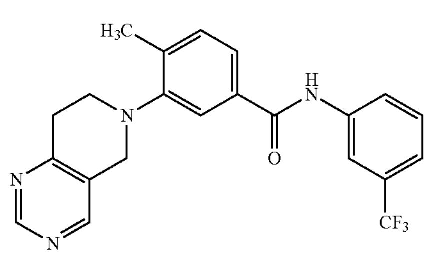 [SMILES: Cc1ccc(C(=O)Nc2cccc(C(F)(F)F)c2)cc1N1CCc2ncncc2C1] | 104 | |

TABLE 2-continued

| Example Number | Structure | VEGFR2 Kinase (IC$_{50}$, nM) | PDGFRβ Kinase (IC$_{50}$, nM) |
|---|---|---|---|
| 153 | 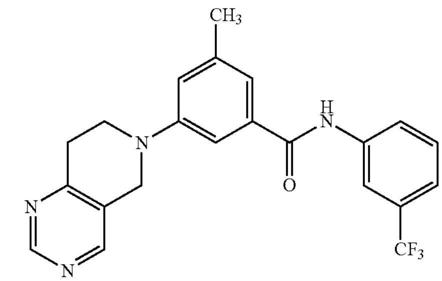 [SMILES: Cc1cc(C(=O)Nc2cccc(C(F)(F)F)c2)cc(N2CCc3ncncc3C2)c1] | | 638 |
| 154 | 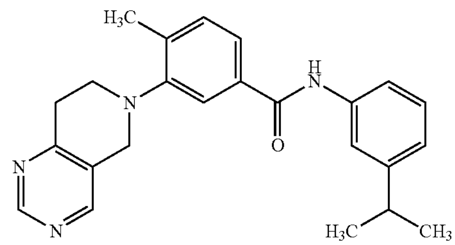 [SMILES: Cc1ccc(C(=O)Nc2cccc(C(C)C)c2)cc1N1CCc2ncncc2C1] | | 11 |
| 155 | 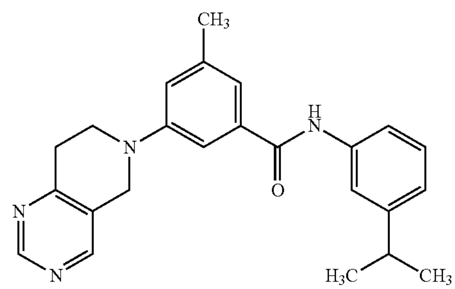 [SMILES: Cc1cc(C(=O)Nc2cccc(C(C)C)c2)cc(N2CCc3ncncc3C2)c1] | | 159 |
| 156 | 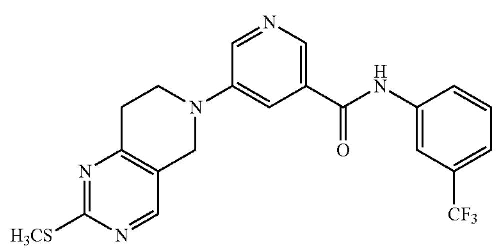 | | >10000 |
| 157 | 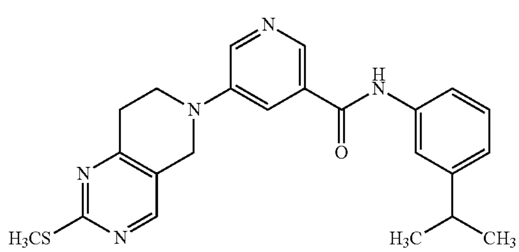 | | >10000 |
| 160 | 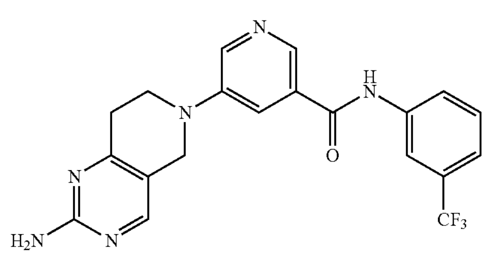 | | 584 |

TABLE 2-continued

| Example Number | Structure | VEGFR2 Kinase (IC$_{50}$, nM) | PDGFRβ Kinase (IC$_{50}$, nM) |
| --- | --- | --- | --- |
| 161 | 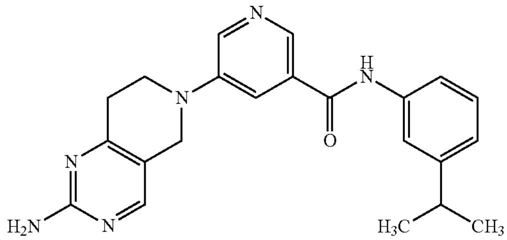 [SMILES: CC(C)c1cccc(NC(=O)c2cncc(N3CCc4nc(N)ncc4C3)c2)c1] | 149 | |
| 162 | 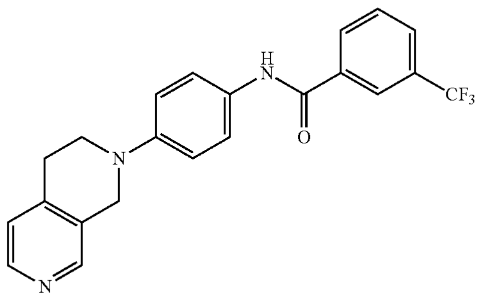 [SMILES: O=C(Nc1ccc(N2CCc3ccncc3C2)cc1)c1cccc(C(F)(F)F)c1] | >10000 | >10000 |
| 163 | 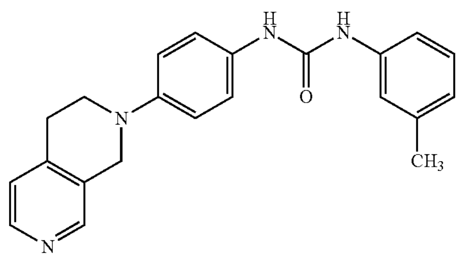 [SMILES: Cc1cccc(NC(=O)Nc2ccc(N3CCc4ccncc4C3)cc2)c1] | 2200 | 1560 |
| 164 | 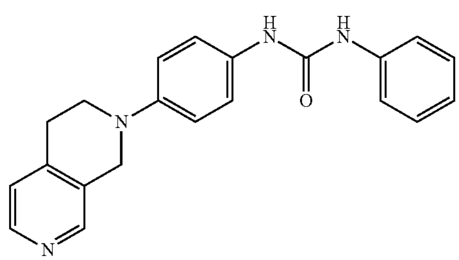 [SMILES: O=C(Nc1ccccc1)Nc1ccc(N2CCc3ccncc3C2)cc1] | >10000 | >10000 |
| 165 | 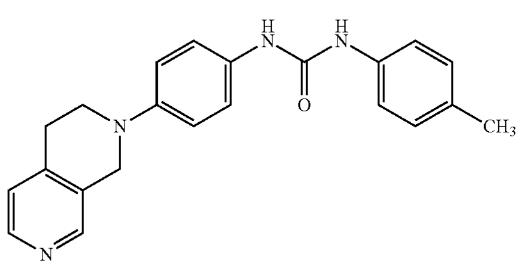 [SMILES: Cc1ccc(NC(=O)Nc2ccc(N3CCc4ccncc4C3)cc2)cc1] | >1000 | >1000 |

TABLE 2-continued

| Example Number | Structure | VEGFR2 Kinase (IC$_{50}$, nM) | PDGFRβ Kinase (IC$_{50}$, nM) |
|---|---|---|---|
| 166 | 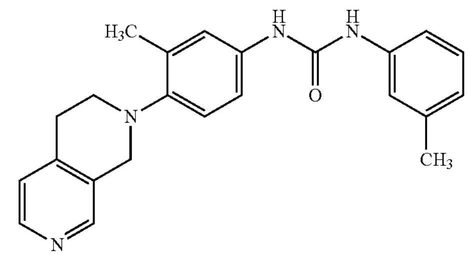 [SMILES: Cc1cccc(NC(=O)Nc2ccc(N3CCc4ccncc4C3)c(C)c2)c1] | 308 | 36 |
| 167 | 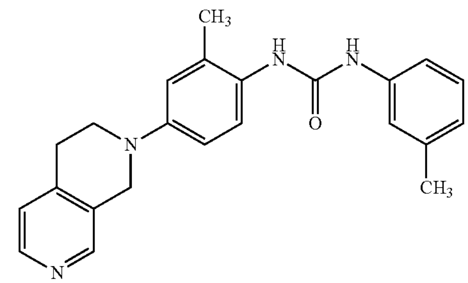 [SMILES: Cc1cccc(NC(=O)Nc2ccc(N3CCc4ccncc4C3)cc2C)c1] | 454 | 1050 |
| 168 | 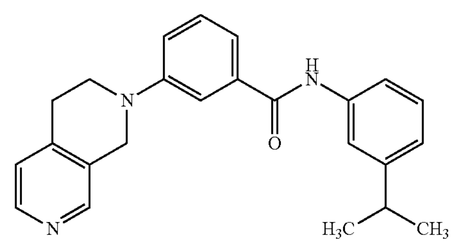 [SMILES: CC(C)c1cccc(NC(=O)c2cccc(N3CCc4ccncc4C3)c2)c1] | 39 | 40 |
| 169 | 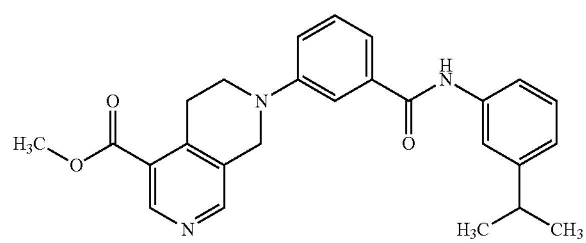 [SMILES: COC(=O)c1cncc2c1CCN(c1cccc(C(=O)Nc3cccc(C(C)C)c3)c1)C2] | 12 | 15 |
| 170 | 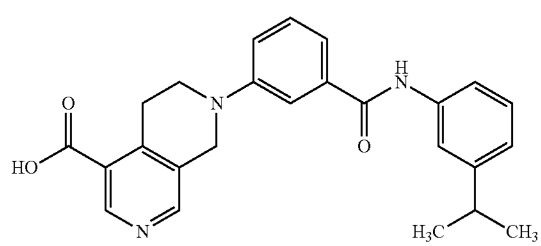 [SMILES: CC(C)c1cccc(NC(=O)c2cccc(N3CCc4c(cncc4C(=O)O)C3)c2)c1] | 54 | |
| 171 | 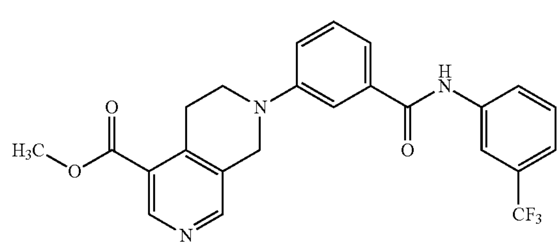 [SMILES: COC(=O)c1cncc2c1CCN(c1cccc(C(=O)Nc3cccc(C(F)(F)F)c3)c1)C2] | 8 | |

TABLE 2-continued

| Example Number | Structure | VEGFR2 Kinase (IC$_{50}$, nM) | PDGFRβ Kinase (IC$_{50}$, nM) |
|---|---|---|---|
| 172 | 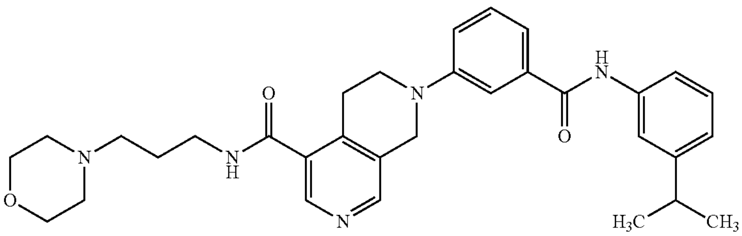 [SMILES: CC(C)c1cccc(NC(=O)c2cccc(N3CCc4c(cncc4C(=O)NCCCN4CCOCC4)C3)c2)c1] | 367 | |
| 173 | 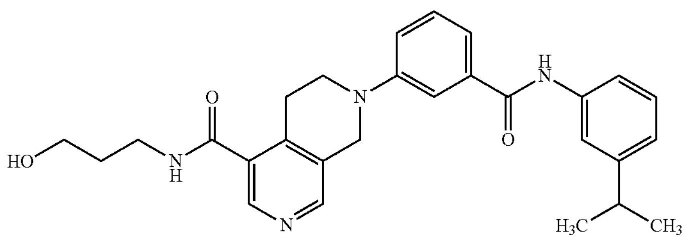 [SMILES: CC(C)c1cccc(NC(=O)c2cccc(N3CCc4c(cncc4C(=O)NCCCO)C3)c2)c1] | 220 | |
| 174 | 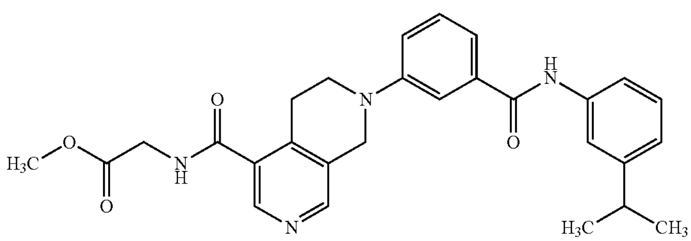 [SMILES: COC(=O)CNC(=O)c1cncc2c1CCN(c1cccc(C(=O)Nc3cccc(C(C)C)c3)c1)C2] | 49 | |
| 175 | 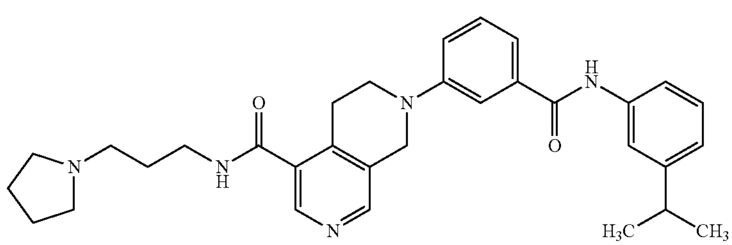 [SMILES: CC(C)c1cccc(NC(=O)c2cccc(N3CCc4c(cncc4C(=O)NCCCN4CCCC4)C3)c2)c1] | 230 | |
| 176 | 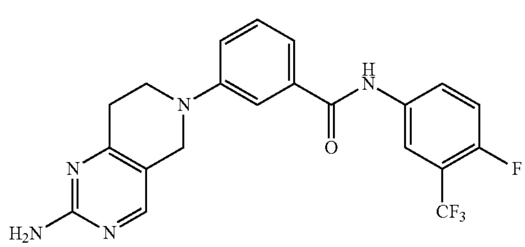 [SMILES: Nc1ncc2c(n1)CCN(c1cccc(C(=O)Nc3ccc(F)c(C(F)(F)F)c3)c1)C2] | 27 | 61 |

It has been, surprisingly, found from the above data that;
Increased selectivity is obtained when the relationship of —XR³ and the condensed N-containing ring, i.e. the pyrido or pyrrolo pyrimidinyl heteroaryl ring, on Ar¹ is meta rather than para;

In the compounds of the present invention, the alkyl and fluoroalkyl-substituted compounds comprising R³ are more selective then the corresponding unsubstituted compounds.

In the alkyl compounds of the present invention, i.e. wherein R³ is alkyl, the branched alkyl compounds are more selective then the corresponding n-alkyl and cycloalkyl compounds.

The invention is further illustrated by the following non-limiting examples.

Preparation 1

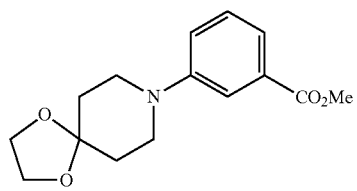 [SMILES: COC(=O)c1cccc(N2CCC3(CC2)OCCO3)c1]

Methyl-3-(1,4-dioxa-8-azaspiro[4.5]dec-8-yl)-benzoate

Procedure adopted from *Tetrahedron Lett.*, 2007, 48, 2519. A thick-walled glass reaction vessel was charged with palladium(II)acetate (235 mg, 1.05 mmol), X-Phos (500 mg, 1.05 mmol, 2-dicyclohexylphosphino-2',4',6'-triisopropylbiphenyl), cesium carbonate (6.82 g, 20.95 mmol) and 5:1 (v/v) toluene:t-BuOH (20 mL). The stirred contents were purged with nitrogen and a solution of 4-piperidone ethylene ketal (2.70 mL, 20.95 mmol) and methyl-3-bromobenzoate (4.95 g, 23.02 mmol) in 5:1 (v/v) toluene:t-BuOH (100 mL) was added. After stirring for 2 minutes, the vessel was sealed and the reaction mixture was heated at 120° C. for 16 hours. Upon cooling to room temperature, the reaction mixture was filtered through celite and the filtrate was concentrated.

Elution through a flash column (silica gel 60, 230-400 mesh, 7:3 hexanes:EtOAc) followed by concentration gave the title compound as an oil (5.64 g, 97%).

Preparation 2

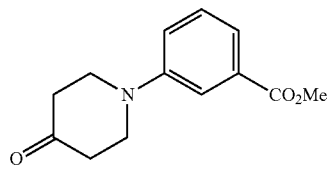 [SMILES: COC(=O)c1cccc(N2CCC(=O)CC2)c1]

Methyl-3-(4-oxopiperidin-1-yl)-benzoate

Method A:
A solution of methyl-3-(1,4-dioxa-8-azaspiro[4.5]dec-8-yl)-benzoate (3.85 g, 13.88 mmol) in 10% aqueous sulfuric acid (40 mL and THF (40 mL) was stirred at ambient temperature for 14 days. The reaction mixture was neutralized by cautious addition of NaHCO₃ and simultaneously diluting with water. The aqueous mixture was extracted with EtOAc (2×75 mL) and the combined organic extracts were dried (MgSO₄), filtered, and concentrated to give the title compound as an oil (2.75 g, 85%) which was used without further purification.

Method B:
A mixture of methyl-3-(1,4-dioxa-8-azaspiro[4.5]dec-8-yl)-benzoate (1.80 g, 6.49 mmol) and p-toluenesulfonic acid monohydrate (123 mg, 0.649 mmol) in water (30 mL) and acetone (15 mL) was heated at reflux for 17 hours. The organic solvent was removed in vacuo and the aqueous mixture was extracted with dichloromethane. The organic extract was washed with saturated NaHCO$_{3(aq.)}$, dried (MgSO₄), filtered and concentrated. Elution through a flash column (silica gel 60, 230-400 mesh, 3:2 hexanes:EtOAc) followed by concentration gave the title compound as a yellow oil (1.20 g, 79%).

Preparation 3

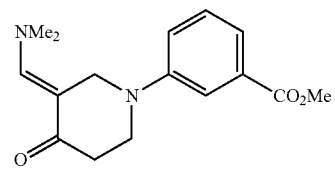 [SMILES: COC(=O)c1cccc(N2CCC(=O)/C(=C/N(C)C)C2)c1]

Methyl-3-(3-dimethylaminomethylene-4-oxopiperidin-1-yl)-benzoate

A solution of methyl-3-(4-oxopiperidin-1-yl)-benzoate (2.72 g, 11.66 mmol) and DMF-dimethylacetal (6.24 mL, 46.64 mmol) in 1,4-dioxane (50 mL) was refluxed for 43 hours. The reaction mixture was concentrated and the residue was eluted through a flash column (silica gel 60, 230-400 mesh, 5% MeOH in EtOAc to 8% MeOH in EtOAc) to obtain the title compound as a red oil which slowly crystallized on standing (1.52 g, 45%).

Preparation 4

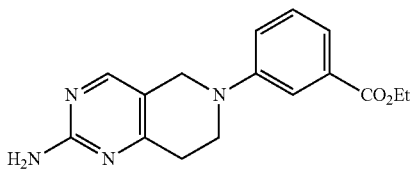 [SMILES: CCOC(=O)c1cccc(N2CCc3nc(N)ncc3C2)c1]

Ethyl-3-(2-amino-7,8-dihydro-5H-pyrido[4,3-d]pyrimidin-6-yl)-benzoate

A solution of methyl-3-(3-dimethylaminomethylene-4-oxopiperidin-1-yl)-benzoate (1.52 g, 5.27 mmol) in EtOH (100 mL) was treated with guanidine carbonate (3.80 g, 21.08 mmol), followed by addition of sodium acetate trihydrate (5.74 g, 42.16 mmol). The reaction mixture was refluxed for 15 hours and the solvent was removed in vacuo. The residue was partitioned between water and ethyl acetate and the mixture was vigorously stirred at ambient temperature for several minutes. The yellow, amorphous precipitate was collected, washed with water, ethyl acetate, and dried to give 776 mg of the title compound. The ethyl acetate layer was dried (MgSO$_4$), filtered, and concentrated.

The residue obtained was triturated with diethyl ether to give an additional 182 mg of the title compound (958 mg total, 61%).

Preparation 5

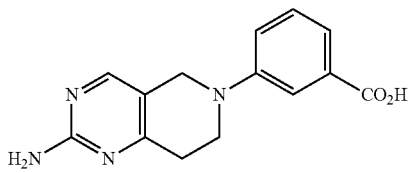 [SMILES: Nc1ncc2c(n1)CCN(c1cccc(C(=O)O)c1)C2]

3-(2-amino-7,8-dihydropyrido[4,3-d]pyrimidin-6 (5H)-yl)benzoic acid

A suspension of ethyl-3-(2-amino-7,8-dihydro-5H-pyrido [4,3-d]pyrimidin-6-yl)-benzoate (958 mg, 3.21 mmol) in 1,4-dioxane (35 mL) was treated with 1.0 N NaOH$_{(aq.)}$ (8.24 mL, 8.24 mmol) and the reaction mixture was refluxed for 21 hours. Upon cooling to room temperature, the reaction mixture was filtered and the filtrate was concentrated. The residue was diluted with water and the pH was adjusted to ~4 with 1.0 N HCl$_{(aq.)}$. The cloudy mixture was treated with ethyl acetate and the aqueous/organic mixture was stirred at room temperature for approx. 1 hour. The precipitate was filtered off, washed with water, ethyl acetate, and dried in vacuo at 50° C. to give the title compound as a yellow, amorphous solid (710.8 mg, 82%).

Example 1

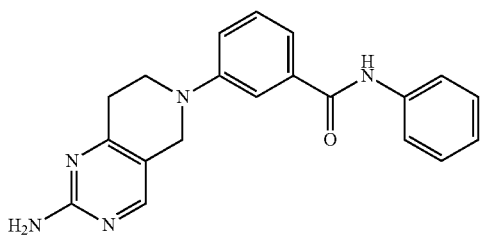 [SMILES: Nc1ncc2c(n1)CCN(c1cccc(C(=O)Nc3ccccc3)c1)C2]

3-(2-amino-7,8-dihydropyrido[4,3-d]pyrimidin-6 (5H)-yl)-N-phenylbenzamide

To a mixture of 3-(2-amino-7,8-dihydropyrido[4,3-d]pyrimidin-6(5H)-yl)benzoic acid (54 mg, 0.20 mmol), aniline (0.027 mL, 0.30 mmol), and N,N-diisopropylethylamine (0.174 mL, 1.0 mmol) in 1.5 mL DMF at room temperature was added HBTU (83 mg, 0.22 mmol). After 1 hour at room temperature, the reaction was briefly warmed to approx. 60° C. and then continued at room temperature. At 2 hours the reaction was partitioned between EtOAc and aqueous Na$_2$CO$_3$ solution, the EtOAc layer washed with H$_2$O, brine, dried with anhydrous Na$_2$SO$_4$ and rotary evaporated. The resulting solid was triturated with EtOAc to give the title compound as an off-white solid (52 mg, 75%). $^1$H NMR (DMSO-d6) δ: 10.15 (s, 1H), 8.13 (s, 1H), 7.74-7.79 (m, 2H), 7.49-7.52 (m, 1H), 7.31-7.41 (m, 4H), 7.22 (dt, J=7.5, 2.3 Hz, 1H), 7.06-7.13 (m, 1H), 6.41 (s, 2H), 4.29 (s, 2H), 3.65 (t, J=6.0 Hz, 2H), 2.77 (t, J=5.9 Hz, 2H).

Example 2

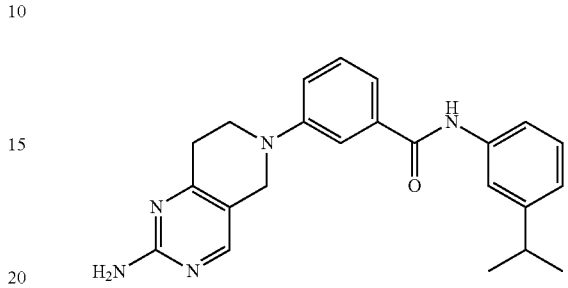

3-(2-amino-7,8-dihydropyrido[4,3-d]pyrimidin-6 (5H)-yl)-N-(3-isopropylphenyl)benzamide A mixture of 3-(2-amino-7,8-dihydropyrido[4,3-d]pyrimidin-6(5H)-yl)benzoic acid (162 mg, 0.60 mmol), N,N-diisopropylethylamine (0.523 mL, 3.0 mmol), and HBTU (250 mg, 0.66 mmol) in 6.0 mL DMF was stirred at room temperature for 3 minutes, briefly warmed to approx. 50° C. to dissolve solids, stirred an additional 10 minutes at room temperature, then 3-isopropylaniline (0.127 mL, 0.90 mmol) added and the reaction heated at 65° C. After 2 hours the mixture was partitioned between EtOAc and aqueous Na$_2$CO$_3$ solution, the EtOAc layer washed with H$_2$O, brine, dried with anhydrous Na$_2$SO$_4$ and rotary evaporated to a solid. The solid was chromatographed eluting with EtOAc/MeOH. The resulting solid was subjected to an EtOAc/NaHCO$_3$ work-up to remove any silica gel impurity and then recrystallized from EtOAc to give the title compound as a pale yellow-beige solid (86 mg, 37%). $^1$H NMR (DMSO-d6) δ: 10.09 (s, 1H), 8.13 (s, 1H), 7.64-7.66 (m, 1H), 7.58-7.63 (m, 1H), 7.50-7.53 (m, 1H), 7.32-7.40 (m, 2H), 7.18-7.29 (m, 2H), 6.96-7.01 (m, 1H), 6.41 (s, 2H), 4.29 (s, 2H), 3.65 (t, J=6.0 Hz, 2H), 2.88 (spt, J=7.0 Hz, 1H), 2.77 (t, J=5.9 Hz, 2H), 1.22 (d, J=7.0 Hz, 6H).

Example 3

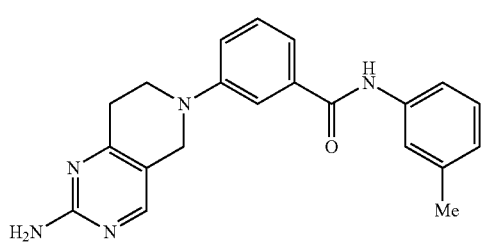

3-(2-amino-7,8-dihydropyrido[4,3-d]pyrimidin-6 (5H)-yl)-N-(m-tolyl)benzamide

A mixture of 3-(2-amino-7,8-dihydropyrido[4,3-d]pyrimidin-6(5H)-yl)benzoic acid (27 mg, 0.10 mmol), N,N-diisopropylethylamine (0.087 mL, 0.50 mmol), and HBTU (42 mg, 0.11 mmol) in 0.9 mL DMF was stirred at room temperature for 3 hours, then meta-toluidine (0.016 mL, 0.15 mmol) added and the reaction continued for 23 hours at room temperature. The reaction mixture was partitioned between EtOAc and aqueous Na₂CO₃ solution, the EtOAc layer washed with H₂O, brine, dried with anhydrous Na₂SO₄ and rotary evaporated. The resulting solid was triturated with an EtOAc/hexane mixture to give the title compound as a light tan solid (22 mg, 62%). ¹H NMR (DMSO-d6) δ: 10.07 (s, 1H), 8.13 (s, 1H), 7.54-7.62 (m, 2H), 7.50 (s, 1H), 7.31-7.41 (m, 2H), 7.19-7.26 (m, 2H), 6.92 (d, J=7.6 Hz, 1H), 6.41 (s, 2H), 4.29 (s, 2H), 3.65 (t, J=6.0 Hz, 2H), 2.77 (t, J=5.9 Hz, 2H), 2.31 (s, 3H).

Example 4

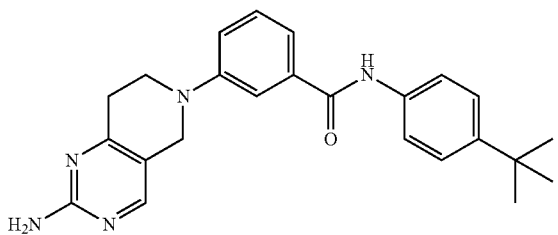 [SMILES: CC(C)(C)c1ccc(NC(=O)c2cccc(N3CCc4nc(N)ncc4C3)c2)cc1]

3-(2-amino-7,8-dihydropyrido[4,3-d]pyrimidin-6 (5H)-yl)-N-(4-(tert-butyl)phenyl)benzamide A mixture of 3-(2-amino-7,8-dihydropyrido[4,3-d]pyrimidin-6(5H)-yl)benzoic acid (27 mg, 0.10 mmol), N,N-diisopropylethylamine (0.087 mL, 0.50 mmol), and HBTU (42 mg, 0.11 mmol) in 0.9 mL DMF was briefly warmed to approx. 50° C. to dissolve solids, then continued stirring at room temperature. After 7 minutes 4-tert-butylaniline (0.024 mL, 0.15 mmol) was added and the reaction continued at room temperature for 17.5 hours. The reaction mixture was partitioned between EtOAc and aqueous Na₂CO₃ solution, the EtOAc layer washed with H₂O, brine, dried with anhydrous Na₂SO₄ and rotary evaporated. The resulting solid was triturated with an EtOAc/hexane mixture to give the title compound as an off-white solid (33 mg, 81%). ¹H NMR (DMSO-d6) δ: 10.08 (s, 1H), 8.13 (s, 1H), 7.65-7.70 (m, 2H), 7.50 (s, 1H), 7.32-7.40 (m, 4H), 7.21 (dt, J=7.0, 2.4 Hz, 1H), 6.41 (s, 2H), 4.29 (s, 2H), 3.65 (t, J=5.9 Hz, 2H), 2.77 (t, J=5.9 Hz, 2H), 1.28 (s, 9H)

Example 5

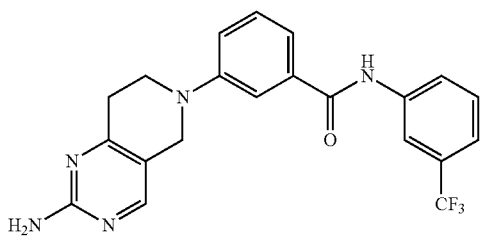 [SMILES: Nc1ncc2c(n1)CCN(c1cccc(C(=O)Nc3cccc(C(F)(F)F)c3)c1)C2]

3-(2-amino-7,8-dihydropyrido[4,3-d]pyrimidin-6 (5H)-yl)-N-(3-(trifluoromethyl)phenyl)benzamide A mixture of 3-(2-amino-7,8-dihydropyrido[4,3-d]pyrimidin-6(5H)-yl)benzoic acid (162 mg, 0.60 mmol), triethylamine (0.335 mL, 2.4 mmol), and HBTU (250 mg, 0.66 mmol) in 4.0 mL DMF was briefly warmed to approx. 40° C. to dissolve solids. After 3 minutes 3-(trifluoromethyl)aniline (0.149 mL, 1.2 mmol) was added and the reaction stirred at 50° C. for 3 hours, at rt for 16 hours, then an additional 1 hour at 50° C. The reaction mixture was partitioned between EtOAc and aqueous NaHCO₃ solution, the EtOAc layer washed with brine, dried with anhydrous Na₂SO₄ and rotary evaporated. The resulting oily solid was chromatographed eluting with CHCl₃, warm EtOAc, CHCl₃:EtOAc (1:1), then 5% MeOH in CHCl₃:EtOAc (1:1) giving a pale yellow solid. This solid was recrystallized from EtOAc giving a white solid (100 mg, 40%). ¹H NMR (DMSO-d6) δ: 10.46 (s, 1H), 8.25 (s, 1H), 8.13 (s, 1H), 8.05 (d, J=8.8 Hz, 1H), 7.60 (t, J=7.9 Hz, 1H), 7.53 (s, 1H), 7.34-7.48 (m, 3H), 7.22-7.27 (m, 1H), 6.41 (s, 2H), 4.30 (s, 2H), 3.66 (t, J=6.0 Hz, 2H), 2.77 (t, J=5.9 Hz, 2H).

In addition during the chromatography an additional product, Example 21, 3-(2-amino-7,8-dihydropyrido[4,3-d]pyrimidin-6(5H)-yl)-N,N-diethylbenzamide was isolated as a yellow solid (3.2 mg).

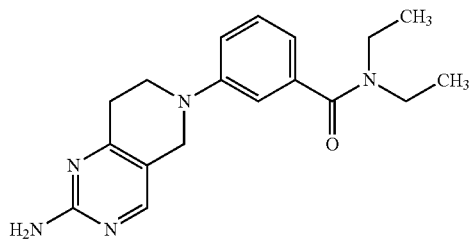

¹H NMR (CDCl₃) δ: 8.11 (s, 1H), 7.28-7.32 (m, 1H), 6.94-7.01 (m, 2H), 6.81-6.85 (m, 1H), 4.97 (br. s., 2H), 4.26 (s, 2H), 3.61 (t, J=6.0 Hz, 2H), 3.53 (br. s., 2H), 3.27 (br. s, 2H), 2.91 (t, J=5.9 Hz, 2H), 1.24 (br. s, 3H), 1.12 (br. s., 3H)

Example 6

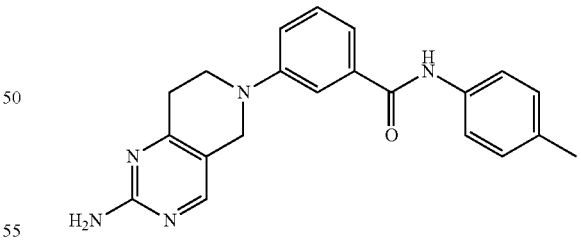

3-(2-amino-7,8-dihydropyrido[4,3-d]pyrimidin-6 (5H)-yl)-N-(p-tolyl)benzamide

In a manner similar to that described in Example 4, the title compound was prepared as a light beige solid (34 mg, 94%). ¹H NMR (DMSO-d6) δ: 10.07 (s, 1H), 8.13 (s, 1H), 7.61-7.67 (m, 2H), 7.48-7.51 (m, 1H), 7.31-7.40 (m, 2H), 7.18-7.23 (m, 1H), 7.15 (d, J=8.2 Hz, 2H), 6.40 (s, 2H), 4.29 (s, 2H), 3.65 (t, J=5.9 Hz, 2H), 2.77 (t, J=5.9 Hz, 2H), 2.28 (s, 3H).

Example 7

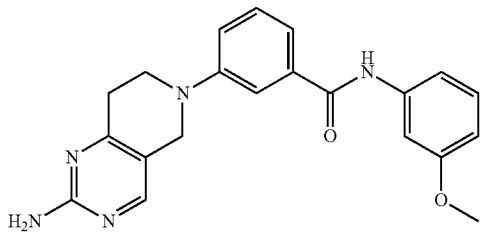 [SMILES: COc1cccc(NC(=O)c2cccc(N3CCc4nc(N)ncc4C3)c2)c1]

3-(2-amino-7,8-dihydropyrido[4,3-d]pyrimidin-6 (5H)-yl)-N-(3-methoxyphenyl)benzamide A mixture of 3-(2-amino-7,8-dihydropyrido[4,3-d]pyrimidin-6(5H)-yl)benzoic acid (41 mg, 0.15 mmol), N,N-diisopropylethylamine (0.105 mL, 0.60 mmol), and HBTU (63 mg, 0.165 mmol) in 1.5 mL DMF was briefly warmed to approx. 50° C. to dissolve solids, then continued stirring at room temperature. After 10 minutes meta-anisidine (0.025 mL, 0.225 mmol) was added and the reaction continued at room temperature for 4 hours. The reaction mixture was partitioned between EtOAc and aqueous $Na_2CO_3$ solution, the EtOAc layer washed with $H_2O$, brine, dried with anhydrous $Na_2SO_4$ and rotary evaporated. The resulting solid was triturated with an acetone/hexane mixture to give the title compound as a light beige solid (41 mg, 73%). $^1$H NMR (DMSO-d6) δ: 10.13 (s, 1H), 8.13 (s, 1H), 7.46-7.51 (m, 2H), 7.31-7.41 (m, 3H), 7.19-7.28 (m, 2H), 6.68 (ddd, J=8.1, 2.4, 0.9 Hz, 1H), 6.41 (s, 2H), 4.29 (s, 2H), 3.75 (s, 3H), 3.65 (t, J=6.0 Hz, 2H), 2.77 (t, J=5.9 Hz, 2H).

Example 8

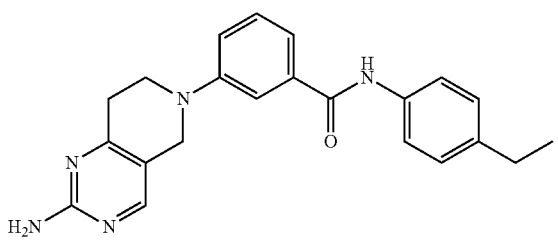 [SMILES: CCc1ccc(NC(=O)c2cccc(N3CCc4nc(N)ncc4C3)c2)cc1]

3-(2-amino-7,8-dihydropyrido[4,3-d]pyrimidin-6 (5H)-yl)-N-(4-ethylphenyl)benzamide

R-2011-10548-73

A mixture of 3-(2-amino-7,8-dihydropyrido[4,3-d]pyrimidin-6(5H)-yl)benzoic acid (41 mg, 0.15 mmol), N,N-diisopropylethylamine (0.105 mL, 0.60 mmol), and HBTU (63 mg, 0.165 mmol) in 1.5 mL DMF was briefly warmed to approx. 50° C. to dissolve solids, then continued stirring at room temperature. After 10 minutes 4-ethylaniline (0.028 mL, 0.225 mmol) was added and the reaction stirred at room temperature for 4 hours, then allowed to stand at room temperature overnight. The reaction was added drop wise to a stirring mixture of 35 mL water containing 4 mL brine and 0.3 mL saturated aqueous $Na_2CO_3$ solution at room temperature. The resulting precipitate was filtered and rinsed with water. The damp solid was dissolved in 40% MeOH in $CHCl_3$ and evaporated to a dry solid. The solid was triturated with an acetone/hexane mixture to give the title compound as a light beige solid (48 mg, 86%). $^1$H NMR (DMSO-d6) δ: 10.08 (s, 1H), 8.13 (s, 1H), 7.63-7.69 (m, 2H), 7.50 (s, 1H), 7.31-7.40 (m, 2H), 7.15-7.24 (m, 3H), 6.41 (s, 2H), 4.29 (s, 2H), 3.65 (t, J=6.0 Hz, 2H), 2.77 (t, J=5.9 Hz, 2H), 2.58 (q, J=7.5 Hz, 2H), 1.18 (t, J=7.6 Hz, 3H).

Example 9

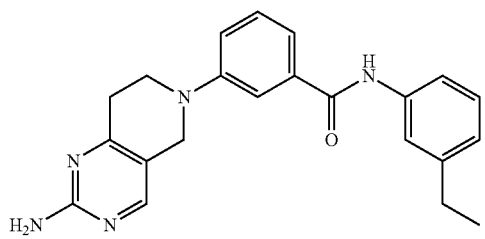

3-(2-amino-7,8-dihydropyrido[4,3-d]pyrimidin-6 (5H)-yl)-N-(3-ethylphenyl)benzamide A mixture of 3-(2-amino-7,8-dihydropyrido[4,3-d]pyrimidin-6(5H)-yl)benzoic acid (41 mg, 0.15 mmol), N,N-diisopropylethylamine (0.105 mL, 0.60 mmol), and COMU (68 mg, 0.158 mmol) in 1.5 mL DMF was stirred at room temperature for 2 minutes, then 3-ethylaniline (0.127 mL, 0.90 mmol) added and the reaction continued for 4 hours at room temperature. The reaction mixture was partitioned between EtOAc and aqueous $Na_2CO_3$ solution, the EtOAc layer washed with $H_2O$, brine, dried with anhydrous $Na_2SO_4$ and rotary evaporated. The resulting solid was chromatographed eluting with portions of $CHCl_3$, then 1:1 $CHCl_3$:EtOAc, and then 5% MeOH/$CHCl_3$. The obtained solid was then triturated with an EtOAc/hexane mixture to give the title compound as a light beige solid (21 mg, 38%). $^1$H NMR (DMSO-d6) δ: 10.08 (s, 1H), 8.13 (s, 1H), 7.61-7.64 (m, 1H), 7.57-7.61 (m, 1H), 7.49-7.52 (m, 1H), 7.32-7.40 (m, 2H), 7.18-7.29 (m, 2H), 6.93-6.98 (m, 1H), 6.41 (s, 2H), 4.29 (s, 2H), 3.65 (t, J=6.0 Hz, 2H), 2.77 (t, J=5.9 Hz, 2H), 2.61 (q, J=7.6 Hz, 2H), 1.20 (t, J=7.6 Hz, 3H)

Example 10

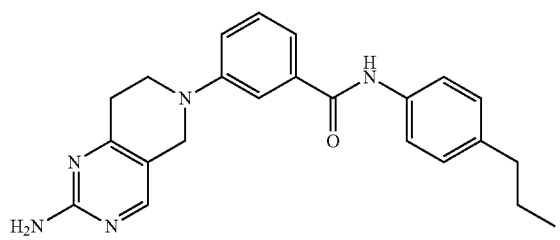 [SMILES: CCCc1ccc(NC(=O)c2cccc(N3CCc4nc(N)ncc4C3)c2)cc1]

3-(2-amino-7,8-dihydropyrido[4,3-d]pyrimidin-6 (5H)-yl)-N-(4-propylphenyl)benzamide To a mixture of 3-(2-amino-7,8-dihydropyrido[4,3-d]pyrimidin-6(5H)-yl)benzoic acid (41 mg, 0.15 mmol), 4-propylaniline (0.029 mL, 0.20 mmol), and N,N-diisopropylethylamine (0.052 mL, 0.30 mmol) in 1.5 mL DMF at room temperature was added COMU (68 mg, 0.158 mmol). The reaction was briefly warmed to approx. 60° C. and then continued at room temperature for 15 hours. The reaction was added drop wise to a stirring mixture of 35 mL water containing 5 mL brine at room temperature, and the resulting precipitate filtered and rinsed with water. The filtrate was partitioned between EtOAc and aqueous $Na_2CO_3$ solution, the EtOAc layer washed with $H_2O$, brine, dried with anhydrous $Na_2SO_4$ and rotary evaporated. The resulting solid was combined with the filtered precipitate and then chromatographed eluting with portions of $CHCl_3$, then 1:1 $CHCl_3$:EtOAc, and then 5% $MeOH/CHCl_3$. The obtained solid was then triturated with an EtOAc/hexane mixture to give the title compound as a light beige solid (18 mg, 32%). $^1H$ NMR (DMSO-d6) δ: 10.07 (s, 1H), 8.13 (s, 1H), 7.62-7.69 (m, 2H), 7.48-7.51 (m, 1H), 7.31-7.40 (m, 2H), 7.21 (dt, J=7.7, 2.0 Hz, 1H), 7.13-7.19 (m, 2H), 6.40 (s, 2H), 4.29 (s, 2H), 3.65 (t, J=6.0 Hz, 2H), 2.77 (t, J=5.9 Hz, 2H), 2.50-2.56 (m, 2H), 1.58 (sxt, J=7.4 Hz, 2H), 0.89 (t, J=7.3 Hz, 3H).

Example 11

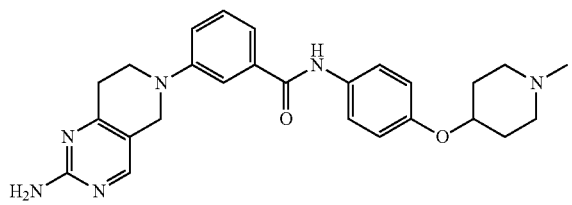 [SMILES: CN1CCC(Oc2ccc(NC(=O)c3cccc(N4CCc5nc(N)ncc5C4)c3)cc2)CC1]

3-(2-amino-7,8-dihydropyrido[4,3-d]pyrimidin-6 (5H)-yl)-N-(4-((1-methylpiperidin-4-yl)oxy)phenyl) benzamide A mixture of 3-(2-amino-7,8-dihydropyrido[4,3-d]pyrimidin-6(5H)-yl)benzoic acid (41 mg, 0.15 mmol), N,N-diisopropylethylamine (0.105 mL, 0.60 mmol), and HBTU (63 mg, 0.165 mmol) in 1.5 mL DMF was briefly warmed to approx. 50° C. to dissolve solids, then continued stirring at room temperature. After 10 minutes 4-((1-methylpiperidin-4-yl)oxy)aniline (46 mg, 0.225 mmol) was added and the reaction continued at room temperature for 3 hours. The reaction mixture was partitioned between EtOAc and aqueous $NaHCO_3$ solution, the EtOAc layer washed with $H_2O$, brine, dried with anhydrous $Na_2SO_4$ and rotary evaporated. The resulting solid was triturated with EtOAc to give the title compound as an off-white solid (48 mg, 70%). $^1H$ NMR (DMSO-d6) δ: 10.02 (s, 1H), 8.13 (s, 1H), 7.60-7.67 (m, 2H), 7.49 (s, 1H), 7.30-7.40 (m, 2H), 7.20 (dt, J=7.7, 2.0 Hz, 1H), 6.90-6.96 (m, 2H), 6.40 (s, 2H), 4.28 (s, 2H), 4.26-4.35 (m, 1H), 3.64 (t, J=5.9 Hz, 2H), 2.77 (t, J=5.9 Hz, 2H), 2.56-2.66 (m, 2H), 2.17 (s, 3H), 2.10-2.21 (m, 2H), 1.86-1.97 (m, 2H), 1.55-1.69 (m, 2H).

Example 12

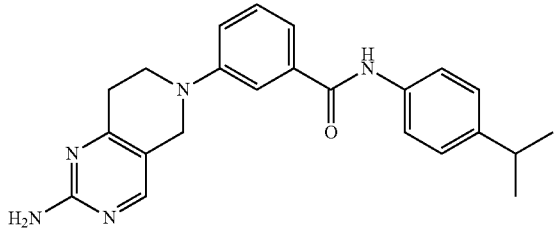 [SMILES: CC(C)c1ccc(NC(=O)c2cccc(N3CCc4nc(N)ncc4C3)c2)cc1]

3-(2-amino-7,8-dihydropyrido[4,3-d]pyrimidin-6 (5H)-yl)-N-(4-isopropylphenyl)benzamide A mixture of 3-(2-amino-7,8-dihydropyrido[4,3-d]pyrimidin-6(5H)-yl)benzoic acid (41 mg, 0.15 mmol), N,N-diisopropylethylamine (0.105 mL, 0.60 mmol), and HBTU (63 mg, 0.165 mmol) in 1.5 mL DMF was briefly warmed to approx. 50° C. to dissolve solids, then continued stirring at room temperature. After 10 minutes 4-isopropylaniline (0.032 mL, 0.225 mmol) was added and the reaction continued at room temperature for 18 hours. The reaction was added drop wise to a stirring mixture of 35 mL water containing 4 mL brine and 0.3 mL saturated aqueous $Na_2CO_3$ solution at room temperature. The resulting precipitate was filtered and rinsed with water. The damp solid was dissolved in 40% MeOH in $CHCl_3$ and evaporated to a dry solid. The solid was triturated with an acetone/hexane mixture to give the title compound as a light beige solid (44 mg, 75%). $^1H$ NMR (DMSO-d6) δ: 10.08 (s, 1H), 8.13 (s, 1H), 7.64-7.70 (m, 2H), 7.49-7.51 (m, 1H), 7.31-7.40 (m, 2H), 7.18-7.25 (m, 3H), 6.40 (s, 2H), 4.29 (s, 2H), 3.65 (t, J=6.0 Hz, 2H), 2.81-2.94 (m, 1H), 2.77 (t, J=5.9 Hz, 2H), 1.20 (d, J=7.0 Hz, 6H).

Preparation 6

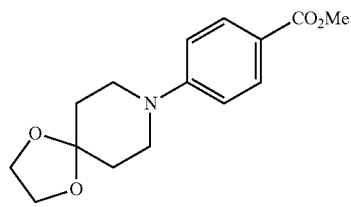 [SMILES: COC(=O)c1ccc(N2CCC3(CC2)OCCO3)cc1]

Methyl-4-(1,4-dioxa-8-azaspiro[4.5]dec-8-yl)-benzoate

Procedure adopted from *Tetrahedron Lett.*, 2007, 48, 2519. A thick-walled glass reaction vessel was charged with palladium(II)acetate (157 mg, 0.698 mmol), X-Phos (332 mg, 0.698 mmol, 2-dicyclohexylphosphino-2',4',6'-triisopropylbiphenyl), cesium carbonate (4.55 g, 13.96 mmol) and 5:1 (v/v) toluene:t-BuOH (20 mL). The stirred contents were purged with nitrogen and a solution of 4-piperidone ethylene ketal (1.80 mL, 13.96 mmol) and methyl-4-bromobenzoate (3.30 g, 15.36 mmol) in 5:1 (v/v) toluene:t-BuOH (100 mL) was added. After stirring for 2 minutes, the vessel was sealed and the reaction mixture was heated at 120° C. for 18 hours. Upon cooling to room temperature, the reaction mixture was filtered through celite and the filtrate was concentrated. Elution through a flash column (silica gel 60, 230-400 mesh, 3:2 hexanes:EtOAc) gave the title compound as an off-white, crystalline solid (3.20 g, 83%).

Preparation 7

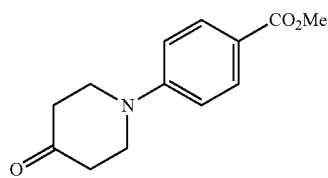 [SMILES: COC(=O)c1ccc(N2CCC(=O)CC2)cc1]

Methyl-4-(4-oxopiperidin-1-yl)-benzoate

A solution of methyl-4-(1,4-dioxa-8-azaspiro[4.5]dec-8-yl)-benzoate (4.87 g, 17.56 mmol) in 10% aqueous sulfuric acid (50 mL) and THF (50 mL) was stirred at ambient temperature for 72 hours. The reaction mixture was neutralized by cautious addition of $NaHCO_3$ and simultaneously diluting with water. The aqueous mixture was extracted with EtOAc (2×75 mL) and the combined organic extracts were dried ($MgSO_4$), filtered, and concentrated to give the title compound as an off-white, amorphous solid (4.06 g, 99%) which was used without further purification.

Preparation 8

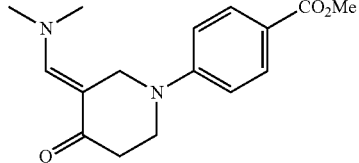 [SMILES: COC(=O)c1ccc(N2CCC(=O)/C(=C/N(C)C)C2)cc1]

Methyl-4-(3-dimethylaminomethylene-4-oxopiperidin-1-yl)-benzoate

A solution of methyl-4-(4-oxopiperidin-1-yl)-benzoate (4.06 g, 17.40 mmol) and DMF-dimethylacetal (9.32 mL, 69.61 mmol) in 1,4-dioxane (100 mL) was refluxed for 40 hours. The reaction mixture was concentrated and the residue was eluted through a flash column (silica gel 60, 230-400 mesh, 5% MeOH in EtOAc to 8% MeOH in EtOAc) to obtain the title compound as an orange, crystalline solid (3.00 g, 60%).

Preparation 9

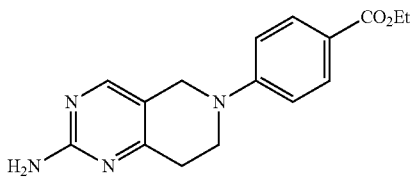 [SMILES: CCOC(=O)c1ccc(N2CCc3nc(N)ncc3C2)cc1]

Ethyl-4-(2-amino-7,8-dihydro-5H-pyrido[4,3-d]pyrimidin-6-yl)-benzoate

A solution of methyl-4-(3-dimethylaminomethylene-4-oxopiperidin-1-yl)-benzoate (3.00 g, 10.40 mmol) in EtOH (200 mL) was treated with guanidine carbonate (7.50 g, 41.60 mmol), followed by sodium acetate trihydrate (11.32 g, 83.20 mmol). The reaction mixture was refluxed for 16 hours and allowed to cool to room temperature. The insolubles were filtered off and the filtrate was concentrated. The residue was partitioned between water and ethyl acetate and the solid was filtered off, washed with water, ethyl acetate, and dried to give the title compound (258 mg). The filtered insoluble material from the reaction mixture was suspended in water, stirred for 30 minutes, and the remaining light yellow, amorphous solid was collected, washed with water, ethyl acetate, and dried to give an additional amount of the title compound (1.95 g, total yield 71%).

Preparation 10

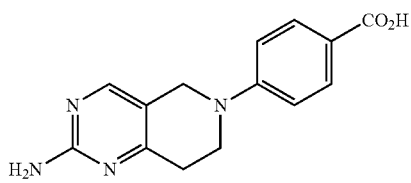 [SMILES: Nc1ncc2c(n1)CCN(c1ccc(C(=O)O)cc1)C2]

4-(2-amino-7,8-dihydropyrido[4,3-d]pyrimidin-6 (5H)-yl)benzoic acid

A suspension of ethyl-4-(2-amino-7,8-dihydro-5H-pyrido [4,3-d]pyrimidin-6-yl)-benzoate (1.14 g, 3.82 mmol) in 1,4-dioxane (35 mL) was treated with 1.0 N $NaOH_{(aq.)}$ (10 mL, 10 mmol) and the reaction mixture was refluxed for 26 hours. The solvent was removed in vacuo and the residue was diluted with water. The pH was adjusted to ~6-7 with 1.0 N $HCl_{(aq.)}$ and the precipitate was collected, washed with water, MeOH, and dried to give a yellow, amorphous solid (1.65 g). The solid was suspended in a 1:1 (v/v) mixture of water:methanol (100 mL) and heated at boiling for 15 minutes with vigorous stirring. The mixture was filtered hot and the product collected was washed with water, methanol, and dried in vacuo at 50° C. to give the title compound (881.7 mg, 85%).

Example 13

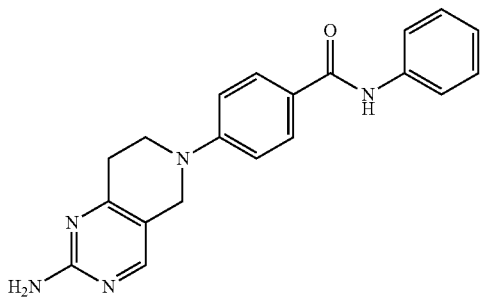 [SMILES: Nc1ncc2c(n1)CCN(c1ccc(C(=O)Nc3ccccc3)cc1)C2]

4-(2-amino-7,8-dihydropyrido[4,3-d]pyrimidin-6(5H)-yl)-N-phenylbenzamide

To a mixture of 4-(2-amino-7,8-dihydropyrido[4,3-d]pyrimidin-6(5H)-yl)benzoic acid (54 mg, 0.20 mmol), aniline (0.027 mL, 0.30 mmol), and N,N-diisopropylethylamine (0.174 mL, 1.0 mmol) in 1.5 mL DMF at room temperature was added HBTU (83 mg, 0.22 mmol). The reaction was stirred at room temperature for 1.5 hours, but also briefly warmed to approx. 60° C. three times during this time. At 2 hours additional 0.025 mL aniline was added and the reaction briefly warmed to approx. 60° C. three times. After 22 hours, the reaction was stored in the freezer for 3 days, then warmed to room temperature, 8 drops 1.0 M NaOH added, and the mixture stirred for 5 minutes. The reaction was partitioned between EtOAc and aqueous $Na_2CO_3$ solution, the EtOAc layer washed with $H_2O$, brine, dried with anhydrous $Na_2SO_4$ and rotary evaporated. The resulting solid was triturated with EtOAc to give the title compound as an off-white solid (37 mg, 53%). $^1$H NMR (DMSO-d6) δ: 9.92 (s, 1H), 8.13 (s, 1H), 7.86-7.92 (m, 2H), 7.73-7.78 (m, 2H), 7.28-7.35 (m, 2H), 7.02-7.10 (m, 3H), 6.43 (s, 2H), 4.36 (s, 2H), 3.71 (t, J=6.0 Hz, 2H), 2.75 (t, J=5.9 Hz, 2H).

Example 14

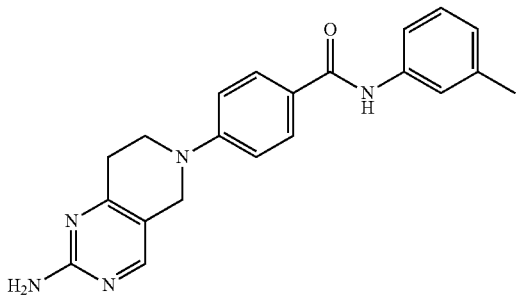 [SMILES: Cc1cccc(NC(=O)c2ccc(N3CCc4nc(N)ncc4C3)cc2)c1]

4-(2-amino-7,8-dihydropyrido[4,3-d]pyrimidin-6(5H)-yl)-N-(m-tolyl)benzamide

A mixture of 4-(2-amino-7,8-dihydropyrido[4,3-d]pyrimidin-6(5H)-yl)benzoic acid (27 mg, 0.10 mmol), N,N-diisopropylethylamine (0.087 mL, 0.50 mmol), and HBTU (42 mg, 0.11 mmol) in 1.0 mL DMF was stirred at room temperature for 10 minutes. Then meta-toluidine (0.022 mL, 0.20 mmol) was added and the reaction heated at 55° C. for 18 hours. The reaction mixture was partitioned between EtOAc and aqueous $Na_2CO_3$ solution, the EtOAc layer washed with $H_2O$, brine, dried with anhydrous $Na_2SO_4$ and rotary evaporated. The resulting solid was triturated with an EtOAc/hexane mixture to give the title compound as a light beige solid (18 mg, 51%). $^1$H NMR (DMSO-d6) δ: 9.84 (s, 1H), 8.12 (s, 1H), 7.85-7.92 (m, 2H), 7.60 (s, 1H), 7.55 (d, J=8.2 Hz, 1H), 7.19 (t, J=7.8 Hz, 1H), 7.03-7.09 (m, 2H), 6.88 (d, J=7.6 Hz, 1H), 6.42 (s, 2H), 4.36 (s, 2H), 3.71 (t, J=6.0 Hz, 2H), 2.75 (t, J=5.9 Hz, 2H), 2.30 (s, 3H)

Example 15

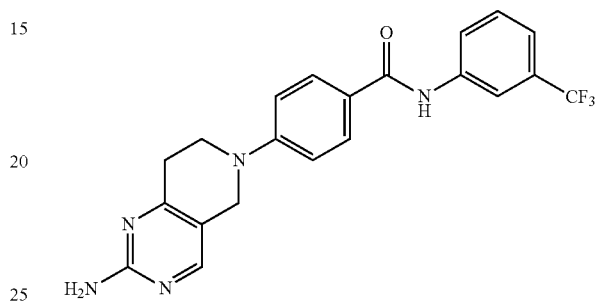

4-(2-amino-7,8-dihydropyrido[4,3-d]pyrimidin-6(5H)-yl)-N-(3-(trifluoromethyl)phenyl)benzamide A mixture of 4-(2-amino-7,8-dihydropyrido[4,3-d]pyrimidin-6(5H)-yl)benzoic acid (27 mg, 0.10 mmol), N,N-diisopropylethylamine (0.087 mL, 0.50 mmol), and HBTU (42 mg, 0.11 mmol) in 1.0 mL DMF was stirred at room temperature for 10 minutes. Then 3-(trifluoromethyl)aniline (0.025 mL, 0.20 mmol) was added and the reaction heated at 55° C. for 18 hours and then 90° C. for 2 hours. The reaction mixture was partitioned between EtOAc and aqueous $Na_2CO_3$ solution, the EtOAc layer washed with dilute aqueous HCl, aqueous $Na_2CO_3$ solution, brine, dried with anhydrous $Na_2SO_4$ and rotary evaporated. The resulting solid was chromatographed eluting with $CHCl_3$, then gradient 2% to 5% MeOH/$CHCl_3$ to give the title compound as a brownish-tan solid (3 mg, 8%). $^1$H NMR ($CDCl_3$) δ: 8.15 (s, 1H), 7.93 (s, 1H), 7.80-7.89 (m, 4H), 7.44-7.51 (m, 1H), 7.35-7.40 (m, 1H), 6.94-7.00 (m, 2H), 5.00 (br. s., 2H), 4.39 (s, 2H), 3.73 (t, J=6.0 Hz, 2H), 2.94 (t, J=6.0 Hz, 2H)

Example 16

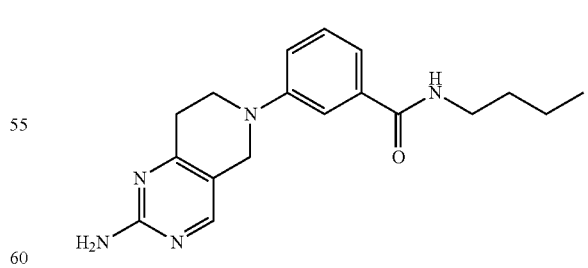

3-(2-amino-7,8-dihydropyrido[4,3-d]pyrimidin-6(5H)-yl)-N-butylbenzamide

A mixture of 3-(2-amino-7,8-dihydropyrido[4,3-d]pyrimidin-6(5H)-yl)benzoic acid (41 mg, 0.15 mmol), N,N-diisopropylethylamine (0.105 mL, 0.60 mmol), and HBTU (63 mg, 0.165 mmol) in 1.5 mL DMF was briefly warmed to approx. 50° C. to dissolve solids, then continued stirring at room temperature. After 10 minutes n-butylamine (0.022 mL, 0.225 mmol) was added and the reaction continued at room temperature for 16.5 hours. The reaction was added drop wise to a stirring mixture of 30 mL water containing 5 mL brine at room temperature, and the resulting precipitate filtered and rinsed with water. The damp solid was dissolved in 20% MeOH in CHCl₃ and evaporated to a dry solid. The solid was triturated with an EtOAc/hexane mixture to give the title compound as a light beige solid (42 mg, 86%). ¹H NMR (acetone-d6) δ: 8.13 (s, 1H), 7.62 (br. s., 1H), 7.53-7.55 (m, 1H), 7.26-7.30 (m, 2H), 7.13-7.20 (m, 1H), 5.74 (br. s., 2H), 4.29 (s, 2H), 3.65 (t, J=6.0 Hz, 2H), 3.38 (td, J=7.1, 5.7 Hz, 2H), 2.81 (t, J=6.0 Hz, 2H), 1.52-1.63 (m, 2H), 1.32-1.45 (m, 2H), 0.93 (t, J=7.3 Hz, 3H).

Example 17

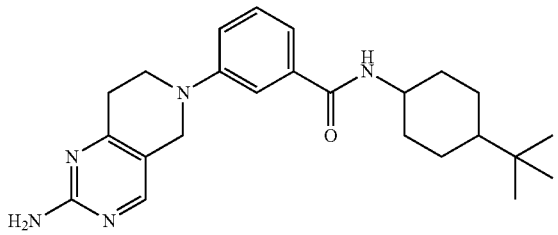 [SMILES: CC(C)(C)C1CCC(NC(=O)c2cccc(N3CCc4nc(N)ncc4C3)c2)CC1]

3-(2-amino-7,8-dihydropyrido[4,3-d]pyrimidin-6 (5H)-yl)-N-(4-(tert-butyl)cyclohexyl)benzamide In a manner similar to that described in Example 16, the title compound was prepared as a mixture of isomers as a light beige solid (49 mg, 81%). ¹H NMR (DMSO-d6) δ: 8.12 (s, 1H), 8.06-8.11 (m, 1H), 7.85 (d, J=6.2 Hz, 0.25H, minor isomer), 7.40 (s, 1H), 7.10-7.33 (m, 3H), 6.40 (s, 2H), 4.21-4.26 (m, 2H), 3.97-4.04 (m, 0.25H, minor isomer), 3.64-3.75 (m, 1H), 3.56-3.63 (m, 2H), 2.75 (t, J=5.9 Hz, 2H), 1.72-2.00 (m, 3H), 1.22-1.56 (m, 3H), 0.92-1.16 (m, 3H), 0.86 (s, 9H).

Example 18

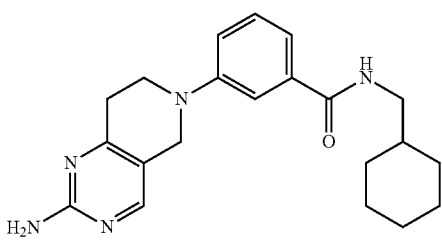 [SMILES: Nc1ncc2c(n1)CCN(c1cccc(C(=O)NCC3CCCCC3)c1)C2]

3-(2-amino-7,8-dihydropyrido[4,3-d]pyrimidin-6 (5H)-yl)-N-(cyclohexylmethyl)benzamide In a manner similar to that described Example 16, the title compound was prepared as a light beige solid (46 mg, 84%). ¹H NMR (DMSO-d6) δ: 8.34 (t, J=5.9 Hz, 1H), 8.11 (s, 1H), 7.41-7.44 (m, 1H), 7.26-7.32 (m, 1H), 7.21-7.26 (m, 1H), 7.11-7.16 (m, 1H), 6.40 (s, 2H), 4.24 (s, 2H), 3.60 (t, J=5.9 Hz, 2H), 3.09 (t, J=6.3 Hz, 2H), 2.75 (t, J=5.9 Hz, 2H), 1.46-1.76 (m, 6H), 1.10-1.25 (m, 3H), 0.83-1.01 (m, 2H).

Example 19

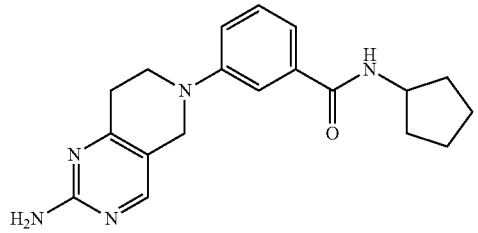

3-(2-amino-7,8-dihydropyrido[4,3-d]pyrimidin-6 (5H)-yl)-N-cyclopentylbenzamide

In a manner similar to that described in Example 16, the title compound was prepared as an off-white solid (37 mg, 72%). ¹H NMR (DMSO-d6) δ: 8.17 (d, J=7.3 Hz, 1H), 8.12 (s, 1H), 7.39-7.41 (m, 1H), 7.26-7.32 (m, 1H), 7.21-7.25 (m, 1H), 7.11-7.15 (m, 1H), 6.40 (s, 2H), 4.24 (s, 2H), 4.15-4.23 (m, 1H), 3.60 (t, J=5.9 Hz, 2H), 2.75 (t, J=5.9 Hz, 2H), 1.82-1.95 (m, 2H), 1.63-1.76 (m, 2H), 1.45-1.61 (m, 4H).

Example 20

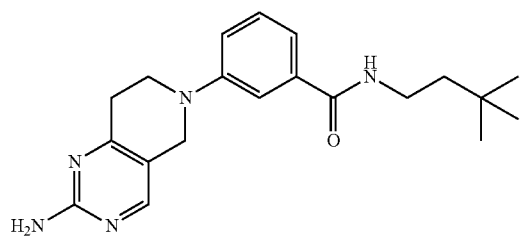 [SMILES: CC(C)(C)CCNC(=O)c1cccc(N2CCc3nc(N)ncc3C2)c1]

3-(2-amino-7,8-dihydropyrido[4,3-d]pyrimidin-6 (5H)-yl)-N-(3,3-dimethylbutyl)benzamide In a manner similar to that described in Example 16, the title compound was prepared as a light beige solid (27 mg, 51%). ¹H NMR (DMSO-d6) δ: 8.31 (t, J=5.4 Hz, 1H), 8.11 (s, 1H), 7.40-7.43 (m, 1H), 7.26-7.32 (m, 1H), 7.19-7.24 (m, 1H), 7.13 (ddd, J=8.1, 2.5, 0.9 Hz, 1H), 6.40 (s, 2H), 4.24 (s, 2H), 3.60 (t, J=6.0 Hz, 2H), 3.23-3.31 (m, 2H), 2.75 (t, J=5.9 Hz, 2H), 1.41-1.49 (m, 2H), 0.93 (s, 9H).

Preparation 11

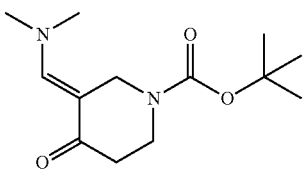 [SMILES: CN(C)/C=C1\CN(C(=O)OC(C)(C)C)CCC1=O]

1-t-Butoxycarbonyl-3-(dimethylamino)methylene-4-piperidone

A solution of N-Boc-4-piperidone (10.0 g, 50.19 mmol) and N,N-dimethylformamide dimethylacetal (20.16 mL, 150.57 mmol) in 1,4-dioxane (100 mL) was heated at reflux for 15 hours. The solvent was removed in vacuo and the residue was eluted through a flash column (silica gel 60, 230-400 mesh, 8% MeOH in EtOAc) to obtain the title compound as an orange oil which crystallized on standing (7.64 g, 60%).

Preparation 12

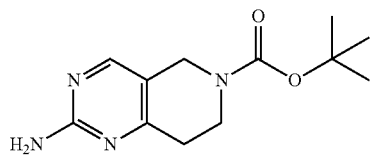

6-t-Butoxycarbonyl-5,6,7,8-tetrahydropyrido[4,3-d]pyrimidin-2-ylamine

A solution of 1-t-Butoxycarbonyl-3-(dimethylamino)methylene-4-piperidone (7.64 g, 30.04 mmol) in methanol (190 mL) was treated with guanidine carbonate (21.65 g, 120.16 mmol), followed by sodium acetate trihydrate (32.70 g, 240.32 mmol). The reaction mixture was heated at reflux for 17 hours and the solvent was removed in vacuo. The residue was diluted with water and the mixture was swirled for a few minutes. The undissolved white solid was collected and washed with water, followed by a small amount of cold ethyl acetate to give the title compound (4.10 g, 55%).

Example 21

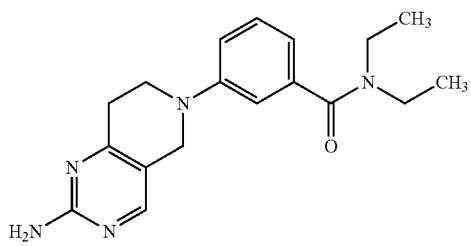 [SMILES: CCN(CC)C(=O)c1cccc(N2CCc3nc(N)ncc3C2)c1]

3-(2-amino-7,8-dihydropyrido[4,3-d]pyrimidin-6(5H)-yl)-N,N-diethylbenzamide

The title compound was produced as a by-product during the preparation of Example 5. The title compound was isolated as a yellow solid (3.2 mg).

Example 22

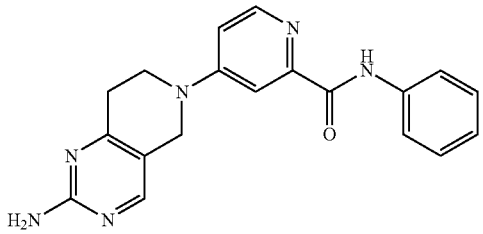

4-(2-amino-7,8-dihydropyrido[4,3-d]pyrimidin-6(5H)-yl)-N-phenylpyridine-2-carboxamide In a manner similar to that described for the Preparations 13-16 and in Example 24, 4-bromopicolinic acid and aniline were converted to the title compound.

Example 23

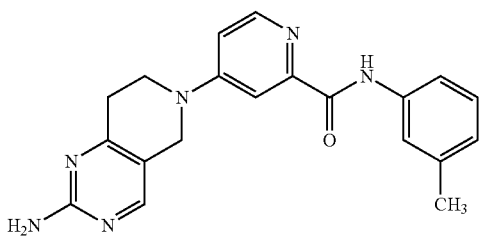 [SMILES: Cc1cccc(NC(=O)c2cc(N3CCc4nc(N)ncc4C3)ccn2)c1]

4-(2-amino-7,8-dihydropyrido[4,3-d]pyrimidin-6(5H)-yl)-N-(3-methylphenyl)pyridine-2-carboxamide In a manner similar to that described for the Preparations 13-16 and in Example 24, 4-bromopicolinic acid and m-toluidine were converted to the title compound.

Preparation 13

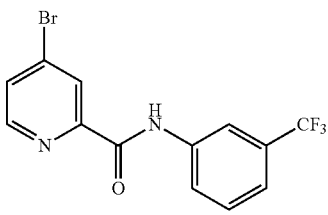 [SMILES: O=C(Nc1cccc(C(F)(F)F)c1)c1cc(Br)ccn1]

4-Bromo-N-[3-(trifluoromethyl)phenyl]pyridine-2-carboxamide

A mixture of 4-bromopicolinic acid (800 mg, 3.96 mmol), 3-(trifluoromethyl)aniline (0.49 ml, 3.96 mmol) and DIEA (3.27 ml, 19.80 mmol) in DMF (12 ml) was treated with HATU (1.66 g, 4.36 mmol) and the reaction mixture was stirred at room temperature for 22 hours. The solvent was removed in vacuo and the residue was taken up in EtOAc. The organic solution was washed with water, dried over MgSO₄, filtered, and concentrated. Elution through a flash column (silica gel 60, 230-400 mesh, 4:1 hexanes:EtOAc) gave pure amide as an off-white, crystalline solid (1.026 g, 75%).

Preparation 14

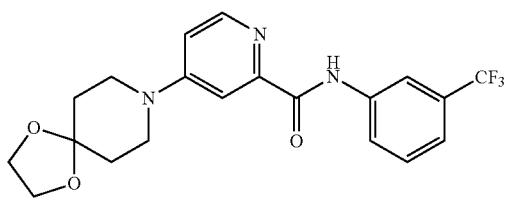 [SMILES: O=C(Nc1cccc(C(F)(F)F)c1)c1cc(N2CCC3(CC2)OCCO3)ccn1]

4-{1,4-Dioxa-8-azaspiro[4.5]decan-8-yl}-N-[3-(trifluoromethyl)phenyl]pyridine-2-carboxamide A mixture of 4-bromo-N-[3-(trifluoromethyl)phenyl]pyridine-2-carboxamide (1.01 g, 2.93 mmol), 4-piperidine ethylene ketal (0.38 ml, 2.93 mmol), palladium(II)acetate (132 mg, 0.586 mmol), rac-BINAP (365 mg, 0.586 mmol), and cesium carbonate (1.37 g, 4.10 mmol) in toluene (15 ml) was stirred at 100° C. for 21 hours. Upon cooling to room temperature, the insolubles were filtered off and washed with EtOAc. The washing was combined with the filtrate and concentrated. Elution through a flash column (silica gel 60, 230-400 mesh, 3:2 hexanes:EtOAc) gave the title compound as a white, crystalline solid (713 mg, 60%).

Preparation 15

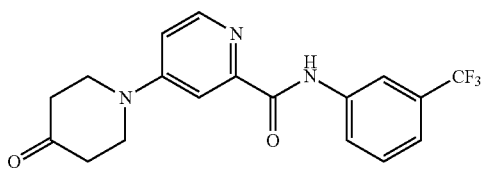 [SMILES: O=C1CCN(c2ccnc(C(=O)Nc3cccc(C(F)(F)F)c3)c2)CC1]

4-(4-Oxopiperidin-1-yl)-N-[3-trifluoromethyl)phenyl]pyridine-2-carboxamide

A mixture of 4-{1,4-Dioxa-8-azaspiro[4.5]decan-8-yl}-N-[3-(trifluoromethyl)phenyl]pyridine-2-carboxamide (710 mg, 1.74 mmol) in THF (7 ml) and 10% $H_2SO_{4(aq.)}$ (7 ml) was stirred at ambient temperature for 41 hours. The reaction mixture was treated with 1.0 N $NaOH_{(aq.)}$ until pH~7-8. The aqueous mixture was extracted with dichloromethane (3×25 ml) and the combined organic extracts were dried (MgSO₄), filtered, and concentrated. Elution through a flash column (silica gel 60, 230-400 mesh, 2:3 hexanes:EtOAc) gave the title compound as a white, amorphous solid (498 mg, 79%).

Preparation 16

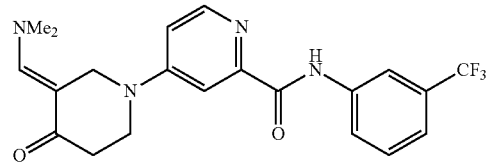 [SMILES: CN(C)/C=C1\CN(c2ccnc(C(=O)Nc3cccc(C(F)(F)F)c3)c2)CCC1=O]

4-[3-(Dimethylamino)methylidene-4-oxopiperidin-1-yl]-N-[3-(trifluoromethyl)phenyl]pyridine-2-carboxamide A solution of 4-(4-oxopiperidin-1-yl)-N-[3-trifluoromethyl)phenyl]pyridine-2-carboxamide (495 mg, 1.36 mmol) and DMF-dimethylacetal (0.55 ml, 4.08 mmol) in 1,4-dioxane (3 ml) was heated at 100° C. for 21 hours. The solvent was removed in vacuo and the residue was eluted through a flash column (silica gel 60, 230-400 mesh, 7% MeOH in EtOAc) to give a viscous, orange oil (419 mg, 74%).

Example 24

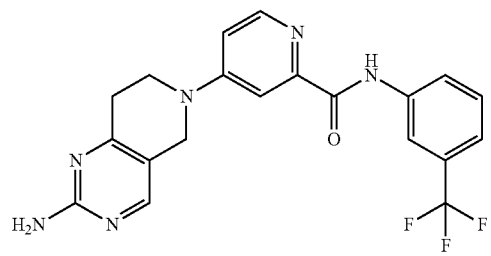 [SMILES: Nc1ncc2c(n1)CCN(c1ccnc(C(=O)Nc3cccc(C(F)(F)F)c3)c1)C2]

4-(2-Amino-5,6,7,8-tetrahydropyrido[4,3-d]pyrimidin-6-yl)-N-[3-(trifluoromethyl)phenyl]pyridine-2-carboxamide A solution of 4-[3-(dimethylamino)methylidene-4-oxopiperidin-1-yl]-N-[3-(trifluoromethyl)phenyl]pyridine-2-carboxamide (417 mg, 0.997 mmol) in EtOH (10 ml) was treated with guanidine carbonate (719 mg, 3.99 mmol), followed by adding sodium acetate trihydrate (1.09 g, 7.98 mmol). The reaction mixture was stirred at 80° C. for 23 hours and concentrated. The residue was partitioned between EtOAc and water resulting in the formation of a yellow, amorphous solid. The solid was collected, washed with water, EtOAc, MeOH, and dried to give the title compound (59 mg, 14%).

Example 25

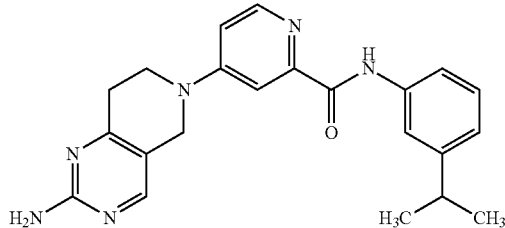

4-(2-Amino-7,8-dihydropyrido[4,3-d]pyrimidin-6 (5H)-yl)-N-(3-isopropylphenyl)pyridine-2-carboxamide In a manner similar to that described for the Preparations 13-16 and in Example 24, 4-bromopicolinic acid and 3-isopropylaniline were converted to the title compound.

Example 26

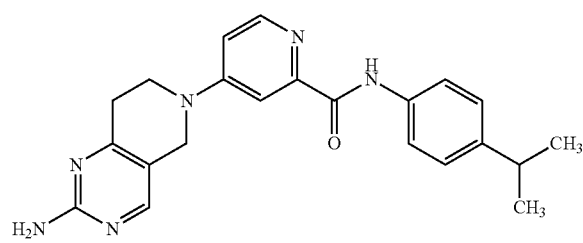

4-(2-amino-7,8-dihydropyrido[4,3-d]pyrimidin-6 (5H)-yl)-N-(4-isopropylphenyl)pyridine-2-carboxamide In a manner similar to that described for the Preparations 13-16 and in Example 24, 4-bromopicolinic acid and 4-isopropyl aniline were converted to the title compound.

Example 36

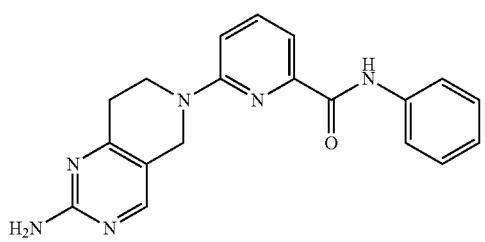

6-(2-amino-7,8-dihydropyrido[4,3-d]pyrimidin-6 (5H)-yl)-N-phenylpyridine-2-carboxamide In a manner similar to that described for the Preparations 13-16 and in Example 24, 6-bromopicolinic acid and aniline were converted to the title compound.

Example 37

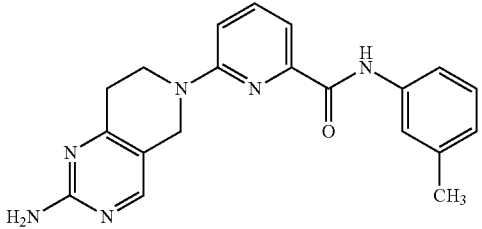

6-(2-amino-7,8-dihydropyrido[4,3-d]pyrimidin-6 (5H)-yl)-N-(3-methylphenyl)pyridine-2-carboxamide In a manner similar to that described for the Preparations 13-16 and in Example 24, 6-bromopicolinic acid and m-toluidine were converted to the title compound.

Example 38

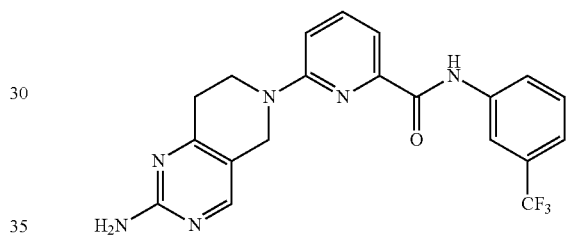

6-(2-amino-7,8-dihydropyrido[4,3-d]pyrimidin-6 (5H)-yl)-N-(3-(trifluoromethyl)phenyl)picolinamide In a manner similar to that described in Example 40, 6-(2-((methylthio)oxy)-7,8-dihydropyrido[4,3-d]pyrimidin-6 (5H)-yl)-N-(3-(trifluoromethyl)phenyl)picolinamide was converted to the title compound.

Example 39

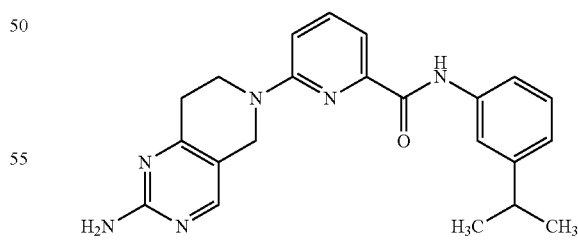

6-(2-amino-7,8-dihydropyrido[4,3-d]pyrimidin-6 (5H)-yl)-N-(3-isopropylphenyl)picolinamide In a manner similar to that described in Example 40, N-(3-isopropylphenyl)-6-(2-((methylthio)oxy)-7,8-dihydropyrido [4,3-d]pyrimidin-6(5H)-yl)picolinamide was converted to the title compound.

Example 40

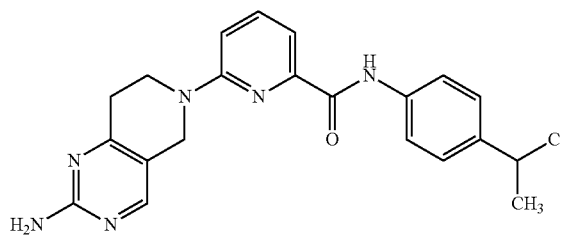

6-{2-Amino-5,6,7,8-tetrahydropyrido[4,3-d]pyrimidin-6-yl}-N-[4-(isopropyl)phenyl]pyridine-2-carboxamide A suspension of 6-(2-Methanesulfinyl-7,8-dihydro-5H-pyrido[4,3-d]pyrimidin-6-yl)-pyridine-2-carboxylic acid (4-isopropyl-phenyl)-amide (405 mg, 0.930 mmol) in 1,4-dioxane (10 ml) was treated with $NH_4OH$ (3 ml, 28-30%) and the reaction mixture was heated in a sealed tube at 100° C. with stirring for 15 hours. Upon cooling to room temperature, the reaction mixture was concentrated and the residue was taken up in water. The aqueous mixture was extracted with ethyl acetate and the organic extract was dried ($MgSO_4$), filtered, and concentrated. Trituration with MeOH gave the title compound as a yellow, amorphous solid (200 mg, 55%).

Example 51

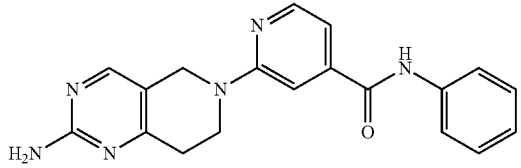 [SMILES: Nc1ncc2c(n1)CCN(c1cc(C(=O)Nc3ccccc3)ccn1)C2]

2-(2-amino-7,8-dihydropyrido[4,3-d]pyrimidin-6(5H)-yl)-N-phenylisonicotinamide

In a manner similar to that described for Example 40, 2-(2-(methylsulfinyl)-7,8-dihydropyrido[4,3-d]pyrimidin-6(5H)-yl)-N-phenylisonicotinamide was converted to the title compound.

Example 52

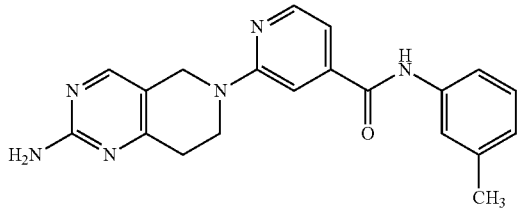

2-(2-amino-7,8-dihydropyrido[4,3-d]pyrimidin-6(5H)-yl)-N-(3-methylphenyl)isonicotinamide In a manner similar to that described for Example 40, 2-(2-(methylsulfinyl)-7,8-dihydropyrido[4,3-d]pyrimidin-6(5H)-yl)-N-(m-tolyl)isonicotinamide was converted to the title compound.

Example 53

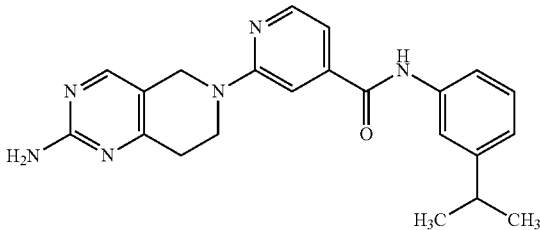 [SMILES: CC(C)c1cccc(NC(=O)c2ccnc(N3CCc4nc(N)ncc4C3)c2)c1]

2-(2-amino-7,8-dihydropyrido[4,3-d]pyrimidin-6(5H)-yl)-N-(3-isopropylphenyl)isonicotinamide In a manner similar to that described for Example 40, 2-(2-(methylsulfinyl)-7,8-dihydropyrido[4,3-d]pyrimidin-6(5H)-yl)-N-(3-(trifluoromethyl)phenyl)isonicotinamide was converted to the title compound.

Example 54

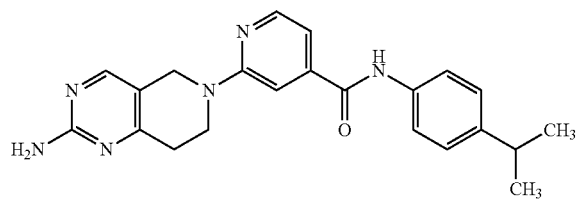

2-(2-amino-7,8-dihydropyrido[4,3-d]pyrimidin-6(5H)-yl)-N-(4-isopropylphenyl)isonicotinamide In a manner similar to that described for Example 40, N-(4-isopropylphenyl)-2-(2-(methylsulfinyl)-7,8-dihydropyrido[4,3-d]pyrimidin-6(5H)-yl)isonicotinamide was converted to the title compound.

Example 55

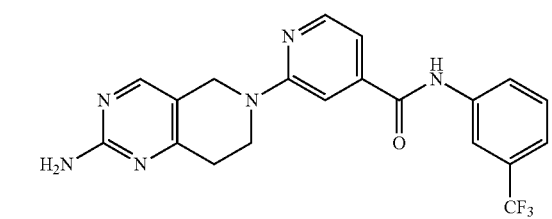 [SMILES: Nc1ncc2c(n1)CCN(c1cc(C(=O)Nc3cccc(C(F)(F)F)c3)ccn1)C2]

2-(2-amino-7,8-dihydropyrido[4,3-d]pyrimidin-6(5H)-yl)-N-[3-(trifluoromethyl)phenyl]isonicotinamide In a manner similar to that described for Example 40, 2-(2-(methylsulfinyl)-7,8-dihydropyrido[4,3-d]pyrimidin-6-(5H)-yl)-N-(3-(trifluoromethyl)phenyl)isonicotinamide was converted to the title compound.

Preparation 17

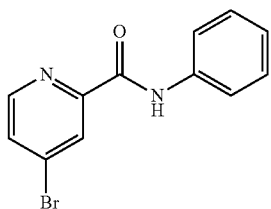 [SMILES: O=C(Nc1ccccc1)c1cc(Br)ccn1]

4-Bromo-pyridine-2-carboxylic acid phenylamide

To a suspension of 4-bromo-pyridine-2-carboxylic acid (1.00 g, 5.00 mmol) in dimethylformamide (10 mL) was added 1-methylmorpholine (1.1 mL, 10 mmol) and O-(7-azabenzotriazol-1-yl)-N,N,N',N'-tetramethyl-uronium hexafluorophosphate (HATU) (2.37 g, 6.23 mmol). The mixture became an orange solution after 10 minutes. Aniline (0.5 mL, 5.5 mmol) was added and the solution was stirred at room temperature for 66 hours. The dimethylformamide was evaporated in vacuo and the residue was partitioned between water and ethyl acetate. The separated water layer was extracted with ethyl acetate. The combined ethyl acetate extract was washed with water and saturated sodium bicarbonate. The organic layer was dried (MgSO$_4$), filtered and evaporated to crude 2. Chromatography on silica gel (40 g) applied in dichloromethane and eluted with hexanes:ethyl acetate (1:1) gave the title compound (0.986 g, 71%).

Preparation 18

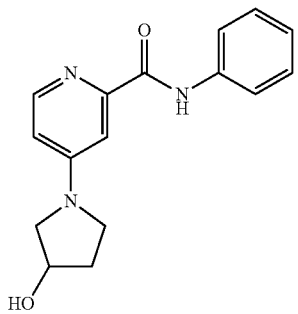 [SMILES: O=C(Nc1ccccc1)c1cc(N2CCC(O)C2)ccn1]

4-(3-Hydroxypyrrolidin-1-yl)-pyridine-2-carboxylic acid phenylamide

A solution of dl-3-pyrrolidinol (0.17 g, 1.95 mmol) and 4-bromo-pyridine-2-carboxylic acid phenylamide (0.36 g, 1.3 mmol) in 1-butanol (25 mL) was heated at 100° C. for 15 hours. The reaction was applied to silica gel (25 g) and eluted with chloroform then chloroform:methanol 9:1 to give the title compound 227 mg (0.80 mmol, 61%).

Preparation 19

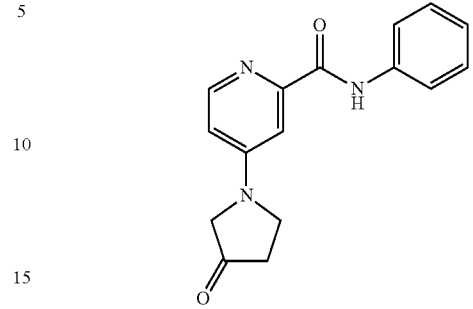

4-(3-Oxopyrrolidin-1-yl)-pyridine-2-carboxylic acid phenylamide

A solution of 4-(3-Hydroxypyrrolidin-1-yl)-pyridine-2-carboxylic acid phenylamide (259 mg, 0.92 mmol) in dichloromethane (5 mL) and dimethylsulfoxide (2.5 mL) was cooled in an ice bath. Diisopropylethylamine (0.48 mL, 2.8 mmol) was added and stirred for 5 minutes. A solution of sulfur trioxide-pyridine complex (0.44 g, 2.8 mmol) in DMSO (2.5 mL) was added dropwise. The reaction was stirred at 0° C. for 3 hours. To the reaction was added 1 M hydrochloric acid (6 mL) and chloroform. The layers were separated. The aqueous layer was treated with saturated aqueous sodium bicarbonate until pH=6. Extraction twice with chloroform gave a crude residue. Purification by chromatography on silica gel (12 g) eluted with chloroform:methanol 39:1 gave the title compound (133 mg, 0.46 mmol, 50%).

Preparation 20

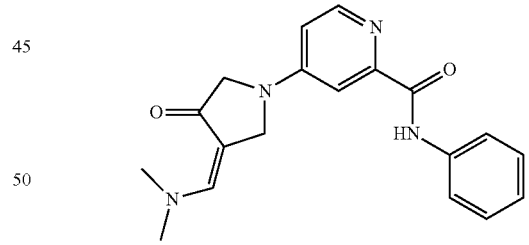

4-(3-((Dimethylamino)methylene)-4-oxopyrrolidin-1-yl)-pyridine-2-carboxylic acid phenylamide A suspension of 4-(3-oxopyrrolidin-1-yl)-pyridine-2-carboxylic acid phenylamide (130 mg, 0.46 mmol) and dimethylformamide dimethylacetal (0.12 mL, 0.90 mmol) in 1,4-dioxane (2 ml) was heated under nitrogen at 100° C. for 4.5 h. The solvent was removed in vacuo and the residue was purified by chromatography on silica gel (25 g) eluted with dichloromethane:methanol 19:1 and gave the title compound (95 mg, 0.28 mmol, yield 61%).

Example 80

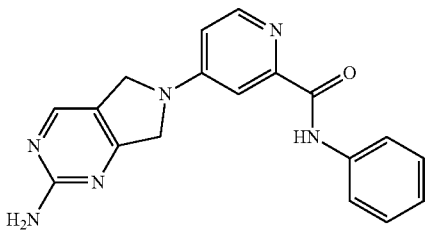 [SMILES: Nc1ncc2c(n1)CN(c1ccnc(C(=O)Nc3ccccc3)c1)C2]

4-(2-Amino-5,7-dihydro-pyrrolo[3,4-d]pyrimidin-6-yl)-pyridine-2-carboxylic acid phenylamide To a solution of sodium ethoxide (0.18 mL, 0.56 mmol, 3M) in ethanol (10 mL) was added guanidine carbonate (50 mg, 0.56 mmol). The suspension was stirred for 45 minutes, then added to a suspension of 4-(3-((Dimethylamino)methylene)-4-oxopyrrolidin-1-yl)-pyridine-2-carboxylic acid phenylamide (95 mg, 0.28 mmol) in ethanol (10 mL). The reaction mixture was heated at 80° C. for 18 hours. Water (20 mL) was added and the mixture stirred for 1 hour. The solid was isolated by filtration and vacuum dried at 50° C. for 115 h and gave the title compound (44 mg, 0.13 mmol, 47%).

Example 81

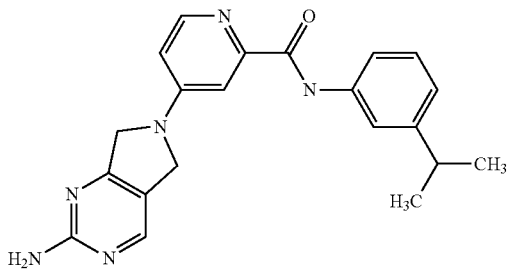 [SMILES: CC(C)c1cccc(NC(=O)c2cc(N3Cc4cnc(N)nc4C3)ccn2)c1]

4-(2-amino-5,7-dihydro-6H-pyrrolo[3,4-d]pyrimidin-6-yl)-N-(3-isopropylphenyl)pyridine-2-carboxamide In a manner similar to that describe in Example 82, N-(3-isopropylphenyl)-4-(2-(methylsulfinyl)-5H-pyrrolo[3,4-d]pyrimidin-6(7H)-yl)picolinamide was converted to the title compound.

Example 82

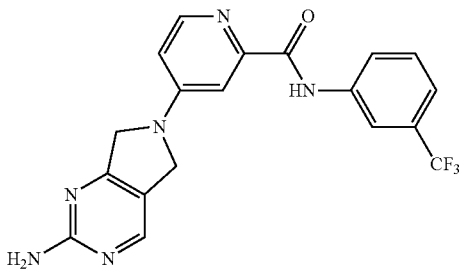 [SMILES: Nc1ncc2c(n1)CN(c1ccnc(C(=O)Nc3cccc(C(F)(F)F)c3)c1)C2]

4-(2-Amino-5,7-dihydro-pyrrolo[3,4-d]pyrimidin-6-yl)-pyridine-2-carboxylic acid (3-trifluoromethyl-phenyl)-amide A mixture of 4-(2-(Methylsulfinyl)-5H-pyrrolo[3,4-d]pyrimidin-6(7H)-yl)-N-(3-(trifluoromethyl)phenyl)picolinamide and 4-(2-(methylsulfonyl)-5H-pyrrolo[3,4-d]pyrimidin-6(7H)-yl)-N-(3-(trifluoromethyl)phenyl)picolinamide was suspended in 1,4-dioxane (7 mL). Ammonium hydroxide (30%, 1.5 mL) was added and the reaction was heated at 90° C. for 16 hours. TLC indicated only partial conversion to the desired amine. The solvent was reduced with a nitrogen stream and then additional ammonium hydroxide (1 mL) was added. The reaction was sealed in a tube and heated at 100° C. for 17 h. The solvent was evaporated in vacuo. The resulting solid was triturated with water and then methanol. The solid was chromatographed on silica gel (4 g) eluted with ethyl acetate:methanol (9:1) to give the title compound (10.6 mg, 0.026 mmol).

Example 83

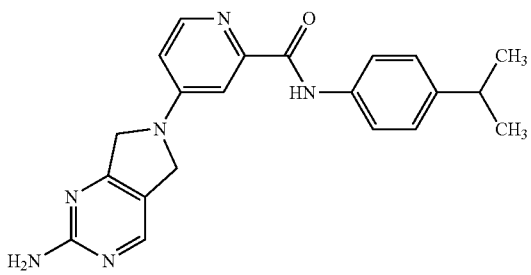 [SMILES: CC(C)c1ccc(NC(=O)c2cc(N3Cc4cnc(N)nc4C3)ccn2)cc1]

4-(2-amino-5,7-dihydro-6H-pyrrolo[3,4-d]pyrimidin-6-yl)-N-(4-isopropylphenyl)pyridine-2-carboxamide In a manner similar to that describe in Example 82, N-(4-isopropylphenyl)-4-(2-(methylsulfinyl)-5H-pyrrolo[3,4-d]pyrimidin-6(7H)-yl)picolinamide was converted to the title compound.

Example 84

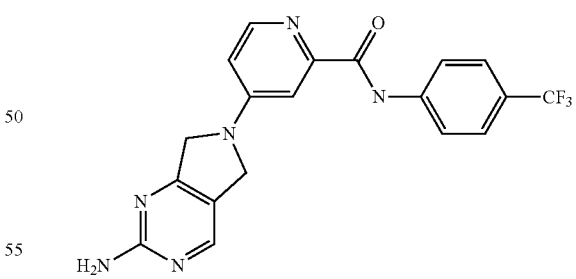

4-(2-amino-5,7-dihydro-6H-pyrrolo[3,4-d]pyrimidin-6-yl)-N-[4-(trifluoromethyl)phenyl]pyridine-2-carboxamide In a manner similar to that describe in Example 82, 4-(2-Methylsulfanyl-5,7-dihydro-pyrrolo[3,4-d]pyrimidin-6-yl)-pyridine-2-carboxylic acid (4-trifluoromethyl-phenyl)-amide was converted to the title compound.

Example 106

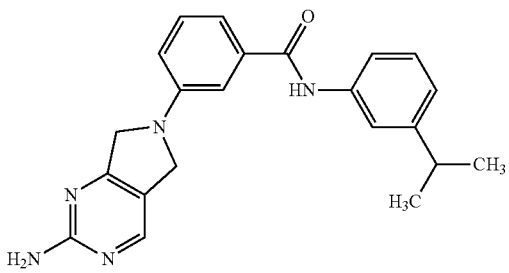

3-(2-amino-5,7-dihydro-6H-pyrrolo[3,4-d]pyrimidin-6-yl)-N-(3-isopropylphenyl)benzamide In a manner similar to that describe in Example 82, N-(3-isopropylphenyl)-3-(2-(methylsulfinyl)-5H-pyrrolo[3,4-d]pyrimidin-6(7H)-yl)benzamide was converted to the title compound.

Example 107

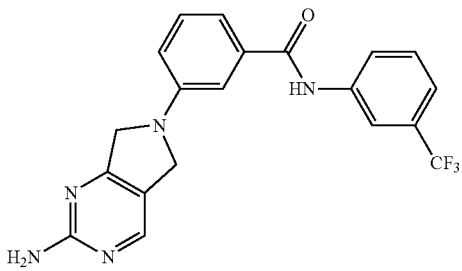

3-(2-amino-5,7-dihydro-6H-pyrrolo[3,4-d]pyrimidin-6-yl)-N-[3-(trifluoromethyl)phenyl]benzamide In a manner similar to that describe in Example 82, 3-(2-(methylsulfinyl)-5H-pyrrolo[3,4-d]pyrimidin-6(7H)-yl)-N-(3-(trifluoromethyl)phenyl)benzamide was converted to the title compound.

Preparation 21

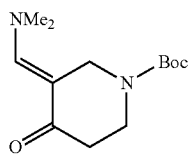 [SMILES: CN(C)/C=C1\CN(C(=O)OC(C)(C)C)CCC1=O]

t-Butyl-3-[(dimethylamino)methylidene]-4-oxopiperidine-1-carboxylate

A solution of N-Boc-4-piperidone (10 g, 50.19 mmol) and DMF-dimethylacetal (20.16 ml, 150.57 mmol) in 1,4-dioxane (100 ml) was heated at reflux for 20 hours. The reaction mixture was concentrated and the residue was eluted through a flash column (silica gel 60, 230-400 mesh, 7% MeOH in EtOAc) to give the title compound as an orange oil which crystallized on standing (10.51 g, 82%).

Preparation 22

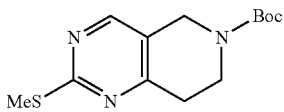

t-Butyl-2-(methylthio)-5,6,7,8-tetrahydropyrido[4,3-d]pyrimidine-6-carboxylate

A suspension of t-Butyl-3-[(dimethylamino)methylidene]-4-oxopiperidine-1-carboxylate (10.95 g, 43.05 mmol) and 2-methyl-2-thiopseudourea hemisulfate (7.79 g, 55.97 mmol) in water (175 ml) was treated with 1.0 N NaOH$_{(aq.)}$ (46.63 ml, 46.63 mmol) and the reaction mixture was heated at 75° C. for 2.5 hours. The aqueous mixture was extracted with dichloromethane and the organic extract was dried (MgSO$_4$), filtered, and concentrated. Elution through a flash column (silica gel 60, 230-400 mesh, 7:3 hexanes:EtOAc) gave the title compound as a yellow oil (4.45 g, 37%).

Preparation 23

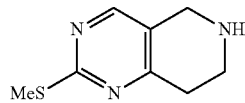 [SMILES: CSc1ncc2c(n1)CCNC2]

2-(Methylthio)-5,6,7,8-tetrahydropyrido[4,3-d]pyrimidine

A solution of t-butyl-2-(methylthio)-5,6,7,8-tetrahydropyrido[4,3-d]pyrimidine-6-carboxylate2 (4.45 g, 15.82 mmol) in acetone (45 ml) was treated dropwise over 10 minutes with 5-6 N HCl solution in 2-propanol (16 ml) and the reaction mixture was stirred at room temperature for 5 hours. The solvent was removed in vacuo and the solid was collected and washed with ethyl acetate (2.94 g). The salt was dissolved in a minimal amount of water and basified to pH=14 with 1.0 N NaOH$_{(aq.)}$. The alkaline mixture was extracted with dichloromethane (4×25 ml) and the combined organic extracts were dried (MgSO$_4$), filtered, and concentrated to give the title compound as a deep red oil which crystallized on standing (2.22 g, 77%)

Preparation 24

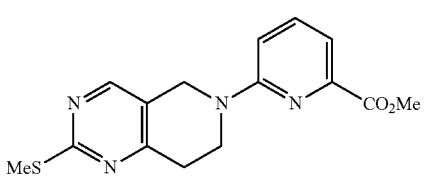 [SMILES: COC(=O)c1cccc(N2CCc3nc(SC)ncc3C2)n1]

Methyl-6-[2-(methylthio)-5,6,7,8-tetrahydropyrido[4,3-d]pyrimidin-6-yl]pyridine-2-carboxylate A mixture of 2-(methylthio)-5,6,7,8-tetrahydropyrido[4,3-d]pyrimidine (892 mg, 4.92 mmol), methyl-6-bromopicolinate (1.06 g, 4.92 mmol), Pd(OAc)$_2$ (110 mg, 0.492 mmol), rac-BINAP (306 mg, 0.492 mmol), and Cs$_2$CO$_3$ (3.85 g, 11.81 mmol) in toluene (45 ml) was heated at 100° C. for 4.5 hours. The insolubles were filtered off and washed with ethyl acetate. The filtrate and washing were combined and concentrated. Elution through a flash column (silica gel 60, 230-400 mesh, 1:1 hexanes:EtOAc) gave the title compound as a viscous yellow oil which gradually solidified on standing (945 mg, 61%).

Preparation 25

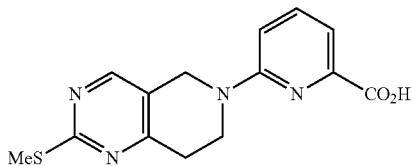 [SMILES: CSc1ncc2c(n1)CCN(c1cccc(C(=O)O)n1)C2]

6-[2-(Methylthio)-5,6,7,8-tetrahydropyrido[4,3-d]pyrimidin-6-yl]pyridine-2-carboxylic acid A solution of methyl-6-[2-(methylthio)-5,6,7,8-tetrahydropyrido[4,3-d]pyrimidin-6-yl]pyridine-2-carboxylate (2.76 g, 8.72 mmol) in 1,4-dioxane (50 ml) was treated with 1.0 N NaOH$_{(aq.)}$ (13.09 ml, 13.09 mmol) and the reaction mixture was stirred at room temperature for 2 hours. The solvent was removed in vacuo and the residue was diluted with water. The aqueous phase was washed with diethyl ether and acidified to pH~5-6 with 1.0 N HCl$_{(aq.)}$. The precipitate was collected, washed with water, ethyl acetate, and dried to give the title compound as a yellow, amorphous solid (2.52 g, 96%).

Example 108

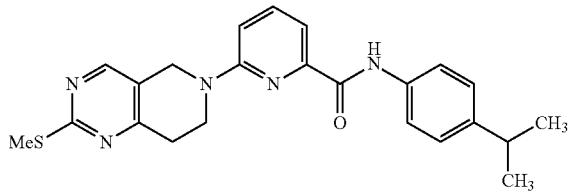 [SMILES: CSc1ncc2c(n1)CCN(c1cccc(C(=O)Nc3ccc(C(C)C)cc3)n1)C2]

N-(4-isopropylphenyl)-6-[2-(methylthio)-7,8-dihydropyrido[4,3-d]pyrimidin-6(5H)-yl]pyridine-2-carboxamide A mixture of 6-[2-(Methylthio)-5,6,7,8-tetrahydropyrido[4,3-d]pyrimidin-6-yl]pyridine-2-carboxylic acid (600 mg, 1.98 mmol), 4-isopropylaniline (0.28 ml, 1.98 mmol) and DIEA (1.64 ml, 9.90 mmol) in DMF (10 ml) was treated with HATU (828 mg, 2.18 mmol) and the reaction mixture was stirred at room temperature for 3 hours. The solvent was removed in vacuo and the residue was partitioned between ethyl acetate and water. The organic layer was washed with water, dried (MgSO$_4$), filtered and concentrated. Elution through a flash column (silica gel 60, 230-400 mesh, 1:1 hexanes:EtOAc) gave the title compound as an oil which crystallized on standing (804 mg, 97%).

Example 109

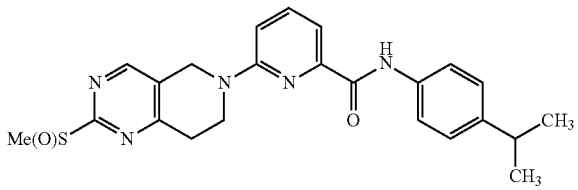

6-(2-Methanesulfinyl-7,8-dihydro-5H-pyrido[4,3-d]pyrimidin-6-yl)-pyridine-2-carboxylic acid(4-isopropyl-phenyl)-amide To a stirred mixture of N-(4-isopropylphenyl)-6-[2-(methylthio)-7,8-dihydropyrido[4,3-d]pyrimidin-6(5H)-yl]pyridine-2-carboxamide (400 mg, 0.953 mmol) in THF (40 ml) and water (16 ml) was added oxone (potassium peroxomonosulfate, 586 mg, 0.953 mmol). After stirring at room temperature for 3 hours, the reaction mixture was quenched by addition of 10% NaHSO$_{3(aq.)}$ (20 ml) and neutralized with sat'd NaHCO$_{3(aq.)}$ (16 ml). The solution was stirred for 20 minutes before extraction with ethyl acetate (2×60 ml). The combined organic extracts were dried (MgSO$_4$), filtered, and concentrated to give the title compound as a light yellow, amorphous solid which was used without further purification (405 mg, 98%).

Example 110

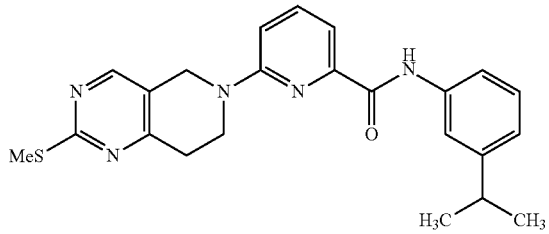

N-(3-isopropylphenyl)-6-(2-(methylthio)-7,8-dihydropyrido[4,3-d]pyrimidin-6(5H)-yl)picolinamide In a manner similar to that described in Example 108, a mixture of 6-[2-(methylthio)-5,6,7,8-tetrahydropyrido[4,3-d]pyrimidin-6-yl]pyridine-2-carboxylic acid and 3-isopropylaniline were converted to the title compound (560 mg).

Example 111

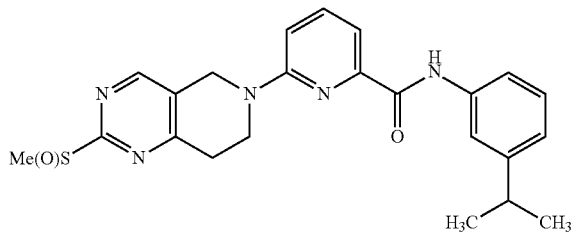

N-(3-isopropylphenyl)-6-(2-((methylthio)oxy)-7,8-dihydropyrido[4,3-d]pyrimidin-6(5H)-yl)picolinamide In a manner similar to that described in Example 109, N-(3-isopropylphenyl)-6-(2-((methylthio)oxy)-7,8-dihydropyrido[4,3-d]pyrimidin-6(5H)-yl)picolinamide was converted to the title compound (427 mg).

Example 112

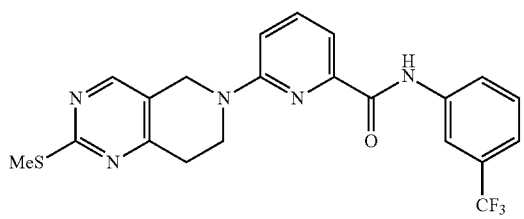

6-(2-(methylthio)-7,8-dihydropyrido[4,3-d]pyrimidin-6(5H)-yl)-N-(3-(trifluoromethyl)phenyl)picolinamide In a manner similar to that described in Example 108, a mixture of 6-[2-(methylthio)-5,6,7,8-tetrahydropyrido[4,3-d]pyrimidin-6-yl]pyridine-2-carboxylic acid and 3-trifluoromethylaniline were converted to the title compound (560 mg).

Example 113

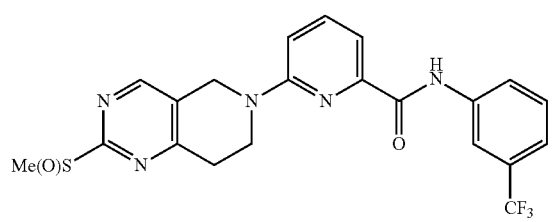

6-(2-((methylthio)oxy)-7,8-dihydropyrido[4,3-d]pyrimidin-6(5H)-yl)-N-(3-(trifluoromethyl)phenyl)picolinamide In a manner similar to that described in Example 109, 6-(2-(methylthio)-7,8-dihydropyrido[4,3-d]pyrimidin-6 (5H)-yl)-N-(3-(trifluoromethyl)phenyl)picolinamide was converted to the title compound.

Example 114

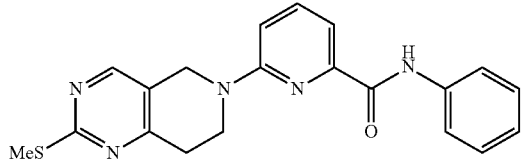 [SMILES: CSc1ncc2c(n1)CCN(c1cccc(C(=O)Nc3ccccc3)n1)C2]

6-[2-(methylthio)-7,8-dihydropyrido[4,3-d]pyrimidin-6(5H)-yl]-N-phenylpyridine-2-carboxamide In a manner similar to that described in Example 108, a mixture of 6-[2-(methylthio)-5,6,7,8-tetrahydropyrido[4,3-d]pyrimidin-6-yl]pyridine-2-carboxylic acid and aniline were converted to the title compound.

Example 115

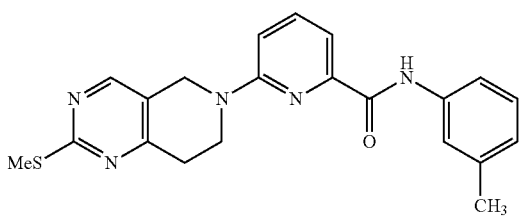

N-(3-methylphenyl)-6-[2-(methylthio)-7,8-dihydropyrido[4,3-d]pyrimidin-6(5H)-yl]pyridine-2-carboxamide In a manner similar to that described in Example 108, a mixture of 6-[2-(methylthio)-5,6,7,8-tetrahydropyrido[4,3-d]pyrimidin-6-yl]pyridine-2-carboxylic acid and m-toluidine were converted to the title compound.

Preparation 26

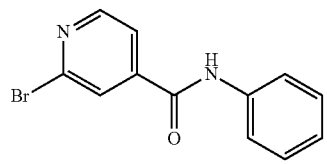 [SMILES: O=C(Nc1ccccc1)c1ccnc(Br)c1]

2-Bromo-N-phenyl-isonicotinamide

In a manner similar to that described in Preparation 17, 2-bromoisonicotinic acid and aniline were converted to the title compound Preparation 27

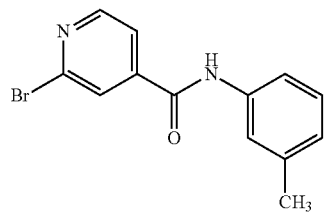

2-Bromo-N-m-tolyl-isonicotinamide

In a manner similar to that described in Preparation 17, 2-bromoisonicotinic acid and m-toluidine were converted to the title compound

Preparation 28

2-Bromo-N-(3-trifluoromethyl-phenyl)-isonicotinamide

In a manner similar to that described in Preparation 17, 2-bromoisonicotinic acid and 3-trifluoromethylaniline were converted to the title compound

Preparation 29

2-Bromo-N-(3-isopropyl-phenyl)-isonicotinamide

In a manner similar to that described in Preparation 17, 2-bromoisonicotinic acid and 3-isopropylaniline were converted to the title compound

Preparation 30

2-Bromo-N-(4-isopropyl-phenyl)-isonicotinamide

In a manner similar to that described in Preparation 17, 2-bromoisonicotinic acid and 4-isopropylaniline were converted to the title compound

Example 116

2-[2-(methylthio)-7,8-dihydropyrido[4,3-d]pyrimidin-6(5H)-yl]-N-phenylisonicotinamide In a manner similar to that described for Example 138, 2-(methylsulfanyl)-5,6,7,8-tetrahydropyrido[4,3-d]-pyrimidine and 2-bromo-N-phenyl-isonicotinamide were converted to the title compound.

Example 117

N-(3-methylphenyl)-2-[2-(methylthio)-7,8-dihydropyrido[4,3-d]pyrimidin-6(5H)-yl]isonicotinamide In a manner similar to that described for Example 138, 2-(methylsulfanyl)-5,6,7,8-tetrahydropyrido[4,3-d]-pyrimidine and 2-bromo-N-m-tolyl-isonicotinamide were converted to the title compound.

Example 118

2-[2-(methylthio)-7,8-dihydropyrido[4,3-d]pyrimidin-6(5H)-yl]-N-[3-(trifluoromethyl)phenyl]isonicotinamide In a manner similar to that described for Example 138, 2-(methylsulfanyl)-5,6,7,8-tetrahydropyrido[4,3-d]-pyrimidine and 2-bromo-N-(3-trifluoromethyl-phenyl)-isonicotinamide were converted to the title compound.

Example 119

N-(3-Isopropyl-phenyl)-2-(2-methylsulfanyl-7,8-dihydro-5H-pyrido[4,3-d]pyrimidin-6-yl)-isonicotinamide In a manner similar to that described for Example 138, 2-(methylsulfanyl)-5,6,7,8-tetrahydropyrido[4,3-d]-pyrimidine and 2-bromo-N-(3-isopropyl-phenyl)-isonicotinamide were converted to the title compound.

Example 120

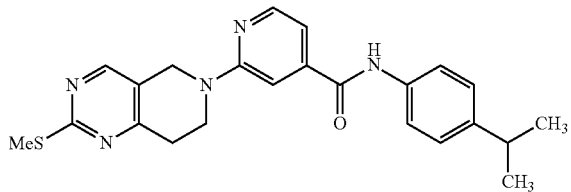 [SMILES: CSc1ncc2c(n1)CCN(c1cc(C(=O)Nc3ccc(C(C)C)cc3)ccn1)C2]

N-(4-Isopropyl-phenyl)-2-(2-methylsulfanyl-7,8-dihydro-5H-pyrido[4,3-d]pyrimidin-6-yl)-isonicotinamide In a manner similar to that described for Example 138, 2-(methylsulfanyl)-5,6,7,8-tetrahydropyrido[4,3-d]-pyrimidine and 2-bromo-N-(4-isopropyl-phenyl)-isonicotinamide were converted to the title compound.

Example 121

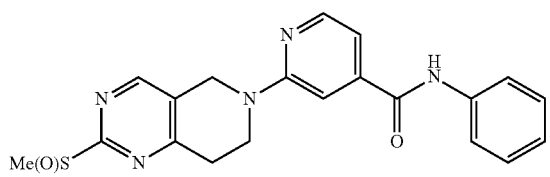

2-(2-(methylsulfinyl)-7,8-dihydropyrido[4,3-d]pyrimidin-6(5H)-yl)-N-phenylisonicotinamide In a manner similar to that described for Example 109, 2-[2-(methylthio)-7,8-dihydropyrido[4,3-d]pyrimidin-6(5H)-yl]-N-phenylisonicotinamide was converted to the title compound.

Example 122

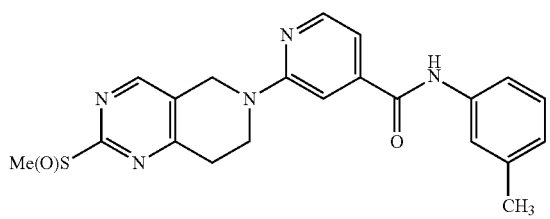

2-(2-(methylsulfinyl)-7,8-dihydropyrido[4,3-d]pyrimidin-6(5H)-yl)-N-(m-tolyl)isonicotinamide In a manner similar to that described for Example 109, N-(3-methylphenyl)-2-[2-(methylthio)-7,8-dihydropyrido[4,3-d]pyrimidin-6(5H)-yl]isonicotinamide was converted to the title compound.

Example 123

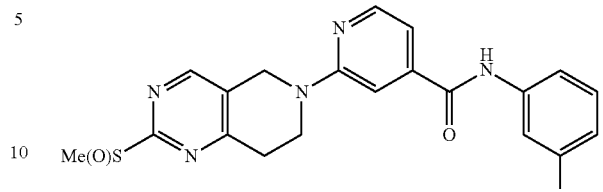

2-(2-(methylsulfinyl)-7,8-dihydropyrido[4,3-d]pyrimidin-6(5H)-yl)-N-(3-(trifluoromethyl)phenyl)isonicotinamide In a manner similar to that described for Example 109, 2-[2-(methylthio)-7,8-dihydropyrido[4,3-d]pyrimidin-6(5H)-yl]-N-[3-(trifluoromethyl)phenyl]isonicotinamide was converted to the title compound.

Example 124

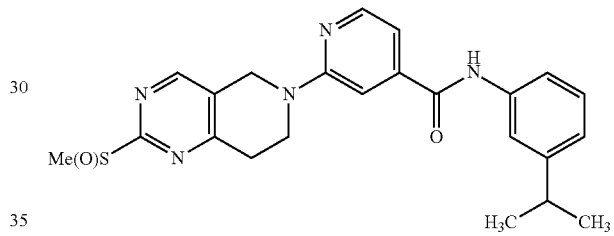

N-(3-isopropylphenyl)-2-(2-(methylsulfinyl)-7,8-dihydropyrido[4,3-d]pyrimidin-6(5H)-yl)isonicotinamide In a manner similar to that described for Example 109, N-(3-isopropyl-phenyl)-2-(2-methylsulfanyl-7,8-dihydro-5H-pyrido[4,3-d]pyrimidin-6-yl)-isonicotinamide was converted to the title compound.

Example 125

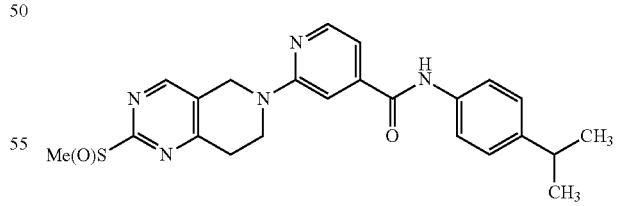

N-(4-isopropylphenyl)-2-(2-(methylsulfinyl)-7,8-dihydropyrido[4,3-d]pyrimidin-6(5H)-yl)isonicotinamide In a manner similar to that described for Example 109, N-(4-Isopropyl-phenyl)-2-(2-methylsulfanyl-7,8-dihydro-5H-pyrido[4,3-d]pyrimidin-6-yl)-isonicotinamide was converted to the title compound.

Preparation 31

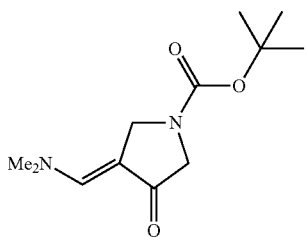 [SMILES: CN(C)/C=C1\CN(C(=O)OC(C)(C)C)CC1=O]

3-Dimethylaminomethylene-4-oxo-pyrrolidine-1-carboxylic acid tert-butyl ester A solution of tert-butyl 3-oxopyrrolidine-1-carboxylate (25.0 g, 135 mmol), dimethylformamide dimethylacetal (27 mL, 202 mmol) and 1,4-dioxane (170 mL) was heated at 100° C. for 17 hours. The dioxane was removed in vacuo. The resulting red solid was triturated with hexanes (180 mL) for one hour, and filtered. The solid was rinsed with hexanes (2×80 mL) and air dried. Chromatography on silica gel eluting with dichloromethane:methanol 39:1 then 19:1 to give the title compound (15.04 g, 46%).

Preparation 32

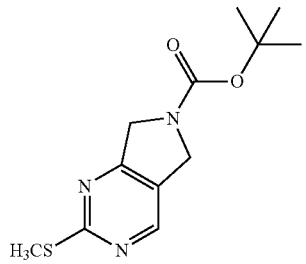

tert-butyl 2-(methylthio)-5,7-dihydro-6H-pyrrolo[3,4-d]pyrimidine-6-carboxylate A suspension of 2-methyl-2-thiopseudourea hemisulfate (3.79 g, 21.2 mmol) in ethanol (30 mL) was cooled in an ice bath. A solution of sodium ethoxide in ethanol (7.1 mL, 21 mmol, ~3 M) was added. The mixture was stirred for 50 minutes. A solution of 3-dimethylaminomethylene-4-oxo-pyrrolidine-1-carboxylic acid tert-butyl ester (1.70 g, 7.07 mmol) in ethanol (10 mL) was added and the mixture was heated at 80° C. for 16 hours. The solvent was removed in vacuo from the cooled mixture. The residue was partitioned between ethyl acetate and aqueous sodium bicarbonate. After separation, the aqueous layer was further extracted with ethyl acetate. The combined organic extracts were washed with brine, dried (MgSO$_4$), filtered and evaporated. The resulting oil was chromatographed on silica gel (40 g) eluted with ethyl acetate to give the title compound (1.43 g, 76%).

Preparation 33

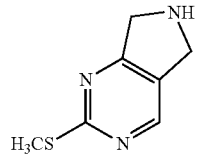

2-(Methylthio)-6,7-dihydro-5H-pyrrolo[3,4-d]pyrimidine

To a solution of tert-butyl 2-(methylthio)-5,7-dihydro-6H-pyrrolo[3,4-d]pyrimidine-6-carboxylate (1.43 g, 5.36 mmol) in dichloromethane (10 mL) was added a solution of trifluoroacetic acid (4.0 mL, 52 mmol) in dichloromethane (5 mL). The solution was stirred at room temperature for 3 hours. The dichloromethane was removed in vacuo. The residue was dissolved in water, treated with 5M sodium hydroxide to pH=14 and extracted with dichloromethane (5×10 mL). The organic layer was dried (MgSO$_4$) filtered and evaporated to give the title compound (870 mg, 97%).

Preparation 34

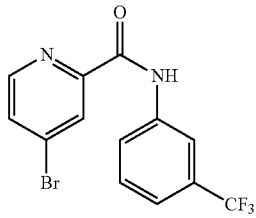 [SMILES: O=C(Nc1cccc(C(F)(F)F)c1)c1cc(Br)ccn1]

4-Bromo-N-(3-(trifluoromethyl)phenyl)picolinamide

To a suspension of 4-bromo-pyridine-2-carboxylic acid (1.00 g, 5.00 mmol) in dimethylformamide (5 mL) was added 1-methylmorpholine (1.1 mL, 10 mmol) and O-(7-azabenzotriazol-1-yl)-N,N,N',N'-tetramethyl-uronium hexafluorophosphate (HATU) (2.37 g, 6.23 mmol). The mixture became an orange solution after 10 minutes. 3-Trifluoromethylaniline (0.5 mL, 5.5 mmol) was added and the solution was stirred at room temperature for 21 hours. The dimethylformamide was evaporated in vacuo and the residue was triturated with water. The resulting solid was filtered and washed twice with water and then vacuum dried at 40° C. to give a crude residue. Chromatography on silica gel (40 g), sample applied in dichloromethane and eluted with hexanes:ethyl acetate (1:1) gave the title compound (1.306 g, 76%).

Preparation 35

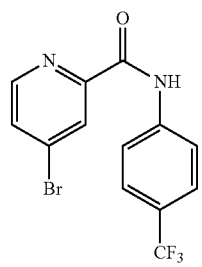 [SMILES: O=C(Nc1ccc(C(F)(F)F)cc1)c1cc(Br)ccn1]

4-Bromo-N-(4-(trifluoromethyl)phenyl)picolinamide

In a manner similar to that describe in Preparation 34, 4-bromo-pyridine-2-carboxylic acid and 4-trifluoromethylaniline were converted to the title compound.

Preparation 36

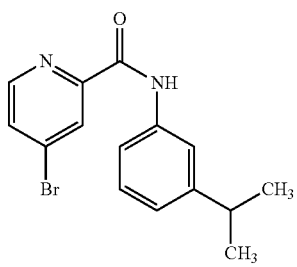 [SMILES: CC(C)c1cccc(NC(=O)c2cc(Br)ccn2)c1]

4-bromo-N-(3-isopropylphenyl)picolinamide

In a manner similar to that describe in Preparation 34, 4-bromo-pyridine-2-carboxylic acid and 3-isopropylaniline were converted to the title compound.

Preparation 37

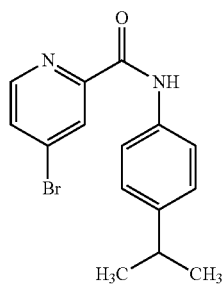

4-bromo-N-(4-isopropylphenyl)picolinamide

In a manner similar to that describe in Preparation 34, 4-bromo-pyridine-2-carboxylic acid and 4-isopropylaniline were converted to the title compound.

Example 126

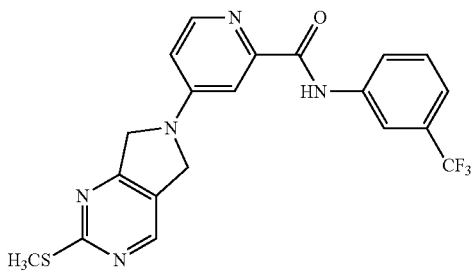

4-(2-Methylsulfanyl-5,7-dihydro-pyrrolo[3,4-d]pyrimidin-6-yl)-pyridine-2-carboxylic acid (3-trifluoromethyl-phenyl)-amide To a toluene (5 mL) solution of 4-Bromo-N-(3-(trifluoromethyl)phenyl)picolinamide (172 mg, 0.50 mmol) and 2-(Methylthio)-6,7-dihydro-5H-pyrrolo[3,4-d]pyrimidine (84 mg, 0.50 mmol) was added cesium carbonate (325 mg, 1.00 mmol). The mixture was purged with nitrogen and then (±)-2,2'-bis(diphenylphosphino)-1,1'-binaphthalene (31 mg, 0.05 mmol) and palladium(II) acetate (11 mg, 0.05 mmol) were added. The reaction was capped and heated at 100° C. for 7 hours. The cooled mixture was filtered. The solid was rinsed twice with ethyl acetate then with chloroform:methanol (9:1). The combined filtrate was evaporated in vacuo. The solid was triturated with hexanes:ethyl acetate (1:1) followed by ethyl acetate:methanol (9:1) and gave the title compound (96 mg). The filtrate was chromatographed on silica gel (12 g) eluted with hexanes:ethyl acetate (1:1) and gave additional title compound (25 mg). The total amount of the title compound obtained was 120 mg (0.28 mmol, yield 56%).

Example 127

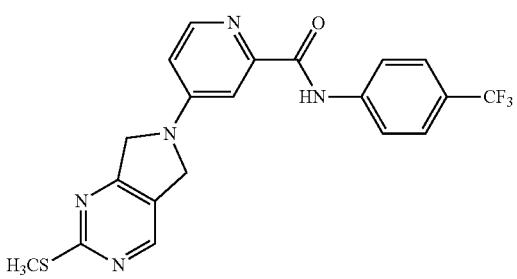

4-(2-Methylsulfanyl-5,7-dihydro-pyrrolo[3,4-d]pyrimidin-6-yl)-pyridine-2-carboxylic acid (4-trifluoromethyl-phenyl)-amide In a manner similar to that describe in Example 126, 2-(methylthio)-6,7-dihydro-5H-pyrrolo[3,4-d]pyrimidine and 4-Bromo-N-(4-(trifluoromethyl)phenyl)picolinamide were converted to the title compound.

Example 128

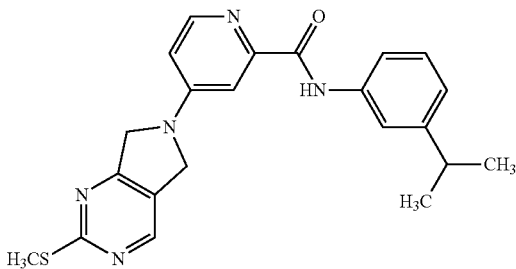

4-(2-Methylsulfanyl-5,7-dihydro-pyrrolo[3,4-d]pyrimidin-6-yl)-pyridine-2-carboxylic acid (3-isopropyl-phenyl)-amide In a manner similar to that describe in Example 126, 2-(methylthio)-6,7-dihydro-5H-pyrrolo[3,4-d]pyrimidine and 4-bromo-N-(3-isopropylphenyl)picolinamide were converted to the title compound.

Example 129

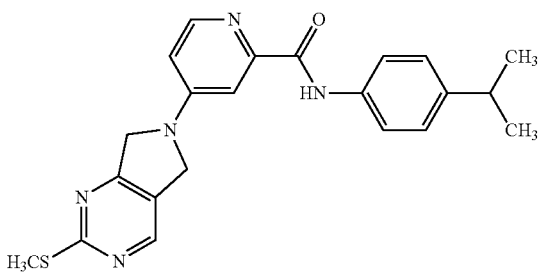

4-(2-Methylsulfanyl-5,7-dihydro-pyrrolo[3,4-d]pyrimidin-6-yl)-pyridine-2-carboxylic acid (4-isopropyl-phenyl)-amide In a manner similar to that describe in Example 126, 2-(methylthio)-6,7-dihydro-5H-pyrrolo[3,4-d]pyrimidine and 4-bromo-N-(4-isopropylphenyl)picolinamide were converted to the title compound.

Example 130

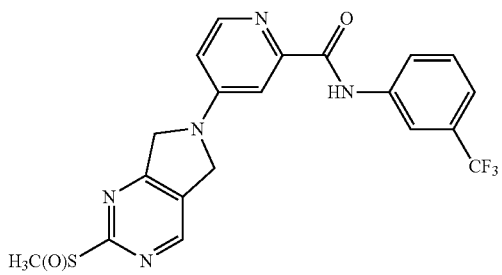

4-(2-(Methylsulfinyl)-5H-pyrrolo[3,4-d]pyrimidin-6(7H)-yl)-N-(3-(trifluoromethyl)phenyl)picolinamide A slurry of 4-(2-Methylsulfanyl-5,7-dihydro-pyrrolo[3,4-d]pyrimidin-6-yl)-pyridine-2-carboxylic acid (3-trifluoromethyl-phenyl)-amide (120 mg, 0.28 mmol) and potassium peroxomonosulfate (Oxone®, 184 mg, 0.30 mmol) in tetrahydrofuran (10 mL) and water (4 mL) was stirred at room temperature for 16 hours. To the reaction was added saturated aqueous sodium bisulfite and saturated aqueous sodium bicarbonate to adjust the pH to 7. The mixture was extracted with chloroform. The extract was washed with water, dried (MgSO$_4$), filtered and evaporated. The resulting solid was dissolved in dichloromethane:methanol (19:1), filtered and applied to chromatography on silica gel (12 g) and eluted with dichloromethane:methanol (19:1) and gave the title compound (15 mg, 0.032 mmol) and 4-(2-(methylsulfonyl)-5H-pyrrolo[3,4-d]pyrimidin-6(7H)-yl)-N-(3-(trifluoromethyl)phenyl)picolinamide (18 mg, 0.040 mmol).

Example 131

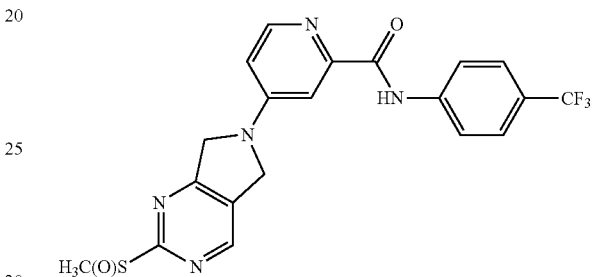

4-(2-Methylsulfanyl-5,7-dihydro-pyrrolo[3,4-d]pyrimidin-6-yl)-pyridine-2-carboxylic acid (4-trifluoromethyl-phenyl)-amide In a manner similar to that describe in Example 130, 4-(2-(methylsulfinyl)-5H-pyrrolo[3,4-d]pyrimidin-6(7H)-yl)-N-(4-(trifluoromethyl)phenyl)picolinamide was converted to the title compound.

Example 132

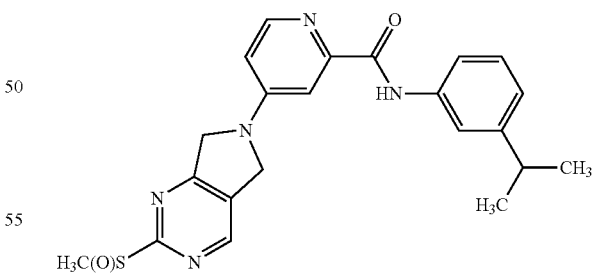

N-(3-isopropylphenyl)-4-(2-(methylsulfinyl)-5H-pyrrolo[3,4-d]pyrimidin-6(7H)-yl)picolinamide In a manner similar to that describe in Example 130, 4-(2-Methylsulfanyl-5,7-dihydro-pyrrolo[3,4-d]pyrimidin-6-yl)-pyridine-2-carboxylic acid (3-isopropyl-phenyl)-amide was converted to the title compound.

Example 133

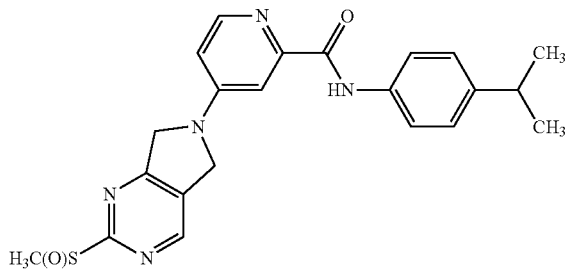

N-(4-isopropylphenyl)-4-(2-(methylsulfinyl)-5H-pyrrolo[3,4-d]pyrimidin-6(7H)-yl)picolinamide In a manner similar to that describe in Example 130, 4-(2-Methylsulfanyl-5,7-dihydro-pyrrolo[3,4-d]pyrimidin-6-yl)-pyridine-2-carboxylic acid (4-isopropyl-phenyl)-amide was converted to the title compound.

Example 134

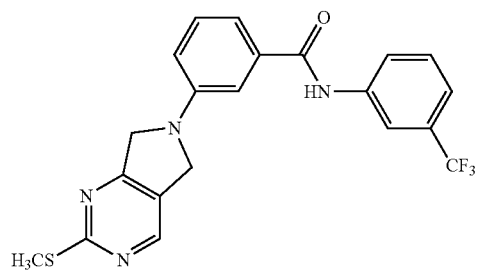

3-[2-(methylthio)-5,7-dihydro-6H-pyrrolo[3,4-d]pyrimidin-6-yl]-N-[3-(trifluoromethyl)phenyl]benzamide In a manner similar to that describe in Example 126, 2-(methylthio)-6,7-dihydro-5H-pyrrolo[3,4-d]pyrimidine and 3-Bromo-N-[3-(trifluoromethyl)phenyl]benzamide were converted to the title compound.

Example 135

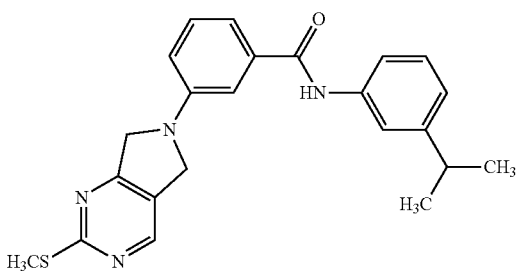

N-(3-isopropylphenyl)-3-[2-(methylthio)-5,7-dihydro-6H-pyrrolo[3,4-d]pyrimidin-6-yl]benzamide In a manner similar to that describe in Example 126, 2-(methylthio)-6,7-dihydro-5H-pyrrolo[3,4-d]pyrimidine and 3-bromo-N-(3-isopropylphenyl)benzamide were converted to the title compound.

Example 136

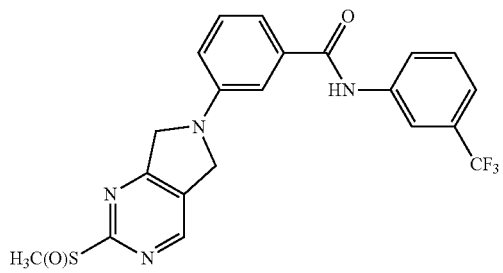

3-(2-(methylsulfinyl)-5H-pyrrolo[3,4-d]pyrimidin-6(7H)-yl)-N-(3-(trifluoromethyl)phenyl)benzamide In a manner similar to that describe in Example 130, 3-[2-(methylthio)-5,7-dihydro-6H-pyrrolo[3,4-d]pyrimidin-6-yl]-N-[3-(trifluoromethyl)phenyl]benzamide was converted to the title compound.

Example 137

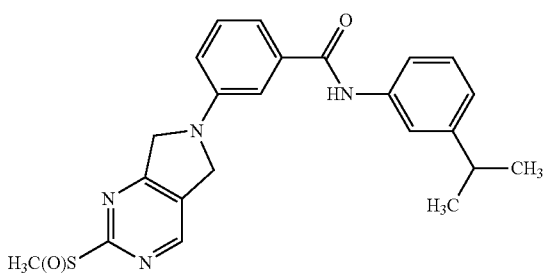

N-(3-isopropylphenyl)-3-(2-(methylsulfinyl)-5H-pyrrolo[3,4-d]pyrimidin-6(7H)-yl)benzamide In a manner similar to that describe in Example 130, N-(3-isopropylphenyl)-3-[2-(methylthio)-5,7-dihydro-6H-pyrrolo[3,4-d]pyrimidin-6-yl]benzamide was converted to the title compound.

Preparation 38

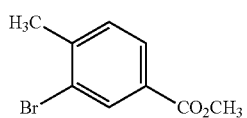

Methyl-3-bromo-4-methylbenzoate

A suspension of 3-bromo-4-methylbenzoic acid (2.0 g, 9.30 mmol) in methanol (20 ml) was treated with sulfuric acid (0.04 ml) and the reaction mixture was stirred at 60° C. for 42 hours. The reaction mixture was concentrated and the residue was taken up in ethyl acetate. The organic solution was washed with sat'd NaHCO3(aq.), dried (MgSO4), filtered, and concentrated to give the title compound as an orange oil which was suitable for use without further purification (2.25 g, quant.).

Preparation 39

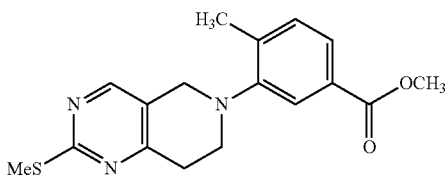 [SMILES: COC(=O)c1ccc(C)c(N2CCc3nc(SC)ncc3C2)c1]

Methyl-4-methyl-3-[2-(methylsulfanyl)-5,6,7,8-tetrahydropyrido[4,3-d]pyrimidin-6-yl]benzoate A mixture of 2-(methylsulfanyl)-5,6,7,8-tetrahydropyrido[4,3-d]pyrimidine (100 mg, 0.552 mmol), methyl-3-bromo-4-methylbenzoate (126 mg, 0.552 mmol), palladium(II)acetate (12.4 mg, 0.0552 mmol), rac-BINAP (34.4 mg, 0.0552 mmol), and cesium carbonate (252 mg, 0.773 mmol) in toluene (10 ml) was heated at 100° C. for 18 hours. Upon cooling, the reaction mixture was diluted with ethyl acetate and the insolubles were filtered off (celite). The filtrate was concentrated and the residue was eluted through a flash column (silica gel 60, 230-400 mesh, 4:1 hexanes:EtOAc to 7:3 hexanes:EtOAc) to obtain the title compound as a light yellow, viscous oil which crystallized on standing (143 mg, 79%).

Preparation 40

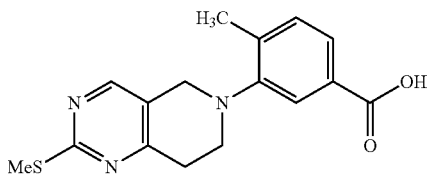 [SMILES: CSc1ncc2c(n1)CCN(c1cc(C(=O)O)ccc1C)C2]

4-Methyl-3-[2-(methylsulfanyl)-5,6,7,8-tetrahydropyrido[4,3-d]pyrimidin-6-yl]benzoic Acid A solution of methyl-4-methyl-3-[2-(methylsulfanyl)-5,6,7,8-tetrahydropyrido[4,3-d]pyrimidin-6-yl]benzoate (82 mg, 0.249 mmol) in 1,4-dioxane (5 ml) was treated with 1.0 N NaOH (aq.) (0.748 ml, 0.748 mmol) and the reaction mixture was heated at 100° C. for 15 hours. The solvent was removed in vacuo and the residue was taken up in water. The aqueous mixture was washed with EtOAc and acidified to pH~2-3 with 1.0 N HCl (aq.). The white, amorphous precipitate which formed was collected, washed with water, and dried to give the title compound (67 mg, 87%).

Preparation 41

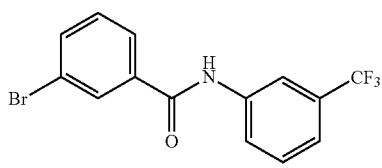 [SMILES: O=C(Nc1cccc(C(F)(F)F)c1)c1cccc(Br)c1]

3-Bromo-N-[3-(trifluoromethyl)phenyl]benzamide

A mixture of 3-bromobenzoic acid (500 mg, 2.49 mmol), 3-(trifluoromethyl)aniline (0.31 ml, 2.49 mmol) and DIEA (2.06 ml, 12.45 mmol) in DMF (6 ml) was treated with HATU (1.04 g, 2.74 mmol) and the reaction mixture was stirred at room temperature for 22 hours. The reaction mixture was partitioned between ethyl acetate and water and the organic phase was washed with sat'd NaCl$_{(aq.)}$, dried (MgSO$_4$), filtered, and concentrated. Elution through a flash column (silica gel 60, 230-400 mesh, 4:1 hexanes:EtOAc) gave a yellow oil which solidified on standing (622 mg, 73%).

Preparation 42

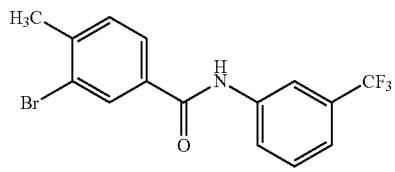 [SMILES: Cc1ccc(C(=O)Nc2cccc(C(F)(F)F)c2)cc1Br]

3-Bromo-4-methyl-N-[3-(trifluoromethyl)phenyl]benzamide

In a manner similar to that described in Preparation 41, 3-bromo-4-methylbenzoic acid (400 mg) and 3-(trifluoromethyl)aniline were converted to the title compound (410 mg, 62%)

Preparation 43

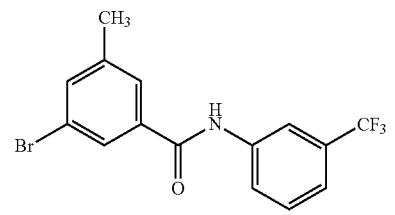 [SMILES: Cc1cc(Br)cc(C(=O)Nc2cccc(C(F)(F)F)c2)c1]

3-Bromo-5-methyl-N-[3-(trifluoromethyl)phenyl]benzamide

In a manner similar to that described in Preparation 41, 3-bromo-5-methylbenzoic acid (400 mg) and 3-(trifluoromethyl)aniline were converted to the title compound (388 mg, 58%).

Preparation 44

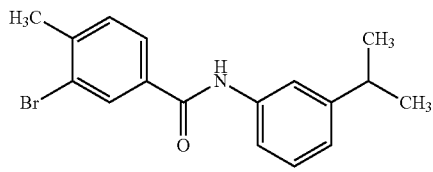 [SMILES: Cc1ccc(C(=O)Nc2cccc(C(C)C)c2)cc1Br]

3-bromo-N-(3-isopropylphenyl)-4-methylbenzamide

In a manner similar to that described in Preparation 41, 3-bromo-5-methylbenzoic acid (400 mg) and 3-isopropylaniline were converted to the title compound (618 mg, 100%).

Preparation 45

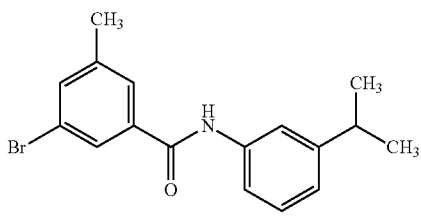 [SMILES: Cc1cc(Br)cc(C(=O)Nc2cccc(C(C)C)c2)c1]

3-bromo-N-(3-isopropylphenyl)-5-methylbenzamide

In a manner similar to that described in Preparation 41, 3-bromo-5-methylbenzoic acid (400 mg) and 3-isopropylaniline were converted to the title compound (615 mg, 99%).

Example 138

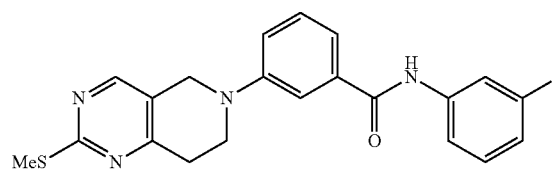

3-[2-(methylthio)-7,8-dihydropyrido[4,3-d]pyrimidin-6(5H)-yl]-N-[3-(trifluoromethyl)phenyl]benzamide A mixture of 3-bromo-N-[3-(trifluoromethyl)phenyl]benzamide (379 mg, 1.10 mmol), 2-(methylsulfanyl)-5,6,7,8-tetrahydropyrido[4,3-d]-pyrimidine (200 mg, 1.10 mmol), RuPhos (15.4 mg, 0.033 mmol), Cl-RuPhos-Pd precatalyst (24 mg, 0.033 mmol), and sodium-t-butoxide (148 mg, 1.54 mmol) in anhydrous THF (30 ml) was heated at 80° C. under nitrogen for 21 hours. Upon cooling, the reaction mixture was diluted with EtOAc and the insolubles were filtered off (celite). The filtrate was concentrated and the residue was eluted through a flash column (silica gel 60, 230-400 mesh, 1:1 hexanes:EtOAc) to obtain a yellow, crystalline solid (389 mg, 80%).

Example 139

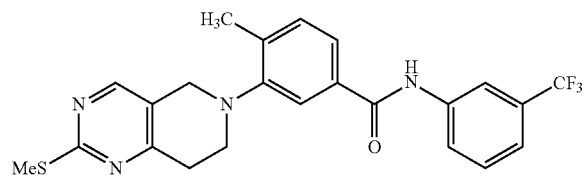 [SMILES: CSc1ncc2c(n1)CCN(c1cc(C(=O)Nc3cccc(C(F)(F)F)c3)ccc1C)C2]

4-methyl-3-[2-(methylthio)-7,8-dihydropyrido[4,3-d]pyrimidin-6(5H)-yl]-N-[3-(trifluoromethyl)phenyl]benzamide In a manner similar to that described for Example 138, 2-(methylsulfanyl)-5,6,7,8-tetrahydropyrido[4,3-d]-pyrimidine and 3-bromo-4-methyl-N-[3-(trifluoromethyl)phenyl]benzamide were converted to the title compound.

Example 140

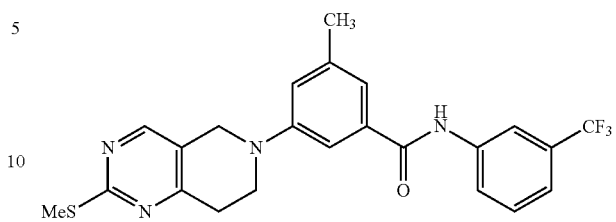

3-methyl-5-[2-(methylthio)-7,8-dihydropyrido[4,3-d]pyrimidin-6(5H)-yl]-N-[3-(trifluoromethyl)phenyl]benzamide In a manner similar to that described for Example 138, 2-(methylsulfanyl)-5,6,7,8-tetrahydropyrido[4,3-d]-pyrimidine and 3-bromo-N-(3-isopropylphenyl)-4-methylbenzamide were converted to the title compound.

Example 141

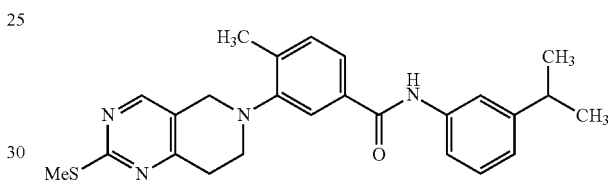

N-(3-isopropylphenyl)-4-methyl-3-[2-(methylthio)-7,8-dihydropyrido[4,3-d]pyrimidin-6(5H)-yl]benzamide A mixture of 4-methyl-3-[2-(methylsulfanyl)-5,6,7,8-tetrahydropyrido[4,3-d]pyrimidin-6-yl]benzoic acid (67 mg, 0.212 mmol), 3-isopropylaniline (0.03 ml, 0.212 mmol) and N,N'-diisopropylethylamine (0.18 ml, 1.06 mmol) in DMF (1.0 ml) was treated with HATU (89 mg, 0.233 mmol). After stirring at room temperature for 1.5 hours, the reaction mixture was partitioned between water and ethyl acetate. The organic phase was washed with sat'd NaCl (aq.), dried (MgSO4), filtered, and concentrated. Trituration of the residue with cold MeOH yielded the title compound as a white, crystalline solid (50 mg, 55%).

Example 142

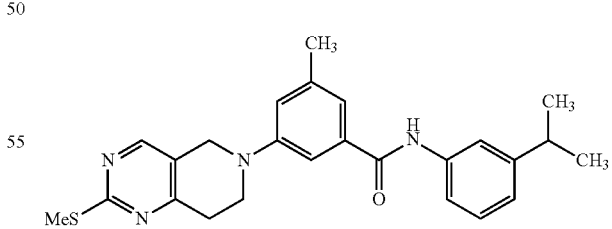

N-(3-isopropylphenyl)-3-methyl-5-[2-(methylthio)-7,8-dihydropyrido[4,3-d]pyrimidin-6(5H)-yl]benzamide In a manner similar to that described for Example 138, 2-(methylsulfanyl)-5,6,7,8-tetrahydropyrido[4,3-d]-pyrimidine and 3-bromo-N-(3-isopropylphenyl)-5-methylbenzamide were converted to the title compound.

Example 143

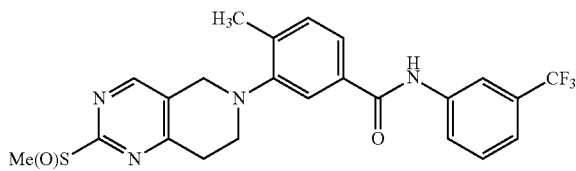

4-methyl-3-(2-(methylsulfinyl)-7,8-dihydropyrido[4,3-d]pyrimidin-6(5H)-yl)-N-(3-(trifluoromethyl)phenyl)benzamide In a manner similar to that described for Example 109, 4-methyl-3-[2-(methylthio)-7,8-dihydropyrido[4,3-d]pyrimidin-6(5H)-yl]-N-[3-(trifluoromethyl)phenyl]benzamide was converted to the title compound.

Example 144

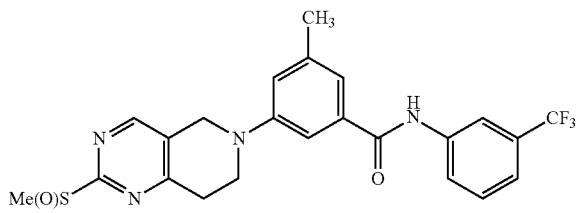

3-methyl-5-(2-(methylsulfinyl)-7,8-dihydropyrido[4,3-d]pyrimidin-6(5H)-yl)-N-(3-(trifluoromethyl)phenyl)benzamide In a manner similar to that described for Example 109, 3-methyl-5-[2-(methylthio)-7,8-dihydropyrido[4,3-d]pyrimidin-6(5H)-yl]-N-[3-(trifluoromethyl)phenyl]benzamide was converted to the title compound.

Example 145

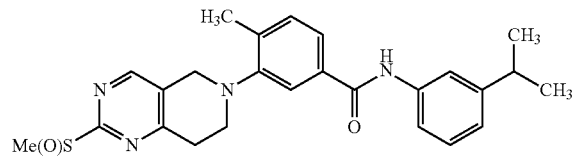

N-(3-isopropylphenyl)-4-methyl-3-(2-(methylsulfinyl)-7,8-dihydropyrido[4,3-d]pyrimidin-6(5H)-yl)benzamide In a manner similar to that described for Example 109, N-(3-isopropylphenyl)-4-methyl-3-[2-(methylthio)-7,8-dihydropyrido[4,3-d]pyrimidin-6(5H)-yl]benzamide was converted to the title compound.

Example 146

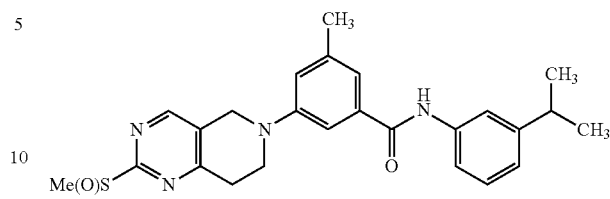

N-(3-isopropylphenyl)-3-methyl-5-(2-(methylsulfinyl)-7,8-dihydropyrido[4,3-d]pyrimidin-6(5H)-yl)benzamide In a manner similar to that described for Example 109, N-(3-isopropylphenyl)-3-methyl-5-[2-(methylthio)-7,8-dihydropyrido[4,3-d]pyrimidin-6(5H)-yl]benzamide was converted to the title compound.

Example 147

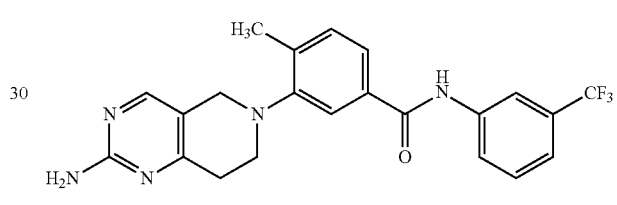

3-(2-amino-7,8-dihydropyrido[4,3-d]pyrimidin-6(5H)-yl)-4-methyl-N-[3-(trifluoromethyl)phenyl]benzamide In a manner similar to that described for Example 82, 4-methyl-3-(2-(methylsulfinyl)-7,8-dihydropyrido[4,3-d]pyrimidin-6(5H)-yl)-N-(3-(trifluoromethyl)phenyl)benzamide was converted to the title compound.

Example 148

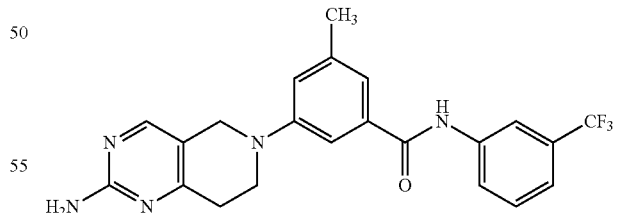

3-(2-amino-7,8-dihydropyrido[4,3-d]pyrimidin-6(5H)-yl)-5-methyl-N-[3-(trifluoromethyl)phenyl]benzamide In a manner similar to that described for Example 82, 3-methyl-5-(2-(methylsulfinyl)-7,8-dihydropyrido[4,3-d]pyrimidin-6(5H)-yl)-N-(3-(trifluoromethyl)phenyl)benzamide was converted to the title compound.

Example 149

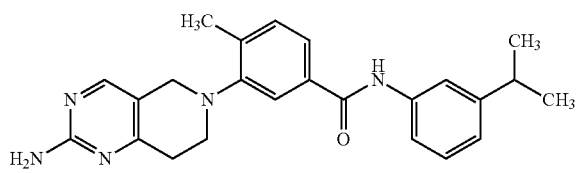 [SMILES: Cc1ccc(C(=O)Nc2cccc(C(C)C)c2)cc1N1CCc2nc(N)ncc2C1]

3-(2-amino-7,8-dihydropyrido[4,3-d]pyrimidin-6 (5H)-yl)-N-(3-isopropylphenyl)-4-methylbenzamide In a manner similar to that described for Example 82, N-(3-isopropylphenyl)-4-methyl-3-(2-(methylsulfinyl)-7,8-dihydropyrido[4,3-d]pyrimidin-6(5H)-yl)benzamide was converted to the title compound.

Example 150

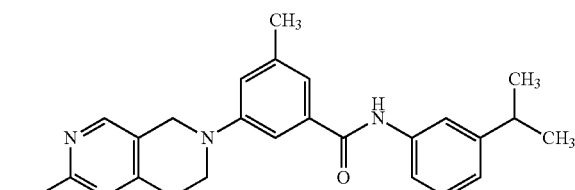

3-(2-amino-7,8-dihydropyrido[4,3-d]pyrimidin-6 (5H)-yl)-N-(3-isopropylphenyl)-5-methylbenzamide In a manner similar to that described for Example 82, N-(3-isopropylphenyl)-3-methyl-5-(2-(methylsulfinyl)-7,8-dihydropyrido[4,3-d]pyrimidin-6(5H)-yl)benzamide was converted to the title compound.

Example 151

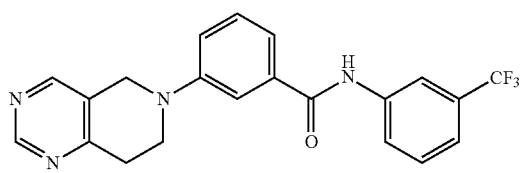 [SMILES: O=C(Nc1cccc(C(F)(F)F)c1)c1cccc(N2CCc3ncncc3C2)c1]

3-(7,8-dihydropyrido[4,3-d]pyrimidin-6(5H)-yl)-N-[3-(trifluoromethyl)phenyl]benzamide A suspension of 3-[2-(methylthio)-7,8-dihydropyrido[4,3-d]pyrimidin-6(5H)-yl]-N-[3-(trifluoromethyl)phenyl]benzamide 3 (150 mg, 0.337 mmol) in ethanol (15 ml) was treated with Raney Nickel (~150 mg, slurry in water) and the reaction mixture was stirred under 1 atm. H₂ at 60° C. for 18 hours. The catalyst was filtered off (celite) and the filtrate was concentrated. Elution through a flash column (silica gel 60, 230-400 mesh, EtOAc) gave the title compound as a yellow oil which solidified to a glass (84 mg, 63%).

Example 152

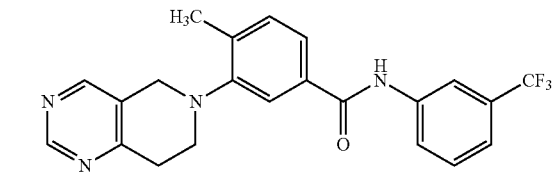 [SMILES: Cc1ccc(C(=O)Nc2cccc(C(F)(F)F)c2)cc1N1CCc2ncncc2C1]

3-(7,8-dihydropyrido[4,3-d]pyrimidin-6(5H)-yl)-4-methyl-N-[3-(trifluoromethyl)phenyl]benzamide In a manner similar to Example 151, 4-methyl-3-[2-(methylthio)-7,8-dihydropyrido[4,3-d]pyrimidin-6(5H)-yl]-N-[3-(trifluoromethyl)phenyl]benzamide was converted to the title compound

Example 153

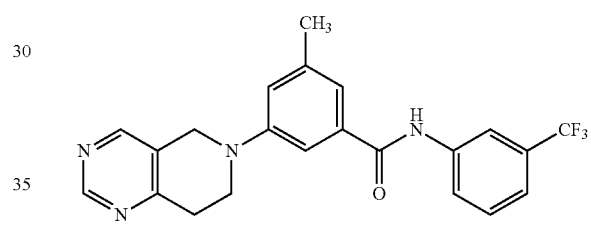

3-(7,8-dihydropyrido[4,3-d]pyrimidin-6(5H)-yl)-5-methyl-N-[3-(trifluoromethyl)phenyl]benzamide In a manner similar to Example 151, 3-methyl-5-[2-(methylthio)-7,8-dihydropyrido[4,3-d]pyrimidin-6(5H)-yl]-N-[3-(trifluoromethyl)phenyl]benzamide was converted to the title compound

Example 154

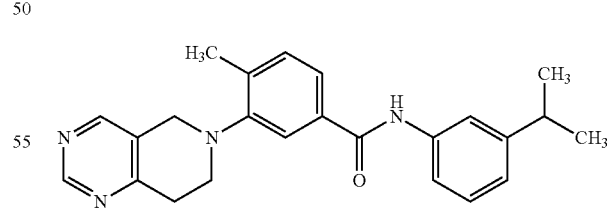

3-(7,8-dihydropyrido[4,3-d]pyrimidin-6(5H)-yl)-N-(3-isopropylphenyl)-4-methylbenzamide In a manner similar to Example 151, N-(3-isopropylphenyl)-4-methyl-3-[2-(methylthio)-7,8-dihydropyrido[4,3-d]pyrimidin-6(5H)-yl]benzamide was converted to the title compound

Example 155

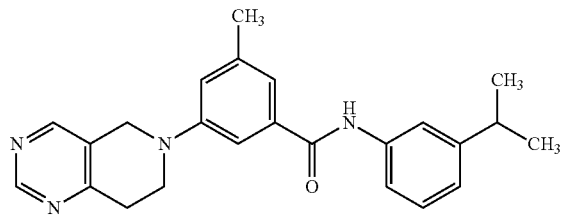 [SMILES: Cc1cc(C(=O)Nc2cccc(C(C)C)c2)cc(N2CCc3ncncc3C2)c1]

3-(7,8-dihydropyrido[4,3-d]pyrimidin-6(5H)-yl)-N-(3-isopropylphenyl)-5-methylbenzamide In a manner similar to Example 151, N-(3-isopropylphenyl)-3-methyl-5-[2-(methylthio)-7,8-dihydropyrido[4,3-d]pyrimidin-6(5H)-yl]benzamide was converted to the title compound.

Preparation 46

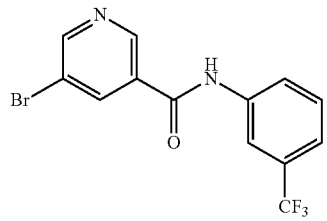 [SMILES: O=C(Nc1cccc(C(F)(F)F)c1)c1cncc(Br)c1]

5-bromo-N-(3-(trifluoromethyl)phenyl)nicotinamide

In a manner similar to that described in Preparation 17, 5-bromonicotinic acid and 3-trifluoromethylaniline were converted to the title compound

Preparation 47

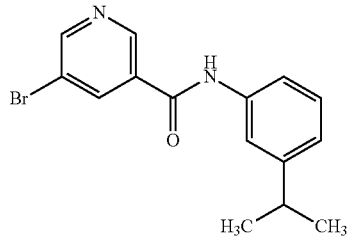 [SMILES: CC(C)c1cccc(NC(=O)c2cncc(Br)c2)c1]

5-bromo-N-(3-isopropylphenyl)nicotinamide

In a manner similar to that described in Preparation 17, 5-bromonicotinic acid and 3-isopropylaniline were converted to the title compound

Example 156

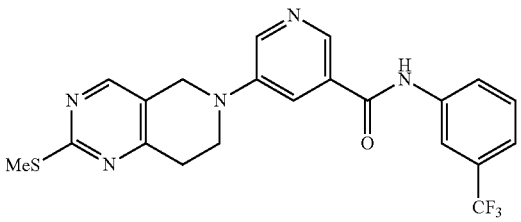 [SMILES: Nc1ncc2c(n1)CCN(c1cncc(C(=O)Nc3cccc(C(F)(F)F)c3)c1)C2]

5-(2-Methylsulfanyl-7,8-dihydro-5H-pyrido[4,3-d]pyrimidin-6-yl)-N-(3-trifluoromethyl-phenyl)-nicotinamide In a manner similar to that described for Example 138, 2-(methylsulfanyl)-5,6,7,8-tetrahydropyrido[4,3-d]-pyrimidine and 5-bromo-N-(3-(trifluoromethyl)phenyl)nicotinamide were converted to the title compound.

Example 157

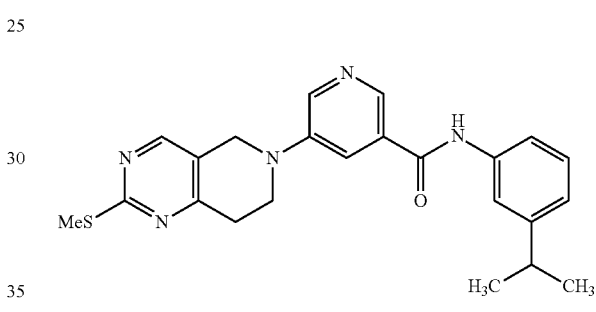

N-(3-Isopropyl-phenyl)-5-(2-methylsulfanyl-7,8-dihydro-5H-pyrido[4,3-d]pyrimidin-6-yl)-nicotinamide In a manner similar to that described for Example 138, 2-(methylsulfanyl)-5,6,7,8-tetrahydropyrido[4,3-d]-pyrimidine and 5-bromo-N-(3-isopropylphenyl)nicotinamide were converted to the title compound.

Example 158

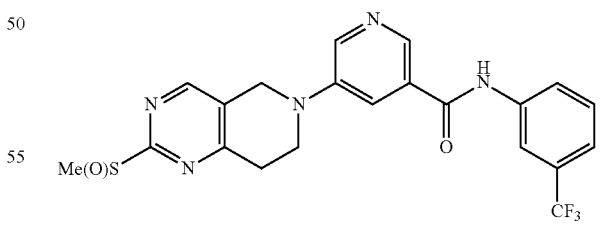

5-(2-(methylsulfinyl)-7,8-dihydropyrido[4,3-d]pyrimidin-6(5H)-yl)-N-(3-(trifluoromethyl)phenyl)nicotinamide In a manner similar to that described for Example 109, 5-(2-Methylsulfanyl-7,8-dihydro-5H-pyrido[4,3-d]pyrimidin-6-yl)-N-(3-trifluoromethyl-phenyl)-nicotinamide was converted to the title compound.

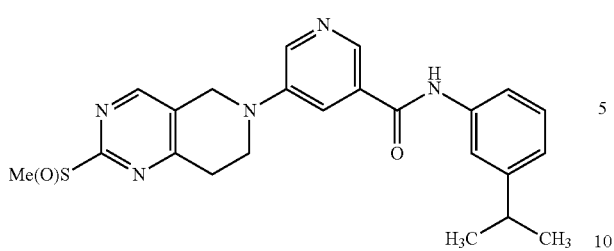

N-(3-Isopropyl-phenyl)-5-(2-methanesulfinyl-7,8-dihydro-5H-pyrido[4,3-d]pyrimidin-6-yl)-nicotinamide In a manner similar to that described for Example 109, N-(3-Isopropyl-phenyl)-5-(2-methylsulfanyl-7,8-dihydro-5H-pyrido[4,3-d]pyrimidin-6-yl)-nicotinamide was converted to the title compound.

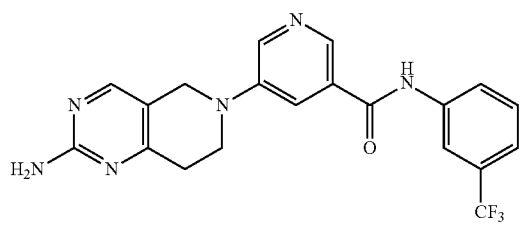

5-(2-amino-7,8-dihydropyrido[4,3-d]pyrimidin-6(5H)-yl)-N-[3-(trifluoromethyl)phenyl]nicotinamide In a manner similar to that described for Example 82, 5-(2-(methylsulfinyl)-7,8-dihydropyrido[4,3-d]pyrimidin-6(5H)-yl)-N-(3-(trifluoromethyl)phenyl)nicotinamide was converted to the title compound.

Example 161

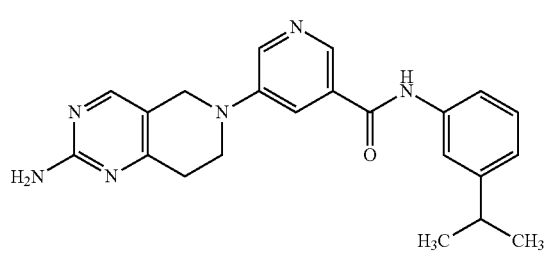 [SMILES: CC(C)c1cccc(NC(=O)c2cncc(N3CCc4nc(N)ncc4C3)c2)c1]

5-(2-amino-7,8-dihydropyrido[4,3-d]pyrimidin-6(5H)-yl)-N-(3-isopropylphenyl)nicotinamide In a manner similar to that described for Example 82, N-(3-Isopropyl-phenyl)-5-(2-methanesulfinyl-7,8-dihydro-5H-pyrido[4,3-d]pyrimidin-6-yl)-nicotinamide was converted to the title compound.

Preparation 48

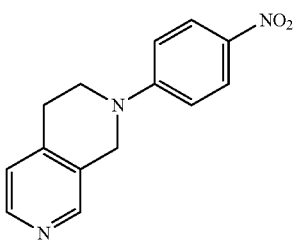 [SMILES: O=[N+]([O-])c1ccc(N2CCc3ccncc3C2)cc1]

2-(4-nitrophenyl)-1,2,3,4-tetrahydro-2,7-naphthyridine

Commercially available 1,2,3,4-tetrahydro-2,7-naphthyridine hydrochloride (14.5 g; 0.085 moles), 4-fluoronitrobenzene (18.0 g; 0.13 moles) and potassium carbonate (37.5 g, 0.27 moles) in anhydrous DMF (100 mL) were heated at 80° C. for 18 hours, cooled and partitioned between ethyl acetate (500 mL) and water (1 L). The layers were separated and the aqueous layer re-extracted with ethyl acetate (300 mL). The combined organic layers were washed with water (400 mL), brine, dried over sodium sulfate and evaporated in vacuo. Chromatography of the residue on silica (250 g) eluting with 20% ethyl acetate in DCM then 7.5% methanol in ethyl acetate gave the title compound (15 g) as an orange solid.

Preparation 49

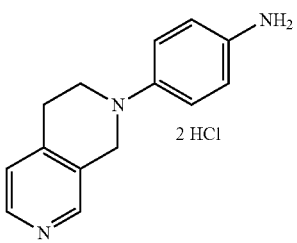 [SMILES: Nc1ccc(N2CCc3ccncc3C2)cc1]

4-(3,4-dihydro-2,7-naphthyridin-2(1H)-yl)aniline dihydrochloride

A solution of 2-(4-nitrophenyl)-1,2,3,4-tetrahydro-2,7-naphthyridine (11.5 g; 0.045 mol) in IMS (230 mL) was hydrogenated under a hydrogen balloon in the presence of 10% Pd/C (1.2 g). After 3.5 hours tlc analysis indicated the reaction was complete. The hydrogen atmosphere was replaced by argon and degassed DCM (100 mL) was added to re-dissolve the precipitated product. The mixture was filtered through Celite and washed through with degassed DCM:IMS (1:1; 200 mL). To the yellow filtrate was quickly added concentrated hydrochloric acid (40 mL) with stirring and a precipitate crashed out after a few seconds. After 10 minutes, the mixture was filtered, washed with 1:1 DCM:IMS then twice with ether. The off-yellow product was dried in vacuo at 50° C. to afford the title compound as a beige solid (11 g) m.p.>220° C. $^1$H NMR (DMSO-d6) δ: 8.82 (s, 1H), 8.68 (d, J=6.2 Hz, 1H), 7.86 (d, J=5.9 Hz, 1H), 7.26-7.32 (m, 2H), 7.10-7.16 (m, 2H), 4.61 (s, 2H), 3.67 (t, J=5.9 Hz, 2H), 3.17 (t, J=5.7 Hz, 2H)

Example 162

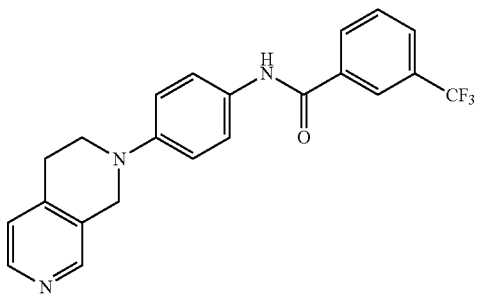 [SMILES: O=C(Nc1ccc(N2CCc3ccncc3C2)cc1)c1cccc(C(F)(F)F)c1]

N-[4-(3,4-dihydro-2,7-naphthyridin-2(1H)-yl)phenyl]-3-(trifluoromethyl)benzamide To a mixture of 4-(3,4-dihydro-2,7-naphthyridin-2(1H)-yl)aniline dihydrochloride (75.0 mg, 0.251 mmol) and N,N-diisopropylethylamine (0.153 mL, 0.88 mmol) in 3.0 mL CH$_2$Cl$_2$ at rt was added 3-(trifluoromethyl)benzoyl chloride (0.041 mL, 0.277 mmol) and the reaction stirred for 15 min at rt. The reaction was evaporated, then partitioned between EtOAc and H$_2$O/brine mixture, the EtOAc layer washed with aqueous Na$_2$CO$_3$ solution, brine, and dried with anhydrous Na$_2$SO$_4$. The EtOAc solution was filtered past a silica gel plug, rinsed with EtOAc, and evaporated to a yellow solid. The solid was recrystallized from EtOAc/hexane to give the title compound as a light tan solid (83 mg, 83%). $^1$H NMR (DMSO-d6) δ: 10.28 (s, 1H), 8.44 (s, 1H), 8.32 (d, J=5.0 Hz, 1H), 8.23-8.30 (m, 2H), 7.95 (d, J=7.9 Hz, 1H), 7.74-7.80 (m, 1H), 7.61-7.68 (m, 2H), 7.19 (dd, J=5.0, 0.6 Hz, 1H), 7.03-7.09 (m, 2H), 4.40 (s, 2H), 3.54 (t, J=5.9 Hz, 2H), 2.93 (t, J=5.9 Hz, 2H).

Example 163

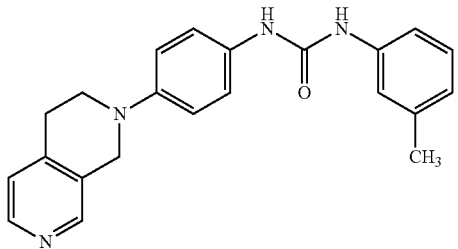 [SMILES: Cc1cccc(NC(=O)Nc2ccc(N3CCc4ccncc4C3)cc2)c1]

1-[4-(3,4-dihydro-2,7-naphthyridin-2(1H)-yl)phenyl]-3-(3-methylphenyl)urea

To a mixture of 4-(3,4-dihydro-2,7-naphthyridin-2(1H)-yl)aniline dihydrochloride (75.0 mg, 0.251 mmol) and N,N-diisopropylethylamine (0.109 mL, 0.63 mmol) in 3.0 mL CH$_2$Cl$_2$ at rt was added meta-tolyl isocyanate (0.047 mL, 0.377 mmol) and the reaction stirred at rt for 2 hours. The reaction was quenched with 1.0 mL MeOH, stirred for 15 min and then evaporated. The sample was partitioned between EtOAc and H$_2$O/brine mixture, the EtOAc layer washed with aqueous Na$_2$CO$_3$ solution, brine, dried with anhydrous Na$_2$SO$_4$, and evaporated to a tan solid. The solid was chromatographed eluting with CH$_2$Cl$_2$, EtOAc, then 3% MeOH/EtOAc to give the title compound as a white solid (79 mg, 88%). $^1$H NMR (DMSO-d6) δ: 8.45 (s, 1H), 8.42 (s, 1H), 8.37 (s, 1H), 8.31 (d, J=5.0 Hz, 1H), 7.29-7.35 (m, 2H), 7.28 (s, 1H), 7.16-7.23 (m, 2H), 7.10-7.16 (m, 1H), 6.96-7.02 (m, 2H), 6.76 (d, J=7.0 Hz, 1H), 4.33 (s, 2H), 3.47 (t, J=5.9 Hz, 2H), 2.91 (t, J=5.7 Hz, 2H), 2.27 (s, 3H).

Example 164

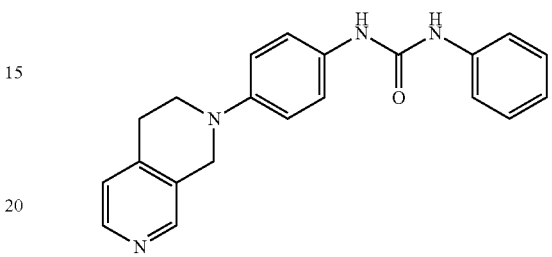

1-[4-(3,4-dihydro-2,7-naphthyridin-2(1H)-yl)phenyl]-3-phenylurea

In a manner similar to that described in Example 163, 4-(3,4-dihydro-2,7-naphthyridin-2(1H)-yl)aniline dihydrochloride (75.0 mg, 0.251 mmol) and phenyl isocyanate (0.041 mL, 0.377 mmol) were reacted to give the title compound as an off-white solid (52 mg, 60%). $^1$H NMR (DMSO-d6) δ 8.53 (s, 1H), 8.42 (s, 1H), 8.39 (s, 1H), 8.31 (d, J=4.7 Hz, 1H), 7.43 (d, J=7.6 Hz, 2H), 7.33 (d, J=9.1 Hz, 2H), 7.26 (t, J=7.8 Hz, 2H), 7.18 (d, J=5.0 Hz, 1H), 6.99 (d, J=9.1 Hz, 2H), 6.94 (t, J=7.3 Hz, 1H), 4.33 (s, 2H), 3.47 (t, J=5.9 Hz, 2H), 2.91 (t, J=5.7 Hz, 2H).

Example 165

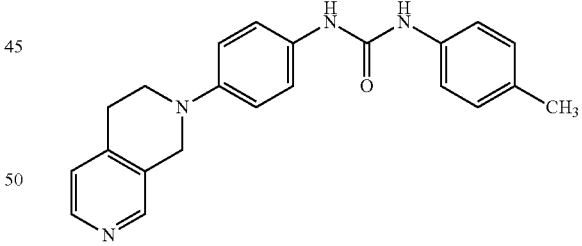

1-[4-(3,4-dihydro-2,7-naphthyridin-2(1H)-yl)phenyl]-3-(4-methylphenyl)urea

In a manner similar to that described in Example 163, 4-(3,4-dihydro-2,7-naphthyridin-2(1H)-yl)aniline dihydrochloride (75.0 mg, 0.251 mmol) and para-tolyl isocyanate (0.047 mL, 0.377 mmol) were reacted to give the title compound as a white solid (64 mg, 71%). $^1$H NMR (DMSO-d6) δ: 8.42 (s, 2H), 8.34 (s, 1H), 8.31 (d, J=5.0 Hz, 1H), 7.29-7.34 (m, 4H), 7.17 (d, J=5.3 Hz, 1H), 7.06 (d, J=8.5 Hz, 2H), 6.95-7.02 (m, 2H), 4.33 (s, 2H), 3.47 (t, J=5.9 Hz, 2H), 2.91 (t, J=5.9 Hz, 2H), 2.23 (s, 3H).

Preparation 50

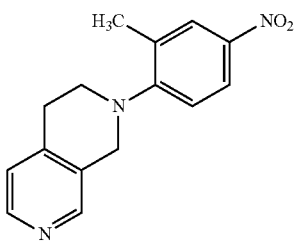 [SMILES: Cc1cc([N+](=O)[O-])ccc1N1CCc2ccncc2C1]

2-(2-methyl-4-nitrophenyl)-1,2,3,4-tetrahydro-2,7-naphthyridine

A mixture of commercially available 1,2,3,4-tetrahydro-2,7-naphthyridine dihydrochloride (456 mg, 2.2 mmol), 2-fluoro-5-nitrotoluene (512 mg, 3.3 mmol), and N,N-diisopropylethylamine (2.0 mL, 11.4 mmol) in 8.0 mL DMSO was heated at 115° C. for 20 hours. The reaction was added to a $H_2O$/brine mixture, then extracted with EtOAc. The EtOAc portion was washed with a $H_2O$/brine mixture, aqueous $Na_2CO_3$ solution, dried with anhydrous $Na_2SO_4$, and evaporated to an oil. An impure sample from a previous reaction (1.0 mmol scale) was combined, and then chromatographed eluting with $CHCl_3$/EtOAc to give the title compound as a yellow solid (365 mg, 42% combined yield). $^1$H NMR ($CDCl_3$) δ: 8.40-8.43 (m, 2H), 8.05-8.11 (m, 2H), 7.14 (d, J=5.0 Hz, 1H), 7.11 (d, J=8.5 Hz, 1H), 4.27 (s, 2H), 3.36 (t, J=5.7 Hz, 2H), 3.04 (t, J=5.6 Hz, 2H), 2.42 (s, 3H).

Preparation 51

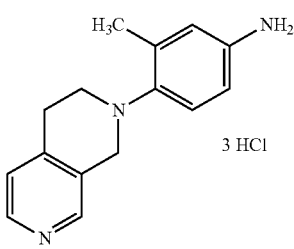 [SMILES: Cc1cc(N)ccc1N1CCc2ccncc2C1]

4-(3,4-dihydro-2,7-naphthyridin-2(1H)-yl)-3-methylaniline trihydrochloride

A mixture of 2-(2-methyl-4-nitrophenyl)-1,2,3,4-tetrahydro-2,7-naphthyridine (23 mg, 0.085 mmol) and platinum oxide (10 mg) in 2 mL MeOH was hydrogenated using 55 PSI hydrogen. After 18 hours, the mixture was filtered past Celite into a solution of MeOH containing excess aqueous HCl. The MeOH solution was evaporated, chased with MeOH and then EtOAc to give the title compound as a beige solid (27 mg, 93%). $^1$H NMR ($CD_3OD$) δ: 8.72 (s, 1H), 8.62 (dd, J=6.0, 0.7 Hz, 1H), 7.95 (d, J=6.2 Hz, 1H), 7.24-7.37 (m, 3H), 4.35 (s, 2H), 3.35 (s, 4H), 2.40 (s, 3H).

Example 166

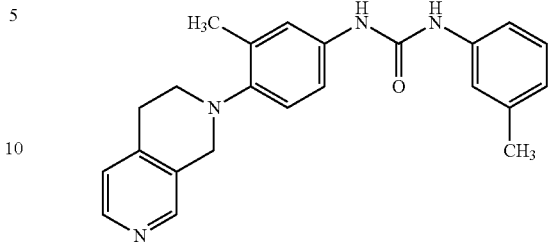

1-[4-(3,4-dihydro-2,7-naphthyridin-2(1H)-yl)-3-methylphenyl]-3-(3-methylphenyl)urea To a mixture of 4-(3,4-dihydro-2,7-naphthyridin-2(1H)-yl)-3-methylaniline trihydrochloride (24.7 mg, 0.071 mmol) and N,N-diisopropylethylamine (0.043 mL, 0.25 mmol) in 1.0 mL $CH_2Cl_2$ at rt was added meta-tolyl isocyanate (0.013 mL, 0.106 mmol) and the reaction stirred at rt for 1.5 hours. The reaction was quenched into a brine/aqueous $Na_2CO_3$ solution, then extracted with EtOAc. The EtOAc layer was washed with brine/aqueous $Na_2CO_3$ solution, dried with anhydrous $Na_2SO_4$, and evaporated to an oily solid. The oil was chromatographed eluting with $CHCl_3$/EtOAc plus 0.5% MeOH to give the title compound as a faint yellow solid (26 mg, 97%). $^1$H NMR (Acetone-d6) δ: 8.35 (s, 1H), 8.32 (d, J=5.0 Hz, 1H), 7.97 (s, 1H), 7.93 (s, 1H), 7.29-7.40 (m, 4H), 7.08-7.17 (m, 3H), 6.80 (d, J=7.3 Hz, 1H), 4.07 (s, 2H), 3.15-3.20 (m, 2H), 2.97-3.03 (m, 2H), 2.30 (s, 3H), 2.29 (s, 3H)

Preparation 52

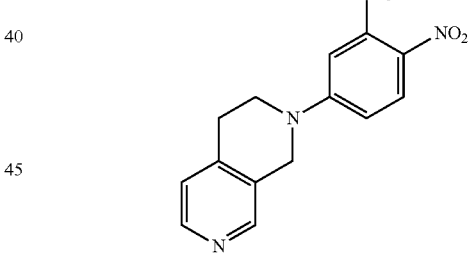

2-(3-methyl-4-nitrophenyl)-1,2,3,4-tetrahydro-2,7-naphthyridine

A mixture of commercially available 1,2,3,4-tetrahydro-2,7-naphthyridine dihydrochloride (207 mg, 1.0 mmol), 5-fluoro-2-nitrotoluene (0.244 mL, 2.0 mmol), and $Na_2CO_3$ (0.53 g, 5.0 mmol) in 3.0 mL NMP was heated at 110° C. for 2.5 hours. The solids were filtered off and then rinsed with EtOAc. The EtOAc portion was washed with a $H_2O$/brine mixture, $H_2O$, brine, dried with anhydrous $Na_2SO_4$, and evaporated to an oil. The oil was chromatographed eluting with $CHCl_3$/EtOAc and the resulting solid triturated with EtOAc/hexane to give the title compound as a yellow solid (123 mg, 45%). $^1$H NMR ($CDCl_3$) δ: 8.48 (s, 1H), 8.44 (d, J=5.3 Hz, 1H), 8.14 (d, J=9.1 Hz, 1H), 7.15 (d, J=5.0 Hz, 1H), 6.76 (dd, J=9.2, 2.8 Hz, 1H), 6.68 (d, J=2.9 Hz, 1H), 4.58 (s, 2H), 3.71 (t, J=5.9 Hz, 2H), 3.01 (t, J=5.9 Hz, 2H), 2.68 (s, 3H)

Preparation 53

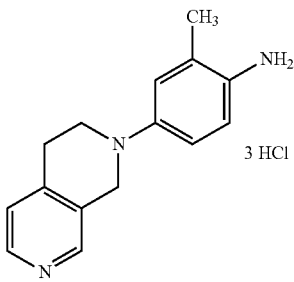 [SMILES: Cc1cc(N2CCc3ccncc3C2)ccc1N]

4-(3,4-dihydro-2,7-naphthyridin-2(1H)-yl)-2-methylaniline trihydrochloride

In a manner similar to that describe in Preparation 163, 2-(3-methyl-4-nitrophenyl)-1,2,3,4-tetrahydro-2,7-naphthyridine (114 mg, 0.42 mmol) was hydrogenated to give the title compound as a light beige solid (148 mg, 100%). $^1$H NMR (DSMO-d6) δ: 8.82 (s, 1H), 8.69 (d, J=6.2 Hz, 1H), 7.89 (d, J=6.2 Hz, 1H), 7.34 (d, J=8.8 Hz, 1H), 7.02 (d, J=2.6 Hz, 1H), 6.94 (dd, J=8.8, 2.6 Hz, 1H), 4.61 (s, 2H), 3.66 (t, J=5.9 Hz, 2H), 3.17 (t, J=5.9 Hz, 2H), 2.33 (s, 3H)

Example 167

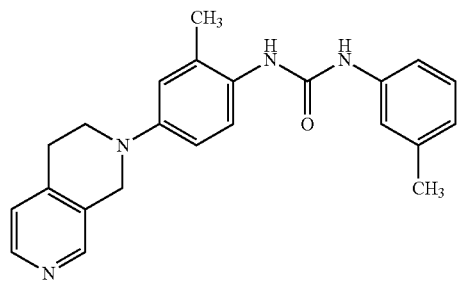 [SMILES: Cc1cccc(NC(=O)Nc2ccc(N3CCc4ccncc4C3)cc2C)c1]

1-[4-(3,4-dihydro-2,7-naphthyridin-2(1H)-yl)-2-methylphenyl]-3-(3-methylphenyl)urea To a mixture of 4-(3,4-dihydro-2,7-naphthyridin-2(1H)-yl)-2-methylaniline trihydrochloride (35 mg, 0.10 mmol) and N,N-diisopropylethylamine (0.061 mL, 0.35 mmol) in 1.5 mL CH$_2$Cl$_2$ at rt was added meta-tolyl isocyanate (0.019 mL, 0.15 mmol) and the reaction stirred at rt for 3 hours. The reaction was quenched into a brine/aqueous Na$_2$CO$_3$ solution, then extracted with EtOAc. The EtOAc layer was washed with brine/aqueous Na$_2$CO$_3$ solution, dried with anhydrous Na$_2$SO$_4$, and evaporated to a solid. The solid was triturated with EtOAc and then with 20% CHCl$_3$/EtOAc to give the title compound as a beige solid (21 mg, 56%). $^1$H NMR (Acetone-d6) δ: 8.44 (s, 1H), 8.31 (d, J=5.0 Hz, 1H), 8.07 (s, 1H), 7.56-7.61 (m, 1H), 7.35-7.38 (m, 1H), 7.26-7.34 (m, 2H), 7.08-7.16 (m, 2H), 6.92-6.95 (m, 1H), 6.87-6.92 (m, 1H), 6.75-6.80 (m, 1H), 4.39 (s, 2H), 3.55 (t, J=5.9 Hz, 2H), 2.98 (td, J=5.9, 0.9 Hz, 2H), 2.27 (s, 3H), 2.26 (s, 3H)

Preparation 54

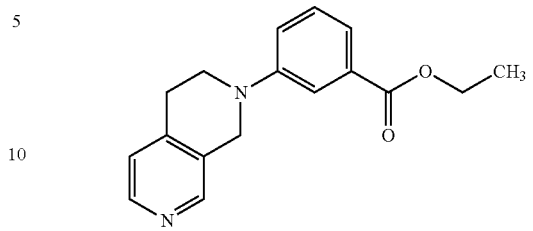

Ethyl 3-(3,4-dihydro-2,7-naphthyridin-2(1H)-yl)benzoate

A mixture of 1,2,3,4-tetrahydro-2,7-naphthyridine dihydrochloride (41.4 mg, 0.20 mmol), cesium carbonate (326 mg, 1.0 mmol), and triethylamine (0.056 mL, 0.40 mmol) in 2.0 mL dioxane was warmed until the amine starting material had dissolved. The reaction filtrate was transferred into another reaction vial and the following added: a spatula portion of cesium carbonate, ethyl 3-bromobenzoate (0.032 mL, 0.20 mmol), palladium acetate (2.2 mg, 0.01 mmol) plus catalytic Pd$_2$(dba)$_3$, and RAC-BINAP (6.2 mg, 0.01 mmol). The reaction was heated at 95° C. for 17 hours, filtered, and evaporated to an oil. The oil was chromatograph eluting with CHCl$_3$/EtOAc to give the title compound as a light yellow oil (3.2 mg, 6%). $^1$H NMR (CDCl$_3$) δ: 8.46 (s, 1H), 8.39 (d, J=5.0 Hz, 1H), 7.66 (dd, J=2.3, 1.5 Hz, 1H), 7.54 (dt, J=7.5, 1.2 Hz, 1H), 7.35 (t, J=7.9 Hz, 1H), 7.16 (dd, J=8.4, 1.9 Hz, 1H), 7.12 (d, J=5.0 Hz, 1H), 4.46 (s, 2H), 4.39 (q, J=7.1 Hz, 2H), 3.62 (t, J=5.9 Hz, 2H), 3.01 (t, J=5.7 Hz, 2H), 1.38-1.44 (m, 3H).

Preparation 55

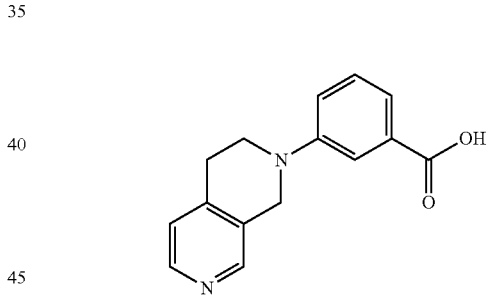

3-(3,4-dihydro-2,7-naphthyridin-2(1H)-yl)benzoic acid

A mixture of ethyl 3-(3,4-dihydro-2,7-naphthyridin-2(1H)-yl)benzoate (51 mg, 0.18 mmol) and 0.5 mL 1.0 M NaOH in 2.0 mL dioxane was heated at 70° C. for 2.3 hours. The pH of the reaction was adjusted to pH 5 using glacial acetic acid. The mixture was evaporated and then chased with MeOH to give a yellow solid film. An impure lot from a previous reaction was combined, and this material triturated with EtOAc. The remaining solid was dissolved in MeOH, and then Bio-rad AG1-X8 basic resin (hydroxide form) was added. The mixture was filtered and the resin rinsed with MeOH and CH$_2$Cl$_2$. The product was eluted from the resin using 10% formic acid in MeOH. The solvent was evaporated, chased with MeOH and EtOAc to give the title compound (used as is for the next step) as a yellow solid (49 mg). $^1$H NMR (CD$_3$OD) δ: 8.42 (s, 1H), 8.29 (d, J=5.3 Hz, 1H), 7.68-7.70 (m, 1H), 7.48-7.51 (m, 1H), 7.33-7.39 (m, 1H), 7.30 (dd, J=2.5, 1.3 Hz, 1H), 7.26 (d, J=4.7 Hz, 1H), 4.48 (s, 2H), 3.64 (t, J=5.9 Hz, 2H), 3.04 (t, J=5.6 Hz, 2H).

Example 168

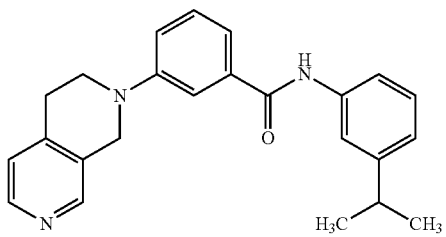

3-(3,4-dihydro-2,7-naphthyridin-2(1H)-yl)-N-(3-isopropylphenyl)benzamide

To a mixture of 3-(3,4-dihydro-2,7-naphthyridin-2(1H)-yl)benzoic acid (15.0 mg, 0.059 mmol), triethylamine (0.016 mL, 0.12 mmol) and catalytic DMAP in 1.0 mL 1,2-dichloroethane at rt was added propylphosphonic anhydride solution (50 wt % in EtOAc, 0.046 mL, 0.077 mmol). After 8 min at rt, 3-isopropylaniline (0.015 mL, 0.106 mmol) was added and the reaction stirred at rt for 18 hours. Then additional 3-isopropylaniline (0.015 mL) and propylphosphonic anhydride solution (0.030 mL) was added and the reaction continued for an additional 3 hours. The reaction was quenched into brine/dilute aqueous $Na_2CO_3$ solution, extracted with EtOAc, the EtOAc layer washed with $H_2O$, brine/dilute aqueous $Na_2CO_3$ solution, dried with anhydrous $Na_2SO_4$ and rotary evaporated to an oil. The oil was chromatographed eluting with $CHCl_3$/EtOAc to give the title compound as a light yellow solid (13 mg, 57%). $^1$H NMR ($CDCl_3$) δ: 8.42 (s, 1H), 8.38 (d, J=5.0 Hz, 1H), 7.94 (s, 1H), 7.55-7.57 (m, 2H), 7.47 (ddd, J=8.1, 2.2, 1.2 Hz, 1H), 7.34-7.40 (m, 1H), 7.29 (t, J=7.8 Hz, 1H), 7.21-7.26 (m, 1H), 7.08-7.14 (m, 2H), 7.01-7.05 (m, 1H), 4.46 (s, 2H), 3.63 (t, J=5.9 Hz, 2H), 2.85-3.02 (m, 3H), 1.27 (d, J=7.0 Hz, 6H).

Preparation 56

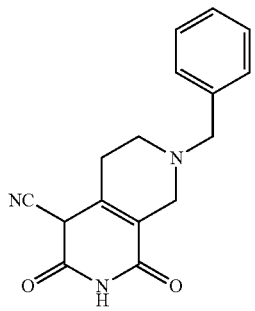 [SMILES: N#CC1C(=O)NC(=O)C2=C1CCN(Cc1ccccc1)C2]

7-Benzyl-1,3-dioxo-1,2,3,4,5,6,7,8-octahydro-[2,7]-naphthyridine-4-carbonitrile

In a 5 L 3-necked flask equipped with a mechanical stirrer and a dropping funnel was placed ethyl 1-benzyl-4-oxo-3-piperidinecarboxylate hydrochloride, (199.3 g, 0.67 mol) in dichloromethane (1.5 L). To this suspension was added saturated sodium bicarbonate (1.5 L) over one hour. After the solid dissolved, the organic layer was separated, washed with brine (250 mL), filtered through 1PS filter paper and concentrated under reduced pressure to give 160.5 g (92%) of ethyl 1-benzyl-4-oxo-3-piperidinecarboxylate as an oil. NMR 60 MHz, ($CDCl_3$), δ 7.3 (s, 5H), 4.2 (q, 2H), 3.6 (s, 2H), 2.3-3.6 (m, 6H), 1.3 (t, 3H).

In a 5 L 3-necked flask equipped with a mechanical stirrer, and a condenser was placed above free base (160 g, 0.613 mol) in methanol (1.2 L). The cyanoacetamide (51.5 g, 0.613 mol) was added followed by addition of a potassium hydroxide solution in methanol (42.9 g, 0.77 mol of KOH in 800 mL MeOH). The resulting mixture was stirred and heated to reflux on steam-bath. The product was started to form as a white solid after few minutes. The reaction mixture was refluxed for 4 hr and cooled to room temperature overnight. The white solid was collected and filter cake was washed with methanol (300 mL). The white solid was transferred into a 2 L 3-necked flask equipped with a mechanical stirrer with the aid of warm water (2 L of 55° C.). The resulting mixture was stirred and acidified to pH=6 with acetic acid (about 35 mL). After 1 hr stirring, the white solid was collected, washed with water (500 mL), pressed well with a rubber dam and air dried in a hood overnight to give 147 g (85%) of the title compound. $^1$H NMR 60 MHz, (hot $d_6$-DMSO), δ 10.3 (br s, 1H), 7.4 (s, 5H), 4.4 (s, 2H), 3.8 (s, 2H), 3.4 (br s, 3H), 2.7 (m, 2H).

Preparation 57

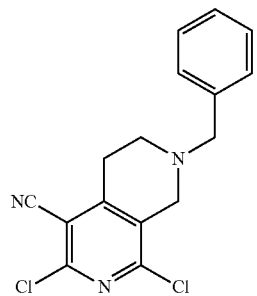 [SMILES: N#Cc1c(Cl)nc(Cl)c2c1CCN(Cc1ccccc1)C2]

7-Benzyl-1,3-dichloro-5,6,7,8-tetrahydro-[2,7]-naphthyridine-4-carbonitrile

A 300 mL glass pressure vessel was charged with 7-benzyl-1,3-dioxo-1,2,3,4,5,6,7,8-octahydro-[2,7]-naphthyridine-4-carbonitrile (17.56 g, 0.0625 mol) and phosphorus oxychloride (60 mL). The vessel was sealed and heated at 180° C. for 4 hr. This process was repeated three more times. All material in these processes were combined and concentrated under reduced pressure. The residue was dissolved in dichloromethane (1.2 L) and added into a 5 L 3-necked flask equipped with a mechanical stirrer containing ice (about 300 g). The resulting mixture was basified to pH=9-10 by adding approximately 650 mL 20% aqueous sodium hydroxide solution. During this addition more ice was added to keep internal temperature under 30° C. The mixture was stirred for 15 min and then was filtered to remove a gel type particle. The organic layer was separated, washed with brine (250 mL), filtered through 1PS filter paper and concentrated under reduced pressure. The oily residue was purified by flash chromatography on silica gel (400 g) with anhydrous sodium sulfate (75 g) on top packed with hexane. The column was eluted with 200 mL portions of 15% ethyl acetate in hexane followed by 35% ethyl acetate in hexane to give the title compound (70.8 g, 89%) as an oil which solidified on standing. $^1$H NMR 60 MHz, (CDCl$_3$), δ 7.3 (s, 5H), 3.7 (s, 2H), 3.6 (s, 2H), 3.0 (m, 4H).

Preparation 58

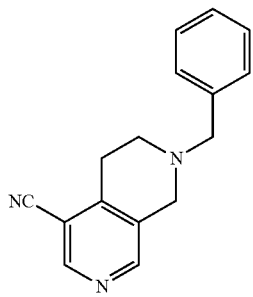 [SMILES: N#Cc1cncc2c1CCN(Cc1ccccc1)C2]

7-Benzyl-5,6,7,8-tetrahydro-[2,7]-naphthyridine-4-carbonitrile

A mixture of 7-benzyl-1,3-dichloro-5,6,7,8-tetrahydro-[2,7]-naphthyridine-4-carbonitrile (70 g, 0.22 mol) and triethylamine (70 mL) in methanol (1 L) was placed in a 2.5 L hydrogenation bottle and hydrogenated over 10% Pd/C (15 g) for 3 hr. The reaction mixture was filtered to remove catalyst. The catalyst on filter paper was washed with methanol (100 mL). The filtrate was concentrated under reduced pressure to give an oil. The oil was dissolved in dichloromethane (500 mL), washed with water (2×200 mL), brine (200 mL), dried over anhydrous magnesium sulfate (10 g), filtered and concentrated under reduced pressure to give an oil. The oil was placed under high vacuum line overnight to give the title compound (48.5 g, 88%). $^1$H NMR 60 MHz, (CDCl$_3$), δ 8.5 (s, 1H), 8.3 (s, 1H), 7.3 (s, 5H), 3.7 (s, 2H), 3.6 (s, 2H), 2.8 (m, 4H).

Preparation 59

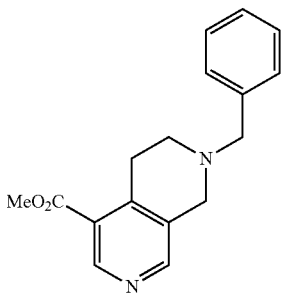 [SMILES: COC(=O)c1cncc2c1CCN(Cc1ccccc1)C2]

7-Benzyl-5,6,7,8-tetrahydro-[2,7]naphthyridine-4-carboxylic acid methyl ester

In a 1 L copper flask was placed 7-benzyl-5,6,7,8-tetrahydro-[2,7]-naphthyridine-4-carbonitrile (44.8 g, 0.18 mol) in ethanol (200 mL). A solution of sodium hydroxide (36 g, 0.9 mol) in water (200 mL) was added and the resulting mixture was refluxed for 8 hr. The reaction mixture was concentrated under reduced pressure. To the residue was added ethanol (150 mL) and toluene (150 mL) and concentrated under reduced pressure. This process was repeated three times. Finally methanol (150 mL) and toluene (150 mL) were added and concentrated under reduced pressure. The solid residue was further dried under high vacuum line overnight. To the residue was added a solution of 30% sulfuric acid in methanol (w/w, 800 mL) and refluxed for 24 hr. The reaction mixture was cooled to room temperature and filtered to remove white solid (inorganic salt). The solid on filter paper was washed with methanol (100 mL) and the filtrate was concentrated under reduced pressure. To the residue was added ice (300 g) and basified with ammonium hydroxide (175 mL. 28-38% ammonia). The mixture was extracted with dichloromethane (2×250 mL). The combined organic layers were washed with brine (150 mL), filtered through 1PS filter paper and concentrated to give a brown oil. The oil was purified by flash chromatography on silica gel (500 g) with anhydrous sodium sulfate (50 g) on top packed with hexane. The column was eluted with 200 mL portions of 25% ethyl acetate in hexane followed by 50% ethyl acetate in hexane. The eluent containing product was concentrated to give the title compound (39.1 g, 77%) as an oil which solidified on standing. $^1$H NMR 60 MHz, (CDCl$_3$), δ 8.8 (s, 1H), 8.2 (s, 1H), 7.3 (s, 5H), 3.8 (s, 3H), 3.6 (s, 2H), 3.5 (s, 2H), 3.2 (m, 2H), 2.6 (m, 2H).

Preparation 60

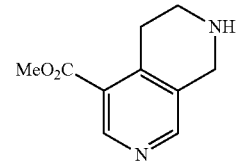 [SMILES: COC(=O)c1cncc2c1CCNC2]

5,6,7,8-tetrahydro-[2,7]naphthyridine-4-carboxylic acid methyl ester

In a 2 L 3-necked flask equipped with a mechanical stirrer and condenser was placed 7-benzyl-5,6,7,8-tetrahydro-[2,7]naphthyridine-4-carboxylic acid methyl ester (11.28 g, 0.04) in methanol (500 mL). To this solution was added ammonium formate (37.8 g, 0.6 mol) and 10% Pd/C (11 g, 50% water wet). The resulting mixture was stirred and heated to reflux for 15 min. The reaction mixture was filtered through glass microfiber filter paper. The catalyst on filter paper was washed with hot methanol (200 mL). The filtrate was concentrated under reduced pressure to give a solid residue. The residue was purified by flash chromatography over silica gel (120 g) with anhydrous sodium sulfate (15 g) on top packed with hexane. The column was eluted with 100 mL portions of dichloromethane for fractions 1-4, 5% of (10% ammonia in methanol) in dichloromethane for fractions 6-9, and 10% of (10% ammonia in methanol) in dichloromethane for fractions 10-18. All fractions checked by TLC [10% of (10% ammonia in methanol) in dichloromethane]. The product was eluted in fractions 11-16 to give the title compound (6.1 g, 79%) as a light yellow solid. $^1$H NMR 60 MHz, (CDCl$_3$), δ 8.8 (s, 1H), 8.2 (s, 1H), 4.0 (s, 2H), 3.8 (s, 3H), 3.0 (s, 4H), 1.7 (s, 1H).

Preparation 61

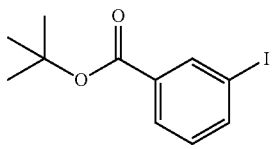

3-iodobenzoic acid tert-butyl ester

To a solution of 3-iodobenzoic acid (50 g, 0.2 mol) in N,N-dimethylformamide (250 mL) was added solid 1,1'-carbonyldiimidazole (32.4 g, 0.2 mol) over 15 min. The resulting mixture was heated at 40° C. for 1 hr, then was added tert-butyl alcohol (29.6 g, 0.4 mol) and 1,8-diazabicyclo[5,4,0]undec-7-ene (30.4 g, 0.2 mol) and heated at 40° C. overnight. The reaction was cooled to room temperature, diluted with water (500 mL) and extracted with hexane (2×500 mL). The combined organic layers were washed with water (2×400 mL), brine (250 mL), dried over anhydrous magnesium sulfate (15 g), filtered and concentrated under reduced pressure to give the title compound (56 g, 92%) as an oil. NMR 60 MHz, (CDCl$_3$), δ 8.3 (m, 1H), 7.8 (m, 2H), 7.0 (m, 1H), 1.6 (s, 9H).

Preparation 62

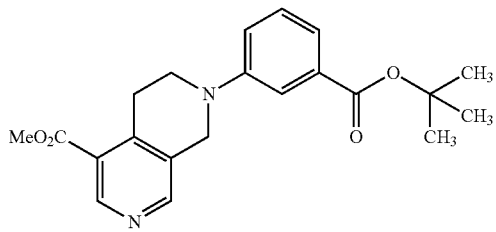 [SMILES: COC(=O)c1cncc2c1CCN(c1cccc(C(=O)OC(C)(C)C)c1)C2]

7-(3-tert-Butoxycarbonyl-phenyl)-5,6,7,8-tetrahydro-[2,7]naphthyridine-4-carboxylic acid methyl ester A 1 L glass pressure vessel was charged with 5,6,7,8-tetrahydro-[2,7]naphthyridine-4-carboxylic acid methyl ester (5.38 g, 0.028 mol) and 3-iodobenzoic acid tert-butyl ester (12.8 g, 0.042 mmol) in toluene (300 mL). The solution was stirred and sparged with argon for 10 min. Palladium(II) acetate (0.38 g, 0.00168 mol, 6 mole %) and cesium carbonate (18.3 g, 0.056 mol) were added and sparged with argon for an additional 10 min. (±)-2,2'-bis(diphenylphosphino)1,1'-binaphthalene (0.96 g, 0.00336, 12 mole %) was added and the vessel was sealed and heated at 100° C. overnight. HPLC analysis and TLC (ethyl acetate:hexane; 1:1) showed the reaction was complete. The reaction mixture was filtered and filter paper was washed with ethyl acetate (250 mL). The filtrate was washed with water (250 mL). The aqueous layer was separated and extracted with ethyl acetate (2×150 mL). The combined organic layers were washed with brine (3×100 mL), filtered through 1PS filter paper and concentrated under reduced pressure to give an oil. The oil was purified by flash chromatography on silica gel (125 g) with anhydrous sodium sulfate (25 g) on top packed with hexane. The column was eluted with 100 mL portions of 10% ethyl acetate in hexane for fractions 1-5, 25% ethyl acetate in hexane for fractions 6-16, 35% ethyl acetate in hexane for fractions 17-24, and 40% ethyl acetate in hexane for fractions 25-32. All fractions checked by TLC. The product was eluted in fractions 19-28 to give the title compound (6.9 g, 67%) as a viscous oil. $^1$H NMR 60 MHz, (CDCl$_3$), δ 9.0 (s, 1H), 8.6 (s, 1H), 7.4 (m. 5H), 4.5 (s, 2H), 4.0 (s, 3H), 3.6 (m, 4H), 1.7 (s, 9H).

Preparation 63

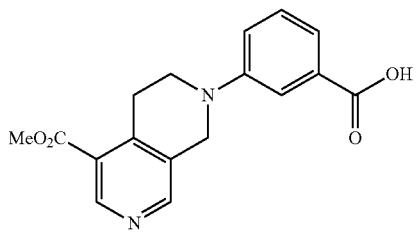 [SMILES: COC(=O)c1cncc2c1CCN(c1cccc(C(=O)O)c1)C2]

3-[5-(methoxycarbonyl)-3,4-dihydro-2,7-naphthyridin-2(1H)-yl]benzoic acid

A mixture of 7-(3-tert-Butoxycarbonyl-phenyl)-5,6,7,8-tetrahydro-[2,7]naphthyridine-4-carboxylic acid methyl ester (6.9 g, 0.0188 mol) and 98% formic acid (30 mL) was heated at 50° C. for 4 hr and at 30° C. overnight. HPLC analysis showed the reaction was not complete. It was heated at 50° C. for an additional 1.5 hr. The reaction mixture was concentrated under reduced pressure. Diluted with dichloromethane (200 mL) and cooled to 0° C. To the mixture (liquid and solid) was added saturated sodium bicarbonate until to get a pH=5-6 at 0° C. The solid was collected, washed with water (50 mL), dichloromethane (50 mL) and air dried. The solid was triturated with acetone (50 mL) for 30 min. The yellow-green solid was collected and dried in a drying pistol with refluxing acetone overnight to give the title compound (3.86 g, 66%). $^1$H NMR 300 MHz (d$_6$-DMSO), δ 13 (brs, 1H), 8.8 (s, 1H), 8.65 (s, 1H), 7.5 (m, 4H), 4.5 (s, 2H), 3.8 (s, 3H), 3.6 (t, 2H), 3.2 (t, 2H).

Example 169

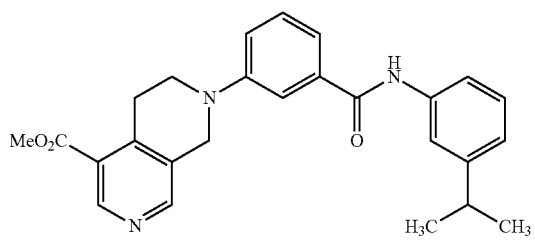 [SMILES: COC(=O)c1cncc2c1CCN(c1cccc(C(=O)Nc3cccc(C(C)C)c3)c1)C2]

Methyl 7-(3-{[(3-isopropylphenyl)amino]carbonyl}phenyl)-5,6,7,8-tetrahydro-2,7-naphthyridine-4-carboxylate To a mixture of 3-[5-(methoxycarbonyl)-3,4-dihydro-2,7-naphthyridin-2(1H)-yl]benzoic acid (63 mg, 0.20 mmol), triethylamine (0.056 mL, 0.40 mmol), and catalytic DMAP in 2.0 mL 1,2-dichloroethane at rt was added propylphosphonic anhydride solution (50 wt % in EtOAc, 0.143 mL, 0.24 mmol). After 10 min at rt, 3-isopropylaniline (0.042 mL, 0.30 mmol) was added and the reaction stirred at rt for 1 hour. The reaction was quenched into aqueous NaHCO₃ solution, extracted with EtOAc, the EtOAc layer washed with H₂O, dilute aqueous NaHCO₃ solution, brine, dried with anhydrous Na₂SO₄ and rotary evaporated. This material was chromatographed eluting with CHCl₃/EtOAc to give the title compound as a light yellow solid (59 mg, 68%). ¹H NMR (Acetone-d6) δ: 9.39 (br. s., 1H), 8.89 (s, 1H), 8.66 (s, 1H), 7.72-7.74 (m, 1H), 7.66-7.71 (m, 2H), 7.35-7.44 (m, 2H), 7.25-7.30 (m, 2H), 7.00 (d, J=7.6 Hz, 1H), 4.60 (s, 2H), 3.91 (s, 3H), 3.66-3.71 (m, 2H), 3.37 (t, J=5.9 Hz, 2H), 2.91 (spt, J=6.9 Hz, 1H), 1.25 (d, J=7.0 Hz, 6H)

Example 170

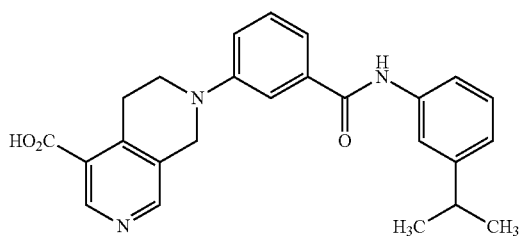 [SMILES: CC(C)c1cccc(NC(=O)c2cccc(N3CCc4c(cncc4C(=O)O)C3)c2)c1]

7-(3-{[(3-isopropylphenyl)amino]carbonyl}phenyl)-5,6,7,8-tetrahydro-2,7-naphthyridine-4-carboxylic acid A mixture of methyl 7-(3-{[(3-isopropylphenyl)amino]carbonyl}phenyl)-5,6,7,8-tetrahydro-2,7-naphthyridine-4-carboxylate (298 mg, 0.694 mmol) and 1.0 M NaOH (3.5 mL, 3.5 mmol) in 8.0 mL dioxane was rapidly stirred at rt for 1.8 hours. The pH of the mixture was adjusted to pH 4 using 10% aqueous HCl, and then water added to form a yellow precipitant. The precipitant was filtered, washed with H₂O then 30% EtOAc/hexane to give the title compound as a yellow solid (232 mg, 81%). ¹H NMR (DMSO-d6 plus D₂O) δ: 10.10 (s, 1H), 8.82 (s, 1H), 8.63 (s, 1H), 7.56-7.65 (m, 2H), 7.54 (s, 1H), 7.33-7.41 (m, 2H), 7.22-7.29 (m, 2H), 6.98 (d, J=7.3 Hz, 1H), 4.55 (s, 2H), 3.60-3.65 (m, 2H), 3.27 (t, J=5.4 Hz, 2H), 2.79-2.94 (m, 1H), 1.21 (d, J=6.7 Hz, 6H)

Example 171

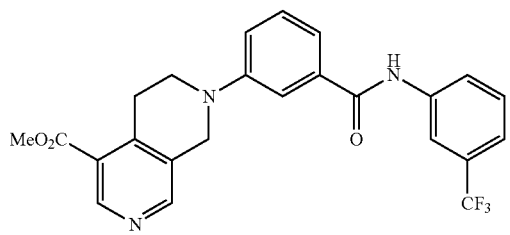 [SMILES: COC(=O)c1cncc2c1CCN(c1cccc(C(=O)Nc3cccc(C(F)(F)F)c3)c1)C2]

Methyl 7-[3-({[3-(trifluoromethyl)phenyl]amino}carbonyl)phenyl]-5,6,7,8-tetrahydro-2,7-naphthyridine-4-carboxylate To a mixture of 3-[5-(methoxycarbonyl)-3,4-dihydro-2,7-naphthyridin-2(1H)-yl]benzoic acid (63 mg, 0.20 mmol), triethylamine (0.084 mL, 0.60 mmol), and catalytic DMAP in 3.0 mL 1,2-dichloroethane at rt was added propylphosphonic anhydride solution (50 wt % in EtOAc, 0.143 mL, 0.24 mmol). After 5 min at rt, 3-(trifluoromethyl)aniline (0.037 mL, 0.30 mmol) was added and the reaction stirred at rt for 18 hours. The reaction was quenched with aqueous NaHCO₃ solution, extracted with EtOAc, the EtOAc layer washed with H₂O, dilute aqueous NaHCO₃ solution, brine, dried with anhydrous Na₂SO₄ and rotary evaporated. This material was chromatographed eluting with CHCl₃/EtOAc to give the title compound as a yellow solid (50 mg, 55%). ¹H NMR (Acetone-d6) δ: 9.75 (br. s., 1H), 8.89 (s, 1H), 8.66 (s, 1H), 8.32 (s, 1H), 8.09 (d, J=7.9 Hz, 1H), 7.69 (s, 1H), 7.60 (t, J=7.9 Hz, 1H), 7.37-7.47 (m, 3H), 7.28-7.34 (m, 1H), 4.61 (s, 2H), 3.92 (s, 3H), 3.67-3.73 (m, 2H), 3.37 (t, J=5.9 Hz, 2H).

Example 172

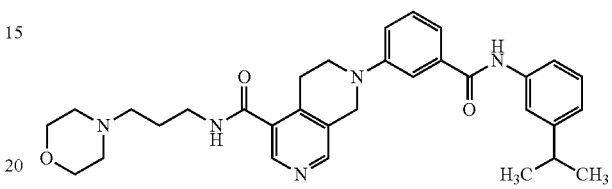

7-(3-{[(3-isopropylphenyl)amino]carbonyl}phenyl)-N-(3-morpholin-4-ylpropyl)-5,6,7,8-tetrahydro-2,7-naphthyridine-4-carboxamide To a mixture of 7-(3-{[(3-isopropylphenyl)amino]carbonyl}phenyl)-5,6,7,8-tetrahydro-2,7-naphthyridine-4-carboxylic acid (25 mg, 0.06 mmol), triethylamine (0.017 mL, 0.12 mmol), and catalytic DMAP in 1.1 mL 1,2-dichloroethane at rt was added propylphosphonic anhydride solution (50 wt % in EtOAc, 0.043 mL, 0.072 mmol). After 5 min at rt, 3-morpholinopropylamine (0.011 mL, 0.072 mmol) was added and the reaction stirred at rt for 1.5 hours. The reaction was partitioned between EtOAc and brine/aqueous NaHCO₃ solution, the EtOAc layer washed with brine/aqueous NaHCO₃ solution, dried with anhydrous Na₂SO₄ and rotary evaporated. This material was chromatographed eluting with CHCl₃/MeOH to give the title compound as an off-white solid (17 mg, 54%). ¹H NMR (CDCl₃) δ: 8.50 (s, 1H), 8.48 (s, 1H), 7.83-7.92 (m, 2H), 7.54 (d, J=4.7 Hz, 2H), 7.46 (d, J=8.2 Hz, 1H), 7.34-7.41 (m, 1H), 7.20-7.33 (m, 2H), 7.13 (d, J=7.9 Hz, 1H), 7.03 (d, J=7.3 Hz, 1H), 4.50 (s, 2H), 3.52-3.63 (m, 8H), 3.23 (t, J=5.7 Hz, 2H), 2.87-2.98 (m, 1H), 2.56 (t, J=6.0 Hz, 2H), 2.47 (br. s., 4H), 1.75-1.85 (m, 2H), 1.27 (d, J=7.0 Hz, 6H)

Example 173

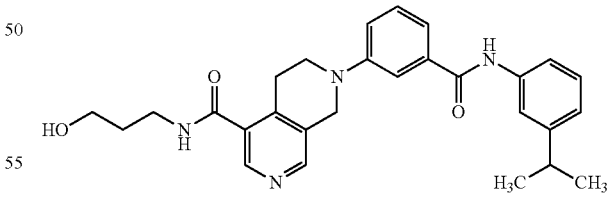

N-(3-hydroxypropyl)-7-(3-{[(3-isopropylphenyl)amino]carbonyl}phenyl)-5,6,7,8-tetrahydro-2,7-naphthyridine-4-carboxamide To a mixture of 7-(3-{[(3-isopropylphenyl)amino]carbonyl}phenyl)-5,6,7,8-tetrahydro-2,7-naphthyridine-4-carboxylic acid (47 mg, 0.113 mmol), triethylamine (0.047 mL, 0.34 mmol), and catalytic DMAP in 3.0 mL 1,2-dichloroethane at rt was added propylphosphonic anhydride solution (50 wt % in EtOAc, 0.081 mL, 0.136 mmol). After 5 min at rt, 3-amino-1-propanol (0.011 mL, 0.147 mmol) was added and the reaction stirred at rt for 2 hours. The reaction was quenched with aqueous NaHCO$_3$ solution, extracted with EtOAc, the EtOAc layer washed with H$_2$O, aqueous NaHCO$_3$ solution, brine, dried with anhydrous Na$_2$SO$_4$ and rotary evaporated. This material was chromatographed eluting with CHCl$_3$/EtOAc plus 10% MeOH to give the title compound as a light yellow solid (20 mg, 37%). $^1$H NMR (CDCl$_3$) δ: 8.46 (s, 1H), 8.41 (s, 1H), 8.02 (s, 1H), 7.54 (s, 1H), 7.44-7.51 (m, 2H), 7.19-7.39 (m, 4H), 7.10 (d, J=8.2 Hz, 1H), 7.03 (d, J=7.6 Hz, 1H), 6.81 (t, J=5.6 Hz, 1H), 4.45 (s, 2H), 3.78 (t, J=5.4 Hz, 2H), 3.53-3.65 (m, 4H), 3.17 (t, J=5.6 Hz, 2H), 2.86-2.97 (m, 1H), 1.77-1.86 (m, 2H), 1.27 (d, J=6.7 Hz, 6H)

Example 174

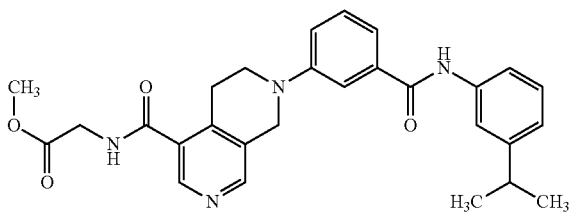 [SMILES: COC(=O)CNC(=O)c1cncc2c1CCN(c1cccc(C(=O)Nc3cccc(C(C)C)c3)c1)C2]

Methyl ({[7-(3-{[(3-isopropylphenyl)amino]carbonyl}phenyl)-5,6,7,8-tetrahydro-2,7-naphthyridin-4-yl]carbonyl}amino)acetate To a mixture of 7-(3-{[(3-isopropylphenyl)amino]carbonyl}phenyl)-5,6,7,8-tetrahydro-2,7-naphthyridine-4-carboxylic acid (40 mg, 0.096 mmol), N,N-diisopropylethylamine (0.067 mL, 0.39 mmol), and catalytic DMAP in 2.5 mL 1,2-dichloroethane at rt was added propylphosphonic anhydride solution (50 wt % in EtOAc, 0.069 mL, 0.116 mmol). After 6 min at rt, glycine methyl ester hydrochloride (18.1 mg, 0.144 mmol) was added and the reaction stirred at rt for 4 hours. The reaction was quenched with aqueous NaHCO$_3$ solution, extracted with EtOAc, the EtOAc layer washed with H$_2$O, aqueous NaHCO$_3$ solution, brine, dried with anhydrous Na$_2$SO$_4$ and rotary evaporated. This material was chromatographed eluting with CHCl$_3$/EtOAc plus 10% MeOH to give the title compound as a light yellow solid (30 mg, 64%). $^1$H NMR (CDCl$_3$) δ: 8.55 (s, 1H), 8.47 (s, 1H), 7.93 (s, 1H), 7.53 (d, J=11.4 Hz, 2H), 7.47 (d, J=7.3 Hz, 1H), 7.33-7.40 (m, 1H), 7.20-7.32 (m, 2H), 7.11 (d, J=7.9 Hz, 1H), 7.03 (d, J=7.6 Hz, 1H), 6.62 (t, J=5.1 Hz, 1H), 4.47 (s, 2H), 4.24 (d, J=5.3 Hz, 2H), 3.81 (s, 3H), 3.56-3.61 (m, 2H), 3.20 (t, J=5.6 Hz, 2H), 2.85-2.99 (m, 1H), 1.27 (d, J=6.7 Hz, 6H)

Example 175

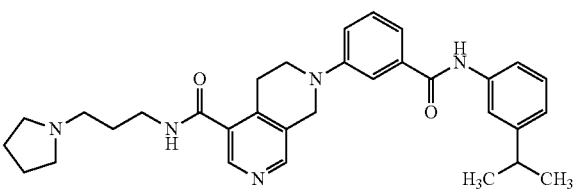 [SMILES: CC(C)c1cccc(NC(=O)c2cccc(N3CCc4c(cncc4C(=O)NCCCN4CCCC4)C3)c2)c1]

7-(3-{[(3-isopropylphenyl)amino]carbonyl}phenyl)-N-(3-pyrrolidin-1-ylpropyl)-5,6,7,8-tetrahydro-2,7-naphthyridine-4-carboxamide To a mixture of 7-(3-{[(3-isopropylphenyl)amino]carbonyl}phenyl)-5,6,7,8-tetrahydro-2,7-naphthyridine-4-carboxylic acid (40 mg, 0.096 mmol), N,N-diisopropylethylamine (0.050 mL, 0.29 mmol), and catalytic DMAP in 2.5 mL 1,2-dichloroethane at rt was added propylphosphonic anhydride solution (50 wt % in EtOAc, 0.069 mL, 0.116 mmol). After 6 min at rt, 1-(3-Aminopropyl)pyrrolidine (16.0 mg, 0.125 mmol) was added and the reaction stirred at rt for 4 hours. The reaction was quenched with aqueous NaHCO$_3$ solution, extracted with EtOAc, the EtOAc layer washed with H$_2$O, aqueous Na$_2$CO$_3$ solution, brine, dried with anhydrous Na$_2$SO$_4$ and rotary evaporated. The sample was triturated with EtOAc, and the filtrate chromatographed eluting with CHCl$_3$/MeOH plus triethylamine to give the title compound as a light beige solid (27 mg, 53%). $^1$H NMR (CDCl$_3$) δ: 8.50 (s, 1H), 8.36-8.44 (m, 2H), 8.10 (s, 1H), 7.58 (s, 1H), 7.46-7.54 (m, 2H), 7.32-7.39 (m, 1H), 7.22-7.31 (m, 2H), 7.10 (d, J=7.6 Hz, 1H), 7.02 (d, J=7.6 Hz, 1H), 4.46 (s, 2H), 3.53-3.61 (m, 4H), 3.22 (t, J=5.4 Hz, 2H), 2.77-2.97 (m, 7H), 1.82-1.99 (m, 6H), 1.27 (d, J=6.7 Hz, 6H)

Example 176

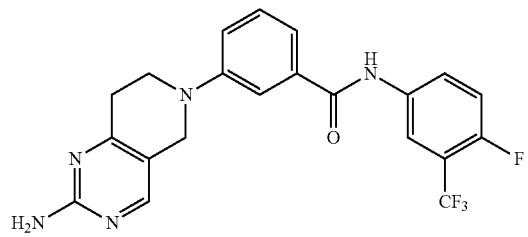 [SMILES: Nc1ncc2c(n1)CCN(c1cccc(C(=O)Nc3ccc(F)c(C(F)(F)F)c3)c1)C2]

3-(2-amino-7,8-dihydropyrido[4,3-d]pyrimidin-6(5H)-yl)-N-[4-fluoro-3-(trifluoromethyl)phenyl]benzamide A mixture of 3-(2-amino-7,8-dihydropyrido[4,3-d]pyrimidin-6(5H)-yl)benzoic acid (54 mg, 0.20 mmol) and 1,1'-Carbonyldiimidazole (36 mg, 0.22 mmol) in 3.0 mL DMSO was stirred at rt for 5 minutes, and then heated at 60° C. for 25 minutes. Then 4-fluoro-3-(trifluoromethyl)aniline (0.051 mL, 0.40 mmol) was added, and the reaction heated at 80° C. for 46 hours. Next, an additional 2 small drops of 4-fluoro-3-(trifluoromethyl)aniline was added and the reaction heated at 160° C. for 1.5 hours. Upon cooling to rt, the reaction mixture was added to a solution of 35 mL H$_2$O plus 5 mL brine, and the resulting precipitate filtered and rinsed with H$_2$O and hexane/EtOAc. The precipitate was chromatographed using CHCl$_3$/MeOH, and the resulting solid chromatographed again using EtOAc/MeOH to give the title compound as a yellow solid (8 mg, 9%). $^1$H NMR (Acetone-d6) δ: 9.77 (br. s., 1H), 8.31 (dd, J=6.4, 2.6 Hz, 1H), 8.10-8.17 (m, 2H), 7.62-7.64 (m, 1H), 7.35-7.44 (m, 3H), 7.24-7.28 (m, 1H), 5.79 (br. s., 2H), 4.35 (s, 2H), 3.70 (t, J=5.9 Hz, 2H), 2.80-2.86 (m, 2H).

Example 177

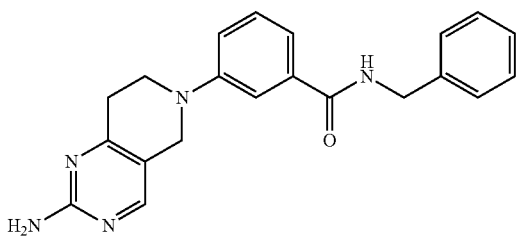 [SMILES: Nc1ncc2c(n1)CCN(c1cccc(C(=O)NCc3ccccc3)c1)C2]

3-(2-amino-7,8-dihydropyrido[4,3-d]pyrimidin-6(5H)-yl)-N-benzylbenzamide

To a mixture of 3-(2-amino-7,8-dihydropyrido[4,3-d]pyrimidin-6(5H)-yl)benzoic acid (54 mg, 0.20 mmol), triethylamine (0.084 mL, 0.60 mmol), and catalytic DMAP in 4.5 mL $CH_2Cl_2$ at rt was added propylphosphonic anhydride solution (50 wt % in EtOAc, 0.131 mL, 0.22 mmol). After 5 min at rt, benzyl amine (0.023 mL, 0.21 mmol) was added and the reaction stirred at rt for 23 hours. The reaction was partitioned between EtOAc and aqueous $Na_2CO_3$ solution, the EtOAc layer washed with aqueous $NaHCO_3$ solution, $H_2O$, brine, dried with anhydrous $Na_2SO_4$ and evaporated to a solid. The solid was chromatographed eluting with $CHCl_3$/EtOAc plus 5% MeOH and then triturated with acetone/hexane to give the title compound as a light beige solid (20 mg, 28%). $^1$H NMR (Acetone-d6) δ: 8.39 (br. s., 1H), 8.12 (s, 1H), 7.58 (br. s., 1H), 7.27-7.38 (m, 5H), 7.16-7.26 (m, 2H), 4.59 (d, J=5.6 Hz, 2H), 4.30 (s, 2H), 3.66 (t, J=5.3 Hz, 2H), 2.82 (t, J=5.3 Hz, 2H).

The present invention is not to be limited in scope by the exemplified embodiments which are intended as illustrations of single aspects of the invention only. Indeed, various modifications of the invention in addition to those described herein will become apparent to those skilled in the art from the foregoing description.

For example, any compound which is a 5,6,7,8-tetrahydropyrido[4,3-d]pyrimidine-N-hydrocarbyl(aryl)(carboxamide) or a 6,7-dihydro-5H-pyrrolo[3,4-d]pyrimidine-N-hydrocarbyl(aryl)(carboxamide) preferably a 2 or 4-amino-5,6,7,8-tetrahydropyrido[4,3-d]pyrimidine-N-hydrocarbyl(aryl)(carboxamide) or a 2 or 4-amino-6,7-dihydro-5H-pyrrolo[3,4-d]pyrimidine-N-hydrocarbyl(aryl)(carboxamide) and binds to the appropriate tyrosine kinase receptor, i.e. the PDGF and VEGF receptors, is contemplated as a compound that may be used in the method of this invention.

Preferably, said aryl is selected from the group consisting of phenyl, pyridinyl, oxazolyl and thiazolyl.

More preferably, said substituted hydrocarbyl is aryl, e.g. phenyl, substituted with a substituent selected from the group consisting of alkyl, alkyloxy, halogen and haloalkyl, e.g. a substituent selected from the group consisting of $C_1$ to $C_7$ alkyl, which alkyl may be substituted with a fluoro, and $C_1$ to $C_7$ alkyloxy, which alkyloxy may be substituted with a nitrogen heteroatom.

Most preferably, said aryl, e.g. phenyl, is substituted with a substituent selected from the group consisting of methyl, isopropyl, t-butyl, trifluoromethyl, methyloxy and 1-methylpiperidin-4-yl oxy.

Alternatively, said substituted hydrocarbyl is alkyl, e.g. an alkyl selected from the group consisting of ethyl, n-butyl, 3,3-dimethylbutyl, cyclopentyl, cyclohexyl, 4-t-butylcyclohexyl and cyclohexylmethyl.

Those skilled in the art will readily understand that for administration the compounds disclosed herein can be admixed with pharmaceutically acceptable excipients which, per se, are well known in the art. Specifically, a drug to be administered systemically, it may be formulated as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the compounds of the present invention and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectable formulations can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds of the present invention administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 ng/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Similarly, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

For topical use, creams, ointments, gels, solutions or suspensions, etc., containing the compound of the present invention are employed. Topical formulations may generally be comprised of a pharmaceutical carrier, cosolvent, emulsifier, penetration enhancer, preservative system, and emollient.

The actual dose of the compounds of the present invention depends on the specific compound, and on the condition to be treated; the selection of the appropriate dose is well within the knowledge of the skilled artisan.

These compounds may be prepared and tested for tyrosine kinase inhibiting activity by the preparatory methods and assays disclosed above.

Such modifications are intended to fall within the scope of the appended claims.

All references cited herein are hereby incorporated by reference in their entirety. Also, the compounds of the present invention may be tested by the various in-vitro and in-vivo assays disclosed in such references to demonstrate the claimed utilities.

We claim:

1. A method of treating an ophthalmic disease selected from the group consisting of diabetic retinopathy, age-related macular degeneration, pterygium, and retinopathy of prematurity, comprising administering to a patient in need of said treatment an effective amount of at least one compound selected from the group consisting of:
    4-(2-amino-7,8-dihydropyrido[4,3-d]pyrimidin-6(5H)-yl)-N-phenylbenzamide;
    3-(2-amino-7,8-dihydropyrido[4,3-d]pyrimidin-6(5H)-yl)-N-(3-isopropylphenyl)benzamide;
    3-(2-amino-7,8-dihydropyrido[4,3-d]pyrimidin-6(5H)-yl)-N-(3-methylphenyl)benzamide;
    3-(2-amino-7,8-dihydropyrido[4,3-d]pyrimidin-6(5H)-yl)-N-(4-tert-butylphenyl)benzamide;
    3-(2-amino-7,8-dihydropyrido[4,3-d]pyrimidin-6(5H)-yl)-N-[3-(trifluoromethyl)phenyl]benzamide;
    3-(2-amino-7,8-dihydropyrido[4,3-d]pyrimidin-6(5H)-yl)-N-(4-methylphenyl)benzamide;
    3-(2-amino-7,8-dihydropyrido[4,3-d]pyrimidin-6(5H)-yl)-N-(3-methoxyphenyl)benzamide;
    3-(2-amino-7,8-dihydropyrido[4,3-d]pyrimidin-6(5H)-yl)-N-(4-ethylphenyl)benzamide;
    3-(2-amino-7,8-dihydropyrido[4,3-d]pyrimidin-6(5H)-yl)-N-(3-ethylphenyl)benzamide;
    3-(2-amino-7,8-dihydropyrido[4,3-d]pyrimidin-6(5H)-yl)-N-(4-propylphenyl)benzamide;
    3-(2-amino-7,8-dihydropyrido[4,3-d]pyrimidin-6(5H)-yl)-N-(4-isopropylphenyl)benzamide;
    3-(2-amino-7,8-dihydropyrido[4,3-d]pyrimidin-6(5H)-yl)-N-(4-tert-butylcyclohexyl)benzamide;
    3-(2-amino-7,8-dihydropyrido[4,3-d]pyrimidin-6(5H)-yl)-N-(3,3-dimethylbutyl)benzamide;
    2-(2-amino-7,8-dihydropyrido[4,3-d]pyrimidin-6(5H)-yl)-N-phenyl-1,3-thiazole-4-carboxamide;
    2-(2-amino-7,8-dihydropyrido[4,3-d]pyrimidin-6(5H)-yl)-N-(3-methylphenyl)-1,3-thiazole-4-carboxamide;
    2-(2-amino-7,8-dihydropyrido[4,3-d]pyrimidin-6(5H)-yl)-N-(3-tert-butylphenyl)-1,3-thiazole-4-carboxamide;
    2-(2-amino-7,8-dihydropyrido[4,3-d]pyrimidin-6(5H)-yl)-N-[3-(trifluoromethyl)phenyl]-1,3-thiazole-4-carboxamide;
    3-(2-Amino-5,7-dihydro-pyrrolo[3,4d]pyrimidin-6-yl)-N-phenyl-benzamide;
    2-(2-amino-5,7-dihydro-6H-pyrrolo[3,4-d]pyrimidin-6-yl)-N-phenyl-1,3-thiazole-4-carboxamide;
    2-(2-amino-5,7-dihydro-6H-pyrrolo[3,4-d]pyrimidin-6-yl)-N-(3-isopropylphenyl)-1,3-thiazole-4-carboxamide;
    2-(2-amino-5,7-dihydro-6H-pyrrolo[3,4-d]pyrimidin-6-yl)-N-[3-(trifluoromethyl)phenyl]-1,3-thiazole-4-carboxamide;
    2-(2-amino-5,7-dihydro-6H-pyrrolo[3,4-d]pyrimidin-6-yl)-N-(4-isopropylphenyl)-1,3-thiazole-4-carboxamide;
    2-(2-amino-5,7-dihydro-6H-pyrrolo[3,4-d]pyrimidin-6-yl)-N-[4-(trifluoromethyl)phenyl]-1,3-thiazole-4-carboxamide;
    3-[2-(methylthio)-7,8-dihydropyrido[4,3-d]pyrimidin-6(5H)-yl]-N-[3-(trifluoromethyl)phenyl]benzamide;
    4-methyl-3-[2-(methylthio)-7,8-dihydropyrido[4,3-d]pyrimidin-6(5H)-yl]-N-[3-(trifluoromethyl)phenyl]benzamide;
    N-(3-isopropylphenyl)-4-methyl-3-[2-(methylthio)-7,8-dihydropyrido[4,3-d]pyrimidin-6(5H)-yl]benzamide;
    4-methyl-3-(2-(methylsulfinyl)-7,8-dihydropyrido[4,3-d]pyrimidin-6(5H)-yl)-N-(3-(trifluoromethyl)phenyl)benzamide;
    3-methyl-5-(2-((methylthio)oxy)-7,8-dihydropyrido[4,3-d]pyrimidin-6(5H)-yl)-N-(3-(trifluoromethyl)phenyl)benzamide;
    N-(3-isopropylphenyl)-4-methyl-3-(2-(methylsulfinyl)-7,8-dihydropyrido[4,3-d]pyrimidin-6(5H)-yl)benzamide;
    N-(3-isopropylphenyl)-3-methyl-5-(2-(methylsulfinyl)-7,8-dihydropyrido[4,3-d]pyrimidin-6(5H)-yl)benzamide;
    3-(2-amino-7,8-dihydropyrido[4,3-d]pyrimidin-6(5H)-yl)-4-methyl-N-[3-(trifluoromethyl)phenyl]benzamide;
    3-(2-amino-7,8-dihydropyrido[4,3-d]pyrimidin-6(5H)-yl)-5-methyl-N-[3-(trifluoromethyl)phenyl]benzamide;
    3-(2-amino-7,8-dihydropyrido[4,3-d]pyrimidin-6(5H)-yl)-N-(3-isopropylphenyl)-4-methylbenzamide;
    3-(2-amino-7,8-dihydropyrido[4,3-d]pyrimidin-6(5H)-yl)-N-(3-isopropylphenyl)-5-methylbenzamide;
    3-(7,8-dihydropyrido[4,3-d]pyrimidin-6(5H)-yl)-N-[3-(trifluoromethyl)phenyl]benzamide;

3-(7,8-dihydropyrido[4,3-d]pyrimidin-6(5H)-yl)-4-methyl-N-[3-(trifluoromethyl)phenyl]benzamide;
3-(7,8-dihydropyrido[4,3-d]pyrimidin-6(5H)-yl)-5-methyl-N-[3-(trifluoromethyl)phenyl]benzamide;
3-(7,8-dihydropyrido[4,3-d]pyrimidin-6(5H)-yl)-N-(3-isopropylphenyl)-4-methylbenzamide;
3-(7,8-dihydropyrido[4,3-d]pyrimidin-6(5H)-yl)-N-(3-isopropylphenyl)-5-methylbenzamide;
5-(2-(methylsulfinyl)-7,8-dihydropyrido[4,3-d]pyrimidin-6(5H)-yl)-N-(3-(trifluoromethyl)phenyl)nicotinamide;
N-(3-isopropylphenyl)-5-(2-(methylsulfinyl)-7,8-dihydropyrido[4,3-d]pyrimidin-6(5H)-yl)nicotinamide;
5-(2-amino-7,8-dihydropyrido[4,3-d]pyrimidin-6(5H)-yl)-N-[3-(trifluoromethyl)phenyl]nicotinamide;
5-(2-amino-7,8-dihydropyrido[4,3-d]pyrimidin-6(5H)-yl)-N-(3-isopropylphenyl)nicotinamide;
1-[4-(3,4-dihydro-2,7-naphthyridin-2(1H)-yl)-3-methylphenyl]-3-(3-methylphenyl)urea;
1-[4-(3,4-dihydro-2,7-naphthyridin-2(1H)-yl)-2-methylphenyl]-3-(3-methylphenyl)urea;
3-(3,4-dihydro-2,7-naphthyridin-2(1H)-yl)-N-(3-isopropylphenyl)benzamide;
methyl 7-(3-{[(3-isopropylphenyl)amino]carbonyl}phenyl)-5,6,7,8-tetrahydro-2,7-naphthyridine-4-carboxylate;
7-(3-{[(3-isopropylphenyl)amino]carbonyl}phenyl)-5,6,7,8-tetrahydro-2,7-naphthyridine-4-carboxylic acid;
methyl 7-[3-({[3-(trifluoromethyl)phenyl]amino}carbonyl)phenyl]-5,6,7,8-tetrahydro-2,7-naphthyridine-4-carboxylate;
7-(3-{[(3-isopropylphenyl)amino]carbonyl}phenyl)-N-(3-morpholin-4-ylpropyl)-5,6,7,8-tetrahydro-2,7-naphthyridine-4-carboxamide;
N-(3-hydroxypropyl)-7-(3-{[(3-isopropylphenyl)amino]carbonyl}phenyl)-5,6,7,8-tetrahydro-2,7-naphthyridine-4-carboxamide;
methyl ({[7-(3-{[(3-isopropylphenyl)amino]carbonyl}phenyl)-5,6,7,8-tetrahydro-2,7-naphthyridin-4-yl]carbonyl}amino)acetate;
7-(3-{[(3-isopropylphenyl)amino]carbonyl}phenyl)-N-(3-pyrrolidin-1-ylpropyl)-5,6,7,8-tetrahydro-2,7-naphthyridine-4-carboxamide;
3-(2-amino-7,8-dihydropyrido[4,3-d]pyrimidin-6(5H)-yl)-N-[4-fluoro-3-(trifluoromethyl)phenyl]benzamide; and
3-(2-amino-7,8-dihydropyrido[4,3-d]pyrimidin-6(5H)-yl)-N-benzylbenzamide;
or a pharmaceutically acceptable salt thereof.

2. The method of claim 1, wherein the compound is selected from the group consisting of:
3-(2-amino-7,8-dihydropyrido[4,3-d]pyrimidin-6(5H)-yl)-N-(3-isopropylphenyl)benzamide;
3-(2-amino-7,8-dihydropyrido[4,3-d]pyrimidin-6(5H)-yl)-N-[3-(trifluoromethyl)phenyl]benzamide;
3-(2-amino-7,8-dihydropyrido[4,3-d]pyrimidin-6(5H)-yl)-N-(3-ethylphenyl)benzamide;
3-(2-amino-7,8-dihydropyrido[4,3-d]pyrimidin-6(5H)-yl)-N-(4-propylphenyl)benzamide;
3-(2-amino-7,8-dihydropyrido[4,3-d]pyrimidin-6 (5H)-yl)-N-(4-isopropylphenyl)benzamide;
N-(3-isopropylphenyl)-4-methyl-3-[2-(methylthio)-7,8-dihydropyrido[4,3-d]pyrimidin-6(5H)-yl]benzamide;
3-(2-amino-7,8-dihydropyrido[4,3-d]pyrimidin-6(5H)-yl)-4-methyl-N-[3-(trifluoromethyl)phenyl]benzamide;
3-(2-amino-7,8-dihydropyrido[4,3-d]pyrimidin-6(5H)-yl)-N-(3-isopropylphenyl)-4-methylbenzamide;
3-(2-amino-7,8-dihydropyrido[4,3-d]pyrimidin-6(5H)-yl)-N-(3-isopropylphenyl)-5-methylbenzamide;
3-(3,4-dihydro-2,7-naphthyridin-2(1H)-yl)-N-(3-isopropylphenyl)benzamide;
methyl 7-(3-{[(3-isopropylphenyl)amino]carbonyl}phenyl)-5,6,7,8-tetrahydro-2,7-naphthyridine-4-carboxylate;
7-(3-{[(3-isopropylphenyl)amino]carbonyl}phenyl)-5,6,7,8-tetrahydro-2,7-naphthyridine-4-carboxylic acid;
methyl 7-[3-({[3-(trifluoromethyl)phenyl]amino}carbonyl)phenyl]-5,6,7,8-tetrahydro-2,7-naphthyridine-4-carboxylate; and
3-(2-amino-7,8-dihydropyrido[4,3-d]pyrimidin-6(5H)-yl)-N-[4-fluoro-3-(trifluoromethyl)phenyl]benzamide;
or a pharmaceutically acceptable salt thereof.

* * * * *